(12) United States Patent
Lee et al.

(10) Patent No.: US 12,121,317 B2
(45) Date of Patent: Oct. 22, 2024

(54) END TOOL FOR SURGICAL INSTRUMENT

(71) Applicant: LIVSMED INC., Seongnam-si (KR)

(72) Inventors: Jaeyeong Lee, Seongnam-si (KR);
Jung Joo Lee, Seongnam-si (KR);
Heejin Kim, Seongnam-si (KR);
Dongkyu Jang, Seongnam-si (KR)

(73) Assignee: LIVSMED INC., Seongnam-si (KR)

( * ) Notice: Subject to any disclaimer, the term of this patent is extended or adjusted under 35 U.S.C. 154(b) by 0 days.

(21) Appl. No.: 18/604,049

(22) Filed: Mar. 13, 2024

(65) Prior Publication Data

US 2024/0216094 A1 Jul. 4, 2024

Related U.S. Application Data

(63) Continuation of application No. PCT/KR2022/013952, filed on Sep. 19, 2022.

(30) Foreign Application Priority Data

Sep. 17, 2021 (KR) .................. 10-2021-0125314
Sep. 28, 2021 (KR) .................. 10-2021-0128403

(51) Int. Cl.
*A61B 34/00* (2016.01)
*A61B 17/29* (2006.01)
*A61B 34/30* (2016.01)

(52) U.S. Cl.
CPC .............. *A61B 34/71* (2016.02); *A61B 17/29* (2013.01); *A61B 2017/2932* (2013.01); *A61B 2034/301* (2016.02); *A61B 2034/302* (2016.02)

(58) Field of Classification Search
CPC . A61B 34/71; A61B 17/29; A61B 2017/2932; A61B 2034/301; A61B 2034/302
See application file for complete search history.

(56) References Cited

U.S. PATENT DOCUMENTS

| | | |
|---|---|---|
| 6,676,684 B1 | 1/2004 | Morely et al. |
| 2004/0199147 A1 | 10/2004 | Nishizawa et al. |
| 2010/0198253 A1 | 8/2010 | Jinno et al. |
| 2015/0150635 A1* | 6/2015 | Kilroy ...................... B25J 17/02 606/130 |
| 2020/0315722 A1* | 10/2020 | Penny .................... A61B 90/08 |

FOREIGN PATENT DOCUMENTS

| | | |
|---|---|---|
| KR | 10-2019-0109449 A | 9/2019 |
| KR | 10-2122508 B1 | 6/2020 |

* cited by examiner

*Primary Examiner* — Brooke Labranche
(74) *Attorney, Agent, or Firm* — Bridgeway IP Law Group, PLLC; Sang Ho Lee; Hyun Woo Shin

(57) ABSTRACT

The present disclosure relates to an end tool of a surgical instrument, and more particularly, to an end tool of a surgical instrument that is mountable on a robotic arm or manually operable for use in laparoscopic surgery or various other surgeries.

21 Claims, 122 Drawing Sheets

END TOOL FOR SURGICAL INSTRUMENT

CROSS-REFERENCE TO RELATED APPLICATION(S)

This application is a continuation application of international application No. PCT/KR2022/013952, filed on Sep. 19, 2022, and claims priority to Korean Patent Application No. 10-2021-0125314, filed on Sep. 17, 2021, and Korean Patent Application No. 10-2021-0128403, filed on Sep. 28, 2021, with the Korean Intellectual Property Office, the disclosures of which are incorporated herein in their entirety by reference.

TECHNICAL FIELD

The present disclosure relates to an end tool of a surgical instrument, and more particularly, to an end tool provided in a surgical instrument that is mountable on a robotic arm or manually operable for use in laparoscopic surgery or various other surgeries.

BACKGROUND ART

In medical terms, surgery refers to the treatment of diseases by cutting, incising, or manipulating a skin, a mucous membrane, or other tissues by using medical devices. In particular, open surgery for incising and opening the skin of a surgical site to treat, shape, or remove an organ or the like therein causes issues such as bleeding, side effects, patient's pain, or scarring. Therefore, recently, surgery performed by forming a certain hole on a skin and inserting only a medical device, for example, a laparoscopic instrument or a surgical instrument, or surgery using a robot has been spotlighted as an alternative.

The surgical instrument refers to a tool for operating on a surgical site by a doctor manipulating an end tool provided at one end of a shaft passing through a hole drilled in the skin with a certain drive part or a robotic arm. The end tool provided in the surgical instrument performs a rotational motion, a gripping motion, a cutting motion, and the like, through a certain structure.

The above-mentioned background art is technical information possessed by the inventor for the derivation of the present disclosure or acquired during the derivation of the present disclosure, and cannot necessarily be said to be a known technique disclosed to the general public prior to the filing of the present disclosure.

DISCLOSURE

Technical Problem

The present disclosure provides an end tool of a surgical instrument that is mountable on a robotic arm or manually operable for use in laparoscopic surgery or various other surgeries, the end tool being capable of independently and seamlessly performing a pitch motion and a yaw motion/actuation motion by compensating for a motion of a jaw wire that occurs during the pitch motion.

Technical Solution

The present disclosure provides an end tool of a surgical instrument, the end tool including: a first jaw; a second jaw formed to face the first jaw; a first jaw pulley coupled to the first jaw and formed to be rotatable around a first shaft; a second jaw pulley coupled to the second jaw, formed to be rotatable around a shaft that is substantially the same as or parallel to the first shaft, and formed to face the first jaw pulley; a pair of first jaw pitch main pulleys formed on one side of the first jaw pulley, and formed to be rotatable around a second shaft forming a predetermined angle with the first shaft; a pair of second jaw pitch main pulleys formed on one side of the second jaw pulley, and formed to be rotatable around a shaft that is substantially the same as or parallel to the second shaft; a first jaw pitch redundant pulley arranged between the first jaw pulley and the pair of first jaw pitch main pulleys, and formed to be rotatable around a third shaft; a second jaw pitch redundant pulley arranged between the second jaw pulley and the pair of second jaw pitch main pulleys, and formed to be rotatable around a fourth shaft; a first jaw wire coupled to the first jaw pulley to rotate the first jaw pulley, and wound around at least portions of the pair of first jaw pitch main pulleys; and a second jaw wire coupled to the second jaw pulley to rotate the second jaw pulley, and wound around at least portions of the pair of second jaw pitch main pulleys.

Advantageous Effects

According to the present disclosure, a pitch motion and a yaw motion/actuation motion may be performed independently and seamlessly by compensating for a motion of a jaw wire that occurs during the pitch motion.

BEST MODE

Figure 1A:
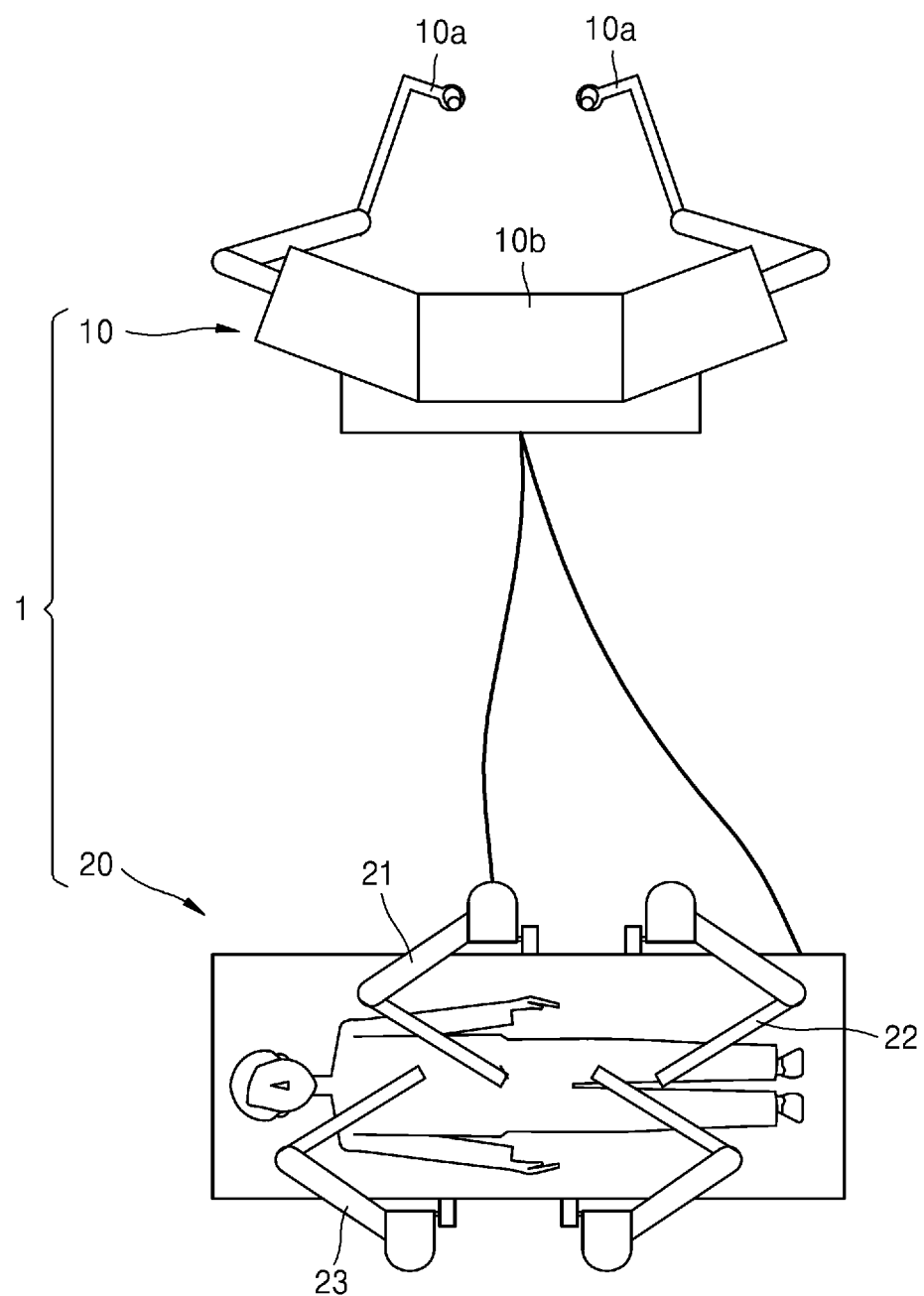
FIGS. 1A-1D are diagrams illustrating an example of use of an end tool of a surgical instrument according to an embodiment of the present disclosure.

In the present disclosure, among two strands of the first jaw wire coupled to the first jaw pulley, when moving from a proximal end to a distal end of the end tool, any one strand of the first jaw wire may be wound around any one of the pair of first jaw pitch main pulleys in any one of a clockwise direction and a counterclockwise direction, and the other strand of the first jaw wire may be wound around the other one of the pair of first jaw pitch main pulleys in the other one of the clockwise direction and the counterclockwise direction.

In the present disclosure, with respect to a plane perpendicular to the first shaft and passing between the first jaw pulley and the second jaw pulley, among two strands of first the jaw wire coupled to the first jaw pulley, any one strand of the first jaw wire comes into contact with an upper side of any one of the pair of first jaw pitch main pulleys, and the other strand of the first jaw wire comes into contact with a lower side of the other one of the pair of first jaw pitch main pulleys.

In the present disclosure, the first jaw wire, when moving from a proximal end to a distal end of the end tool, may sequentially come into contact with the pair of first jaw pitch main pulleys and the first jaw pitch redundant pulley.

In the present disclosure, with respect to a plane perpendicular to the first shaft and passing between the first jaw pulley and the second jaw pulley, any one of two strands of the first jaw wire coupled to the first jaw pulley may sequentially come into contact with a lower side of any one of the pair of first jaw pitch main pulleys, and a lower side of the first jaw pitch redundant pulley, and the other one of the two strands of the first jaw wire coupled to the first jaw pulley may sequentially come into contact with an upper side of the other one of the pair of first jaw pitch main pulleys, and a lower side of the first jaw pitch redundant pulley.

In the present disclosure, the end tool may further include: a first jaw auxiliary pulley formed between the first jaw pulley and the first jaw pitch redundant pulley; and a second jaw auxiliary pulley formed between the second jaw pulley and the second jaw pitch redundant pulley.

In the present disclosure, the first jaw wire may be located on a common internal tangent of the first jaw pulley and the first jaw auxiliary pulley, and a rotation angle of the first jaw pulley may be increased by the first jaw auxiliary pulley.

In the present disclosure, the end tool may further include: one or more first jaw pitch sub-pulleys formed on one side of the pair of first jaw pitch main pulleys and rotatable around a shaft that is substantially parallel to the second shaft; and one or more second jaw pitch sub-pulleys formed on one side of the pair of second jaw pitch main pulleys and rotatable around a shaft that is substantially parallel to the second shaft.

In the present disclosure, the one or more first jaw pitch sub-pulleys or the one or more second jaw pitch sub-pulleys may include only one pulley.

In the present disclosure, the end tool may further include: an end tool hub formed to accommodate at least portions of the first jaw and the second jaw; and a pitch hub axially coupled to the end tool hub to be rotatable with respect to the end tool hub.

In the present disclosure, a yaw motion may be performed as the first jaw and the second jaw are rotated around the first shaft, and a pitch motion may be performed as the end tool hub is rotated around the second shaft.

In the present disclosure, the end tool may further include: an end tool pitch pulley formed at a proximal end of the end tool hub; and a pitch wire coupled to the end tool pitch pulley to rotate the end tool pitch pulley.

In the present disclosure, when the end tool pitch pulley is rotated by the pitch wire, as the entire end tool hub is rotated together with the end tool pitch pulley, lengths by which the first jaw wire is wound around the pair of first jaw pitch main pulleys and the pair of second jaw pitch main pulleys may change.

In the present disclosure, when the end tool pitch pulley is rotated by the pitch wire, the first jaw wire may be moved by an external force to a certain extent, in order to compensate for changes in the lengths by which the first jaw wire is wound around the pair of first jaw pitch main pulleys and the pair of second jaw pitch main pulleys.

In the present disclosure, the first jaw pitch redundant pulley or the second jaw pitch redundant pulley may be formed with the end tool hub as one body.

In the present disclosure, the third shaft and the fourth shaft may be substantially parallel to the second shaft.

In the present disclosure, the third shaft and the fourth shaft may be formed to be inclined with respect to the first shaft and the second shaft, respectively.

In the present disclosure, a groove on the first jaw pulley around which the first jaw wire is wound, and a groove on the second jaw pulley around which the second jaw wire is wound may be formed to be spaced apart from each other to a certain extent.

In the present disclosure, a groove on the first jaw pulley around which the first jaw wire is wound, and a groove on the second jaw pulley around which the second jaw wire is wound may be formed adjacent to each other.

In the present disclosure, the first jaw pitch redundant pulley or the second jaw pitch redundant pulley may include only one pulley.

The present disclosure provides a surgical instrument including: the end tool of the surgical instrument of any one of claims 1 to 20; a drive part configured to provide a certain driving force necessary for rotation of the end tool; and a connection part extending in a first direction (an X-axis) and connecting the drive part to the end tool as the end tool is coupled to one end of the connection part, and the drive part is coupled to the other end of the connection part.

In the present disclosure, when a drive part pitch pulley of the drive part is rotated for a pitch motion, a drive part first jaw pulley and a drive part second jaw pulley of the drive part may be rotated together to compensate for the pitch motion.

The present disclosure provides an end tool of a surgical instrument, the end tool including: a first jaw; a second jaw coupled to be rotatable with respect to the first jaw; an end tool hub formed to accommodate at least portions of the first jaw and the second jaw; a pitch hub axially coupled to the end tool hub to be rotatable with respect to the end tool hub; a first pin inserted through the end tool hub and extending in a first direction; a second pin inserted through the end tool hub and formed on one side of the first pin to be parallel to the first pin; a two-and-a-halfth pin inserted through the end tool hub, and formed on one side of the second pin to extend in a second direction that forms a predetermined angle with the first direction; a third pin inserted through the end tool hub and the pitch hub, and formed on one side of the two-and-a-halfth pin to be parallel to the two-and-a-halfth pin; a fourth pin inserted through the pitch hub, and formed on one side of the third pin to be parallel to the third pin; a first jaw pulley coupled to the first jaw and formed to be rotatable around the first pin; a second jaw pulley coupled to the second jaw and formed to be rotatable around the first pin; a first auxiliary pulley formed on one side of the first jaw pulley to be rotatable around the second pin; a second jaw auxiliary pulley formed on one side of the second jaw pulley to be rotatable around the second pin; one or more first jaw pitch redundant pulleys formed on one side of the first jaw auxiliary pulley to be rotatable around the two-and-a-halfth pin; one or more second jaw pitch redundant pulleys formed on one side of the second jaw auxiliary pulley to be rotatable around the two-and-a-halfth pin; a pair of first jaw pitch main pulleys formed on one side of the one or more first jaw pitch redundant pulleys to be rotatable around the third pin; a pair of second jaw pitch main pulleys formed on one side of the one or more second jaw pitch redundant pulleys to be rotatable around the third pin; one or more first jaw pitch sub-pulleys formed on one side of the pair of first jaw pitch main pulleys to be rotatable around the fourth pin; one or more second jaw pitch sub-pulleys formed on one side of the pair of second jaw pitch main pulleys to be rotatable around the fourth pin; a first jaw wire coupled to the first jaw pulley to rotate the first jaw pulley, and wound around at least portions of the pair of first jaw pitch main pulleys; and a second jaw wire coupled to the second jaw pulley to rotate the second jaw pulley, and wound around at least portions of the pair of second jaw pitch main pulleys.

In the present disclosure, among two strands of the first jaw wire coupled to the first jaw pulley, when moving from a proximal end to a distal end of the end tool, any one strand of the first jaw wire may be wound around any one of the pair of first jaw pitch main pulleys in any one of a clockwise direction and a counterclockwise direction, and the other strand of the first jaw wire may be wound around the other one of the pair of first jaw pitch main pulleys in the other one of the clockwise direction and the counterclockwise direction.

In the present disclosure, with respect to a plane perpendicular to the first pin and passing between the first jaw pulley and the second jaw pulley, among two strands of first the jaw wire coupled to the first jaw pulley, any one strand of the first jaw wire may come into contact with an upper side of any one of the pair of first jaw pitch main pulleys, and the other strand of the first jaw wire may come into contact with a lower side of the other one of the pair of first jaw pitch main pulleys.

In the present disclosure, the first jaw wire, when moving from a proximal end to a distal end of the end tool, may sequentially come into contact with the one or more first jaw pitch sub-pulleys, the pair of first jaw pitch main pulleys, and the one or more first jaw pitch redundant pulleys.

In the present disclosure, with respect to a plane perpendicular to the first pin and passing between the first jaw pulley and the second jaw pulley, any one of two strands of the first jaw wire coupled to the first jaw pulley may sequentially come into contact with an upper side of the one or more first jaw pitch sub-pulleys, a lower side of any one of the pair of first jaw pitch main pulleys, and a lower side of the one or more first jaw pitch redundant pulleys, and the other one of the two strands of the first jaw wire coupled to the first jaw pulley may sequentially come into contact with a lower side of the one or more first jaw pitch sub-pulleys, an upper side of the other one of the pair of first jaw pitch main pulleys, and a lower side of the first jaw pitch redundant pulley.

In the present disclosure, the end tool may further include: an end tool pitch pulley formed at a proximal end of the end tool hub; and a pitch wire coupled to the end tool pitch pulley to rotate the end tool pitch pulley.

In the present disclosure, when the end tool pitch pulley is rotated by the pitch wire, as the entire end tool hub is rotated together with the end tool pitch pulley, lengths by which the first jaw wire is wound around the pair of first jaw pitch main pulleys and the pair of second jaw pitch main pulleys may change.

In the present disclosure, when the end tool pitch pulley is rotated by the pitch wire, the first jaw wire may be moved by an external force to a certain extent, in order to compensate for changes in the lengths by which the first jaw wire is wound around the pair of first jaw pitch main pulleys and the pair of second jaw pitch main pulleys.

In the present disclosure, the first pin, the second pin, the two-and-a-halfth pin, the third pin, and the fourth pin may be sequentially arranged in a direction from a distal end of the end tool toward a proximal end of the end tool.

In the present disclosure, the first jaw pulley, the first jaw auxiliary pulley, the one or more first jaw pitch redundant pulleys, the pair of first jaw pitch main pulleys, and the one or more first jaw pitch sub-pulleys may be sequentially arranged in a direction from a distal end of the end tool toward a proximal end of the end tool.

In the present disclosure, the first jaw wire may be located on a common internal tangent of the first jaw pulley and the first jaw auxiliary pulley, and a rotation angle of the first jaw pulley may be increased by the first jaw auxiliary pulley.

In the present disclosure, a surgical instrument characterized in that a yaw motion may be performed as the first jaw and the second jaw are rotated around the first pin, and a pitch motion may be performed as the end tool hub is rotated around the third pin.

In the present disclosure, a groove on the first jaw pulley around which the first jaw wire is wound, and a groove on the second jaw pulley around which the second jaw wire is wound may be formed to be spaced apart from each other to a certain extent.

In the present disclosure, a groove on the first jaw pulley around which the first jaw wire is wound, and a groove on the second jaw pulley around which the second jaw wire is wound may be formed adjacent to each other.

In the present disclosure, the one or more first jaw pitch redundant pulleys or the one or more second jaw pitch redundant pulleys may include only one pulley.

In the present disclosure, the one or more first jaw pitch redundant pulleys or the one or more second jaw pitch redundant pulleys may be formed with the end tool hub as one body.

In the present disclosure, the one or more first jaw pitch sub-pulleys or the one or more second jaw pitch sub-pulleys may include only one pulley.

The present disclosure provides an end tool of a surgical instrument, the end tool including: a first jaw; a second jaw coupled to be rotatable with respect to the first jaw; an end tool hub formed to accommodate at least portions of the first jaw and the second jaw; a pitch hub axially coupled to the end tool hub to be rotatable with respect to the end tool hub; a first pin inserted through the end tool hub and extending in a first direction; a second pin inserted through the end tool hub, and formed on one side of the first pin to extend in a second direction that forms a predetermined angle with the first direction; a third pin inserted through the end tool hub and the pitch hub, and formed on one side of the second pin to extend in a third direction that forms predetermined angles with the first direction and the second direction; a fourth pin inserted through the pitch hub, and formed on one side of the third pin to be parallel to the third pin; a first jaw pulley coupled to the first jaw and formed to be rotatable around the first pin; a second jaw pulley coupled to the second jaw and formed to be rotatable around the first pin; a first auxiliary pulley formed on one side of the first jaw pulley to be rotatable around the second pin; a second jaw auxiliary pulley formed on one side of the second jaw pulley to be rotatable around the second pin; a pair of first jaw pitch main pulleys formed on one side of the first jaw auxiliary pulley to be rotatable around the third pin; a pair of second jaw pitch main pulleys formed on one side of the second jaw auxiliary pulley to be rotatable around the third pin; one or more first jaw pitch sub-pulleys formed on one side of the pair of first jaw pitch main pulleys to be rotatable around the fourth pin; one or more second jaw pitch sub-pulleys formed on one side of the pair of second jaw pitch main pulleys to be rotatable around the fourth pin; a first jaw wire coupled to the first jaw pulley to rotate the first jaw pulley, and wound around at least portions of the pair of first jaw pitch main pulleys; and a second jaw wire coupled to the second jaw pulley to rotate the second jaw pulley, and wound around at least portions of the pair of second jaw pitch main pulleys.

In the present disclosure, among two strands of the first jaw wire coupled to the first jaw pulley, when moving from a proximal end to a distal end of the end tool, any one strand of the first jaw wire may be wound around any one of the pair of first jaw pitch main pulleys in any one of a clockwise direction and a counterclockwise direction, and the other strand of the first jaw wire may be wound around the other one of the pair of first jaw pitch main pulleys in the other one of the clockwise direction and the counterclockwise direction.

In the present disclosure, with respect to a plane perpendicular to the first pin and passing between the first jaw pulley and the second jaw pulley, among two strands of first the jaw wire coupled to the first jaw pulley, any one strand of the first jaw wire may come into contact with an upper side of any one of the pair of first jaw pitch main pulleys, and the other strand of the first jaw wire may come into contact with a lower side of the other one of the pair of first jaw pitch main pulleys.

In the present disclosure, the first jaw wire, when moving from a proximal end to a distal end of the end tool, may sequentially come into contact with the one or more first jaw pitch sub-pulleys, the pair of first jaw pitch main pulleys, the first jaw auxiliary pulley, and the first jaw pulley.

In the present disclosure, with respect to a plane perpendicular to the first pin and passing between the first jaw pulley and the second jaw pulley, any one of two strands of the first jaw wire coupled to the first jaw pulley may sequentially come into contact with an upper side of the one or more first jaw pitch sub-pulleys, a lower side of any one of the pair of first jaw pitch main pulleys, and the first jaw pulley, and the other one of the two strands of the first jaw wire coupled to the first jaw pulley may sequentially come into contact with a lower side of the one or more first jaw pitch sub-pulleys, an upper side of the other one of the pair of first jaw pitch main pulleys, the first jaw auxiliary pulley, and the first jaw pulley.

In the present disclosure, the end tool may further include: an end tool pitch pulley formed at a proximal end of the end tool hub; and a pitch wire coupled to the end tool pitch pulley to rotate the end tool pitch pulley.

In the present disclosure, when the end tool pitch pulley is rotated by the pitch wire, as the entire end tool hub is rotated together with the end tool pitch pulley, lengths by which the first jaw wire is wound around the pair of first jaw pitch main pulleys and the pair of second jaw pitch main pulleys may change.

In the present disclosure, when the end tool pitch pulley is rotated by the pitch wire, the first jaw wire may be moved by an external force to a certain extent, in order to compensate for changes in the lengths by which the first jaw wire is wound around the pair of first jaw pitch main pulleys and the pair of second jaw pitch main pulleys.

In the present disclosure, the first pin, the second pin, the third pin, and the fourth pin may be sequentially arranged in a direction from a distal end of the end tool toward a proximal end of the end tool.

In the present disclosure, the first jaw pulley, the first jaw auxiliary pulley, the pair of first jaw pitch main pulleys, and the one or more first jaw pitch sub-pulleys may be sequentially arranged in a direction from a distal end of the end tool toward a proximal end of the end tool.

In the present disclosure, the first jaw wire may be located on a common internal tangent of the first jaw pulley and the first jaw auxiliary pulley, and a rotation angle of the first jaw pulley may be increased by the first jaw auxiliary pulley.

In the present disclosure, a yaw motion may be performed as the first jaw and the second jaw are rotated around the first pin, and a pitch motion may be performed as the end tool hub is rotated around the third pin.

In the present disclosure, the second pin may include a first sub-shaft formed in a first jaw pulley coupling part of the end tool hub, and a second sub-shaft formed in a second jaw pulley coupling part of the end tool hub, the first jaw auxiliary pulley may be coupled to the first sub-shaft, and the second jaw auxiliary pulley may be coupled to the second sub-shaft.

In the present disclosure, the first sub-shaft and the second sub-shaft may be formed to be inclined to a certain extent with respect to the first pin and the third pin.

In the present disclosure, with respect to a first plane perpendicular to the first pin and passing between the first jaw pulley and the second jaw pulley, the first jaw wire may cross the first plane while passing through the first jaw auxiliary pulley.

In the present disclosure, with respect to a first plane perpendicular to the first pin and passing between the first jaw pulley and the second jaw pulley, the first jaw wire may come into contact with the pair of first jaw pitch main pulleys on a lower side of the first plane, and come into contact with the first jaw auxiliary pulley on an upper side of the first plane.

Other aspects, features, advantages other than those described above will become apparent from the following drawings, claims, and detailed description of the present disclosure.

Mode for Invention

As the present disclosure allows for various changes and numerous embodiments, example embodiments will be illustrated in the drawings and described in detail. However, this is not intended to limit the present disclosure to particular modes of practice, and it is to be appreciated that all modifications, equivalents, and/or alternatives that do not depart from the spirit and technical scope are encompassed in the disclosure. In describing the present disclosure, detailed explanations of the related art are omitted when it is deemed that they may unnecessarily obscure the gist of the present disclosure.

While such terms as "first," "second," and the like may be used to describe various components, such components are not be limited by the above terms. These terms are used only to distinguish one component from another.

Terms used in the present application are merely used to describe example embodiments, and are not intended to limit the present disclosure. Singular forms are intended to include plural forms as well, unless the context clearly indicates otherwise. In the present specification, it is to be understood that the terms such as "including," "having," and "comprising" are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

Hereinafter, embodiments of the present disclosure will be described below in detail with reference to the accompanying drawings, and in describing the embodiments of the present disclosure with reference to the drawings, the same or corresponding components are given the same reference numerals, and repetitive descriptions thereof will be omitted.

Further, in describing the various embodiments of the present disclosure, it is to be understood that each embodiment is not intended to be interpreted or implemented independently, and that the technical ideas described in each embodiment may be interpreted or implemented in combination with other embodiments described separately.

Surgical Instrument

FIG. 1 is a diagram illustrating an example of use of an end tool of a surgical instrument according to an embodiment of the present disclosure. In this regard, FIG. 1A is a conceptual diagram illustrating a surgical robotic system equipped with an end tool of a surgical instrument, according to an embodiment of the present disclosure, FIG. 1B is a perspective view illustrating a slave robot of the surgical robotic system of FIG. 1A, and FIG. 1C is a perspective view illustrating a surgical instrument mounted on the slave robot of FIG. 1A. In addition, FIG. 1D is a perspective view illustrating an example of a hand-held surgical instrument equipped with an end tool, according to an embodiment of the present disclosure.

Figure 1B:
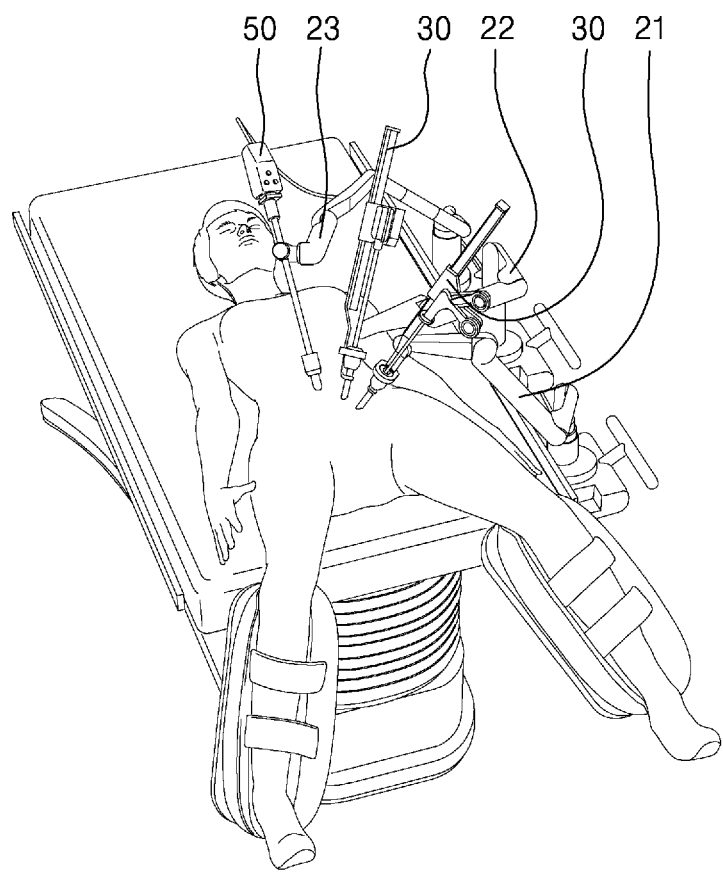
Figure 1C:
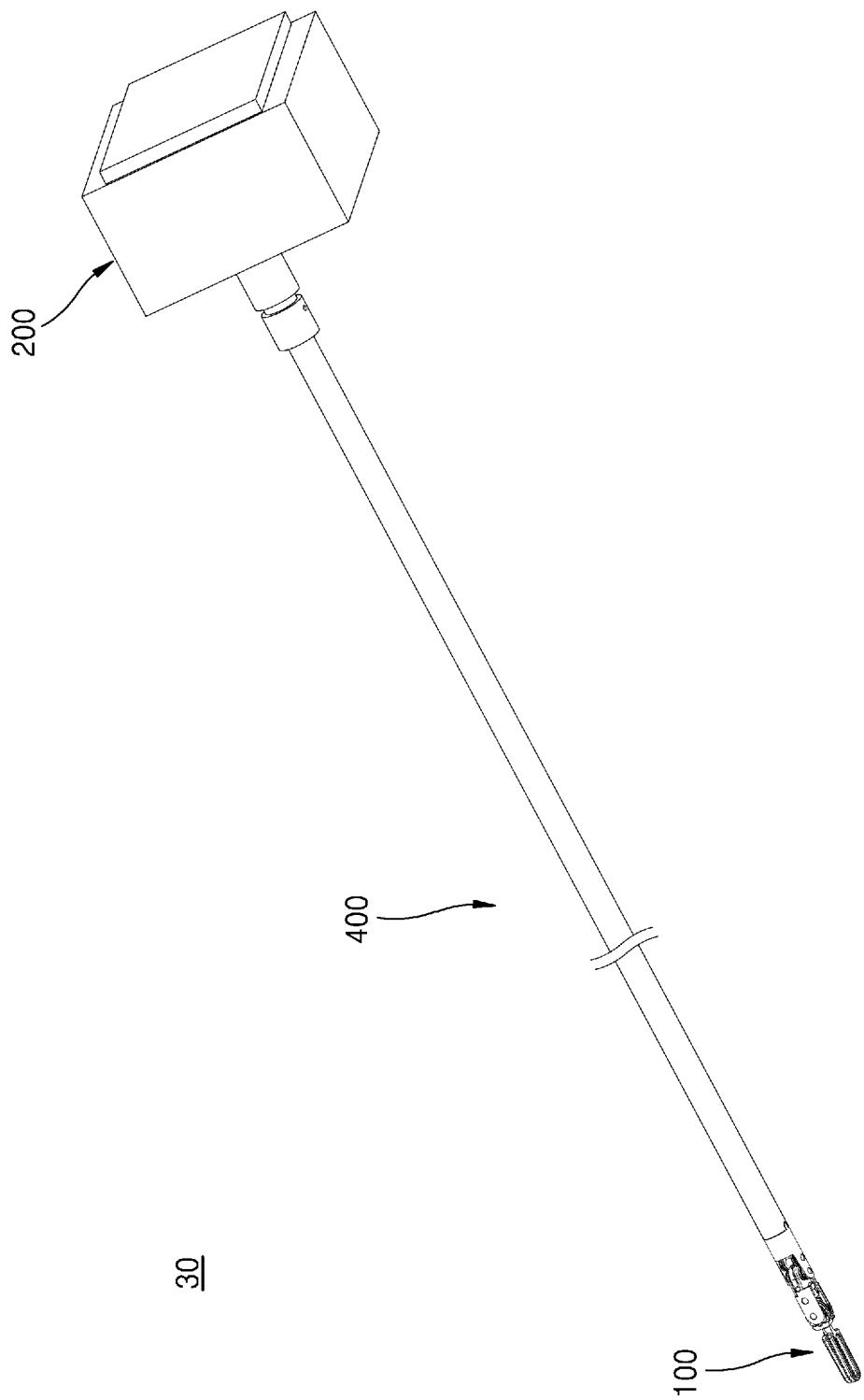

Referring to FIGS. 1A, 1B, and 1C, a surgical robotic system 1 includes a master robot 10, a slave robot 20, and a surgical instrument 30.

The master robot 10 includes a manipulation member 10a and a display member 10b, and the slave robot 20 includes one or more robotic arm units 21, 22, and 23.

In detail, the master robot 10 includes the manipulation member 10a to allow an operator to hold and manipulate the manipulation member 10a with both hands. In addition, an image captured through a laparoscope 50 is displayed as an image on the display member 10b of the master robot 10. In addition, a predetermined virtual manipulation panel may be displayed on the display member 10b independently of or together with the image captured through the laparoscope 50. Detailed descriptions of the arrangement and configuration of the virtual manipulation panel will be omitted.

Meanwhile, the slave robot 20 may include the one or more robotic arm units 21, 22, and 23. In this regard, each of the robotic arm units 21, 22, and 23 may be provided in the form of a module that may operate independently of each other, and in this case, an algorithm for preventing collisions between the robotic arm units 21, 22, and 23 may be applied to the surgical robotic system 1.

In this regard, surgical instruments 30 may be attached to two or more of the robotic arm units 21, 22, and 23, and laparoscopes 50 may be attached to one or more of the robotic arm units 21, 22, and 23. In addition, a surgeon may select the robotic arm unit 21, 22, or 23 to be controlled through the master robot 10. As such, the surgeon may directly control a total of three or more surgical instruments through the master robot 10 without the need for a surgical assistant, and thus manipulate various instruments accurately and freely as intended by the surgeon.

Continuing to refer to FIG. 1C, the surgical instrument 30 of the surgical robotic system 1 may include an end tool 100, a drive part 200, and a connection part 400.

In this regard, the connection part 400 may be formed in the shape of a hollow shaft and accommodate one or more wires (to be described below) therein, and the drive part 200 may be coupled to one end of the connection part 400, and the end tool 100 is coupled to the other end of the connection part 400 such that the connection part 400 serves to connect the drive part 200 to the end tool 100.

The drive part 200 is formed at one end of the connection part 400 and provides an interface that may be coupled to the robotic arm unit 21, 22, or 23. Thus, when the master robot 10 is operated by a user, a motor (not shown) of the robotic arm unit 21, 22, or 23 operate to allow the end tool 100 of the surgical instrument 30 to perform a corresponding motion, and a driving force of the motor (not shown) is transmitted to the end tool 100 through the drive part 200. In other words, it may also be described that the drive part 200 itself serves as an interface connecting the surgical instrument 30 to the slave robot 20.

The end tool 100 may be formed at the other end of the connection part 400 and may be inserted into a surgical site to perform a motion necessary for surgery. The end tool 100 will be described in more detail below with reference to FIG. 2 and the subsequent drawings.

Figure 1D:
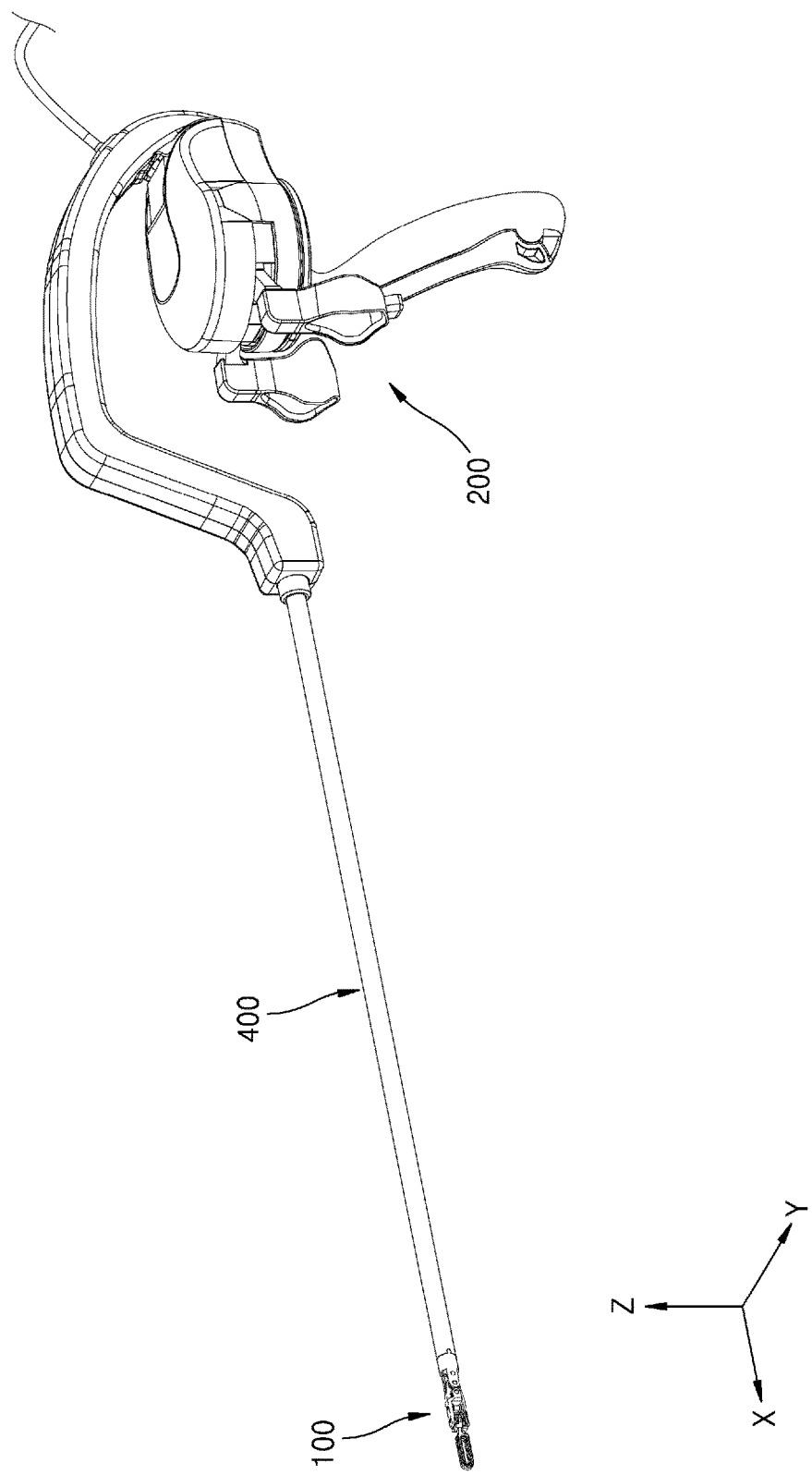

Meanwhile, referring to FIG. 1D, a hand-held surgical instrument 40 may include the end tool 100, the drive part 200, and the connection part 400.

In this regard, the connection part 400 may be formed in the shape of a hollow shaft and accommodate one or more wires (to be described below) therein, and the drive part 200 may be coupled to one end of the connection part 400, and the end tool 100 is coupled to the other end of the connection part 400 such that the connection part 400 serves to connect the drive part 200 to the end tool 100.

The drive part 200 is formed at one end of the connection part 400 and provided as an interface to be directly manipulated by a doctor, for example, in a tongs shape, a stick shape, a lever shape, or the like, and when the doctor manipulates the drive part 200, the end tool 100, which is connected to the interface and inserted into the body of a surgical patient, performs a certain motion, thereby performing surgery. In this regard, although FIG. 1D illustrates that the drive part 200 is formed in the shape of a handle that may be rotated while fingers are inserted therein, the present disclosure is not limited thereto, and various types of drive parts 200 that may be connected to the end tool 100 to manipulate the end tool 100 may be possible.

The end tool 100 may be formed at the other end of the connection part 400 and may be inserted into a surgical site to perform a motion necessary for surgery. The end tool 100 will be described in more detail below with reference to FIG. 2 and the subsequent drawings.

An end tool of a surgical instrument according to an embodiment of the present disclosure may be provided in the surgical instrument of the surgical robotic system illustrated in FIGS. 1A, 1B, and 1C, or may be provided in the hand-held surgical instrument illustrated in FIG. 1D.

Hereinafter, an end tool that may be provided in a surgical instrument of a surgical robotic system or a hand-held surgical instrument will be described in more detail.

First Embodiment of End Tool of Surgical Instrument

Figure 2:
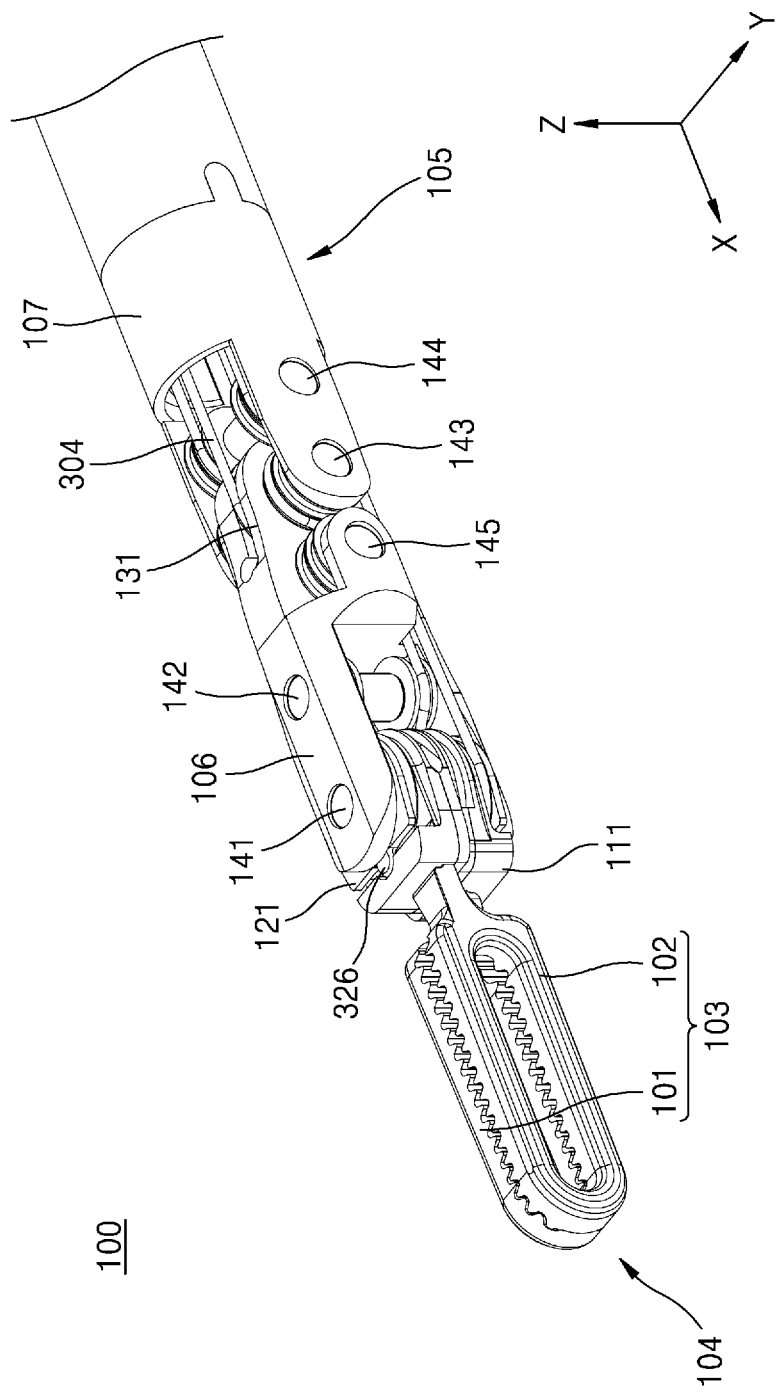
FIGS. 2 and 3 are perspective views illustrating an end tool of a surgical instrument according to a first embodiment of the present disclosure.
Figure 3:
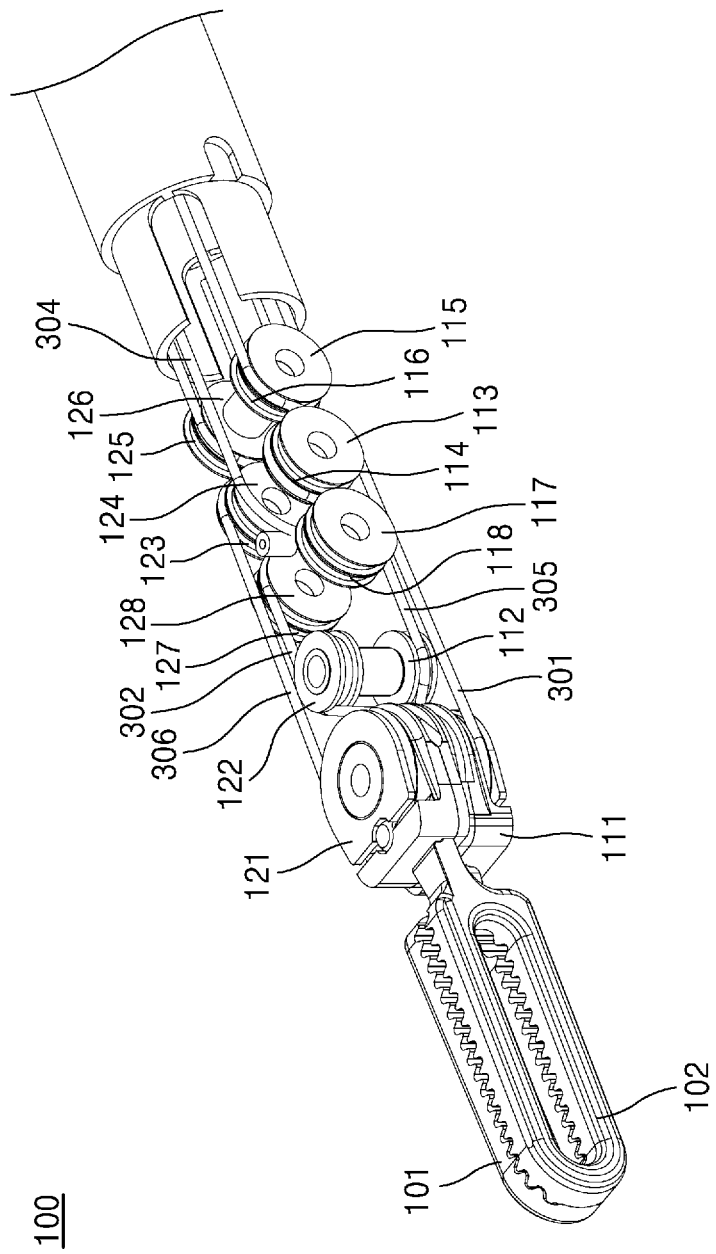
Figure 4:
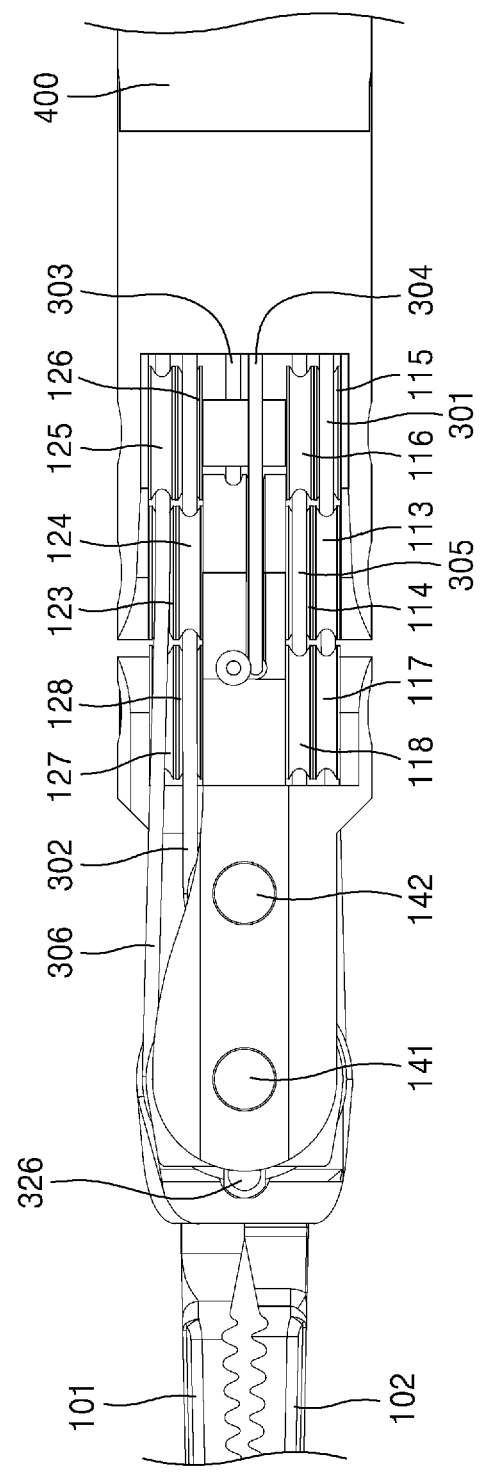
FIG. 4 is a plan view of the end tool of FIG. 2.
Figure 5:
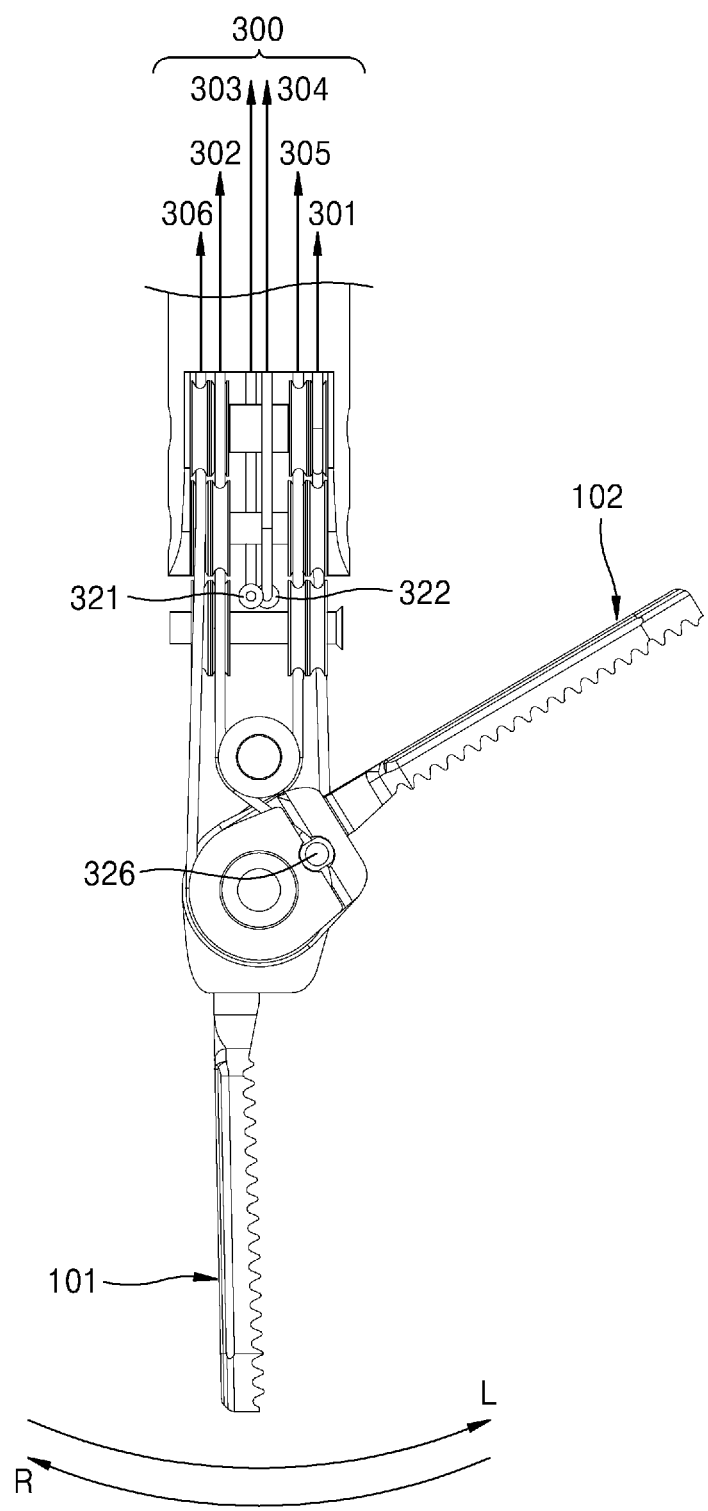
FIGS. 5 and 6 are plan views of the end tool of FIG. 2.
Figure 6:
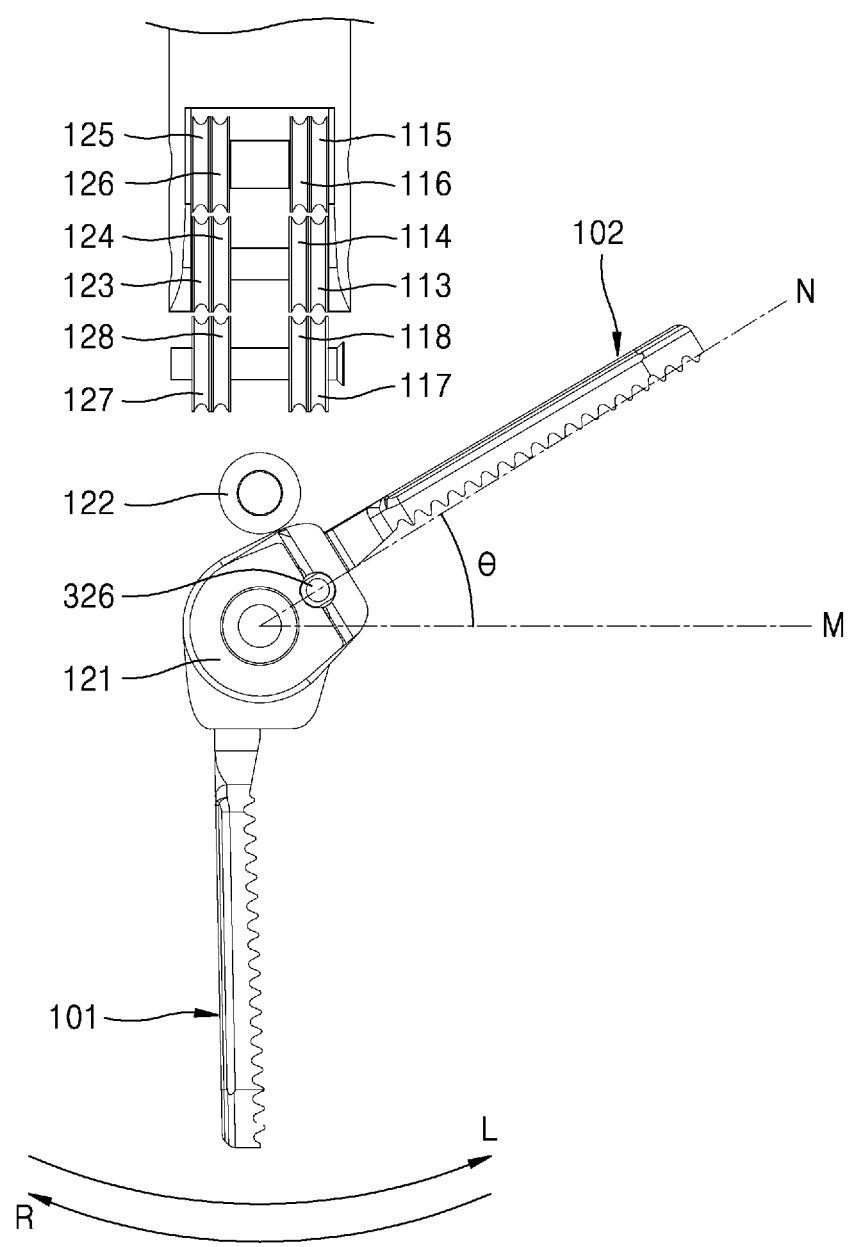
Figure 7A:
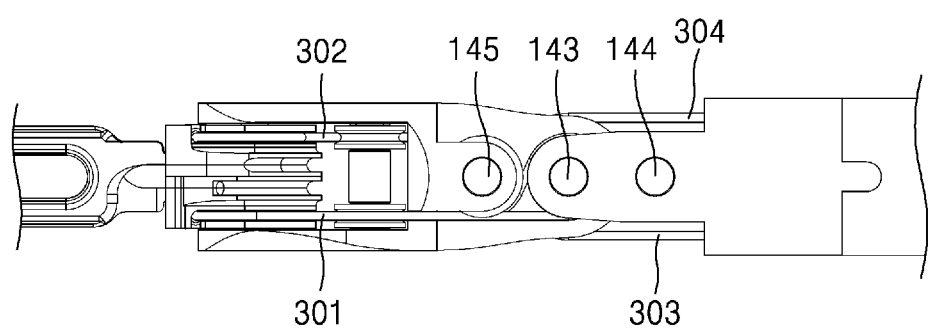
FIGS. 7A-7C are side views of the end tool of FIG. 2.
Figure 7B:
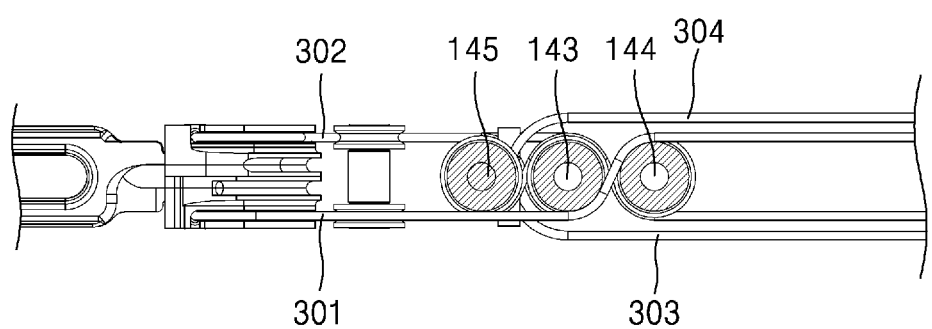
Figure 7C:
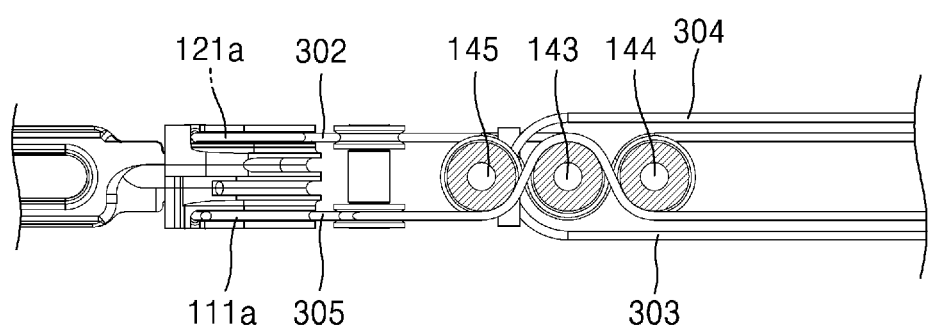
Figure 8:
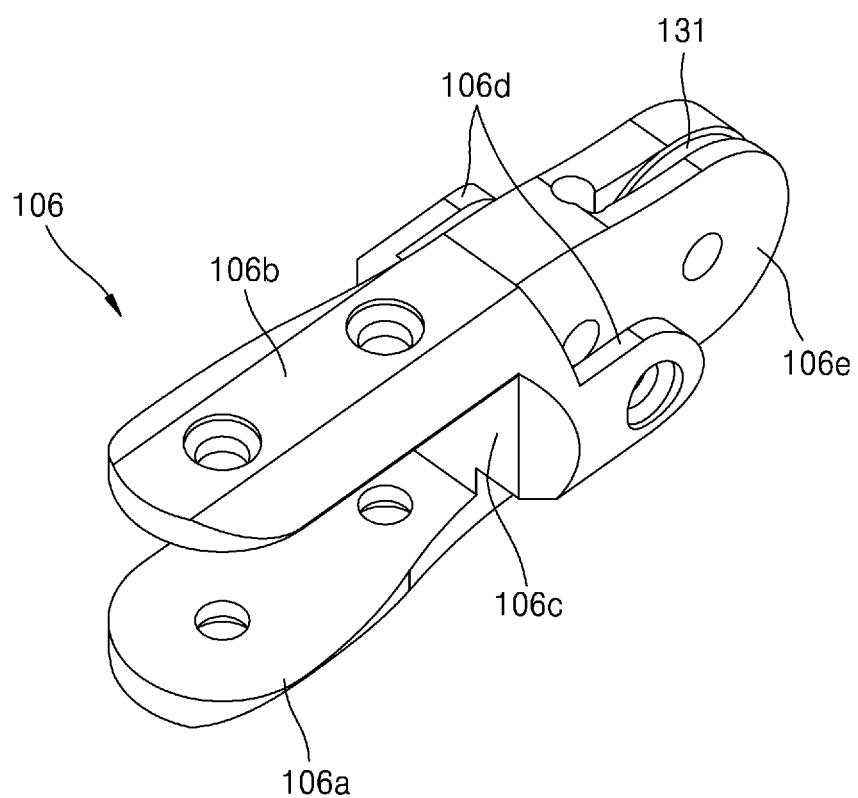
FIG. 8 is a perspective view of an end tool hub of the end tool of FIG. 2.
Figure 9:
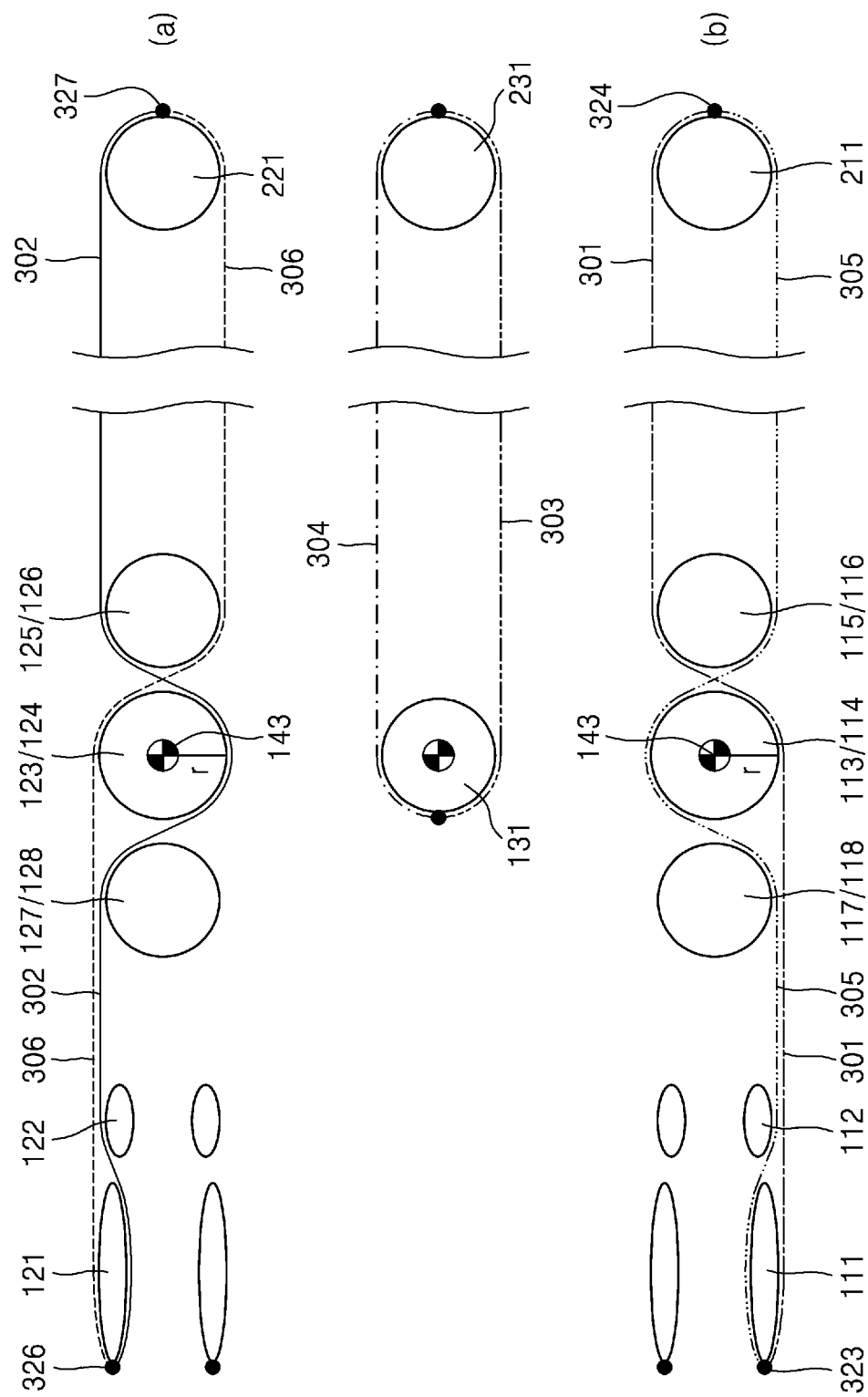
FIGS. 9-11B are conceptual diagrams of pitch motion compensation of a surgical instrument according to a first embodiment of the present disclosure.

FIGS. 2 and 3 are perspective views illustrating an end tool of a surgical instrument according to a first embodiment of the present disclosure. FIG. 4 is a plan view of the end tool of FIG. 2. FIGS. 5 and 6 are plan views of the end tool of FIG. 2. FIG. 7 is a side view of the end tool of FIG. 2. FIG. 8 is a perspective view of an end tool hub of the end tool of FIG. 2. FIGS. 9, 10, and 11 are conceptual diagrams of pitch motion compensation of a surgical instrument according to an embodiment of the present disclosure.

Figure 12:
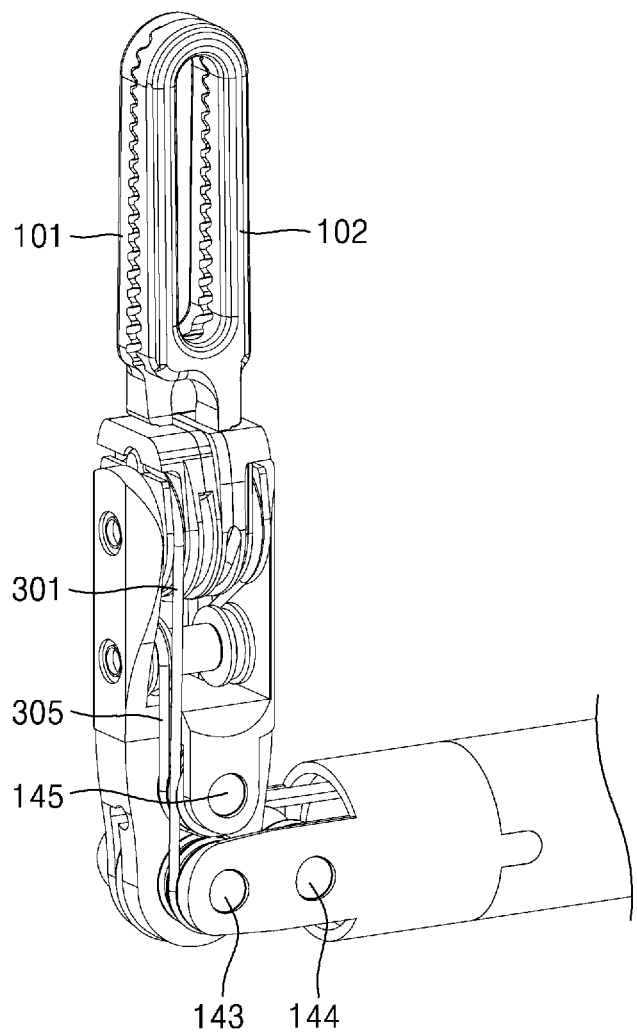
FIGS. 12 and 13 are perspective views illustrating a state in which the end tool of the surgical instrument of FIG. 2 is pitch-rotated by −90°.
Figure 13:
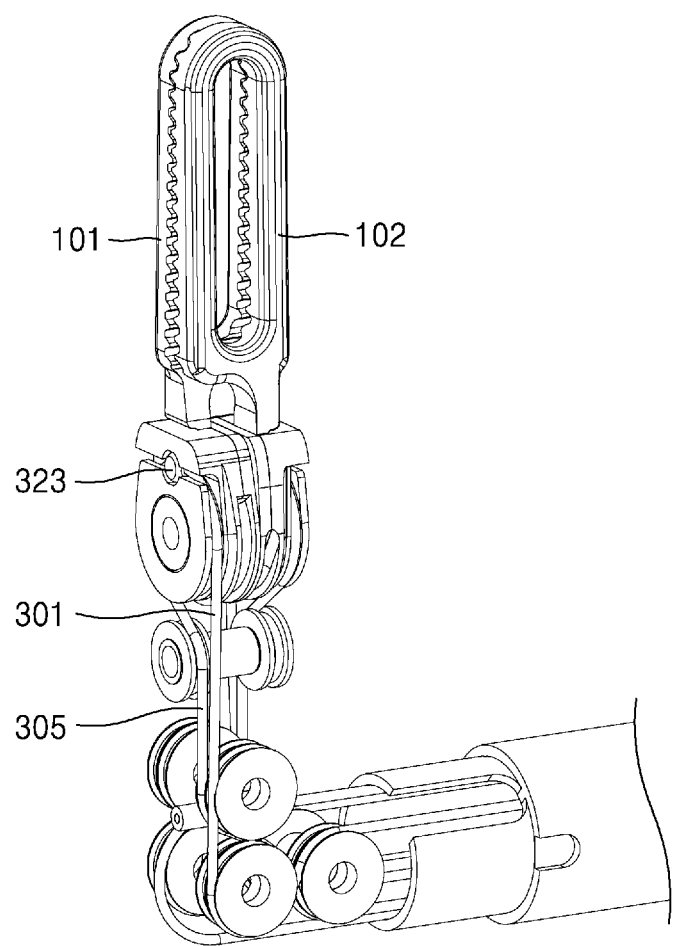
Figure 14:
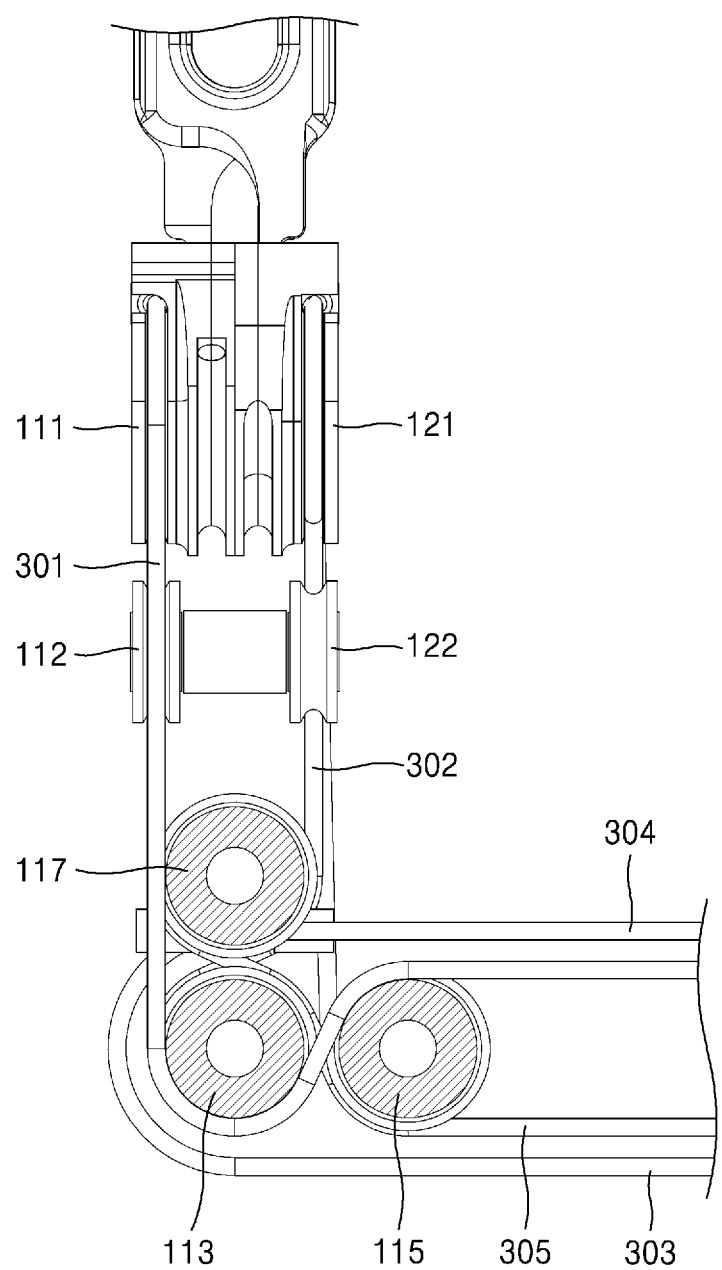
FIGS. 14 and 15 are side views illustrating a state in which the end tool of the surgical instrument of FIG. 2 is pitch-rotated by −90°.
Figure 15:
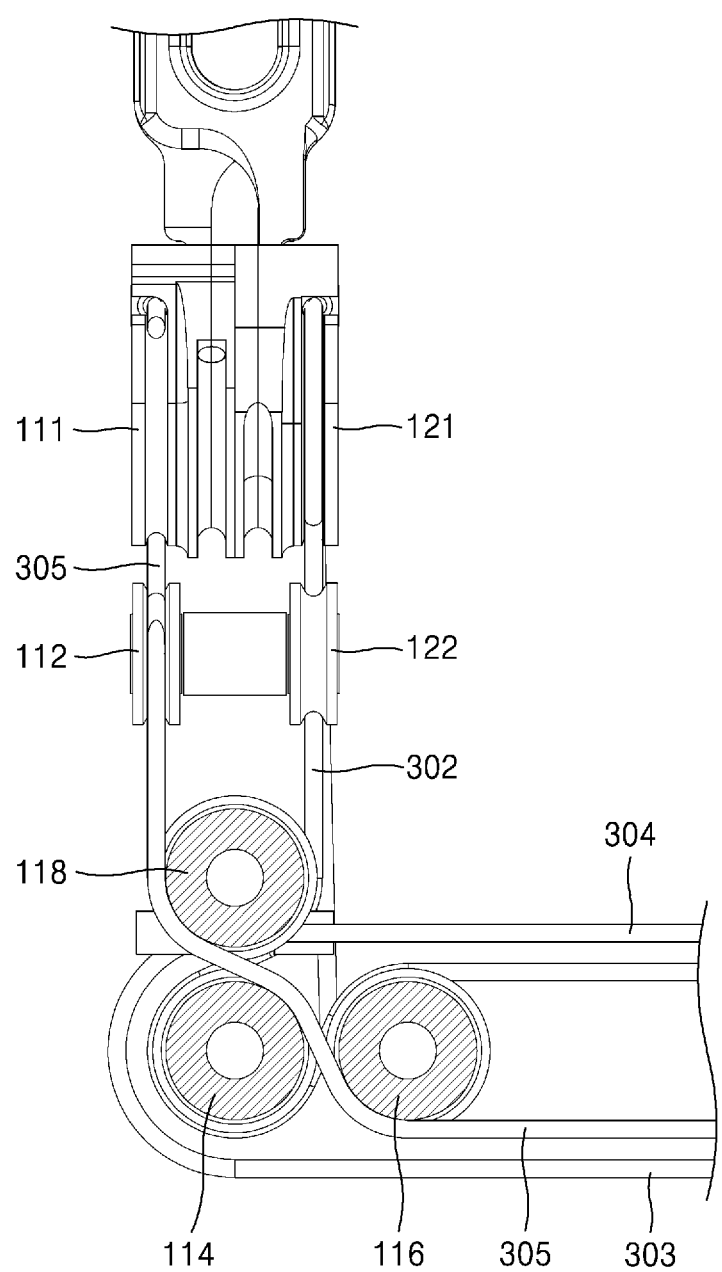
Figure 16:
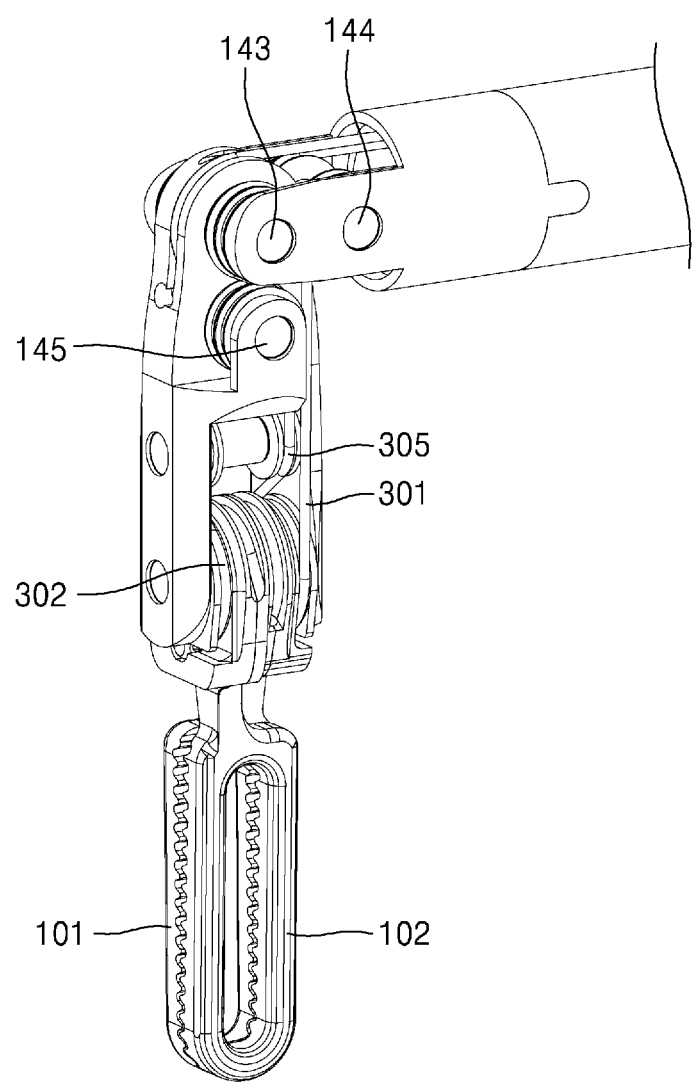
FIGS. 16 and 17 are perspective views illustrating a state in which the end tool of the surgical instrument of FIG. 2 is pitch-rotated by +90°.
Figure 17:
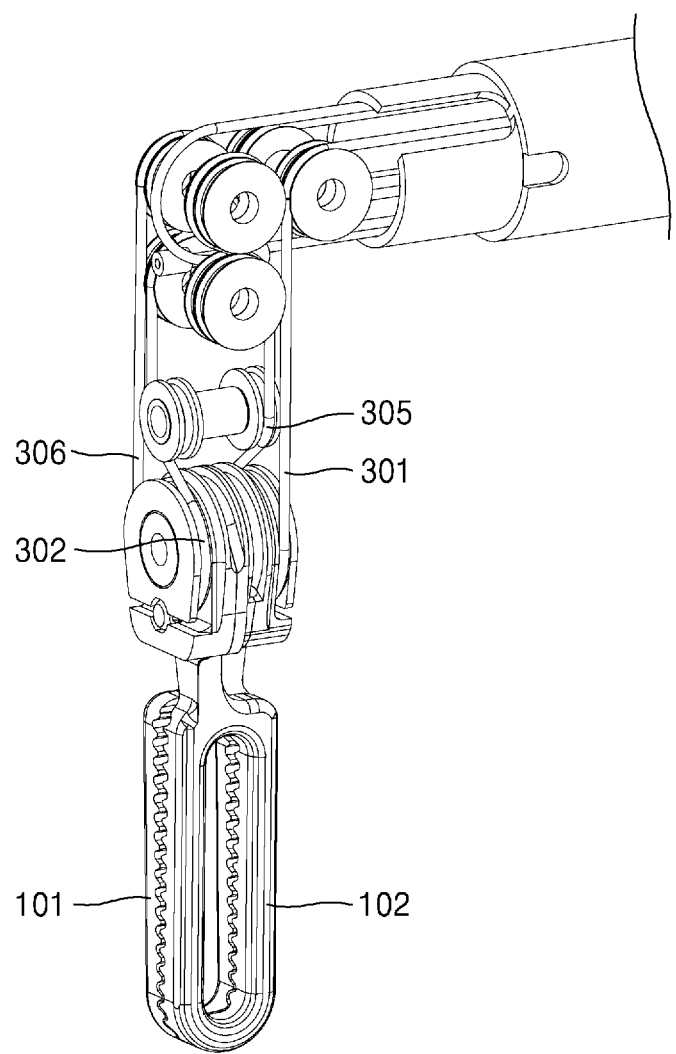
Figure 18:
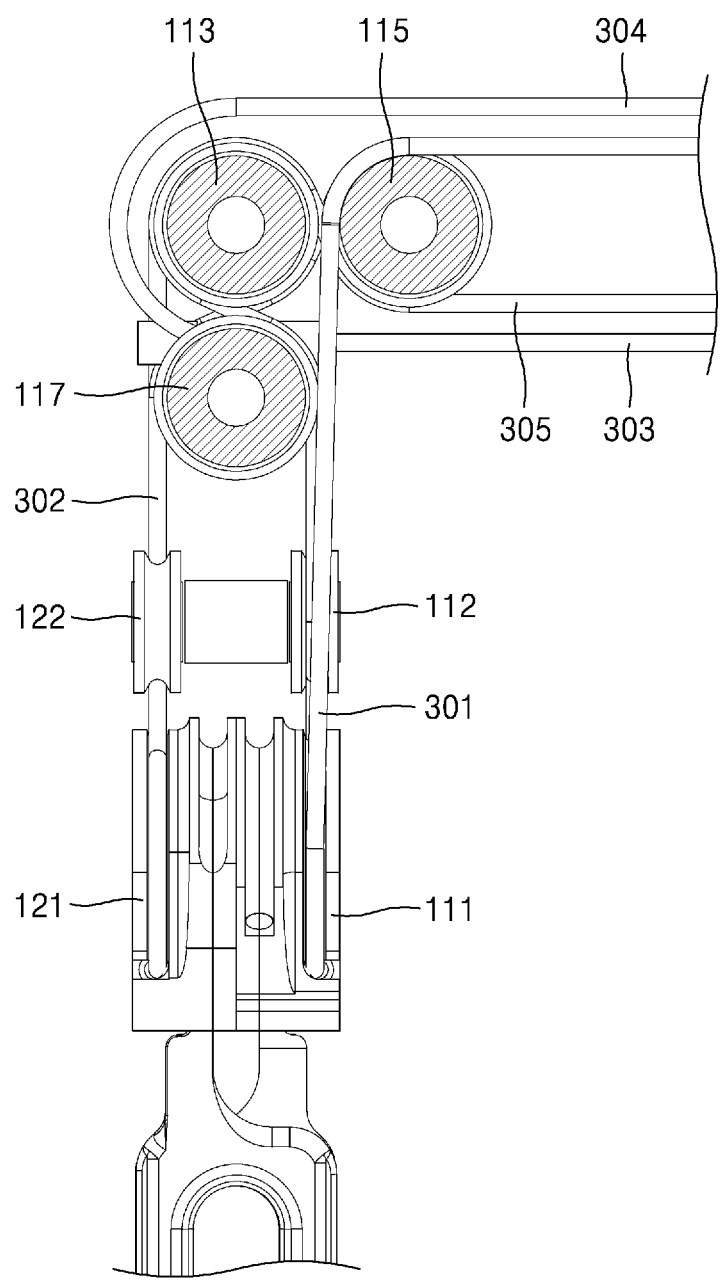
FIGS. 18 and 19 are side views illustrating a state in which the end tool of the surgical instrument of FIG. 2 is pitch-rotated by +90°.
Figure 19:
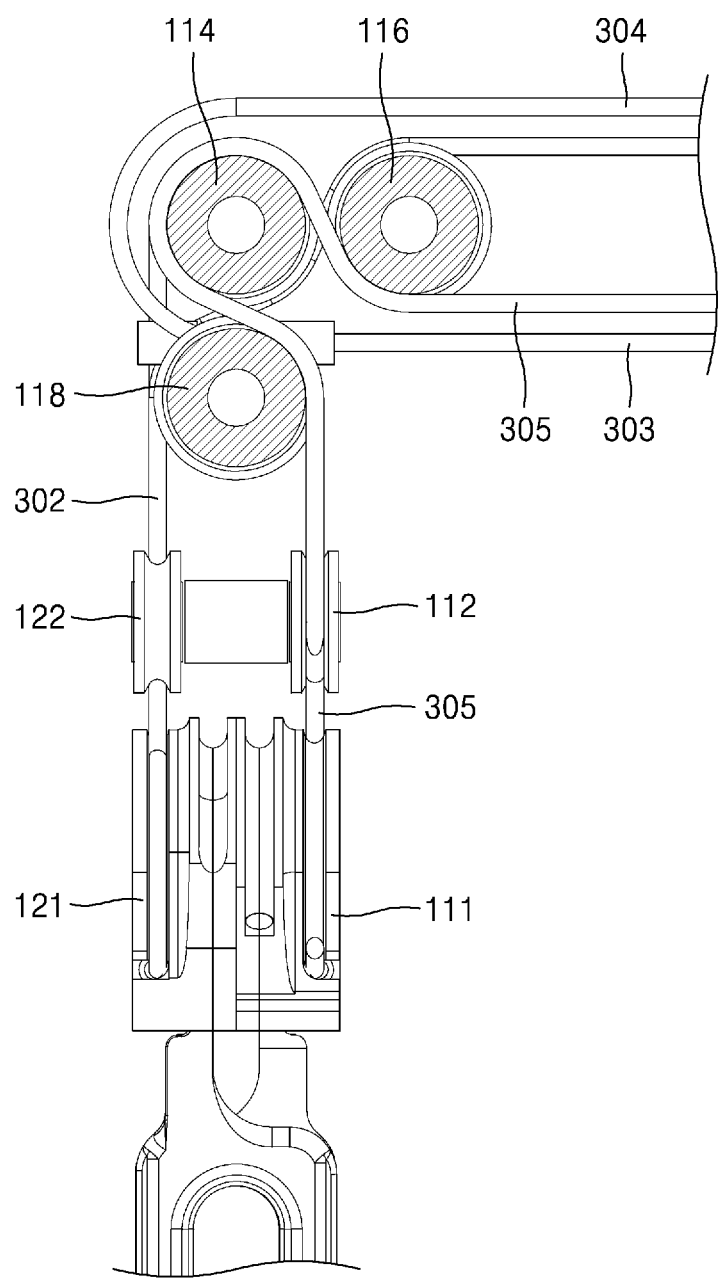

In addition, FIGS. 12 and 13 are perspective views illustrating a state in which the end tool of the surgical instrument of FIG. 2 is pitch-rotated by −90°. FIGS. 14 and 15 are side views illustrating a state in which the end tool of the surgical instrument of FIG. 2 is pitch-rotated by −90°. FIGS. 16 and 17 are perspective views illustrating a state in which the end tool of the surgical instrument of FIG. 2 is pitch-rotated by +90°. FIGS. 18 and 19 are side views illustrating a state in which the end tool of the surgical instrument of FIG. 2 is pitch-rotated by +90°.

In this regard, FIG. 3 illustrates a state in which an end tool hub 106 is removed from the end tool of FIG. 2. In addition, FIG. 5 is a diagram mainly illustrating wires in the end tool of FIG. 2, and FIG. 6 is a diagram mainly illustrating pulleys in the end tool of FIG. 2. In addition, FIGS. 8 and 9 are cross-sectional views illustrating a state in which the end tool hub 106 is removed from the end tool of FIG. 7.

As described above with reference to FIG. 1, the surgical instrument (see 30 of FIG. 1C or 40 of FIG. 1D) according to the first embodiment of the present disclosure may include the end tool 100, a drive part (see 200 of FIG. 1C or 200 of FIG. 1D), and the connection part 400. In addition, the end tool 100 may include a power transmission part 300.

Referring to FIGS. 2 to 11, the end tool 100 is formed at an end of the connection part 400, and is inserted into a surgical site to perform a motion required for surgery. As an example of the end tool 100, a pair of jaws 101 and 102 for performing a grip motion may be used as illustrated in FIG. 2. However, the concept of the present disclosure is not limited thereto, and various other surgical instruments may be used as the end tool 100. For example, a one-armed cautery may be used as the end tool. The end tool 100 is connected to the drive part (see 200 of FIG. 1C or 200 of FIG. 1D) by the power transmission part 300, to receive a driving force of the drive part (see 200 of FIG. 1C or 200 of FIG. 1D) through the power transmission part 300, and thus perform a motion necessary for surgery, such as gripping, cutting, or suturing.

In this regard, the end tool 100 of the surgical instrument according to the first embodiment of the present disclosure is formed to be rotatable in two or more directions, and for example, the end tool 100 may be formed to perform a pitch motion around a rotation axis 143 of FIG. 2 and simultaneously perform a yaw motion and an actuation motion around a rotation axis 141 of FIG. 2.

In this regard, the pitch, yaw, and actuation motions used in the present disclosure are defined as follows.

First, the pitch motion refers to a motion of the end tool 100 rotating in a vertical direction with respect to an extension direction of the connection part 400 (the X-axis direction of FIG. 2), that is, a motion of rotating around the Y-axis of FIG. 2. In other words, the pitch motion refers to a motion of the end tool 100, which extends from the connection part 400, rotating in the vertical direction around the Y-axis with respect to the connection part 400.

Next, the yaw motion refers to a motion of the end tool 100 rotating in a horizontal direction, that is, a motion of rotating around the Z-axis of FIG. 2, with respect to the extension direction of the connection part 400 (the X-axis direction of FIG. 2). In other words, the yaw motion refers to a motion of the end tool 100, which extends from the connection part 400, rotating in the horizontal direction around the Y-axis with respect to the connection part 400. That is, the yaw motion refers to a motion of the two jaws 101 and 102, which are formed on the end tool 100, rotating around the Z-axis in the same direction.

Meanwhile, the actuation motion refers to a motion of the end tool 100 rotating around the same rotation axis as that of the yaw motion, but with the two jaws 101 and 102 rotating in the opposite directions to be closed or opened. That is, the actuation motion refers to a motion of the two jaws 101 and 102, which are formed on the end tool 100, rotating around the Z-axis in the opposite directions.

In other words, yaw rotation may refer to a motion of a jaw pulley, which will be described below, rotating around the rotation axis 141, which is a jaw pulley rotation axis, and pitch rotation may refer to a motion of the jaw pulley revolving around the rotation axis 143, which is a pitch main rotation axis.

The power transmission part 300 may connect the drive part (see 200 of FIG. 1C or 200 of FIG. 1D) to the end tool 100, to transmit a driving force of the drive part (see 200 of FIG. 1C or 200 of FIG. 1D) to the end tool 100, and may include a plurality of wires, pulleys, links, sections, gears, or the like.

Hereinafter, the power transmission part 300 and the end tool 100 including the power transmission part 300 will be described in more detail.

(Power Transmission Part)

Hereinafter, the power transmission part 300 of the end tool of the surgical instrument of FIG. 2 will be described in more detail.

Referring to FIGS. 5, 6, 10, and the like, the power transmission part 300 of the end tool 100 of the surgical instrument according to an embodiment of the present disclosure may include a wire 301, a wire 302, a wire 303, a wire 304, a wire 305, and a wire 306.

In this regard, the wire 301 and the wire 305 may be paired to serve as a first jaw wire. The wire 302 and the wire 306 may be paired to serve as a second jaw wire. In this regard, a component encompassing the wire 301 and the wire 305, which are first jaw wires, and the wire 302 and the wire 306, which are second jaw wires, may be referred to as jaw wires. In addition, the wire 303 and the wire 304 may be paired to serve as a pitch wire.

In this regard, the drawings illustrate that a pair of wires are associated with a rotational motion of a first jaw 101, and a pair of wires are associated with a rotational motion of a second jaw 102, but the concept of the present disclosure is not limited thereto. For example, a pair of wires may be associated with the yaw motion, and a pair of wires may be associated with the actuation motion.

In addition, the power transmission part 300 of the surgical instrument according to an embodiment of the present disclosure may include a coupling member 321, a coupling member 322, a coupling member 323, a coupling member 324, a coupling member 326, a coupling member 327, a coupling member 329, and the like, which are coupled to ends of the respective wires to combine the wires with the pulleys. In this regard, each of the coupling members may have various shapes as necessary, such as a ball shape, a tube shape, or the like.

In this regard, the coupling member 321, which is a pitch wire coupling member, may be coupled to an end of the wire 303, which is a pitch wire, on the side of the end tool 100, and the coupling member 322, which is a pitch wire coupling member, may be coupled to an end of the wire 304, which is a pitch wire, on the side of the end tool 100, such that they serve as pitch wire-end tool coupling members. Meanwhile, the pitch wire-drive part coupling member 329 may be coupled to ends of the wire 303 and the wire 304, which are pitch wires, on the side of the drive part (see 200 of FIG. 1).

Meanwhile, the coupling member 323, which is a first jaw wire coupling member, may be coupled to ends of the wire 301 and the wire 305, which are first jaw wires, on the side of the end tool 100, to serve as a first jaw wire-end tool coupling member. Meanwhile, the first jaw wire-drive part coupling member 324 may be coupled to ends of the wire 301 and the wire 305, which are first jaw wires, on the side of the drive part (see 200 of FIG. 1).

Meanwhile, the coupling member 326, which is a second jaw wire coupling member, may be coupled to ends of the wire 302 and the wire 306, which are second jaw wires, on the side of the end tool 100, to serve as a second jaw wire-end tool coupling member. Meanwhile, the second jaw wire-drive part coupling member 327 may be coupled to ends of the wire 302 and the wire 306, which are second jaw wires, on the side of the drive part (see 200 of FIG. 1).

In this regard, the coupling members are classified as being included in the power transmission part 300, but the coupling members on the side of the end tool 100 may be classified as being included in the end tool 100, and the coupling members on the side of the drive part (see 200 of FIG. 1) may be classified as being included in the drive part (see 200 of FIG. 1).

The coupling relationship between the wires, the coupling members, and each pulley will be described as follows.

First, the wire 302 and the wire 306, which are second jaw wires, may be a single wire. When the coupling member 326, which is a second jaw wire-end tool coupling member, is fit into a middle point of the first jaw wire, and the coupling member 326 is fixed through crimping, both strands of the second jaw wires around the coupling member 326 may be referred to as the wire 302 and the wire 306, respectively.

Alternatively, the wire 302 and the wire 306, which are second jaw wires, may be formed as separate wires and connected to each other by the coupling member 326.

In addition, by coupling the coupling member 326 to a pulley 121, the wire 302 and the wire 306 may be fixedly coupled to the pulley 121. Accordingly, the pulley 121 may be rotated as the wire 302 and the wire 306 are pulled and released.

The second jaw wire-drive part coupling member 327 may be coupled to ends of the wire 302 and the wire 306 that are opposite to the ends to which the coupling member 326 is coupled. That is, by fitting the opposite ends of the wire 302 and the wire 306 into the second jaw wire-drive part coupling member 327, and then crimping the coupling member 327, each of the wire 302 and the wire 306 may be fixed to the second jaw wire-drive part coupling member 327.

In addition, by coupling the second jaw wire-drive part coupling member 327, which is coupled to the wire 302 and the wire 306, to a pulley 221, each of the wire 302 and the wire 306 may be fixedly coupled to the pulley 221. Accordingly, when the pulley 221 is rotated by a motor or a human force, the pulley 121 of the end tool 100 may be rotated as the wire 302 and the wire 306 are pulled and released.

In this regard, as illustrated in the drawings, a drive part second jaw pulley may include the pulley 221, which is a single pulley, the second jaw wire-drive part coupling member may also include the coupling member 327, which is a single coupling member, and the wire 302 and the wire 306 may be coupled to the single coupling member 327 and thus coupled to the single drive part second jaw pulley 221. Alternatively, although not illustrated in the drawings, the drive part second jaw pulley may include two pulleys, and the second jaw wire-drive part coupling member may also include two coupling members.

In the same manner, each of the wire 301 and the wire 305, which are first jaw wires, is coupled to the first jaw wire-end tool coupling member 323 and the first jaw wire-drive part coupling member 324. In addition, the first jaw wire-end tool coupling member 323 is coupled to a pulley 111, and the first jaw wire-drive part coupling member 324 is coupled to a pulley 211. Accordingly, when the pulley 211 is rotated by a motor or a human force, the pulley 111 of the end tool 100 may be rotated as the wire 301 and the wire 305 are pulled and released.

In the same way, one end of the wire 303, which is a pitch wire, may be coupled to the coupling member 321, which is a pitch wire-end tool coupling member, and one end of the wire 304, which is a pitch wire, may be coupled to the coupling member 322, which is a pitch wire-end tool coupling member. In addition, the other end of each of the wire 303 and the wire 304 may be coupled to the pitch wire-drive part coupling member 329. In addition, each of the coupling member 321 and the coupling member 322 is coupled to a pulley 131, and the pitch wire-drive part coupling member 329 is coupled to a drive part pitch pulley 231. Accordingly, when the drive part pitch pulley 231 is rotated by a motor or a human force, the pulley 131 of the end tool 100 may be rotated as the wire 303 and the wire 304 are pulled and released.

Accordingly, the wire 301 and the wire 305, which are both strands of the first jaw wires, may be combined with the coupling member 323, which is a first jaw wire-end tool coupling member, and the first jaw wire-drive part coupling member 324, so as to form a closed loop together. Similarly, each of the second jaw wire and pitch wire may be formed to form a closed loop.

(End Tool)

Hereinafter, the end tool 100 of the surgical instrument of FIG. 2 will be described in more detail.

Continuing to refer to FIGS. 2 to 11, the end tool 100 of the first embodiment of the present disclosure includes a pair of jaws for performing a grip motion, that is, the first jaw 101 and the second jaw 102. In this regard, a component encompassing each of the first jaw 101 and the second jaw 102 or both the first jaw 101 and the second jaw 102 may be referred to as a jaw 103.

In addition, the end tool 100 may include the pulley 111, a pulley 112, a pulley 113, a pulley 114, a pulley 115, a pulley 116, a pulley 117, and a pulley 118, which are associated with a rotational motion of the first jaw 101. In addition, the end tool 100 may include the pulley 121, a pulley 122, a pulley 123, a pulley 124, a pulley 125, a pulley 126, a pulley 127, and a pulley 128, which are associated with a rotational motion of the second jaw 102.

In this regard, the drawings illustrate that a group of pulleys are associated with the rotational motion of the first jaw 101, and a group of pulleys are associated with the rotational motion of the second jaw 102, but the concept of the present disclosure is not limited thereto. For example, one group of pulleys within the end tool may be associated with a yaw motion, and one group of pulleys within an end tool may be associated with an actuation motion. In this regard, the pulleys included in the end tool 100, including the pulleys described above, may be collectively referred to as end tool pulleys.

In this regard, although the drawings illustrate that the pulleys facing each other are arranged in parallel with each other, the concept of the present disclosure are not limited thereto, and the pulleys may be formed in various positions and sizes suitable for the configuration of the end tool.

Further, the end tool 100 of the first embodiment of the present disclosure may include the end tool hub 106 and a pitch hub 107.

The rotation axis 141, a rotation axis 142, and a rotation axis 145, which will be described below, are inserted through the end tool hub 106. In addition, the end tool hub 106 may internally accommodate at least portions of the pulley 111 and the pulley 121 that are axially coupled to the rotation axis 141. In addition, the end tool hub 106 may internally accommodate at least portions of the pulley 112 and the pulley 122 that are axially coupled to the rotation axis 142. In addition, the pulley 117/pulley 118 and the pulley 127/pulley 128 that are axially coupled to the rotation axis 145 may be coupled to the end tool hub 106.

In detail, referring to FIG. 8 and the like, the end tool hub 106 includes a first jaw pulley coupling part 106a, a second jaw pulley coupling part 106b, a guide part 106c, a pitch redundant pulley accommodation part 106d, and a pitch pulley coupling part 106e.

In detail, the first jaw pulley coupling part 106a and the second jaw pulley coupling part 106b are formed to face each other such that the pulley 111 and the pulley 121 are accommodated therein. In addition, a through hole is formed in each of the first jaw pulley coupling part 106a and the second jaw pulley coupling part 106b such that the rotation axis 141 passes through and axially couples the first jaw pulley coupling part 106a, the pulley 111, the pulley 121, and the second jaw pulley coupling part 106b. In addition, the rotation axis 142 passes through and axially couples the first jaw pulley coupling part 106a, the pulley 112, the pulley 122, and the second jaw pulley coupling part 106b.

The first jaw pulley coupling part 106a and the second jaw pulley coupling part 106b are connected to each other by the guide part 106c. That is, the first jaw pulley coupling part 106a and the second jaw pulley coupling part 106b parallel to each other are coupled by the guide part 106c formed in a direction substantially perpendicular thereto, such that the first jaw pulley coupling part 106a, the second jaw pulley coupling part 106b, and the guide part 106c form a substantially "C" shape in which the pulley 111, the pulley 112, the pulley 121, and the pulley 122 are accommodated.

In this regard, the pulley 111, which is a first jaw pulley, may be arranged adjacent to the first jaw pulley coupling part 106a of the end tool hub 106, and the pulley 121, which is a second jaw pulley, may be arranged adjacent to the second jaw pulley coupling part 106b of the end tool hub 106, such that a predetermined space may be formed between the wire 301/wire 305, which are first jaw wires, and the wire 302/wire 306, which are second jaw wires.

Meanwhile, the pitch redundant pulley accommodation part 106d may be formed on the side of the proximal end of the guide part 106c of the end tool hub 106. In addition, the pulley 117, the pulley 118, the pulley 127, and the pulley 128, which are pitch redundant pulleys, may be accommodated in the pitch redundant pulley accommodation part 106d, and these pitch redundant pulleys may be axially coupled to the end tool hub 106 by the rotation axis 145.

Meanwhile, the pulley 131 that serves as an end tool pitch pulley may be formed in the pitch pulley coupling part 106e at one end of the end tool hub 106. In this regard, the pulley 131 may be formed with the end tool hub 106 as one body. That is, one end of the end tool hub 106 may be formed in a disk shape or a semicircular shape, and a groove around which a wire may be wound may be formed on an outer circumferential surface of the groove, such that a kind of guide channel is formed. Alternatively, the pulley 131 may be formed as a separate member from the end tool hub 106 and coupled to the end tool hub 106. The wire 303 and the wire 304 described above are coupled to the pulley 131 serving as an end tool pitch pulley, and a pitch motion is performed as the pulley 131 is rotated around the rotation axis 143.

The rotation axis 143 and a rotation axis 144, which will be described below, may be inserted through the pitch hub 107, and the pitch hub 107 may be axially coupled to the end tool hub 106 and the pulley 131 by the rotation axis 143. Thus, the end tool hub 106 and the pulley 131 (coupled to the end tool hub 106) may be formed to be rotatable around the rotation axis 143 with respect to the pitch hub 107.

In addition, the pitch hub 107 may internally accommodate at least portions of the pulley 113, the pulley 114, the pulley 123, and the pulley 124 that are axially coupled to the rotation axis 143. In addition, the pitch hub 107 may internally accommodate at least portions of the pulley 115, the pulley 116, the pulley 125, and the pulley 126 that are axially coupled to the rotation axis 144.

In addition, the end tool 100 of the first embodiment of the present disclosure may include the rotation axis 141, the rotation axis 142, the rotation axis 145, the rotation axis 143, and the rotation axis 144. As described above, the rotation axis 141, the rotation axis 142, and the rotation axis 145 may be inserted through the end tool hub 106, and the rotation axis 143 and the rotation axis 144 may be inserted through the pitch hub 107.

The rotation axis 141, the rotation axis 142, the rotation axis 145, the rotation axis 143, and the rotation axis 144 may be arranged sequentially from a distal end 104 of the end tool 100 toward a proximal end 105. Accordingly, starting from the distal end 104, the rotation axis 141 may be referred to as a first pin, the rotation axis 142 may be referred to as a second pin, the rotation axis 145 may be referred to as a two-and-a-halfth pin, the rotation axis 143 may be referred to as a third pin, and the rotation axis 144 may be referred to as a fourth pin.

In this regard, the rotation axis 141 may function as a jaw pulley rotation axis, the rotation axis 142 may function as a jaw auxiliary pulley rotation axis, the rotation axis 143 may function as a pitch main rotation axis, and the rotation axis 144 may function as a pitch sub-rotation axis of the end tool 100. In addition, the rotation axis 145 arranged between the rotation axis 142 and the rotation axis 143 may function as a pitch redundant rotation axis of the end tool 100.

One or more pulleys may be fit into each of the rotation axes 141, 142, 143, 144, and 145, and this will be described in detail below.

The pulley 111 functions as a first jaw pulley, the pulley 121 functions as a second jaw pulley, and these two components may be collectively referred to as a jaw pulley.

The pulley 111 and the pulley 121, which are jaw pulleys, are formed to face each other, and are formed to be rotatable independently of each other around the rotation axis 141, which is a jaw pulley rotation axis. In this regard, the drawings illustrate that the pulley 111 and the pulley 121 are formed to be rotated around one rotation axis 141, but it is needless to say that each jaw pulley may be formed to be rotatable around a separate shaft. In this regard, the first jaw 101 may be fixedly coupled to the pulley 111 to be rotated together with the pulley 111, and the second jaw 102 may be fixedly coupled to the pulley 121 to be rotated together with the pulley 121. Yaw and actuation motions of the end tool 100 are performed according to rotation of the pulley 111 and the pulley 121. That is, when the pulley 111 and the pulley 121 are rotated in the same direction around the rotation axis 141, the yaw motion is performed, and when the pulley 111 and the pulley 121 are rotated in opposite directions around the rotation axis 141, the actuation motion is performed.

In this regard, the first jaw 101 and the pulley 111 may be formed as separate members and coupled to each other, or the first jaw 101 and the pulley 111 may be formed as one body. Similarly, the second jaw 102 and the pulley 121 may be formed as separate members and coupled to each other, or the second jaw 102 and the pulley 121 may be formed as one body.

In this regard, in the pulley 111, which is a first jaw pulley, a groove 111a around which the wire 301/wire 305, which are first wires, are wound, is arranged adjacent to the first jaw pulley coupling part 106a of the end tool hub 106, in the pulley 121, which is a second jaw pulley, a groove 121a around which the wire 301/wire 305, which are second wires, are wound, is arranged adjacent to the first jaw pulley coupling part 106a of the end tool hub 106. Thus, a predetermined space may be formed between the wire 301/wire 305, which are first jaw wires, and the wire 302 and the wire 306, which are second jaw wires. As such, as the wire 301/wire 305, which are first jaw wires, and the wire 302 and the wire 306, which are second jaw wires, are arranged to be spaced apart from each other, the wires may be wound around the respective pulleys while maintaining a straight line.

The pulley 112 functions as a first jaw auxiliary pulley, the pulley 122 functions as a second jaw auxiliary pulley, and these two components may be collectively referred to as a jaw auxiliary pulley.

In detail, the pulley 112 and the pulley 122, which are jaw auxiliary pulleys, may be additionally provided on one side of the pulley 111 and the pulley 121. In other words, the pulley 112, which is a jaw auxiliary pulley, may be arranged between the pulley 111 and the pulley 113/pulley 114. In addition, the pulley 122, which is a jaw auxiliary pulley, may be arranged between pulley 121 and pulley 123/pulley 124. The pulley 112 and the pulley 122 may be formed to be rotatable independently of each other around the rotation axis 142. In this regard, the drawings illustrate that the pulley 112 and the pulley 122 are formed to be rotated around one rotation axis 142, but it is needless to say that the pulley 112 and the pulley 122 may be formed to be rotatable around separate shafts, respectively. Such an auxiliary pulley will be described below in more detail.

The pulley 113 and the pulley 114 may function as first jaw pitch main pulleys, the pulley 123 and the pulley 124 may function as second jaw pitch main pulleys, and these two components may be collectively referred to as a pitch main pulley.

The pulley 115 and the pulley 116 may function as first jaw pitch sub-pulleys, the pulley 125 and the pulley 126 may function as second jaw pitch sub-pulleys, and these two components may be collectively referred to as a pitch sub-pulley.

Meanwhile, according to the present disclosure, the pulley 117, the pulley 118, the pulley 127, and the pulley 128 pulley, which are pitch redundant pulleys, are further arranged between the pulley 112 and the pulley 122, which are jaw auxiliary pulleys, and the pulley 113, the pulley 114, the pulley 123, and the pulley 124, which are pitch main pulleys.

The pulley 117 and the pulley 118 may function as first jaw pitch redundant pulleys, the pulley 127 and the pulley 128 may function as second jaw pitch redundant pulleys, and these two components may be collectively referred to as a pitch redundant pulley.

In addition, the rotation axis 145 functioning as a pitch redundant rotation axis may be further provided, and the rotation axis 145 may be inserted through the end tool hub 106. In this regard, the rotation axis 145 may be formed to be substantially parallel to the rotation axis 143, which is a pitch main rotation axis, and the rotation axis 144, which is a pitch sub-rotation axis. In this regard, the rotation axis 145 is arranged between the rotation axis 142, which is the second pin, and the rotation axis 143, which is the third pin, and thus may be referred to as the two-and-a-halfth pin in terms of its position.

The pitch redundant pulleys may serve to change insertion/withdrawal paths of jaw wires entering from the proximal end of the end tool to the distal end, or coming out from the distal end to the proximal end. This will be described in more detail below.

Accordingly, the rotation axis 141, the rotation axis 142, the rotation axis 145, the rotation axis 143, and the rotation axis 144 may be sequentially arranged from the distal end 104 of the end tool 100 toward the proximal end 105.

In addition, the pulley 111, the pulley 112, the pulley 117/pulley 118, the pulley 113/pulley 114, and the pulley 115/pulley 116, which are associated with rotation of the first jaw 101, may be sequentially arranged from the distal end 104 of the end tool 100 toward the proximal end 105.

In addition, the pulley 121, the pulley 122, the pulley 127/pulley 128, the pulley 123/pulley 124, and the pulley 125/pulley 126, which are associated with rotation of the second jaw 102, may be sequentially arranged from the distal end 104 of the end tool 100 toward the proximal end 105.

Hereinafter, the pulley 112 and the pulley 122 serving as auxiliary pulleys will be described in more detail.

The pulley 112 and the pulley 122 may come into contact with the wire 305, which is a first jaw wire, and the wire 302, which is a second jaw wire to change the arrangement path of the wire 305 and the wire 302 to a certain extent, and thus perform a function of increasing a rotation angle of each of the first jaw 101 and the second jaw 102.

That is, when no auxiliary pulley is arranged, each of the first jaw and the second jaw may be rotated up to the right angle, however, in an embodiment of the present disclosure, by additionally arranging the pulley 112 and the pulley 122, which are auxiliary pulleys, the maximum rotation angle may be increased by θ as illustrated in FIG. 6. This enables an opening motion of the two jaws of the end tool 120 for the actuation motion in a state in which the two jaws are yaw-rotated by 90° in the L direction. This is because the second jaw 102 may be rotated by the additional angle θ as illustrated in FIG. 6. Similarly, the actuation motion may be performed even in a state in which the two jaws are yaw-rotated in the R direction. In other words, a feature of increasing the range of yaw rotation in which an actuation motion is possible may be obtained through the pulley 112 and the pulley 122.

This will be described in more detail as follows.

When no auxiliary pulley is arranged, as the first jaw wire is fixedly coupled to the first jaw pulley, and the second jaw wire is fixedly coupled to the second jaw pulley, each of the first jaw pulley and the second jaw pulley may be rotated only up to 90°. In this case, when the actuation motion is performed in a state in which the first jaw and the second jaw are located at a 90° line, the first jaw may be opened, but the second jaw may not be rotated beyond 90°. Thus, there was a problem that, in a state in which the first jaw and the second jaw perform a yaw motion over a certain angle, the actuation motion is not smoothly performed.

In order to address such a problem, in the end tool 100 of the surgical instrument of the present disclosure, the pulley 112 and the pulley 122, which are auxiliary pulleys, are additionally arranged at one sides of the pulley 111 and the pulley 121, respectively. As described above, as the arrangement path of the wire 305, which is a first jaw wire, and the wire 302, which is a second jaw wire, are changed to a certain extent by arranging the pulley 112 and the pulley 122, a tangential direction of the wire 305 and the wire 302 is changed, and accordingly, the coupling member 326 for coupling the wire 302 and the pulley 121 may be rotated up to a line N of FIG. 6. That is, the coupling member 326, which is a coupling part of the wire 302 and the pulley 121, is rotatable until the coupling member 326 is located on a common internal tangent of the pulley 121 and the pulley 122. Similarly, the coupling member 323, which is a coupling part of the wire 305 and the pulley 111, is rotatable until the coupling member 323 is located on a common internal tangent of the pulley 111 and the pulley 112, such that the range of rotation in the L direction may be increased.

In other words, the wire 301 and the wire 305, which are both strands of the first jaw wire wound around the pulley 111 by the pulley 112, are arranged at one side with respect to a plane perpendicular to the Y-axis and passing through the X-axis. Simultaneously, the wire 302 and the wire 306, which are both strands of the second jaw wire wound around the pulley 121 by the pulley 122, are arranged at the other side with respect to the plane perpendicular to the Y-axis and passing through the X-axis.

In other words, the pulley 113 and the pulley 114 are arranged at one side with respect to the plane perpendicular to the Y-axis and passing through the X-axis, and the pulley 123 and the pulley 124 are arranged at the other side with respect to the plane perpendicular to the Y-axis and passing through the X-axis.

In other words, the wire 305 is located on the internal tangent of the pulley 111 and the pulley 112, and the rotation angle of the pulley 111 is increased by the pulley 112. In addition, the wire 302 is located on the internal tangent of the pulley 121 and the pulley 122, and the rotation angle of the pulley 121 is increased by the pulley 122.

According to the present disclosure, as the radii of rotation of the jaw 101 and the jaw 102 increase, an effect of increasing a yaw motion range in which a normal opening/closing actuation motion is performed may be obtained.

Hereinafter, components associated with the rotation of the pulley 111 will be described.

The pulley 113 and the pulley 114 are paired to function as first jaw pitch main pulleys. That is, the pulley 113 and the pulley 114 function as main rotation pulleys for a pitch motion of the first jaw 101. In this regard, the wire 301, which is a first jaw wire, is wound around the pulley 113, and the wire 305, which is a first jaw wire, is wound around the pulley 114.

The pulley 115 and the pulley 116 are paired to function as first jaw pitch sub-pulleys. That is, the pulley 115 and the pulley 116 function as sub-rotation pulleys for a pitch motion of the first jaw 101. In this regard, the wire 301, which is a first jaw wire, is wound around the pulley 115, and the wire 305, which is a first jaw wire, is wound around the pulley 116.

The pulley 117 and the pulley 118 are paired to function as first jaw redundant pulleys. That is, the pulley 117 and the pulley 118 function as redundant rotation pulleys for a pitch motion of the first jaw 101. In this regard, the wire 301, which is a first jaw wire, is wound around the pulley 117, and the wire 305, which is a first jaw wire, is wound around the pulley 118.

In this regard, the pulley 117 and the pulley 118 are arranged on one side of the pulley 111 and the pulley 112 to face each other. In this regard, the pulley 117 and the pulley 118 are formed to be rotatable independently of each other around the rotation axis 145, which is a pitch redundant rotation axis. In addition, the pulley 113 and the pulley 114 are arranged on one sides of the pulley 117 and the pulley 118, respectively, to face each other. In this regard, the pulley 113 and the pulley 114 are formed to be rotatable independently of each other around the rotation axis 143, which is a pitch main rotation axis. In addition, the pulley 115 and the pulley 116 are arranged on one sides of the pulley 113 and the pulley 114, respectively, to face each other. In this regard, the pulley 115 and the pulley 116 are formed to be rotatable independently of each other around the rotation axis 144, which is a pitch sub-rotation axis. In this regard, the drawings illustrate that the pulley 117, the pulley 118, the pulley 113, the pulley 114, the pulley 115, and the pulley 116 are formed to be rotatable around the Y-axis direction, but the concept of the present disclosure is not limited thereto, and the rotation axes of the respective pulleys may be formed in various directions according to their configurations.

The wire 301, which is a first jaw wire, is wound to sequentially come into contact with at least portions of the pulley 115, the pulley 113, the pulley 117, and the pulley 111. In addition, the wire 305 connected to the wire 301 by the coupling member 323 is wound to sequentially come into contact with at least portions of the pulley 111, the pulley 112, the pulley 118, the pulley 114, and the pulley 116.

In other words, the wire 301 and the wire 305, which are first jaw wires, are wound to sequentially come into contact with at least portions of the pulley 115, the pulley 113, the pulley 117, the pulley 111, the pulley 112, the pulley 118, the pulley 114, and the pulley 116, and are formed to move along the above pulleys while rotating the above pulleys.

Accordingly, when the wire 301 is pulled in the direction of an arrow 301 of FIG. 7, the coupling member 323 to which the wire 301 is coupled and the pulley 111 coupled to the coupling member 323 are rotated in the direction of an arrow L of FIG. 7. On the contrary, when the wire 305 is pulled in the direction of an arrow 305 of FIG. 7, the coupling member 323 to which the wire 305 is coupled and the pulley 111 coupled to the coupling member 323 are rotated in the direction of an arrow R of FIG. 7.

Next, components associated with the rotation of the pulley 121 will be described.

The pulley 123 and the pulley 124 are paired to function as second jaw pitch main pulleys. That is, the pulley 123 and the pulley 124 function as main rotation pulleys for a pitch motion of the second jaw 102. In this regard, the wire 306, which is a second jaw wire, is wound around the pulley 123, and the wire 302, which is a second jaw wire, is wound around the pulley 124.

The pulley 125 and the pulley 126 are paired to function as second jaw pitch sub-pulleys. That is, the pulley 125 and the pulley 126 may function as sub-rotation pulleys for a pitch motion of the second jaw 102. In this regard, the wire 306, which is a second jaw wire, is wound around the pulley 125, and the wire 302, which is a second jaw wire, is wound around the pulley 126.

The pulley 127 and the pulley 128 are paired to function as second jaw pitch redundant pulleys. That is, the pulley 127 and the pulley 128 function as redundant rotation pulleys for a pitch motion of the second jaw 102. In this regard, the wire 306, which is a second jaw wire, is wound around the pulley 127, and the wire 302, which is a second jaw wire, is wound around the pulley 128.

In this regard, the pulley 127 and the pulley 128 are arranged on one side of the pulley 121 and the pulley 122 to face each other. In this regard, the pulley 127 and the pulley 128 are formed to be rotatable independently of each other around the rotation axis 145, which is a pitch redundant rotation axis. In addition, the pulley 123 and the pulley 124 are arranged on one sides of the pulley 127 and the pulley 128, respectively, to face each other. In this regard, the pulley 123 and the pulley 124 are formed to be rotatable independently of each other around the rotation axis 143, which is a pitch main rotation axis. In addition, the pulley 125 and the pulley 126 are arranged on one sides of the pulley 123 and the pulley 124, respectively, to face each other. In this regard, the pulley 125 and the pulley 126 are formed to be rotatable independently of each other around the rotation axis 144, which is a pitch sub-rotation axis. In this regard, the drawings illustrate that the pulley 127, the pulley 128, the pulley 123, the pulley 124, the pulley 125, and the pulley 126 are formed to be rotatable around the Y-axis direction, but the concept of the present disclosure is not limited thereto, and the rotation axes of the respective pulleys may be formed in various directions according to their configurations.

The wire 306, which is a second jaw wire, is wound to sequentially come into contact with at least portions of the pulley 125, the pulley 123, the pulley 127, and the pulley 121. In addition, the wire 302 connected to the wire 306 by the coupling member 326 is wound to sequentially come into contact with at least portions of the pulley 121, the pulley 122, the pulley 128, the pulley 124, and the pulley 126.

In other words, the wire 306 and the wire 302, which are second jaw wires, are wound to sequentially come into contact with at least portions of the pulley 125, the pulley 123, the pulley 127, the pulley 121, the pulley 122, the pulley 128, the pulley 124, and the pulley 126, and are formed to move along the above pulleys while rotating the above pulleys.

Accordingly, when the wire 306 is pulled in the direction of an arrow 306 of FIG. 7, the coupling member 326 to which the wire 306 is coupled and the pulley 121 coupled to the coupling member 326 are rotated in the direction of the arrow R of FIG. 7. On the contrary, when the wire 302 is pulled in the direction of an arrow 302 of FIG. 6, the coupling member 326 to which the wire 302 is coupled and the pulley 121 coupled to the coupling member 326 are rotated in the direction of the arrow L of FIG. 7.

In this regard, according to the present disclosure, two strands of jaw wires wound around one jaw pulley are wound around pitch main pulleys in opposite directions, such that a pitch motion is easily controlled.

In detail, when the side above, in the +Z-axis direction, a plane passing between the pulley 111, which is a first jaw pulley, and the pulley 121, which is a second jaw pulley (i.e., an XY plane) is defined as an upper side and the side below the plane in the −Z-axis direction is defined as a lower side, any one (e.g., the wire 301) of the two strands of the first jaw wires may enter the pulley 113, which is a first jaw pitch main pulley, from the lower side of the XY plane, and the other strand (e.g., the wire 305) may come out of the pulley 114, which is a first jaw pitch main pulley, from the upper side of the XY plane. In other words, it may be described as a structure in which the jaw wire enters the first jaw pitch main pulley from the lower side and comes out from the upper side. (The second jaw wire enters the second jaw pitch main pulley from the upper side and comes out from the lower side)

In other words, the wire 301, which is one strand of the first jaw wires, sequentially comes into contact with the upper side of the pulley 115, the lower side of the pulley 113, and the lower side of the pulley 117, and then comes into contact with the pulley 111. Next, the wire 305, which is the other strand of the first jaw wires, is wound around the pulley 111 and the pulley 112, and then sequentially comes into contact with the lower side of the pulley 118, the upper side of the pulley 114, and the lower side of the pulley 116, and then comes out toward the connection part 400. Accordingly, the first jaw wire comes out of the connection part 400, enters the pulley 113 from the lower side, then passes through each pulley, then passes through the upper side of the pulley 114, and then enters back the connection part 400.

Similarly, the wire 306, which is one strand of the second jaw wires, sequentially comes into contact with the lower side of the pulley 125, the upper side of the pulley 123, and the upper side of the pulley 127, and then comes into contact with the pulley 121. Next, the wire 302, which is the other strand of the second jaw wires, is wound around the pulley 121 and the pulley 122, and then sequentially comes into contact with the upper side of the pulley 128, the lower side of the pulley 124, and the upper side of the pulley 126, and then comes out toward the connection part 400. Accordingly, the second jaw wire comes out of the connection part 400, enters the pulley 123 from the upper side, then passes through each pulley, then passes through the lower side of the pulley 124, and then enters back the connection part 400.

In other words, it may also be described that any one wire of two strands of the first jaw wires is wound around the first jaw pitch main pulley in any one of the clockwise direction and the counterclockwise direction, and the other wire is wound around the first jaw pitch main pulley in the other one of the clockwise direction and the counterclockwise direction. That is, as illustrated in FIG. 10, the wire 301 is wound in the clockwise direction while entering the end tool 100 from the connection part 400, and the wire 305 is wound in the counterclockwise direction while entering the end tool 100 from the connection part 400.

Similarly, it may also be described that any one wire of two strands of the second jaw wires is wound around the second jaw pitch main pulley in any one of the clockwise direction and the counterclockwise direction, and the other wire is wound around the second jaw pitch main pulley in the other one of the clockwise direction and the counterclockwise direction. That is, as illustrated in FIG. 10, the wire 302 is wound in the clockwise direction while entering the end tool 100 from the connection part 400, and the wire 306 is wound in the counterclockwise direction while entering the end tool 100 from the connection part 400.

As such, as two strands of jaw wires wound around one jaw pulley are wound around pitch main pulleys in opposite directions, an effect of facilitating control of a pitch motion may be obtained. This will be described in more detail below.

Meanwhile, when viewed from an XZ plane, two strands of respective jaw wires are arranged on the same side with respect to the XZ plane. In detail, when the side above, in the +Y-axis direction, a plane passing between the pulley 114, which is a first jaw pitch main pulley, and the pulley 124, which is a second jaw pitch main pulley (i.e., an XZ plane) is defined as a first side and the side below the plane in the −Y-axis direction is defined as a second side, any one (e.g., the wire 301) of the two strands of the first jaw wires may be arranged on the first side of the XZ plane, and the other strand (e.g., the wire 305) may also be arranged on the first side. Similarly, any one of the two strands of the second jaw wires (e.g., the wire 306) may be arranged on the second side of XZ plane, and the other strand (e.g., the wire 302) may be also arranged on the second side. In other words, it may be described as a structure in which one jaw wire enters from the first side and comes out from the first side. (It may also be described as a structure in which one jaw wire enters from the second side and comes out from the second side)

(Pitch Motion)

The end tool 100 of the surgical instrument of the present disclosure may include the pulley 131, which is an end tool pitch pulley, the drive part (see 200 of FIG. 1) may include the drive part pitch pulley 231, and the power transmission part 300 may further include the wire 303 and the wire 304, which are pitch wires.

In detail, the pulley 131 of the end tool 100 is rotatable around the rotation axis 143, which is a pitch main rotation axis, and may be formed with the end tool hub 106 as one body (or to be fixedly coupled to the end tool hub 106). In addition, the wire 303 and the wire 304 may serve to connect the pulley 131 of the end tool 100 to the drive part pitch pulley 231 of the drive part (see 200 of FIG. 1).

Thus, when the drive part pitch pulley 231 of the drive part (see 200 of FIG. 1) is rotated, the rotation of the drive part pitch pulley 231 is transmitted to the pulley 131 of the end tool 100 through the wire 303 and the wire 304 such that the pulley 131 is rotated together therewith, and accordingly, the end tool 100 performs a pitch motion while rotating.

However, there was a problem that, when the drive part pitch pulley 231 is rotated to perform the pitch motion in this manner, and the drive part does not provide separate pitch compensation for the jaw wires, in the end tool, along with the pitch motion, the jaws are also rotated around the rotation axis 141, which is a jaw pulley rotation axis, and accordingly, a genuine pitch motion is not performed.

Hereinafter, the pitch compensation will be described in more detail.

Figure 10A:
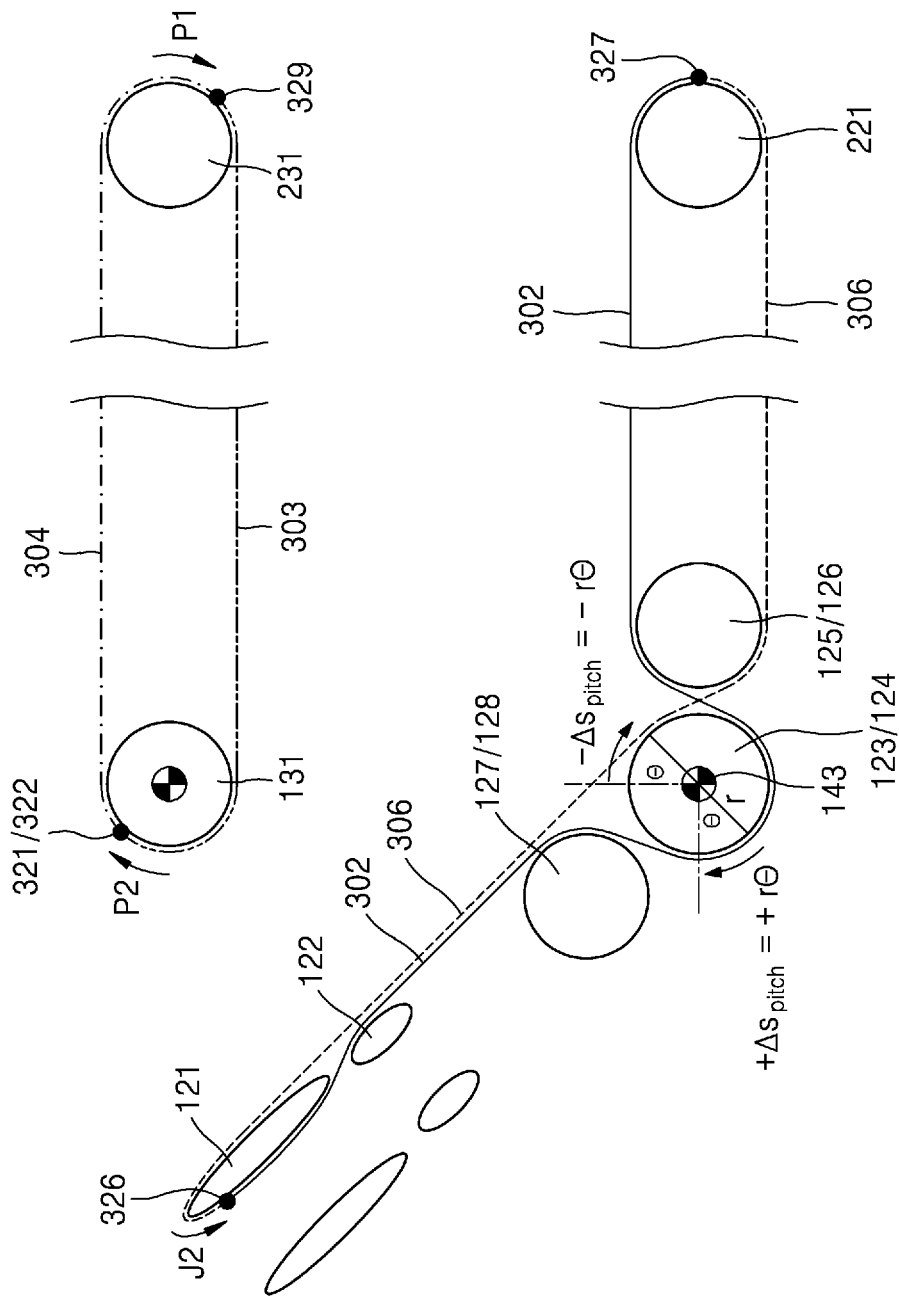
Figure 10B:
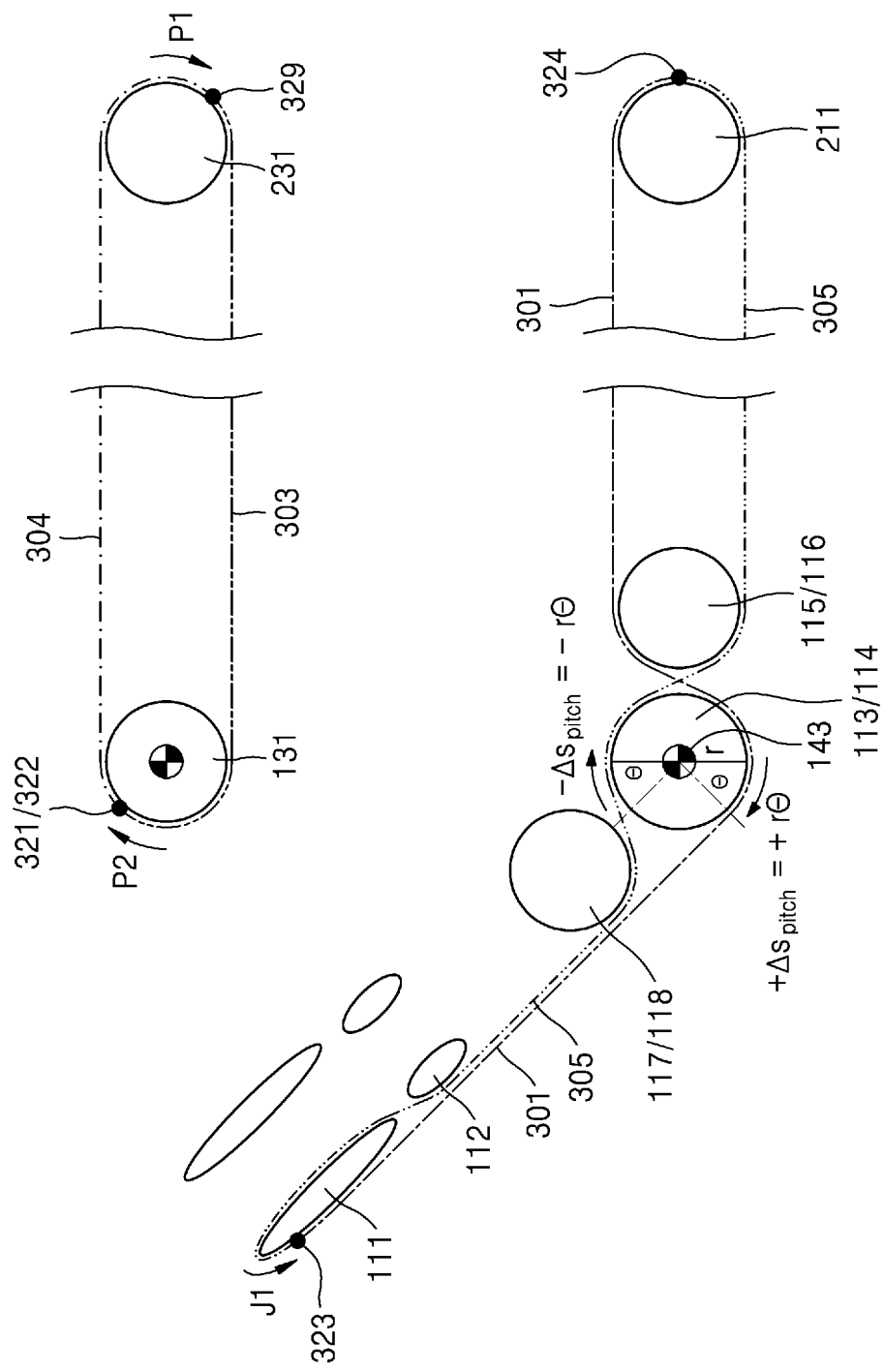
Figure 11A:
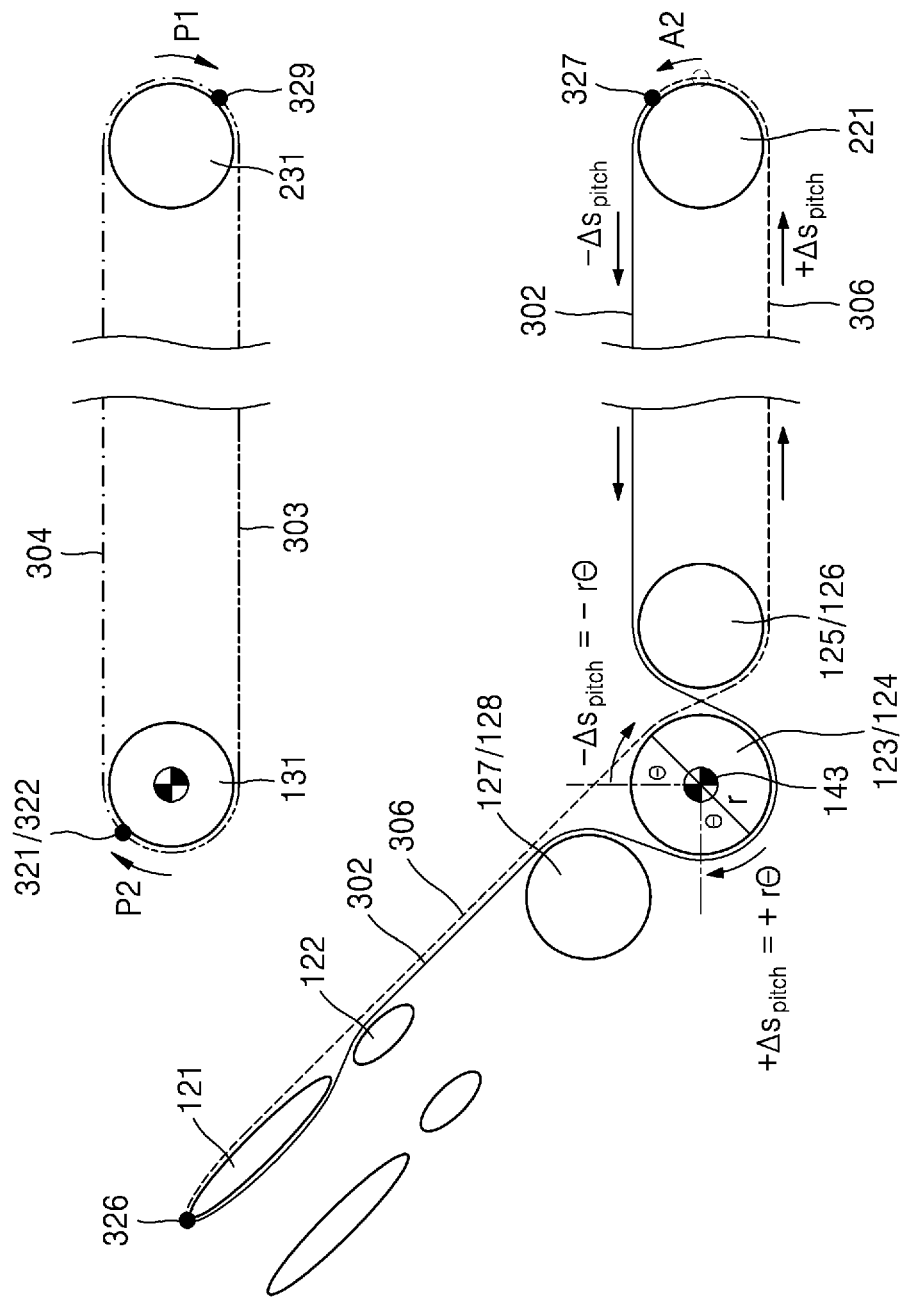
Figure 11B:
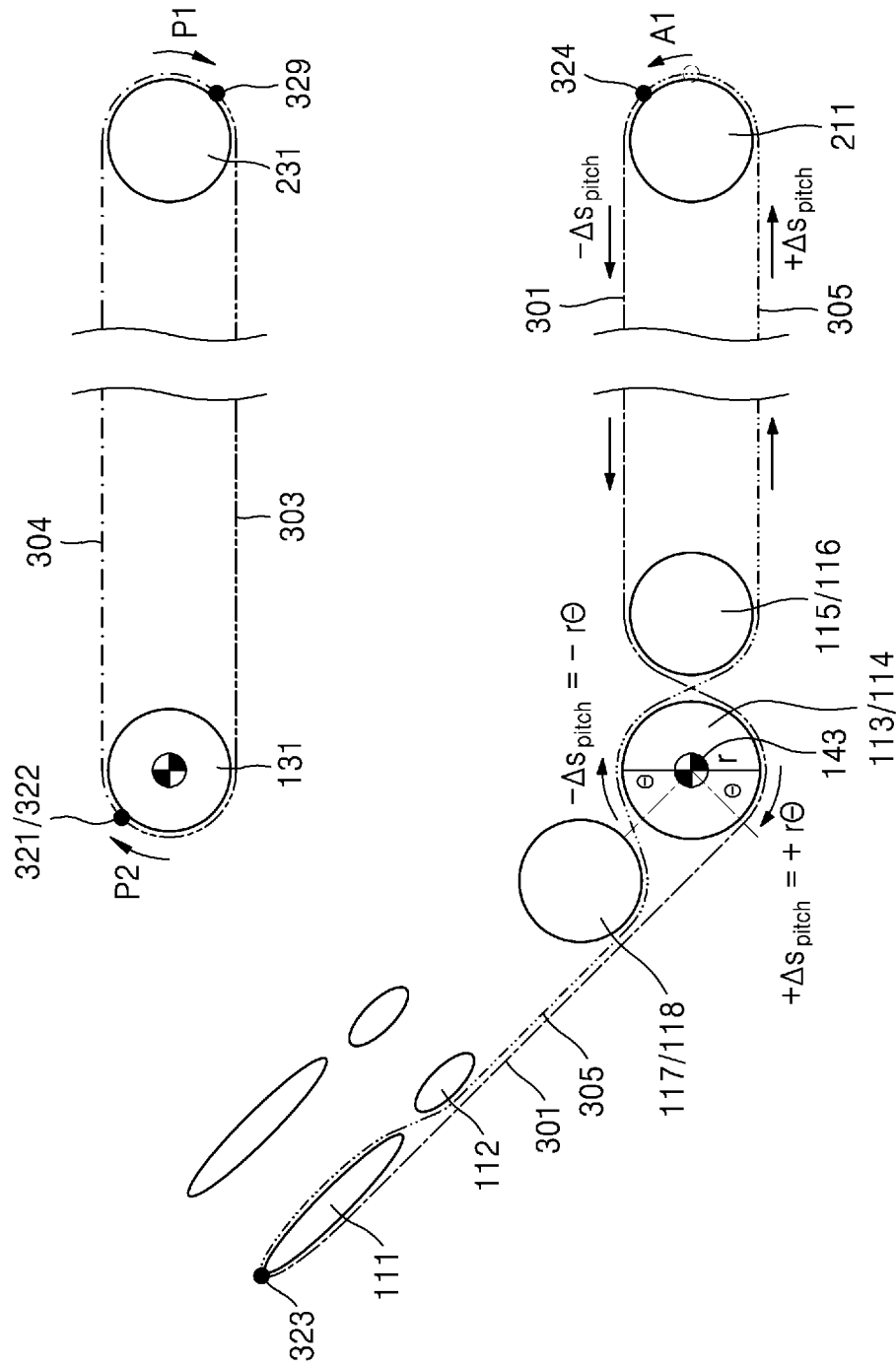

FIGS. 9, 10, and 11 are conceptual diagrams illustrating a pitch motion of the surgical instrument illustrated in FIG. 2. In detail, FIG. 9 is a diagram illustrating a surgical instrument in a neutral state, FIG. 10 is a diagram illustrating a surgical instrument when pitch compensation is not performed, and FIG. 11 is a diagram illustrating a surgical instrument when pitch compensation is performed. In this regard, for convenience of description, FIGS. 9A, 10A, and 11A mainly illustrate pulleys and wires associated with rotation of a first jaw, and FIGS. 9B, 10B, and 11B mainly illustrate pulleys and wires associated with rotation of a second jaw.

In this regard, in the surgical instrument according to an embodiment of the present disclosure, when performing a pitch motion of the end tool 100, the pitch motion is performed as the drive part first jaw pulley 211 and the drive part second jaw pulley 221 are rotated to wind or unwind the jaw wires.

As described above, when the drive part pitch pulley 231 is rotated to perform the pitch motion, and separate pitch compensation for the jaw wires is not performed, in the end tool, along with the pitch motion, the jaws are also rotated around the rotation axis 141, which is a jaw pulley rotation axis, and accordingly, a genuine pitch motion is not performed.

In detail, referring to FIGS. 9 and 10, when the drive part pitch pulley 231 of the drive part (see 200 of FIG. 1) is rotated to perform the pitch motion of the end tool, the rotation of the drive part pitch pulley 231 is transmitted to the pulley 131 of the end tool 100 through the wire 303 and the wire 304, thus, the pulley 131 is also rotated together, and accordingly, the end tool 100 is rotated to perform the pitch motion.

That is, when the drive part pitch pulley 231 is rotated in the direction of an arrow P1 of FIG. 10A, the rotation of the drive part pitch pulley 231 is transmitted to the pulley 131 of the end tool 100 through the wire 303 and the wire 304, thus, the pulley 131 is rotated in the direction of an arrow P2 of FIG. 10A, and accordingly, the end tool hub (see 106 of FIG. 2) is rotated with respect to the pitch hub (see 107 of FIG. 2). In addition, the first jaw 101 and the second jaw 102, which are coupled to the end tool hub (see 106 of FIG. 2), the first jaw pulley 111, the second jaw pulley 122, and the first jaw auxiliary pulley 112 are also rotated with respect to the pitch hub (see 107 of FIG. 2) together with the end tool hub (see 106 of FIG. 2).

In this regard, however, the wire 301 and the wire 302, which are jaw wires, are wound around the pulley 113/pulley 114 more by $\Delta S_{pitch}$, and the wire 305 and the wire 306 are unwound from the pulley 114/pulley 114 more by $\Delta S_{pitch}$.

Thus, when compensation for the excess is not performed, the first jaw pulley 111 is rotated to a certain extent in the direction of an arrow J1 of FIG. 10B, and the second jaw pulley 121 is rotated to a certain extent in the direction of an arrow J2 of FIG. 10A.

Thus, there is a problem that, when compensation for motions of the jaw wires is not performed, in the end tool, along with the pitch motion, the jaws are rotated around the rotation axis 141, which is a jaw pulley rotation axis, accordingly, a genuine pitch motion is not performed, and the pitch motion and a yaw motion are mixedly performed.

In order to perform motion compensation for performing the pitch motion, in the surgical instrument according to an embodiment of the present disclosure, when performing the pitch motion of end tool 100, the pitch motion may be performed as the drive part first jaw pulley 211 and the drive part second jaw pulley 221 are rotated to wind or unwind the jaw wires, such that a kind of compensation for the pitch motion is performed.

That is, during the pitch motion, the drive part first jaw pulley 211 is rotated to a certain extent in the direction of an arrow A1 of FIG. 11B. Then, the wire 301 is unwound from the drive part first jaw pulley 211 to a certain extent (e.g., $\Delta S_{pitch}$), and is wound around the first jaw pitch main pulley 113 to that extent. At the same time, the wire 305 is wound around the drive part first jaw pulley 211 to a certain extent (e.g., $\Delta S_{pitch}$), and is unwound from the first jaw pitch main pulley 114 to that extent.

Similarly, during the pitch motion, the drive part first jaw pulley 221 is rotated to a certain extent in the direction of an arrow A2 of FIG. 11A. Then, the wire 302 is unwound from the drive part second jaw pulley 221 to a certain extent (e.g., $\Delta S_{pitch}$), and is wound around the second jaw pitch main pulley 123 to that extent. At the same time, the wire 306 is wound around the drive part second jaw pulley 221 to a certain extent (e.g., $\Delta S_{pitch}$), and is unwound from the second jaw pitch main pulley 124 to that extent.

In other words, when the drive part pitch pulley 231 is rotated, the drive part first jaw pulley 211 and the drive part second jaw pulley 221 are also rotated, and accordingly, lengths by which the jaw wires are wound around the drive part first jaw pulley 211 and the drive part second jaw pulley 221, respectively, are changed. That is, the jaw wire, which is wound on the side of the end tool 100 by the rotation of the drive part pitch pulley 231, is unwound on the side of the drive part (see 200 of FIG. 1) to the same extent, and the jaw wire, which is unwound on the side of the end tool 100, is wound on the side of the drive unit (see 200 of FIG. 1) to the same extent, such that the pitch motion does not affect the yaw motion.

In other words, when the end tool 100 performs the pitch motion by the rotation of the drive part pitch pulley 231, the jaw wire (responsible for a yaw motion and an actuation motion) also moves by the pitch motion. That is, as pitch rotation is performed around the rotation axis 143 of the end tool 100, one strand of the jaw wires coupled to one jaw is pulled and the other strand is released. At the same time, one strand of the jaw wires coupled to the other jaw is pulled and the other strand is released. Thus, it may also be described that, in the present disclosure, in order to compensate for such motions of the jaw wires, when the drive part pitch pulley 231 is rotated for the pitch motion of the end tool, the drive part first jaw pulley 211 and the drive part second jaw pulley 221 are also rotated such that the total lengths of the jaw wires within the drive part are changed, and thus, the jaw wires on the side of the drive part are released (or pulled) by the amount by which the jaw wires are pulled (or released) on the side of the end tool, to compensate for motions of the jaw wires during the pitch motion of the end tool.

As such, the end tool 100 of a surgical instrument according to an embodiment of the present disclosure may obtain an effect of facilitating control of the pitch motion as the two strands of the jaw wires wound around one jaw pulley are wound around the pitch main pulleys in opposite directions. That is, during the pitch motion, the drive part first jaw pulley 211 and the drive part second jaw pulley 221 are rotated to wind or unwind the jaw wires, and thus perform a kind of compensation for the pitch motion, enabling the pitch motion of the end tool 100.

First Modified Example of First Embodiment

Hereinafter, the end tool 100 of the surgical instrument according to a first modified example of the first embodiment of the present disclosure will be described. In this regard, the end tool 100 of the surgical instrument according to the first modified example of the first embodiment of the present disclosure is different from the end tool of the surgical instrument according to the first embodiment of the present disclosure described above in that some of the pulleys are omitted. Hereinafter, the configuration that is different from that of the first embodiment will be described in detail.

Figure 20:
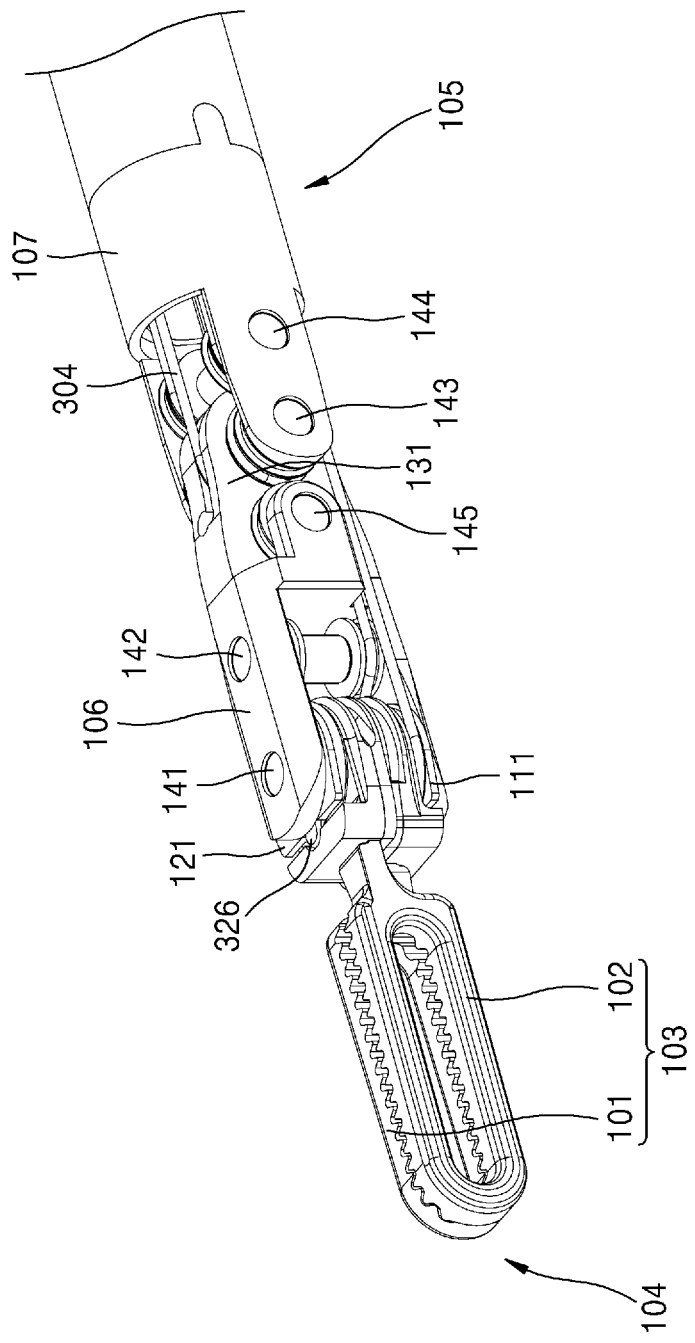
FIGS. 20 and 21 are perspective views illustrating an end tool of a surgical instrument according to a first modified example of the first embodiment of the present disclosure.
Figure 21:
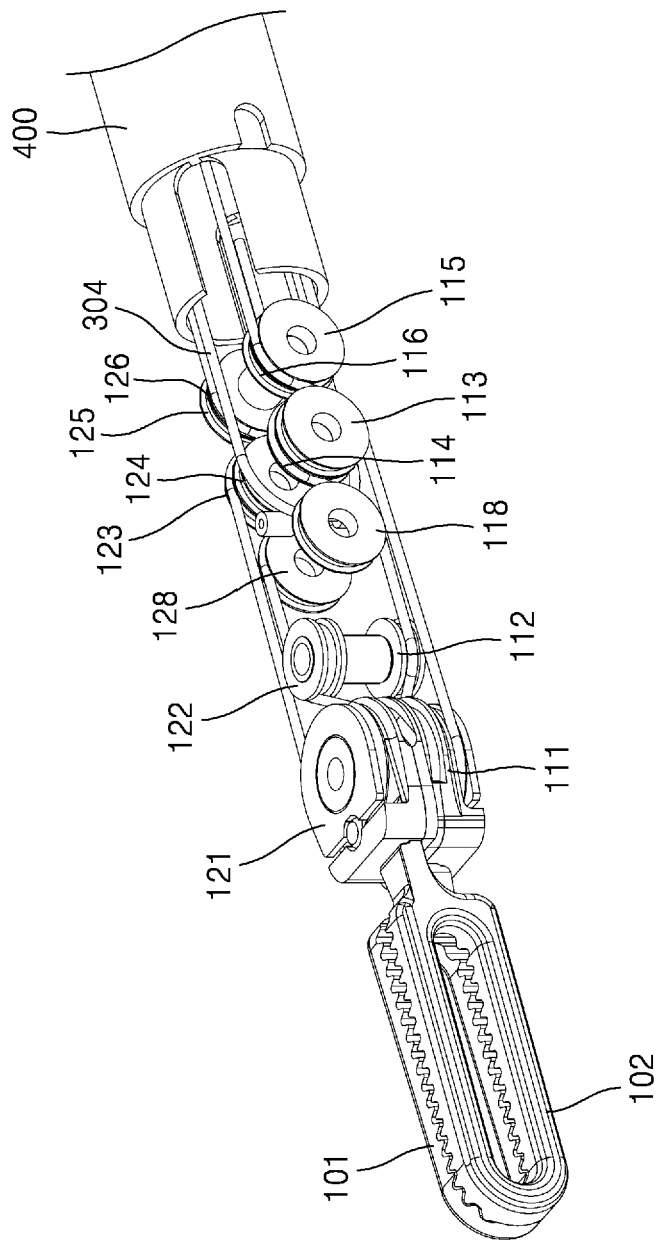
Figure 22:
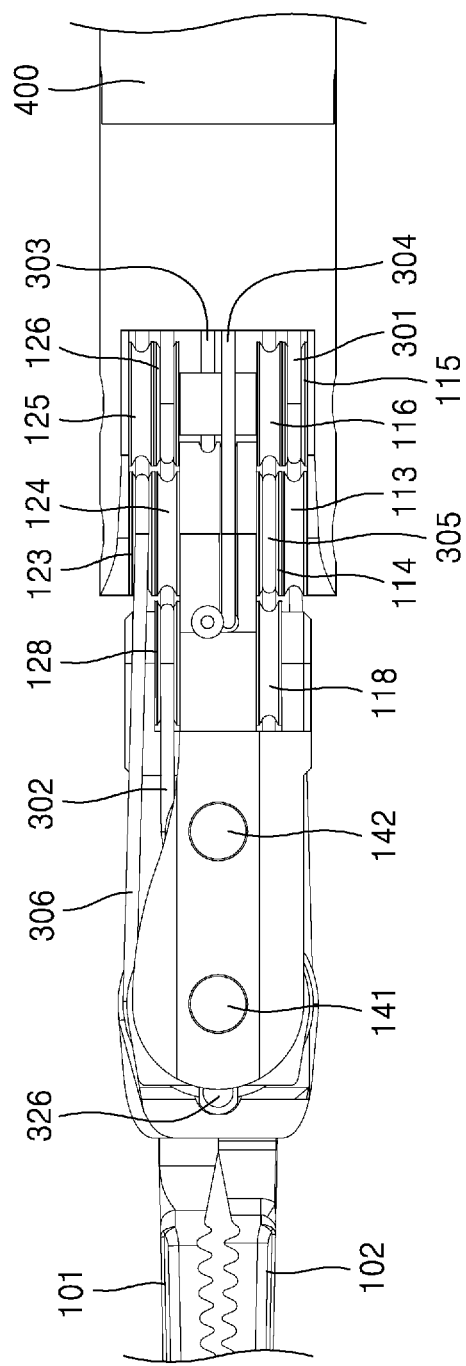
FIG. 22 is a plan view of the end tool of FIG. 20.
Figure 23:
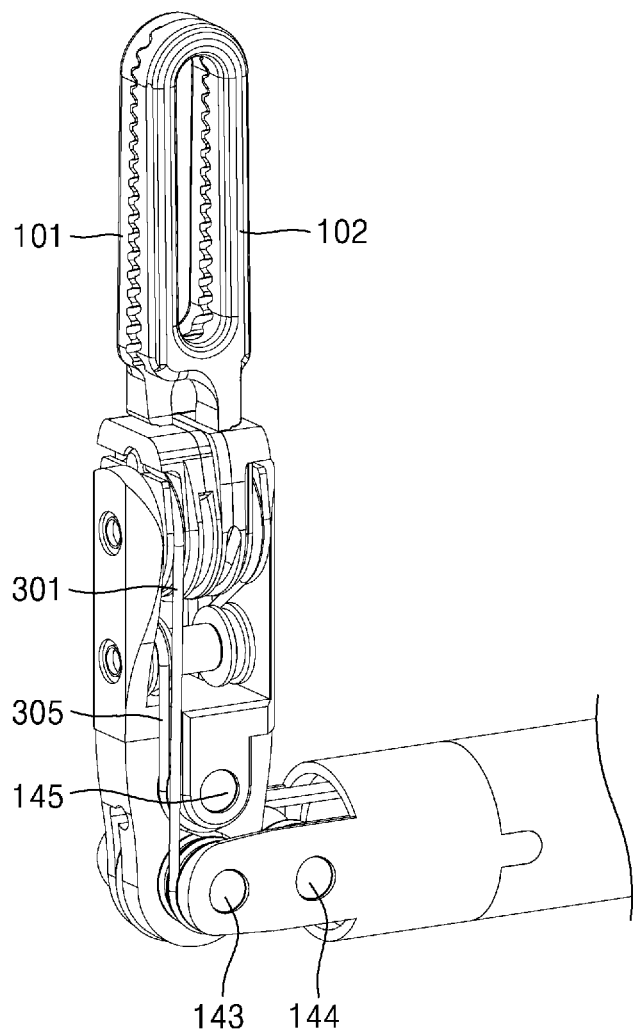
FIGS. 23 and 24 are perspective views illustrating a state in which the end tool of the surgical instrument of FIG. 20 is pitch-rotated by −90°.
Figure 24:
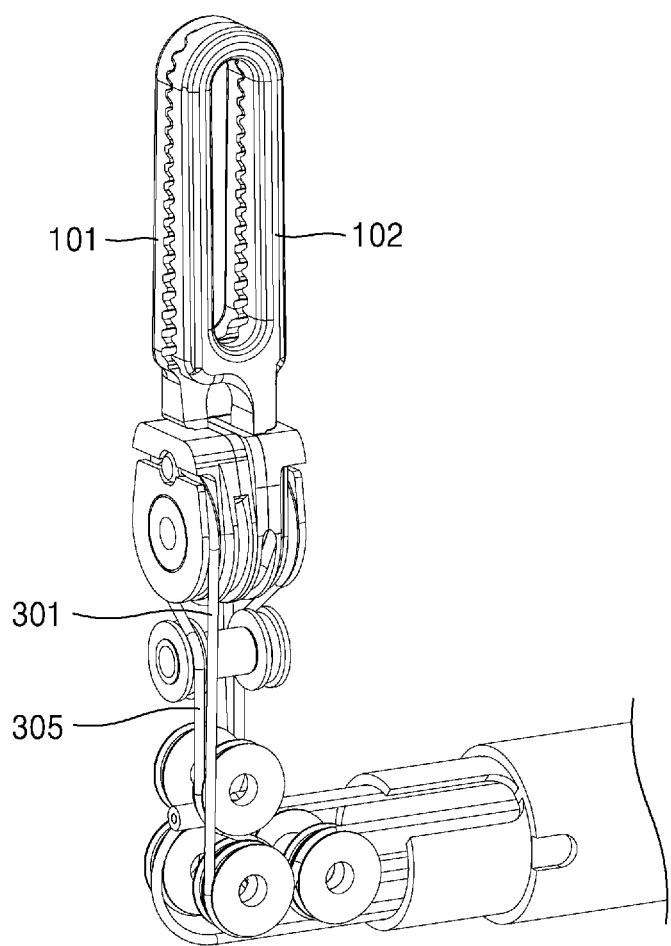
Figure 25:
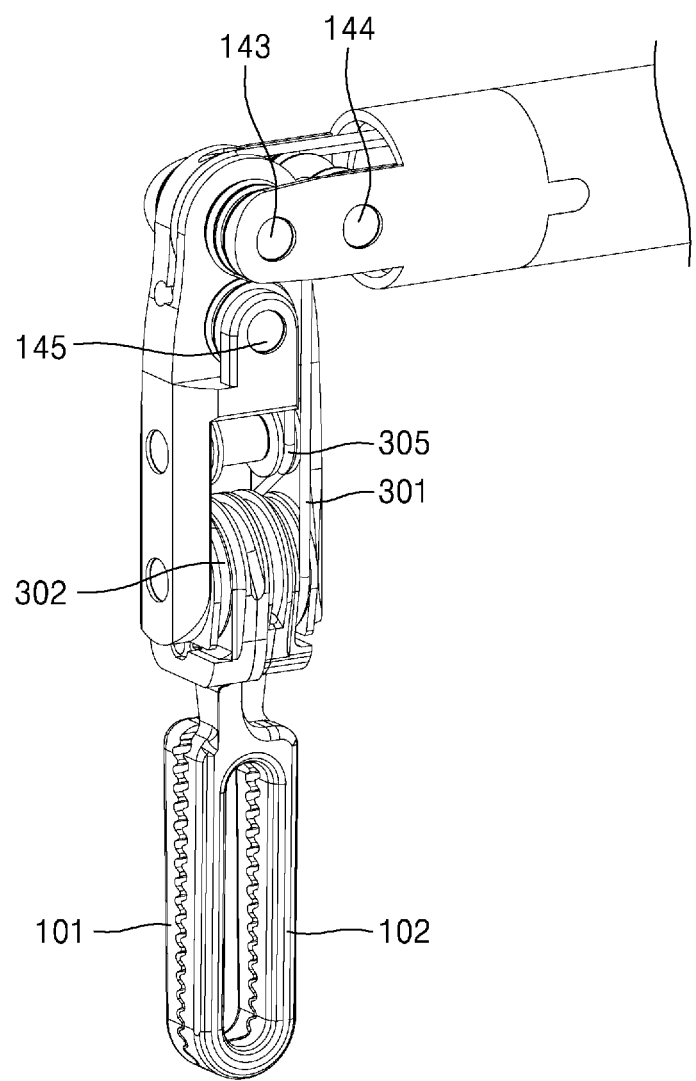
FIGS. 25 and 26 are side views illustrating a state in which the end tool of the surgical instrument of FIG. 20 pitch-rotated by −90°.
Figure 26:
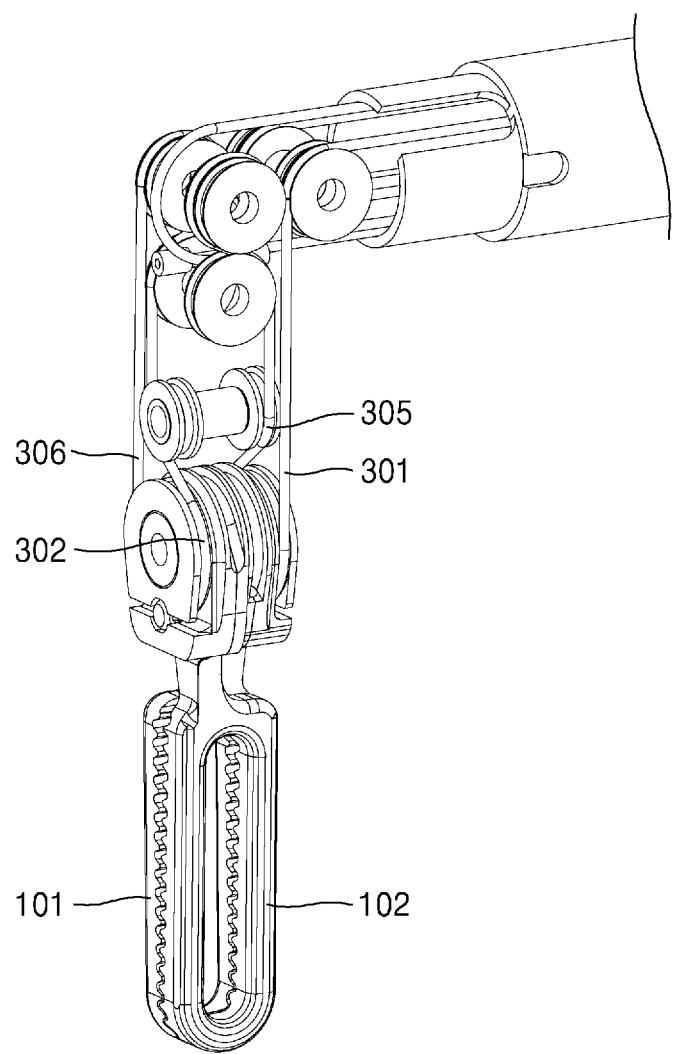

FIGS. 20 and 21 are perspective views illustrating an end tool of a surgical instrument according to a first modified example of the first embodiment of the present disclosure. FIG. 22 is a plan view of the end tool of FIG. 20. FIGS. 23 and 24 are perspective views illustrating a state in which the end tool of the surgical instrument of FIG. 20 is pitch-rotated by −90°. FIGS. 25 and 26 are side views illustrating a state in which the end tool of the surgical instrument of FIG. 20 pitch-rotated by −90°.

Referring to FIGS. 20 to 26, the end tool 100 according to the first modified example of the first embodiment of the present disclosure includes a pair of jaws for performing a grip motion, that is, the first jaw 101 and the second jaw 102. In this regard, a component encompassing each of the first jaw 101 and the second jaw 102 or both the first jaw 101 and the second jaw 102 may be referred to as the jaw 103.

In addition, the end tool 100 of the first embodiment of the present disclosure may include the end tool hub 106 and the pitch hub 107.

In addition, the end tool 100 of the first modified example of the first embodiment of the present disclosure may include the rotation axis 141, the rotation axis 142, the rotation axis 145, the rotation axis 143, and the rotation axis 144. As described above, the rotation axis 141, the rotation axis 142, and the rotation axis 145 may be inserted through the end tool hub 106, and the rotation axis 143 and the rotation axis 144 may be inserted through the pitch hub 107.

In the present modified example, the end tool hub 106, the pitch hub 107, and the rotation axes 141, 142, 143, 144, and 145 are substantially the same as the end tool hub 106, the pitch hub 107, and the rotation axes 141, 142, 143, 144, and 145 that are described above with reference to FIG. 2 and the like, respectively, and thus, detailed descriptions thereof will be omitted.

Meanwhile, the end tool 100 may include the pulley 111, the pulley 112, the pulley 113, the pulley 114, the pulley 115, the pulley 116, and the pulley 118, which are associated with a rotational motion of the first jaw 101. In addition, the end tool 100 may include the pulley 121, the pulley 122, the pulley 123, the pulley 124, the pulley 125, the pulley 126, and the pulley 128, which are associated with a rotational motion of the second jaw 102.

In this regard, in the end tool 100 of the surgical instrument according to the first modified example of the first embodiment of the present disclosure, each of the first jaw pitch redundant pulley and the second jaw pitch redundant pulley includes only one pulley.

In detail, the end tool 100 of the surgical instrument according to the first embodiment of the present disclosure illustrated in FIG. 6 and the like includes a pair of pulleys 117 and 118 as first jaw pitch redundant pulleys, and a pair of pulleys 127 and 128 as second jaw pitch redundant pulleys.

On the contrary, the end tool 100 of the surgical instrument according to the first modified example of the first embodiment of the present disclosure is different from the first embodiment of the present disclosure illustrated in FIG. 6 and the like, in that it includes a single pulley 118 as a first jaw pitch redundant pulley, and a single pulley 128 as a second jaw pitch redundant pulley.

Accordingly, the pulley 111, the pulley 112, the pulley 118, the pulley 113/pulley 114, and the pulley 115/pulley 116, which are associated with rotation of the first jaw 101, may be sequentially arranged from the distal end 104 of the end tool 100 toward the proximal end 105.

In addition, the pulley 121, the pulley 122, the pulley 128, the pulley 123/pulley 124, and the pulley 125/pulley 126, which are associated with rotation of the second jaw 102, may be sequentially arranged from the distal end 104 of the end tool 100 toward the proximal end 105.

In this regard, the pulley 117 and pulley 127 of the end tool 100 of the first embodiment of the present disclosure illustrated in FIG. 6 and the like are not pulleys around which wires are wound, but pulleys through which the wires pass in a straight line, and thus may be omitted as in the present modified example.

In other words, in the first embodiment of the present disclosure, two rows of first jaw pitch redundant pulleys and two rows of second jaw pitch redundant pulleys are provided, whereas in the first modified example of the first embodiment of the present disclosure, one row of a first jaw pitch redundant pulley and one row of a second jaw pitch redundant pulley are provided.

In this regard, the pulley 118 is arranged on one side of the pulley 111 and the pulley 112. In this regard, the pulley 118 is formed to be rotatable around the rotation axis 145, which is a pitch redundant rotation axis. In addition, the pulley 113 and the pulley 114 are arranged on one side of the pulley 118 to face each other. In this regard, the pulley 113 and the pulley 114 are formed to be rotatable independently of each other around the rotation axis 143, which is a pitch main rotation axis. In addition, the pulley 115 and the pulley 116 are arranged on one sides of the pulley 113 and the pulley 114, respectively, to face each other. In this regard, the pulley 115 and the pulley 116 are formed to be rotatable independently of each other around the rotation axis 144, which is a pitch sub-rotation axis. In this regard, the drawings illustrate that the pulley 118, the pulley 113, the pulley 114, the pulley 115, and the pulley 116 are formed to be rotatable around the Y-axis direction, but the concept of the present disclosure is not limited thereto, and the rotation axes of the respective pulleys may be formed in various directions according to their configurations.

The wire 301, which is a first jaw wire, is wound to sequentially come into contact with at least portions of the pulley 115, the pulley 113, and the pulley 111. In addition, the wire 305 connected to the wire 301 by the coupling member 323 is wound to sequentially come into contact with at least portions of the pulley 111, the pulley 112, the pulley 118, the pulley 114, and the pulley 116.

In other words, the wire 301 and the wire 305, which are first jaw wires, are wound to sequentially come into contact with at least portions of the pulley 115, the pulley 113, the pulley 111, the pulley 112, the pulley 118, the pulley 114, and the pulley 116, and are formed to move along the above pulleys while rotating the above pulleys.

Meanwhile, the pulley 128 is arranged on one side of the pulley 121 and the pulley 122. In this regard, the pulley 128 is formed to be rotatable around the rotation axis 145, which is a pitch redundant rotation axis. In addition, the pulley 123 and the pulley 124 are arranged on one side of the pulley 128 to face each other. In this regard, the pulley 123 and the pulley 124 are formed to be rotatable independently of each other around the rotation axis 143, which is a pitch main rotation axis. In addition, the pulley 125 and the pulley 126 are arranged on one sides of the pulley 123 and the pulley 124, respectively, to face each other. In this regard, the pulley 125 and the pulley 126 are formed to be rotatable independently of each other around the rotation axis 144, which is a pitch sub-rotation axis. In this regard, the drawings illustrate that the pulley 128, the pulley 123, the pulley 124, the pulley 125, and the pulley 126 are formed to be rotatable around the Y-axis direction, but the concept of the present disclosure is not limited thereto, and the rotation axes of the respective pulleys may be formed in various directions according to their configurations.

The wire 306, which is a second jaw wire, is wound to sequentially come into contact with at least portions of the pulley 125, the pulley 123, and the pulley 121. In addition, the wire 302 connected to the wire 306 by the coupling member 326 is wound to sequentially come into contact with at least portions of the pulley 121, the pulley 122, the pulley 128, the pulley 124, and the pulley 126.

In other words, the wire 306 and the wire 302, which are second jaw wires, are wound to sequentially come into contact with at least portions of the pulley 125, the pulley 123, the pulley 121, the pulley 122, the pulley 128, the pulley 124, and the pulley 126, and are formed to move along the above pulleys while rotating the above pulleys.

Accordingly, in the first embodiment of the present disclosure, two rows of first jaw pitch redundant pulleys and two rows of second jaw pitch redundant pulleys are provided, whereas in the first modified example of the first embodiment of the present disclosure, one row of a first jaw pitch redundant pulley and one row of a second jaw pitch redundant pulley are provided, and thus, an effect of reducing the number of parts and simplifying a manufacturing process may be achieved.

Second Modified Example of First Embodiment

Hereinafter, the end tool 100 of the surgical instrument according to a second modified example of the first embodiment of the present disclosure will be described. In this regard, the end tool 100 of the surgical instrument according to the second modified example of the first embodiment of the present disclosure is different from the end tool of the surgical instrument according to the first embodiment of the present disclosure described above, in the configuration of the end tool hub. Hereinafter, the configuration that is different from that of the first embodiment will be described in detail.

Figure 27:
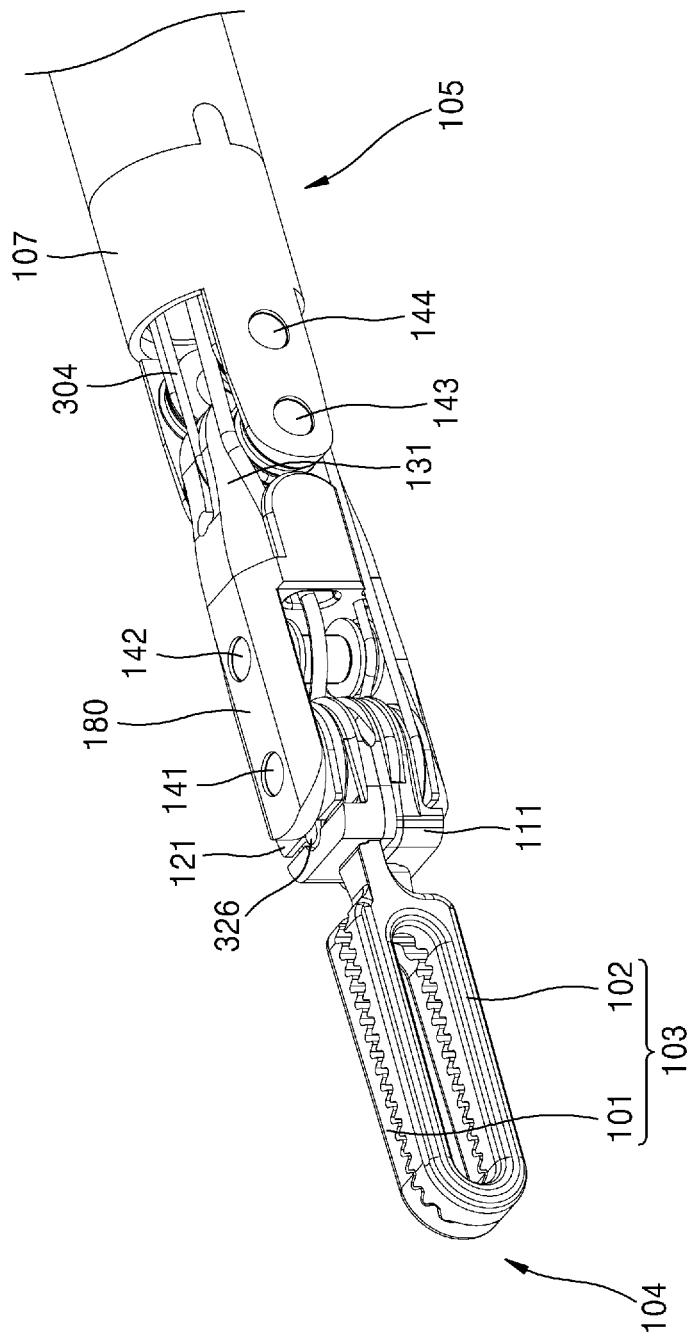
FIGS. 27 and 28 are perspective views illustrating the end tool of the surgical instrument according to the second modified example of the first embodiment of the present disclosure.
Figure 28:
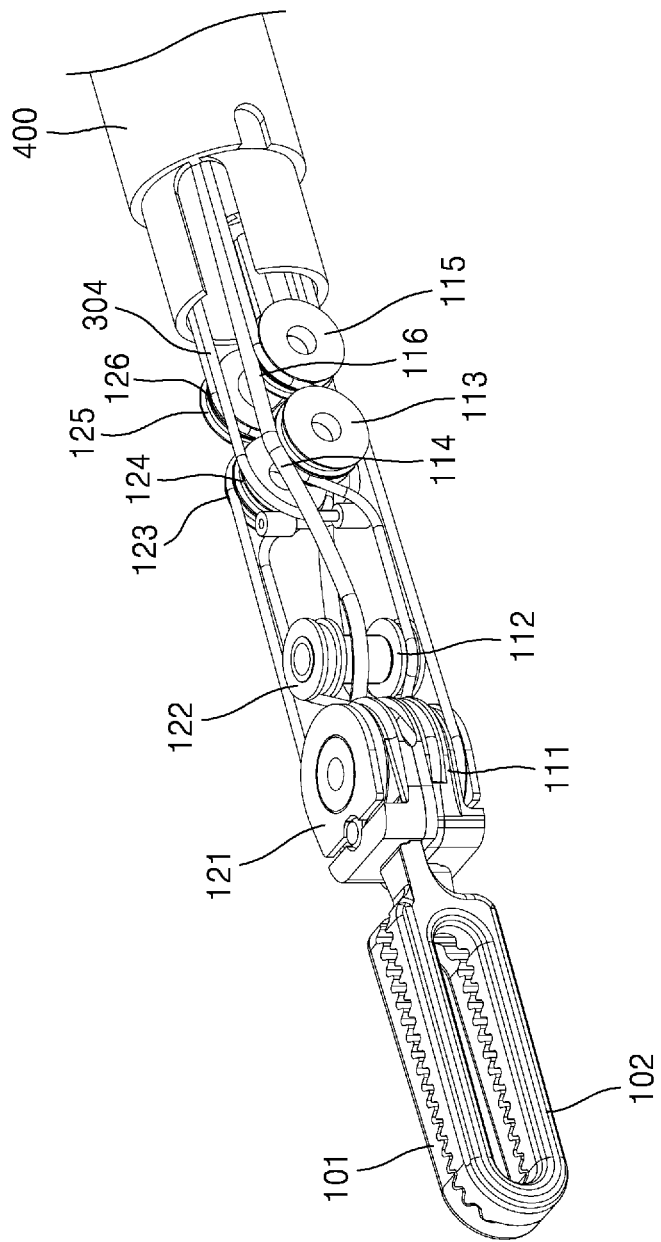
Figure 29:
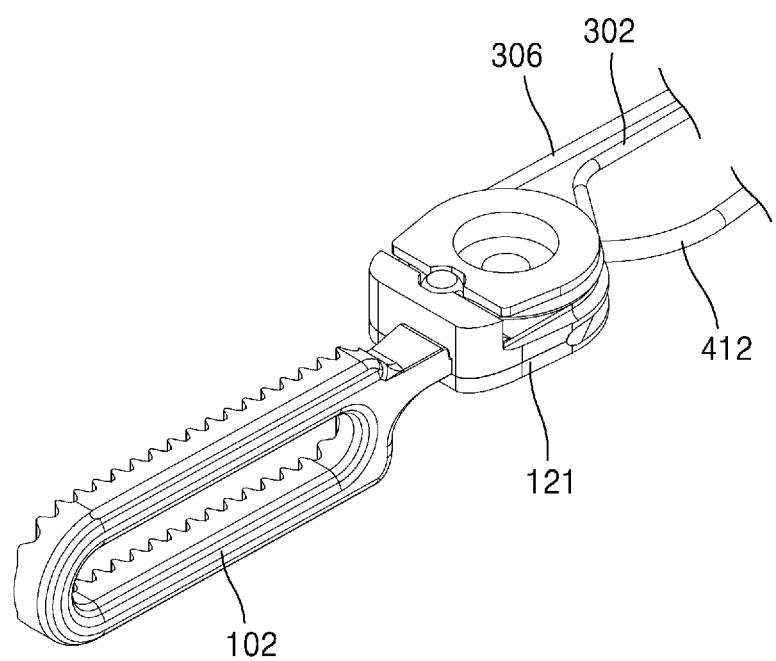
FIG. 29 is a combined perspective view illustrating a second jaw of the end tool of FIG. 27.
Figure 30:
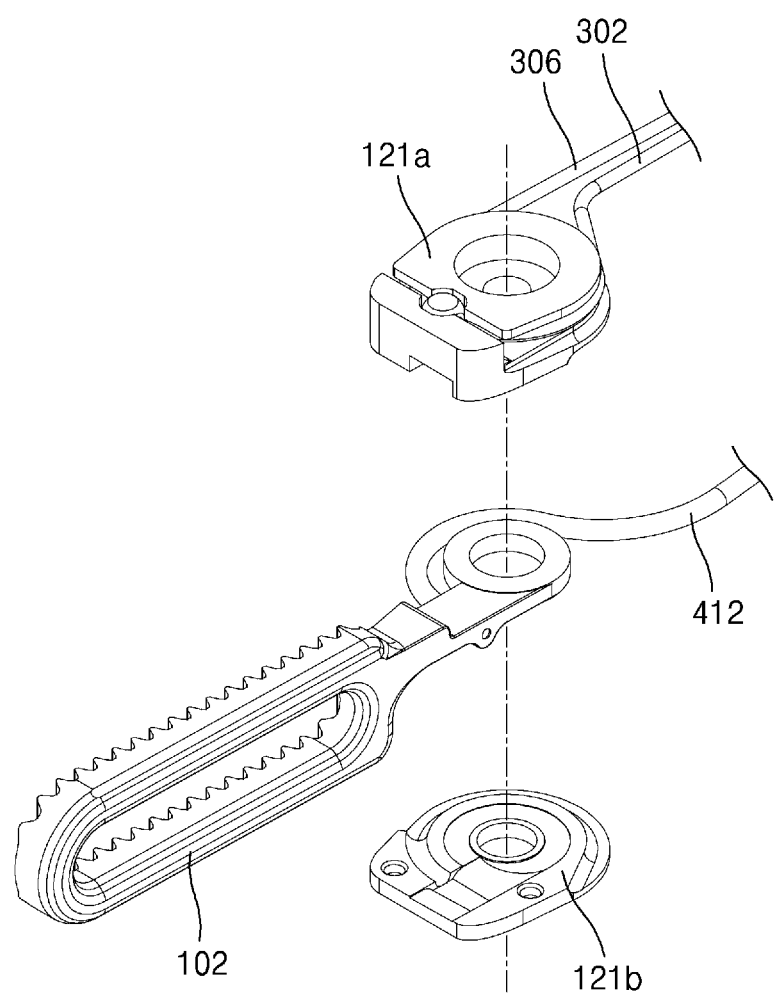
FIG. 30 is an exploded perspective view illustrating the second jaw of the end tool of FIG. 27.
Figure 31:
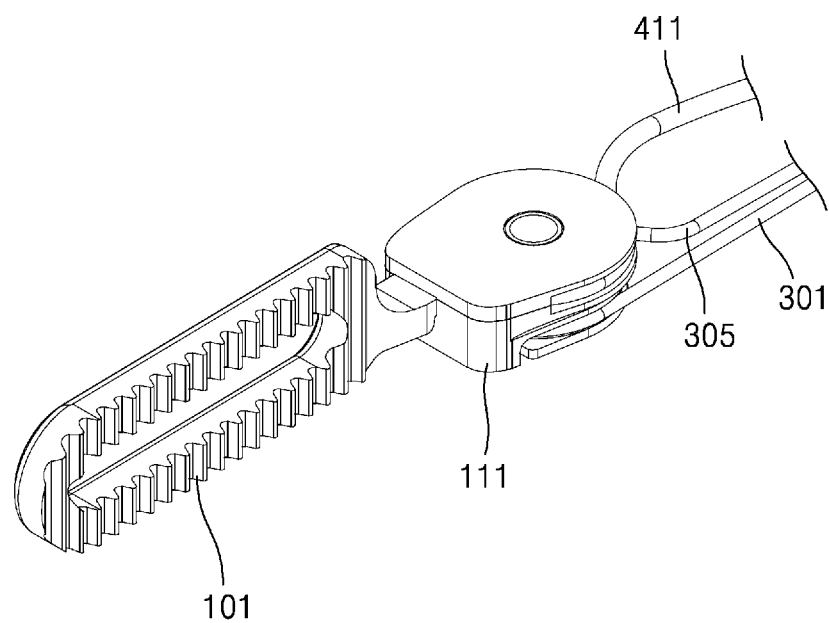
FIG. 31 is a combined perspective view illustrating a first jaw of the end tool of FIG. 27.
Figure 32:
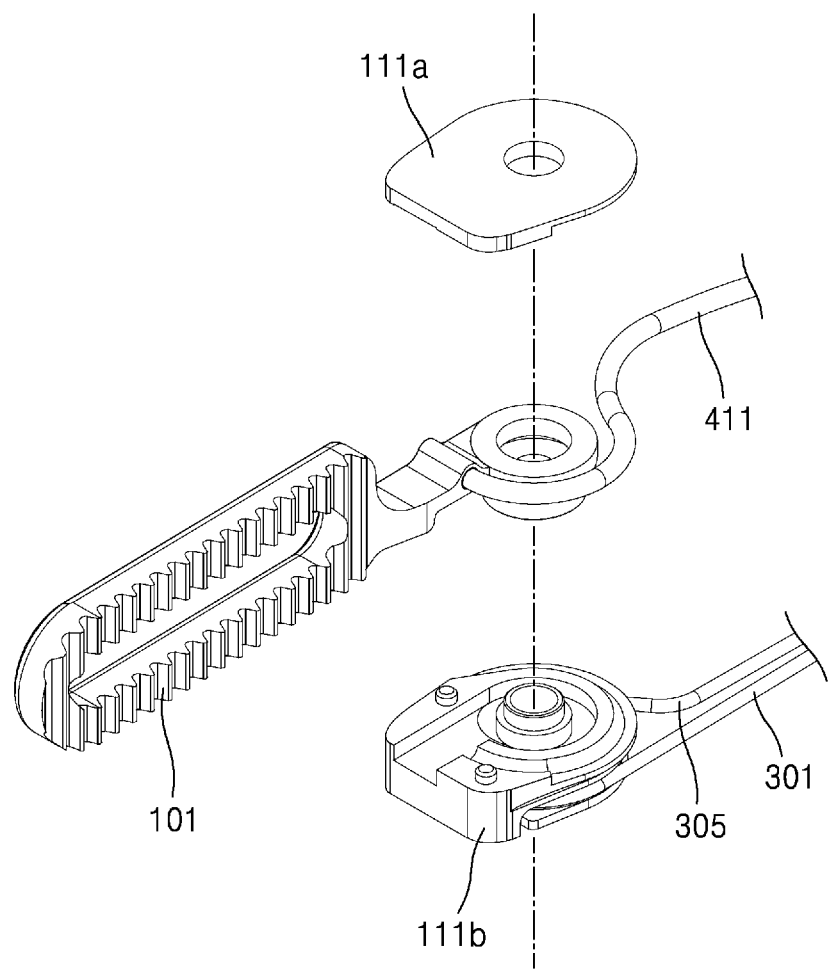
FIG. 32 is an exploded perspective view illustrating the first jaw of the end tool of FIG. 27.
Figure 33:
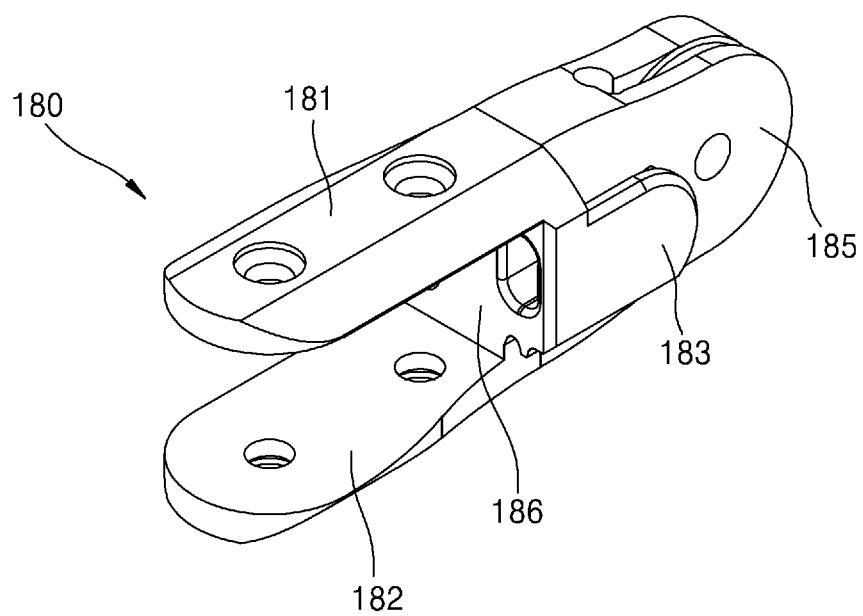
FIGS. 33 and 34 are perspective views illustrating an end tool hub of the end tool of FIG. 27.
Figure 34:
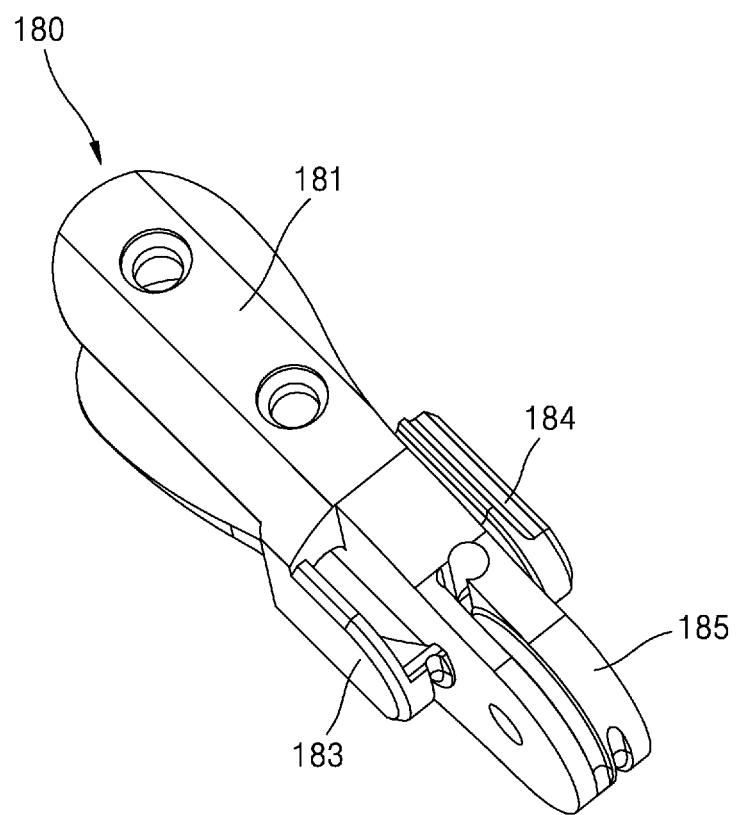
Figure 35:
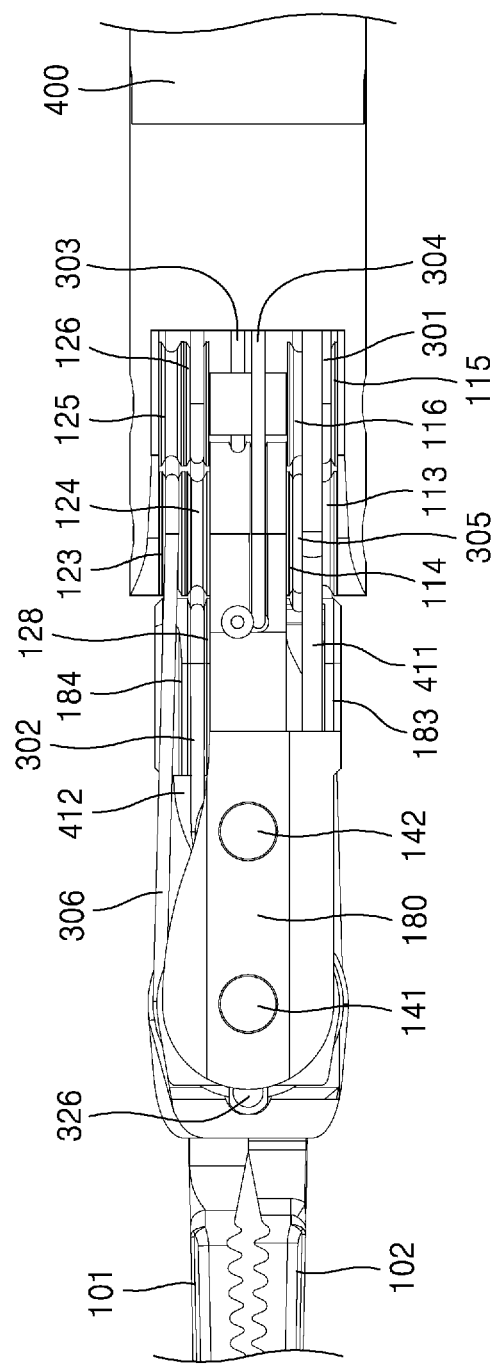
FIG. 35 is a plan view of the end tool of FIG. 27.
Figure 36:
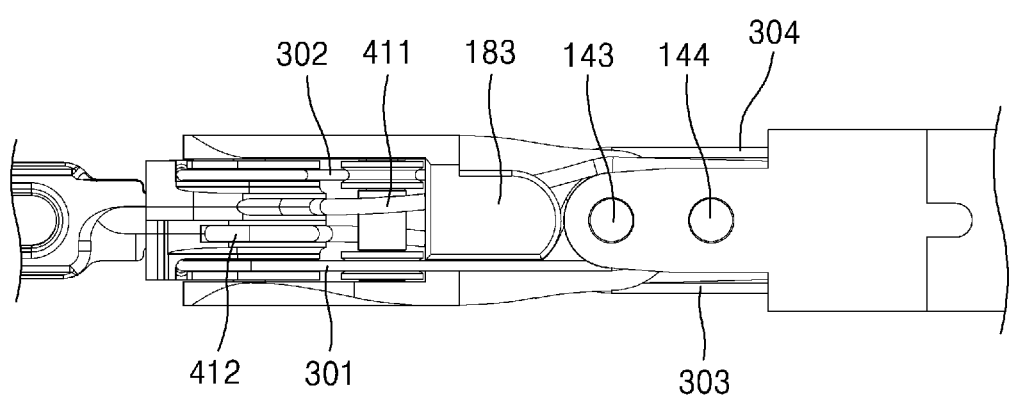
FIGS. 36 and 37 are side views of the end tool of FIG. 27.
Figure 37:
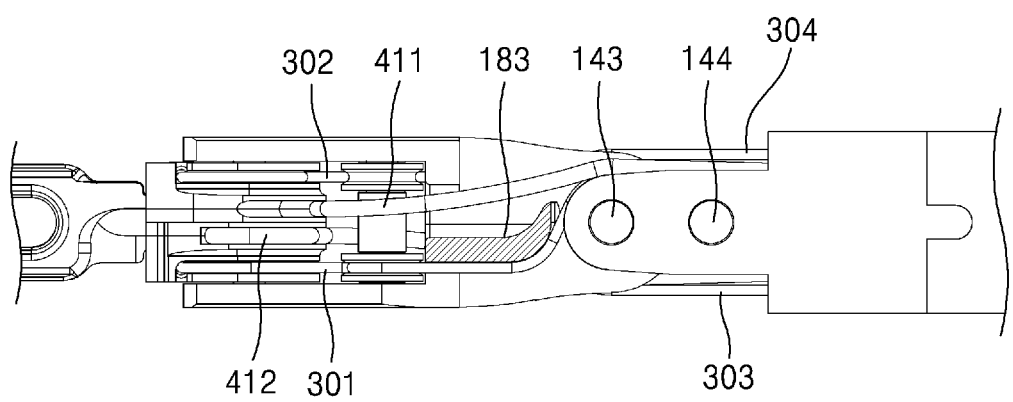
Figure 38:
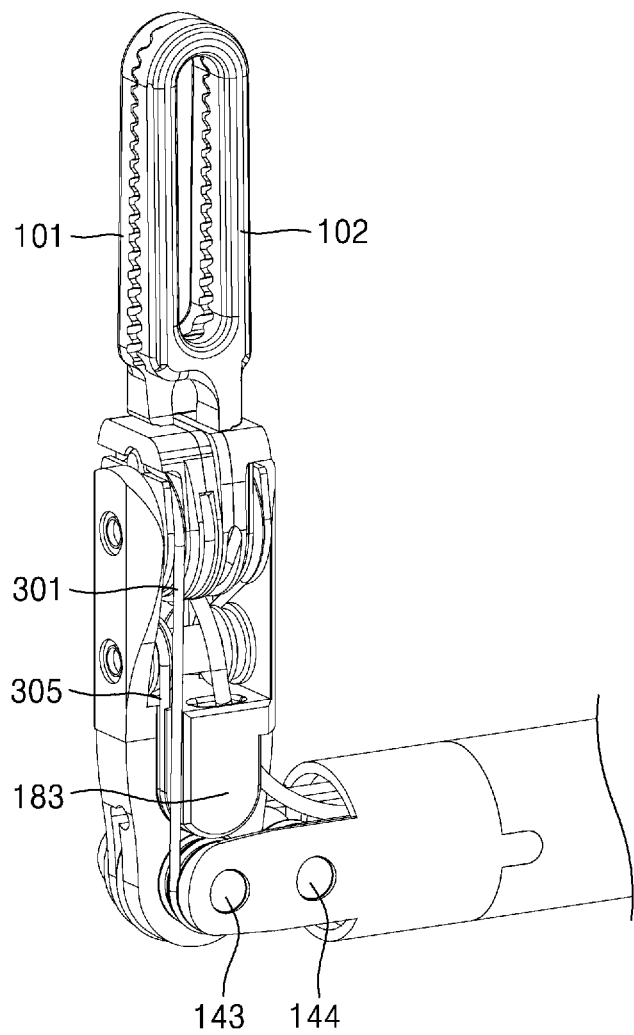
FIGS. 38 and 39 are perspective views illustrating a state in which the end tool of the surgical instrument of FIG. 27 is pitch-rotated by −90°.
Figure 39:
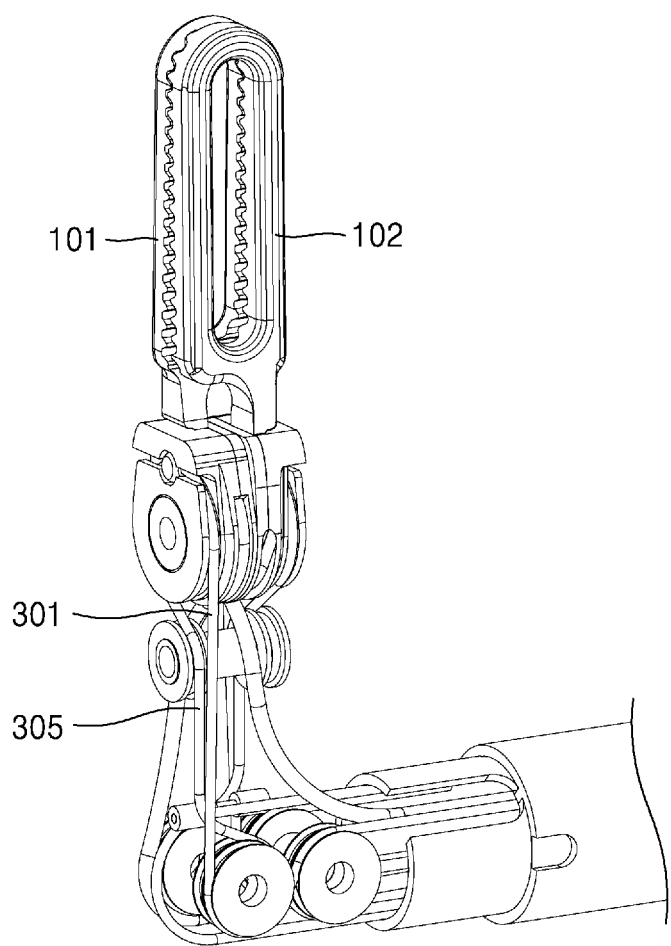
Figure 40:
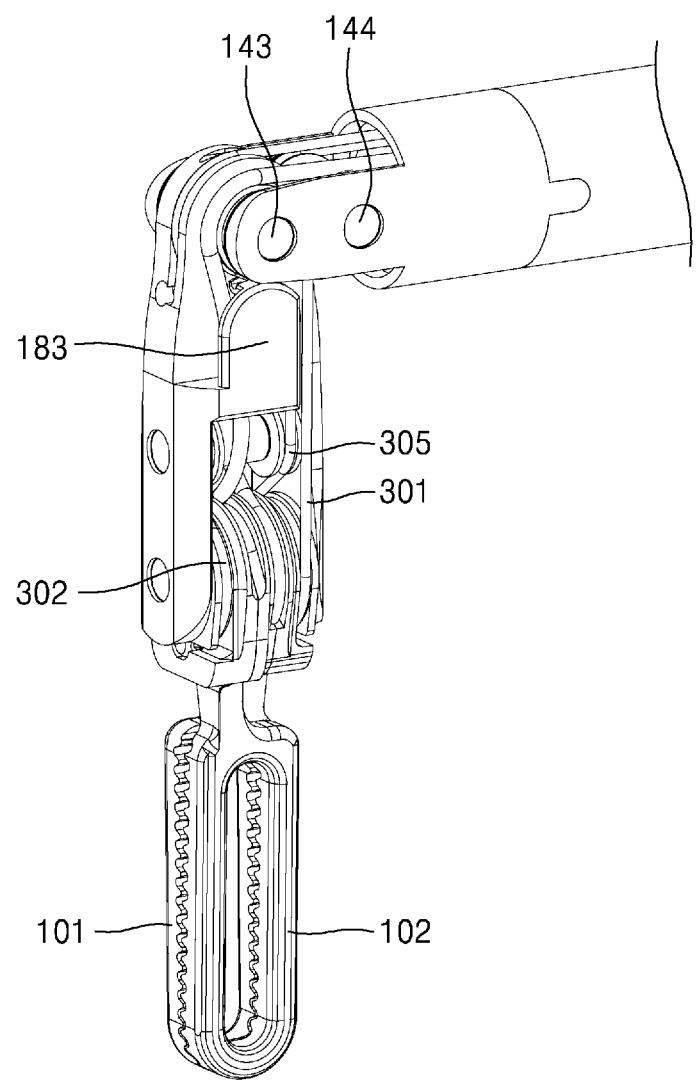
FIGS. 40 and 41 are perspective views illustrating a state in which the end tool of the surgical instrument of FIG. 27 is pitch-rotated by +90°.
Figure 41:
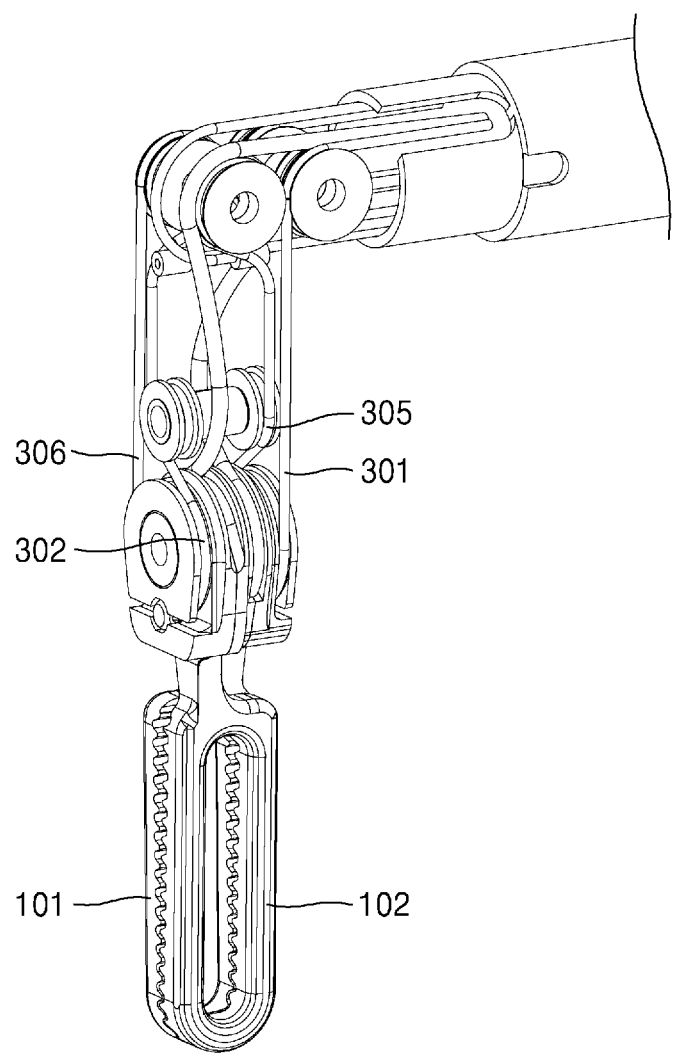

FIGS. 27 and 28 are perspective views illustrating the end tool of the surgical instrument according to the second modified example of the first embodiment of the present disclosure. FIG. 29 is a combined perspective view illustrating a second jaw of the end tool of FIG. 27. FIG. 30 is an exploded perspective view illustrating the second jaw of the end tool of FIG. 27. FIG. 31 is a combined perspective view illustrating a first jaw of the end tool of FIG. 27. FIG. 32 is an exploded perspective view illustrating the first jaw of the end tool of FIG. 27. FIGS. 33 and 34 are perspective views illustrating an end tool hub of the end tool of FIG. 27. FIG. 35 is a plan view of the end tool of FIG. 27. FIGS. 36 and 37 are side views of the end tool of FIG. 27. FIGS. 38 and 39 are perspective views illustrating a state in which the end tool of the surgical instrument of FIG. 27 is pitch-rotated by −90°. FIGS. 40 and 41 are perspective views illustrating a state in which the end tool of the surgical instrument of FIG. 27 is pitch-rotated by +90°.

Referring to FIGS. 27 to 41, the end tool 100 according to the second modified example of the first embodiment of the present disclosure includes a pair of jaws for performing a grip motion, that is, the first jaw 101 and the second jaw 102. In this regard, a component encompassing each of the first jaw 101 and the second jaw 102 or both the first jaw 101 and the second jaw 102 may be referred to as the jaw 103.

Meanwhile, an electric wire 411 may be coupled to the first jaw 101, and an electric wire 412 may be coupled to the second jaw 102.

In addition, the end tool 100 of the second modified example of the first embodiment of the present disclosure may include an end tool hub 180 and the pitch hub 107. The end tool hub 180 will be described in more detail below.

In addition, the end tool 100 of the second modified example of the first embodiment of the present disclosure may include the rotation axis 141, the rotation axis 142, the rotation axis 145, the rotation axis 143, and the rotation axis 144. As described above, the rotation axis 141, the rotation axis 142, and the rotation axis 145 may be inserted through the end tool hub 106, and the rotation axis 143 and the rotation axis 144 may be inserted through the pitch hub 107.

Meanwhile, the end tool 100 may include the pulley 111, the pulley 112, the pulley 113, the pulley 114, the pulley 115, and the pulley 116, which are associated with a rotational motion of the first jaw 101. In addition, the end tool 100 may include the pulley 121, the pulley 122, the pulley 123, the pulley 124, the pulley 125, and the pulley 126, which are associated with a rotational motion of the second jaw 102.

In the present modified example, the first jaw 101, the second jaw 102, the pitch hub 107, the respective pulleys, the respective rotation axes, and the like are substantially the same as those of the end tool 100 of the first embodiment described above with reference to FIG. 2 and the like, and thus, detailed descriptions thereof will be omitted.

Hereinafter, the end tool hub 180 of the second modified example of the first embodiment of the present disclosure will be described in more detail, and in particular, a first pitch redundant pulley part 183 and a second pitch redundant pulley part 184 of the end tool hub 180, which serve as pitch redundant pulleys, will be mainly described.

The end tool hub 180 includes a first jaw pulley coupling part 181, a second jaw pulley coupling part 182, the first pitch redundant pulley part 183, the second pitch redundant pulley part 184, and a pitch pulley coupling part 185.

In detail, the first jaw pulley coupling part 181 and the second jaw pulley coupling part 182 are formed to face each other such that the pulley 111, the pulley 112, the pulley 121, and the pulley 122 are accommodated therein. In addition, a through hole is formed in each of the jaw pulley coupling parts 181 and 182 such that the rotation axis 141 passes through and axially couples the jaw pulley coupling parts 181 and 182, the pulley 111, and the pulley 121. In addition, a through hole is formed in each of the jaw pulley coupling parts 181 and 182 such that the rotation axis 142 passes through and axially couples the jaw pulley coupling parts 181 and 182, the pulley 112, and the pulley 122.

The first jaw pulley coupling part 181 and the second jaw pulley coupling part 182 are connected to each other by a guide part 186. That is, the first jaw pulley coupling part 181 and the second jaw pulley coupling part 182 parallel to each other are coupled by the guide part 186 formed in a direction substantially perpendicular thereto, such that the first jaw pulley coupling part 181, the second jaw pulley coupling part 182, and the guide part 186 form a substantially "C" shape in which the pulley 111, the pulley 112, the pulley 121, and the pulley 122 are accommodated.

In other words, it may also be described that the first jaw pulley coupling part 181 and the second jaw pulley coupling part 182 are formed to extend in the X-axis direction from both ends of the guide part 186 that is elongated in the Z-axis direction.

The first pitch redundant pulley part 183 may be formed on one side surface of the guide part 186, and the second pitch redundant pulley part 184 may be formed on the other side surface.

In detail, the first pitch redundant pulley part 183 and the second pitch redundant pulley part 184, each of which is formed in the shape of a disk like a pulley and has a groove formed on the outer circumferential surface thereof, around which a wire may be wound, may be formed on both side surfaces of the guide part 186, respectively.

In addition, the wire 305, which is a first jaw wire, may be wound around the first pitch redundant pulley part 183, and the wire 302, which is a second jaw wire, may be wound around the second pitch redundant pulley part 184.

Meanwhile, the wire 301, which is a first jaw wire, may pass through a side surface of the first pitch redundant pulley part 183, and the wire 306, which is a second jaw wire, may pass through a side surface of the second pitch redundant pulley part 184.

Meanwhile, the pulley 131 that serves as an end tool pitch pulley may be formed in the pitch pulley coupling part 185 at one end of the end tool hub 180. In this regard, the pulley 131 may be formed with the end tool hub 180 as one body. That is, one end of the end tool hub 180 may be formed in a disk shape or a semicircular shape, and a groove around which a wire may be wound may be formed on an outer circumferential surface of the groove, such that a kind of guide channel is formed. Alternatively, the pulley 131 may be formed as a separate member from the end tool hub 180 and coupled to the end tool hub 180. The wire 303 and the wire 304 described above are coupled to the pulley 131 serving as an end tool pitch pulley, and a pitch motion is performed as the pulley 131 is rotated around the rotation axis 143.

As such, as the first pitch redundant pulley part 183 and the second pitch redundant pulley part 184 is formed in the existing end tool hub 180 without adding a separate structure such as a pitch redundant pulley, it is possible to increase the range of rotation without adding additional parts or manufacturing processes.

Third Modified Example of First Embodiment

Hereinafter, the end tool 100 of the surgical instrument according to a third modified example of the first embodiment of the present disclosure will be described. In this regard, the end tool 100 of the surgical instrument according to the third modified example of the first embodiment of the present disclosure is different from the end tool of the surgical instrument according to the first embodiment of the present disclosure described above in that some of the pulleys are omitted. Hereinafter, the configuration that is different from that of the first embodiment will be described in detail.

Figure 42:
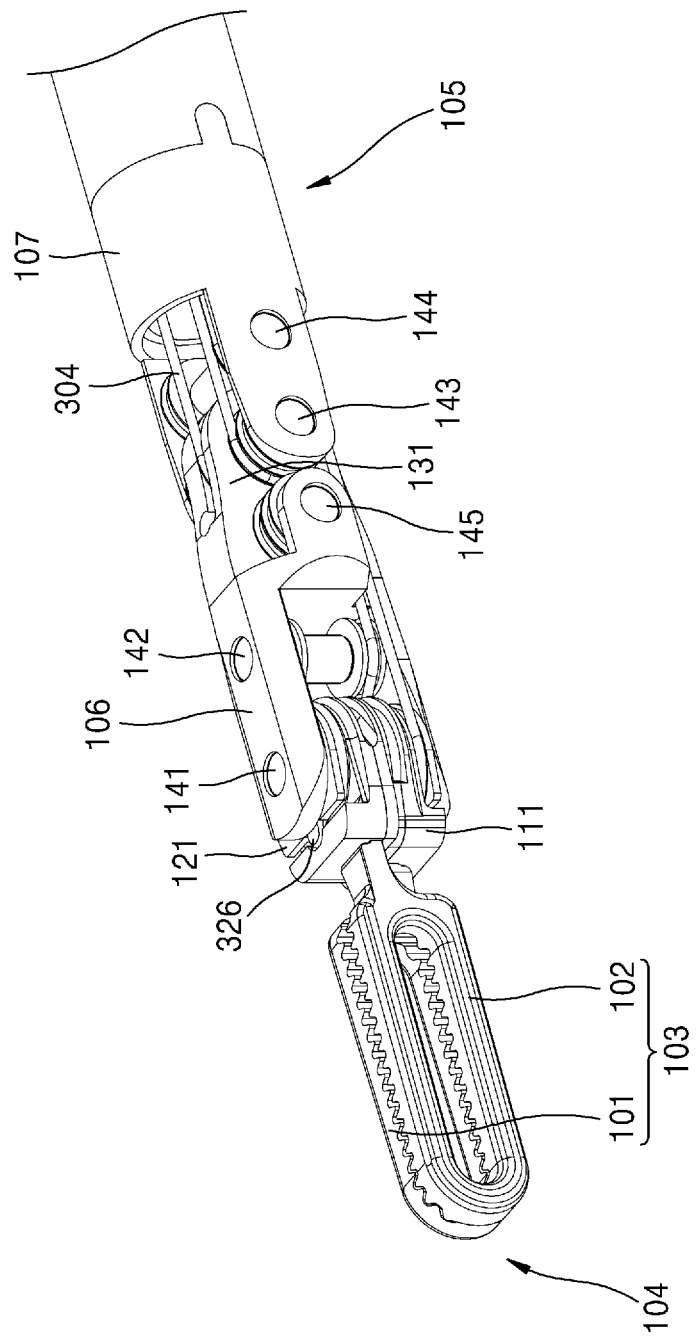
FIGS. 42 and 43 are perspective views illustrating the end tool of the surgical instrument according to a third modified example of the first embodiment of the present disclosure.
Figure 43:
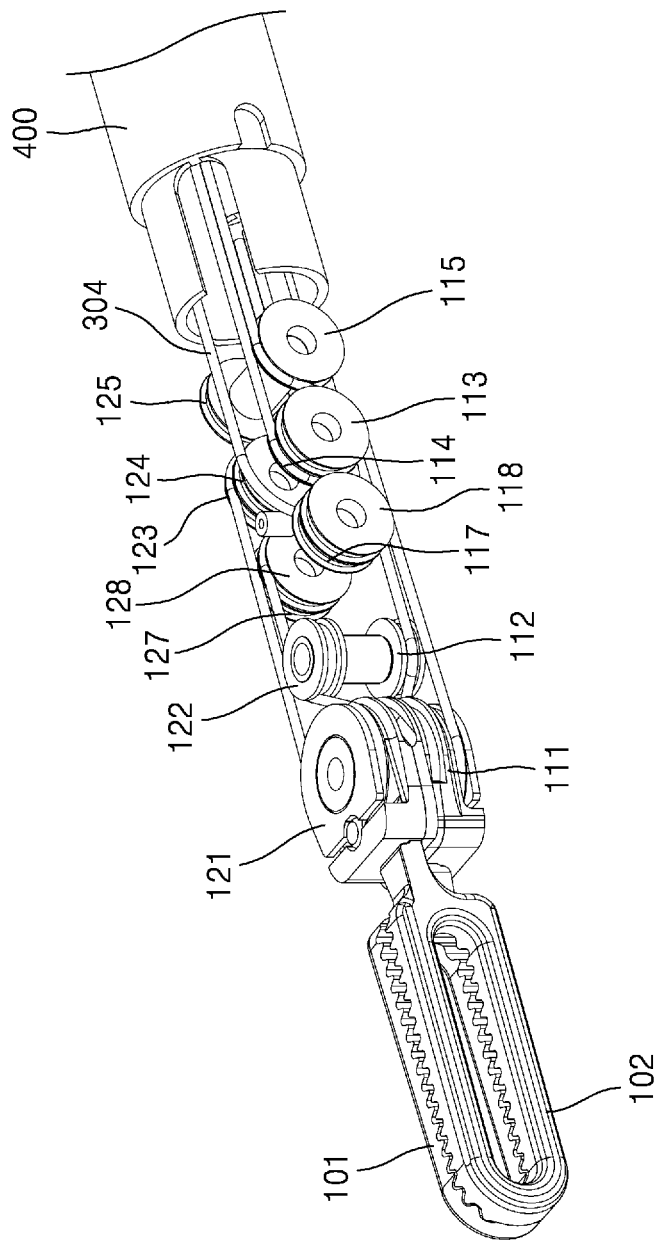
Figure 44:
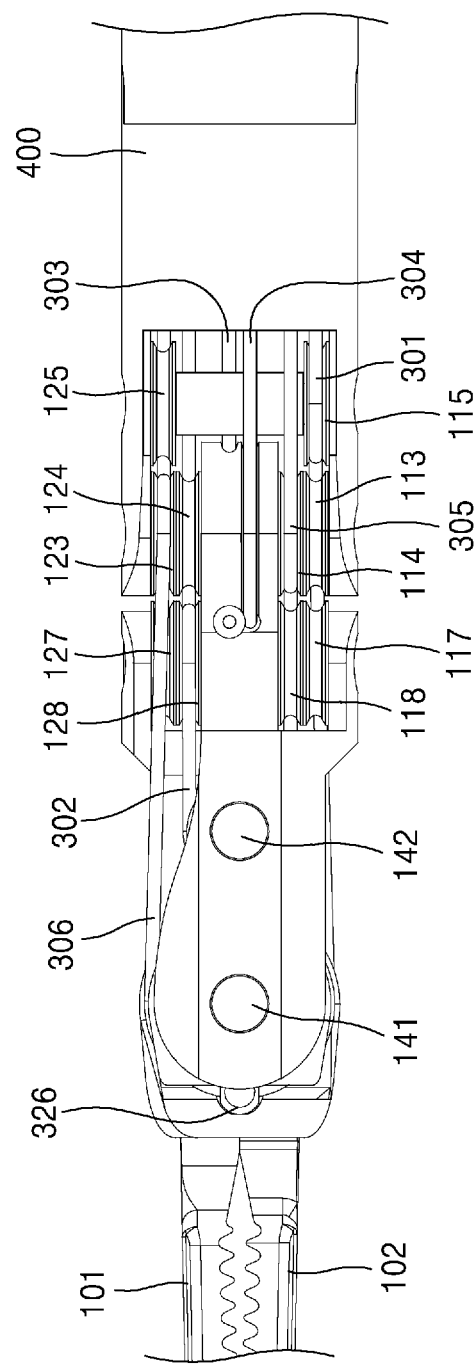
FIGS. 44 and 45 are plan views of the end tool of FIG. 42.
Figure 45:
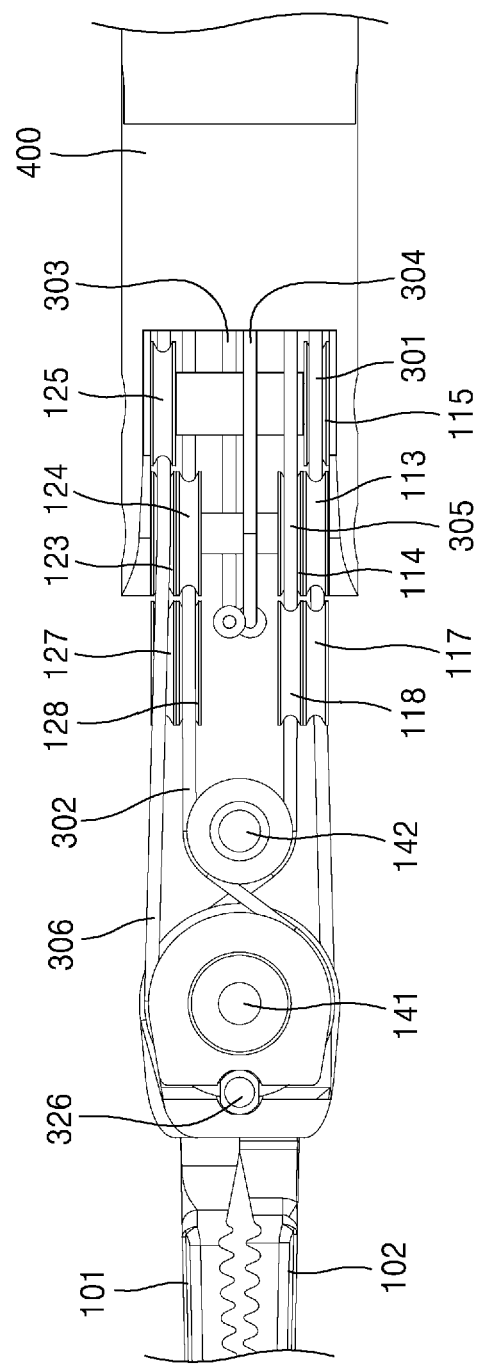
Figure 46:
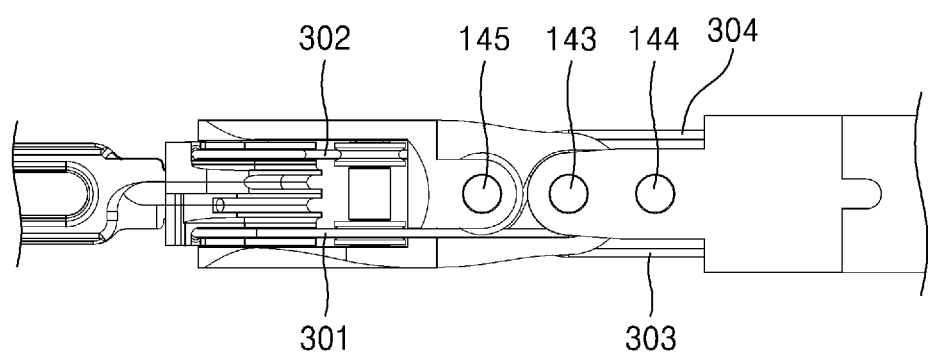
FIGS. 46, 47, and 48 are side views of the end tool of FIG. 42.
Figure 47:
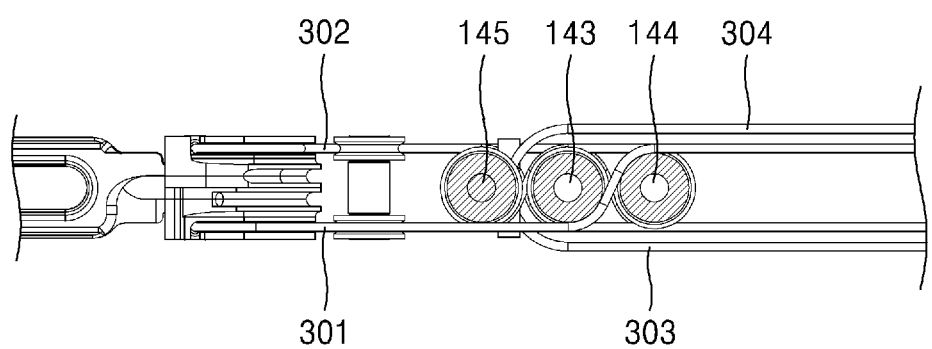
Figure 48:
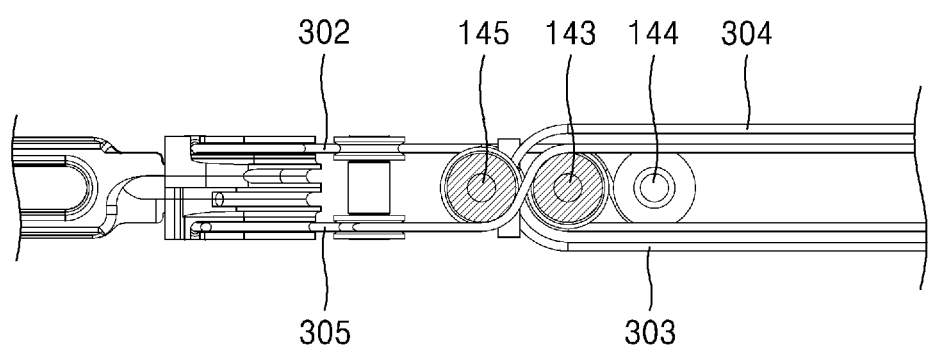
Figure 49:
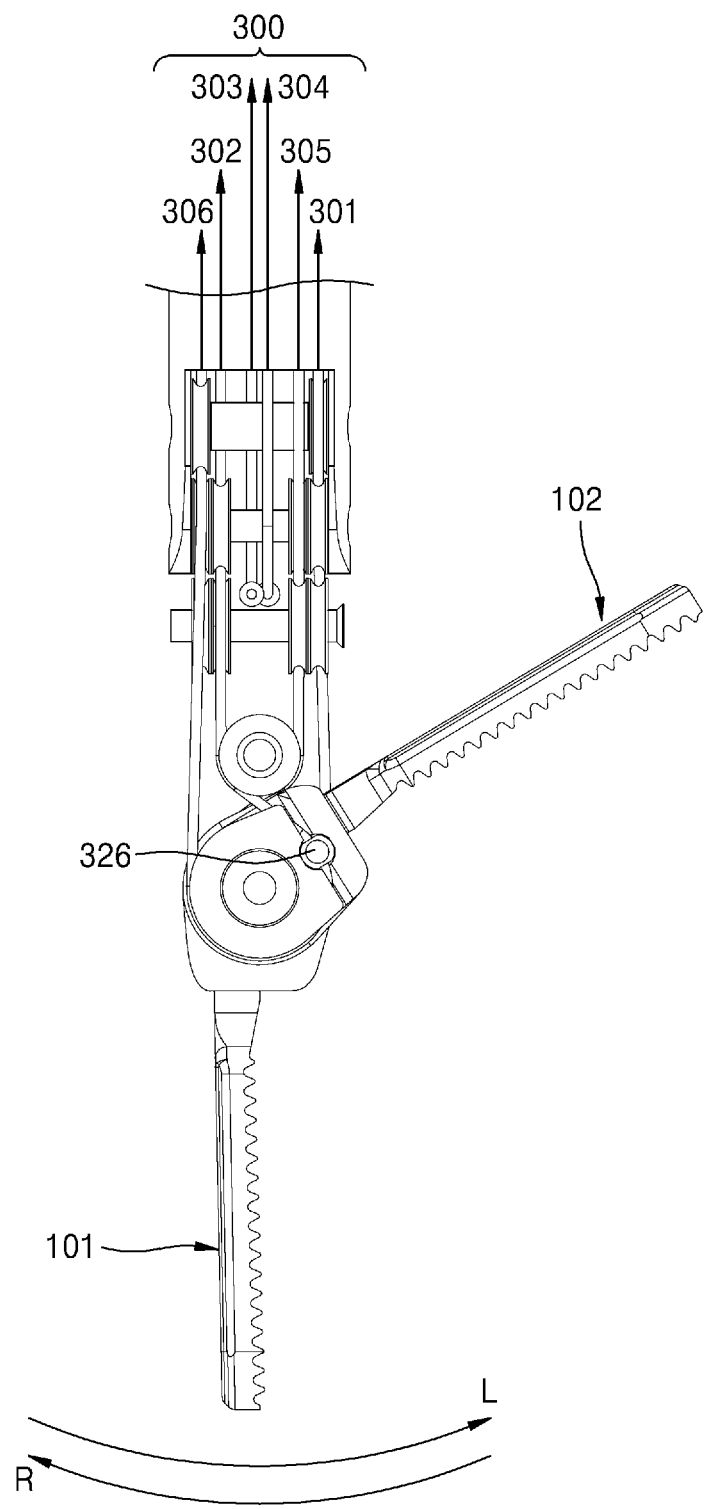
FIGS. 49 and 50 are plan views of the end tool of FIG. 42.
Figure 50:
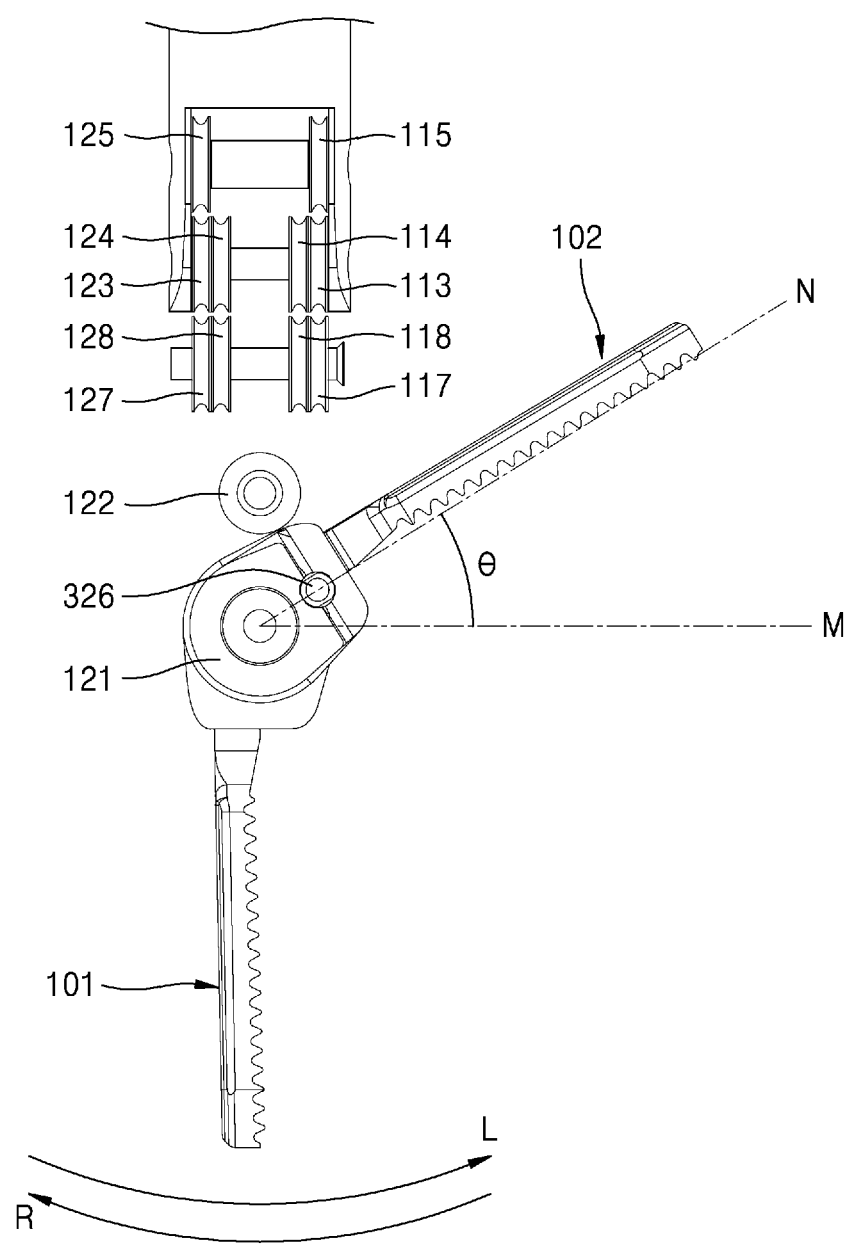
Figure 51:
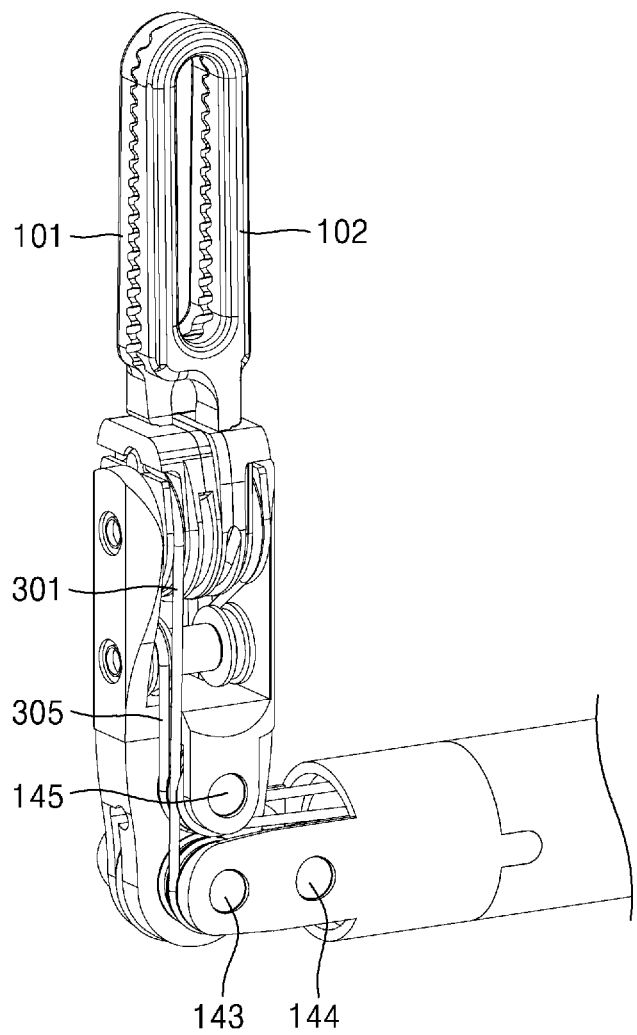
FIGS. 51 and 52 are perspective views illustrating a state in which the end tool of the surgical instrument of FIG. 42 is pitch-rotated by −90°.
Figure 52:
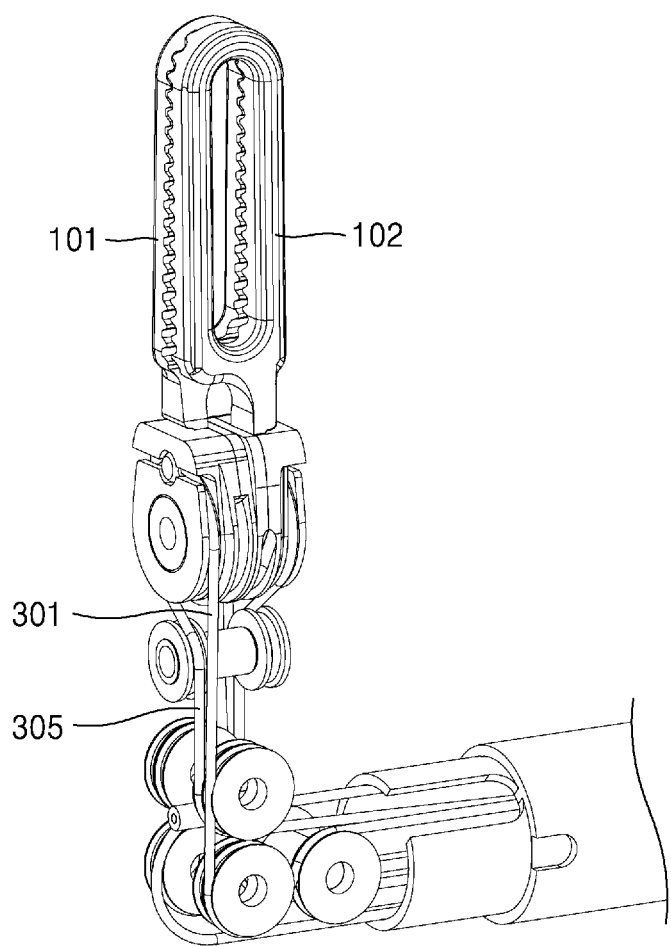
Figure 53:
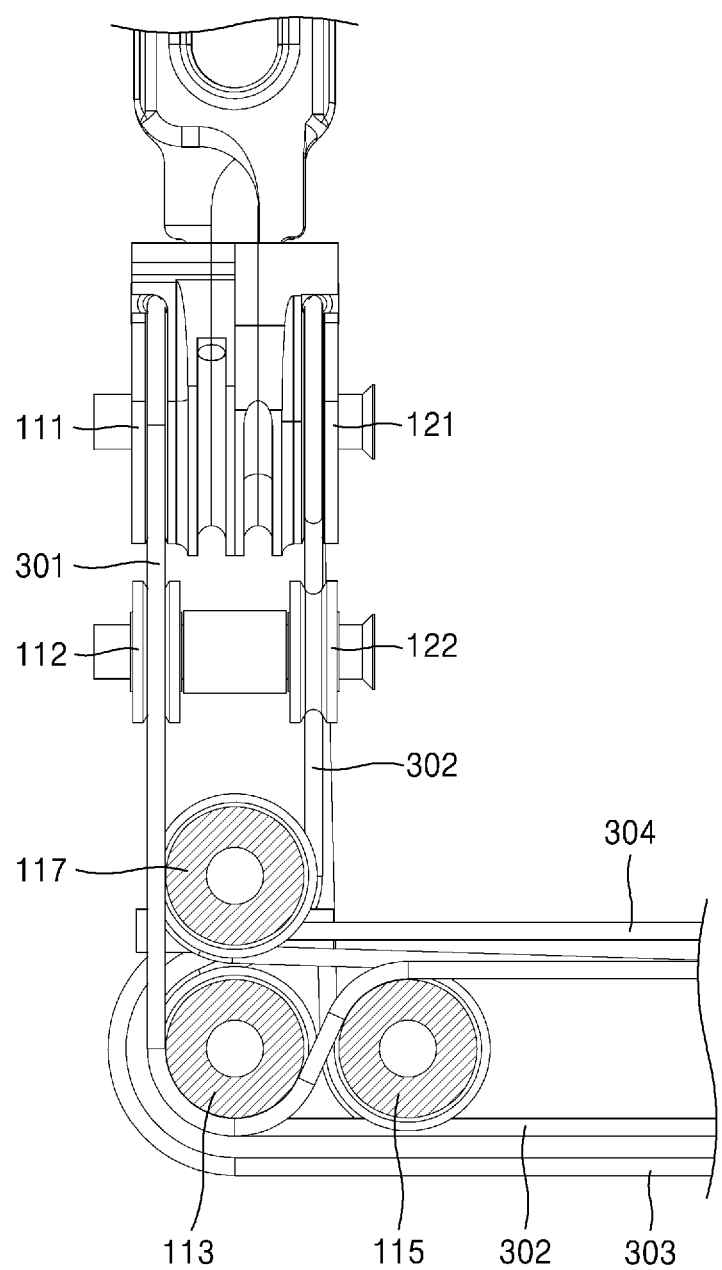
FIGS. 53 and 54 are side views illustrating a state in which the end tool of the surgical instrument of FIG. 42 is pitch-rotated by −90°.
Figure 54:
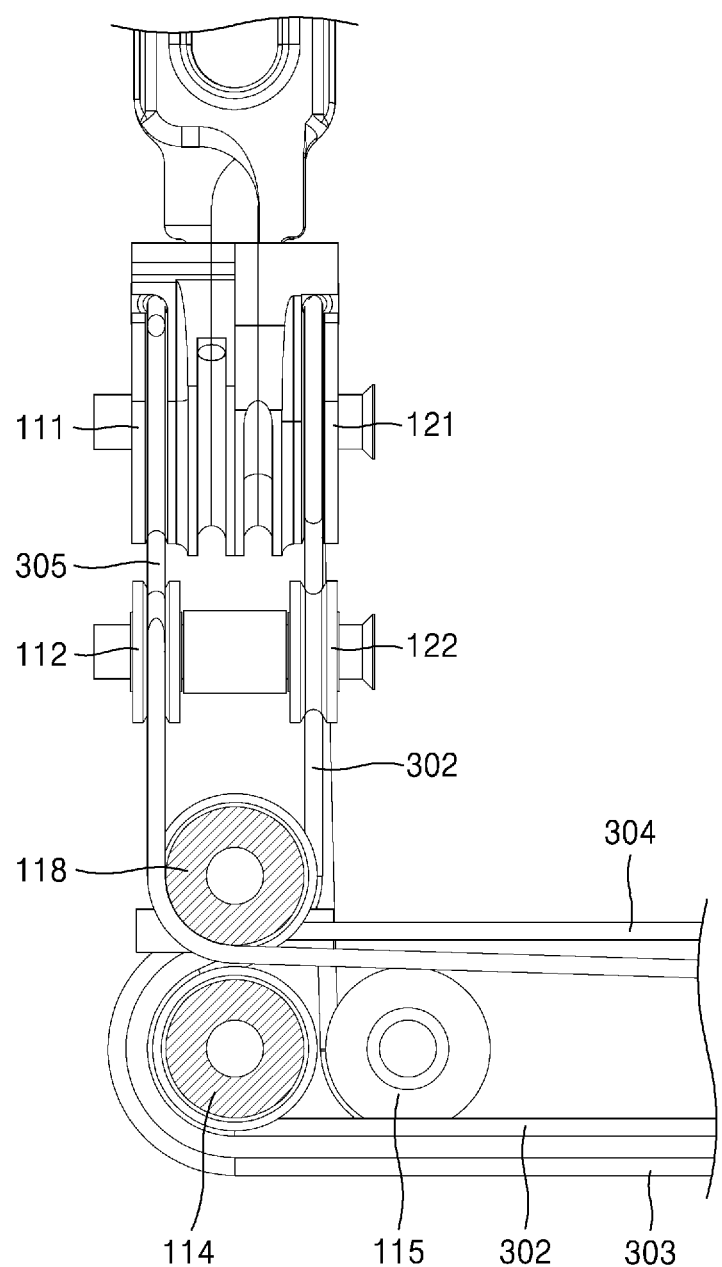
Figure 55:
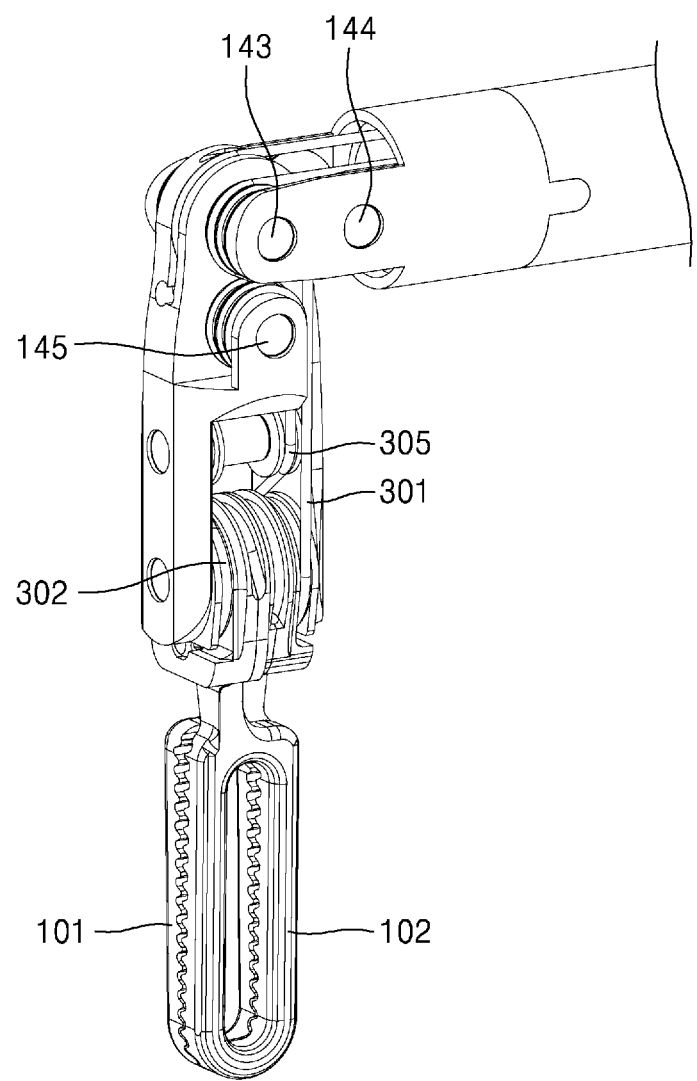
FIGS. 55 and 56 are perspective views illustrating a state in which the end tool of the surgical instrument of FIG. 42 is pitch-rotated by +90°.
Figure 56:
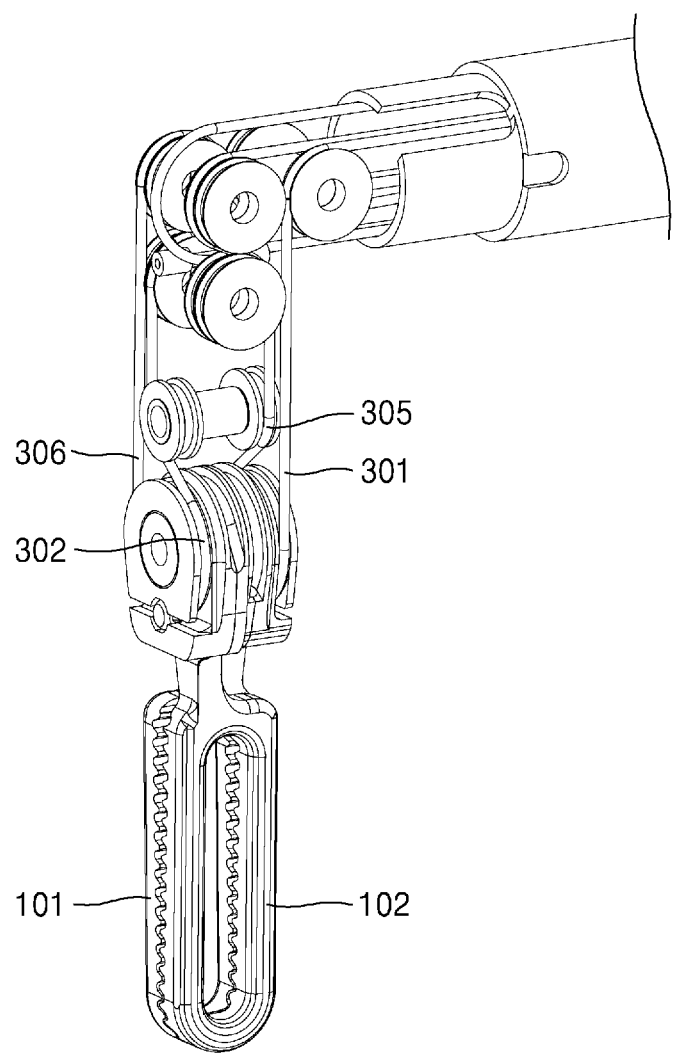
Figure 57:
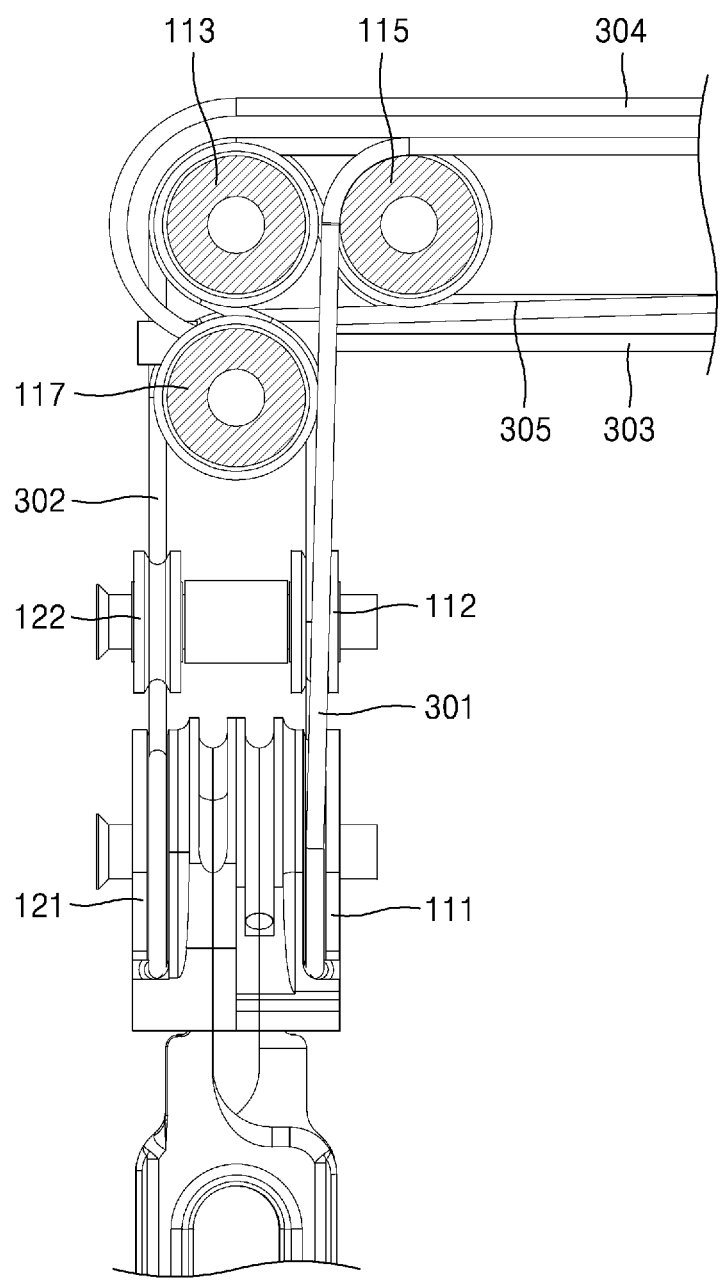
FIGS. 57 and 58 are side views illustrating a state in which the end tool of the surgical instrument of FIG. 42 is pitch-rotated by +90°.
Figure 58:
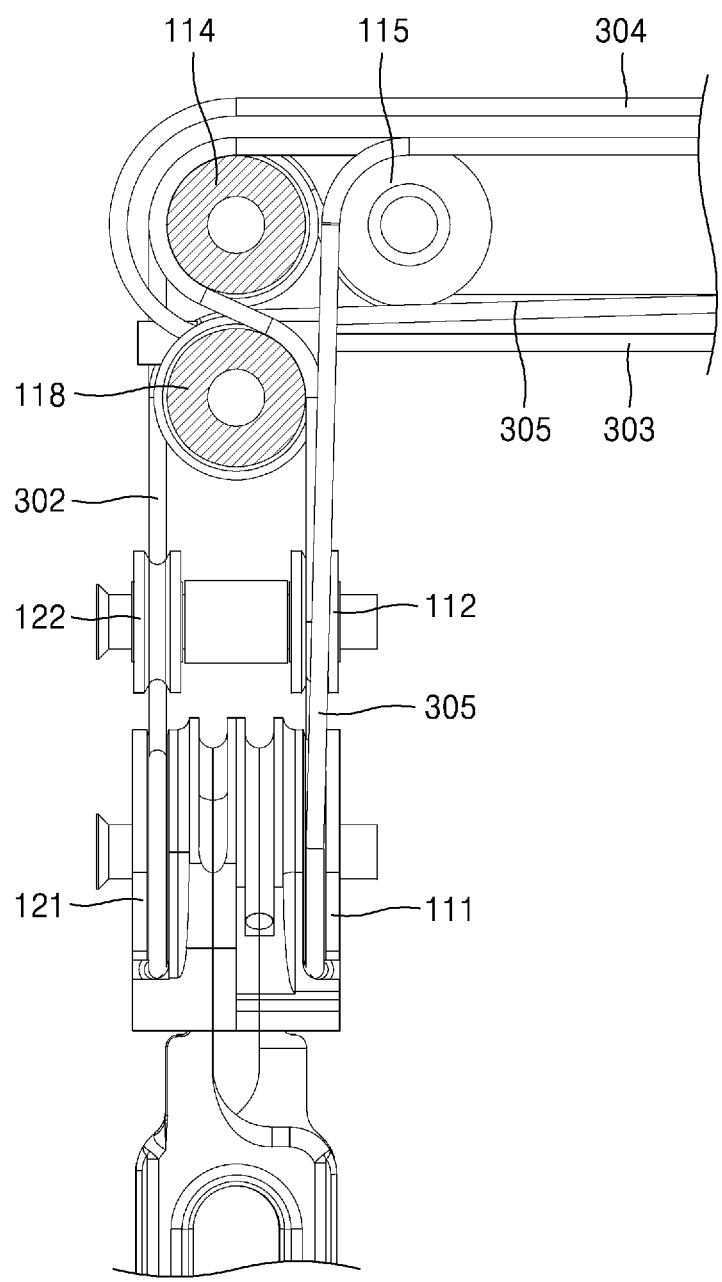

FIGS. 42 and 43 are perspective views illustrating the end tool of the surgical instrument according to the third modified example of the first embodiment of the present disclosure. FIGS. 44 and 45 are plan views of the end tool of FIG. 42. FIGS. 46, 47, and 48 are side views of the end tool of FIG. 42. FIGS. 49 and 50 are plan views of the end tool of FIG. 42. FIGS. 51 and 52 are perspective views illustrating a state in which the end tool of the surgical instrument of FIG. 42 is pitch-rotated by −90°. FIGS. 53 and 54 are side views illustrating a state in which the end tool of the surgical instrument of FIG. 42 is pitch-rotated by −90°. FIGS. 55 and 56 are perspective views illustrating a state in which the end tool of the surgical instrument of FIG. 42 is pitch-rotated by +90°. FIGS. 57 and 58 are side views illustrating a state in which the end tool of the surgical instrument of FIG. 42 is pitch-rotated by +90°.

Referring to FIGS. 42 to 58, the end tool 100 according to the third modified example of the first embodiment of the present disclosure includes a pair of jaws for performing a grip motion, that is, the first jaw 101 and the second jaw 102. In this regard, a component encompassing each of the first jaw 101 and the second jaw 102 or both the first jaw 101 and the second jaw 102 may be referred to as the jaw 103.

In addition, the end tool 100 of the first embodiment of the present disclosure may include the end tool hub 106 and the pitch hub 107.

In addition, the end tool 100 of the third modified example of the first embodiment of the present disclosure may include the rotation axis 141, the rotation axis 142, the rotation axis 145, the rotation axis 143, and the rotation axis 144. As described above, the rotation axis 141, the rotation axis 142, and the rotation axis 145 may be inserted through the end tool hub 106, and the rotation axis 143 and the rotation axis 144 may be inserted through the pitch hub 107.

In the present modified example, the end tool hub 106, the pitch hub 107, and the rotation axes 141, 142, 143, 144, and 145 are substantially the same as the end tool hub 106, the pitch hub 107, and the rotation axes 141, 142, 143, 144, and 145 that are described above with reference to FIG. 2 and the like, respectively, and thus, detailed descriptions thereof will be omitted.

Meanwhile, the end tool 100 may include the pulley 111, the pulley 112, the pulley 113, the pulley 114, the pulley 115, the pulley 117, and the pulley 118, which are associated with a rotational motion of the first jaw 101. In addition, the end tool 100 may include the pulley 121, the pulley 122, the pulley 123, the pulley 124, the pulley 125, the pulley 127, and the pulley 128, which are associated with a rotational motion of the second jaw 102.

In this regard, in the end tool 100 of the surgical instrument according to the third modified example of the first embodiment of the present disclosure, each of the first jaw pitch sub-pulley and the second jaw pitch sub-pulley includes only one pulley.

In detail, the end tool 100 of the surgical instrument according to the first embodiment of the present disclosure illustrated in FIG. 6 and the like includes a pair of pulleys 115 and 116 as first jaw pitch sub-pulleys, and a pair of pulleys 125 and 126 as second jaw pitch sub-pulleys.

On the contrary, the end tool 100 of the surgical instrument according to the third modified example of the first embodiment of the present disclosure is different from the first embodiment of the present disclosure illustrated in FIG. 6 and the like, in that it includes a single pulley 115 as a first jaw pitch sub-pulley, and a single pulley 125 as a second jaw pitch sub-pulley.

Accordingly, the pulley 111, the pulley 112, the pulley 117/pulley 118, the pulley 113/pulley 114, and the pulley 115, which are associated with rotation of the first jaw 101, may be sequentially arranged from the distal end 104 of the end tool 100 toward the proximal end 105.

In addition, the pulley 121, the pulley 122, the pulley 127/pulley 128, the pulley 123/pulley 124, and the pulley 125, which are associated with rotation of the second jaw 102, may be sequentially arranged from the distal end 104 of the end tool 100 toward the proximal end 105.

In this regard, the pulley 116 and pulley 126 of the end tool 100 of the first embodiment of the present disclosure illustrated in FIG. 6 and the like are not pulleys around which wires are wound, but pulleys through which the wires pass in a straight line, and thus may be omitted as in the present modified example.

In other words, in the first embodiment of the present disclosure, two rows of first jaw pitch sub-pulleys and two rows of second jaw pitch sub-pulleys are provided, whereas in the third modified example of the first embodiment of the present disclosure, one row of a first jaw pitch sub-pulley and one row of a second jaw pitch sub-pulley are provided.

In this regard, the pulley 117/pulley 118 are arranged on one side of the pulley 111 and the pulley 112. In this regard, the pulley 117/pulley 118 are formed to be rotatable around the rotation axis 145, which is a pitch redundant rotation axis. In addition, the pulley 113 and the pulley 114 are arranged on one side of the pulley 117/pulley 118 to face each other. In this regard, the pulley 113 and the pulley 114 are formed to be rotatable independently of each other around the rotation axis 143, which is a pitch main rotation axis. In addition, the pulley 115 is arranged on one side of each of the pulley 113 and the pulley 114. In this regard, the pulley 115 is formed to be rotatable around the rotation axis 144, which is a pitch sub-rotation axis. In this regard, the drawings illustrate that the pulley 117, the pulley 118, the pulley 113, the pulley 114, and the pulley 115 are formed to be rotatable around the Y-axis direction, but the concept of the present disclosure is not limited thereto, and the rotation axes of the respective pulleys may be formed in various directions according to their configurations.

The wire 301, which is a first jaw wire, is wound to sequentially come into contact with at least portions of the pulley 115, the pulley 113, the pulley 117, and the pulley 111. In addition, the wire 305 connected to the wire 301 by the coupling member 323 is wound to sequentially come into contact with at least portions of the pulley 111, the pulley 112, the pulley 118, and the pulley 114.

In other words, the wire 301 and the wire 305, which are first jaw wires, are wound to sequentially come into contact with at least portions of the pulley 115, the pulley 113, the pulley 117, the pulley 111, the pulley 112, the pulley 118, and the pulley 114, and are formed to move along the above pulleys while rotating the above pulleys.

Meanwhile, the pulley 127/pulley 128 are arranged on one side of the pulley 121 and the pulley 122. In this regard, the pulley 127/pulley 128 are formed to be rotatable around the rotation axis 145, which is a pitch redundant rotation axis. In addition, the pulley 123 and the pulley 124 are arranged on one side of the pulley 127/pulley 128 to face each other. In this regard, the pulley 123 and the pulley 124 are formed to be rotatable independently of each other around the rotation axis 143, which is a pitch main rotation axis. In addition, the pulley 125 is arranged on one side of the pulley 123 and the pulley 124. In this regard, the pulley 125 is formed to be rotatable around the rotation axis 144, which is a pitch sub-rotation axis. In this regard, the drawings illustrate that the pulley 127, the pulley 128, the pulley 123, the pulley 124, the pulley 125, and the pulley 126 are formed to be rotatable around the Y-axis direction, but the concept of the present disclosure is not limited thereto, and the rotation axes of the respective pulleys may be formed in various directions according to their configurations.

The wire 306, which is a second jaw wire, is wound to sequentially come into contact with at least portions of the pulley 125, the pulley 123, the pulley 127, and the pulley 121. In addition, the wire 302 connected to the wire 306 by the coupling member 326 is wound to sequentially come into contact with at least portions of the pulley 121, the pulley 122, the pulley 128, and the pulley 124.

In other words, the wire 306 and the wire 302, which are second jaw wires, are wound to sequentially come into contact with at least portions of the pulley 125, the pulley 123, the pulley 127, the pulley 121, the pulley 122, the pulley 128, and the pulley 124, and are formed to move along the above pulleys while rotating the above pulleys.

Accordingly, in the first embodiment of the present disclosure, two rows of first jaw pitch sub-pulleys and two rows of second jaw pitch sub-pulleys are provided, whereas in the third modified example of the first embodiment of the present disclosure, one row of a first jaw pitch sub-pulley and one row of a second jaw pitch sub-pulley are provided, and thus, an effect of reducing the number of parts and simplifying a manufacturing process may be achieved.

Second Embodiment of End Tool of Surgical Instrument

Hereinafter, an end tool 1100 of a surgical instrument according to a second embodiment of the present disclosure will be described. In this regard, the end tool 1100 of the surgical instrument according to the second embodiment of the present disclosure is different from the end tool (see 100 of FIG. 2 and the like) of the surgical instrument according to the first embodiment of the present disclosure described above, in the arrangement of the jaw pulleys and the jaw wires. The configuration that is different from that of the first embodiment will be described in detail below.

Figure 59:
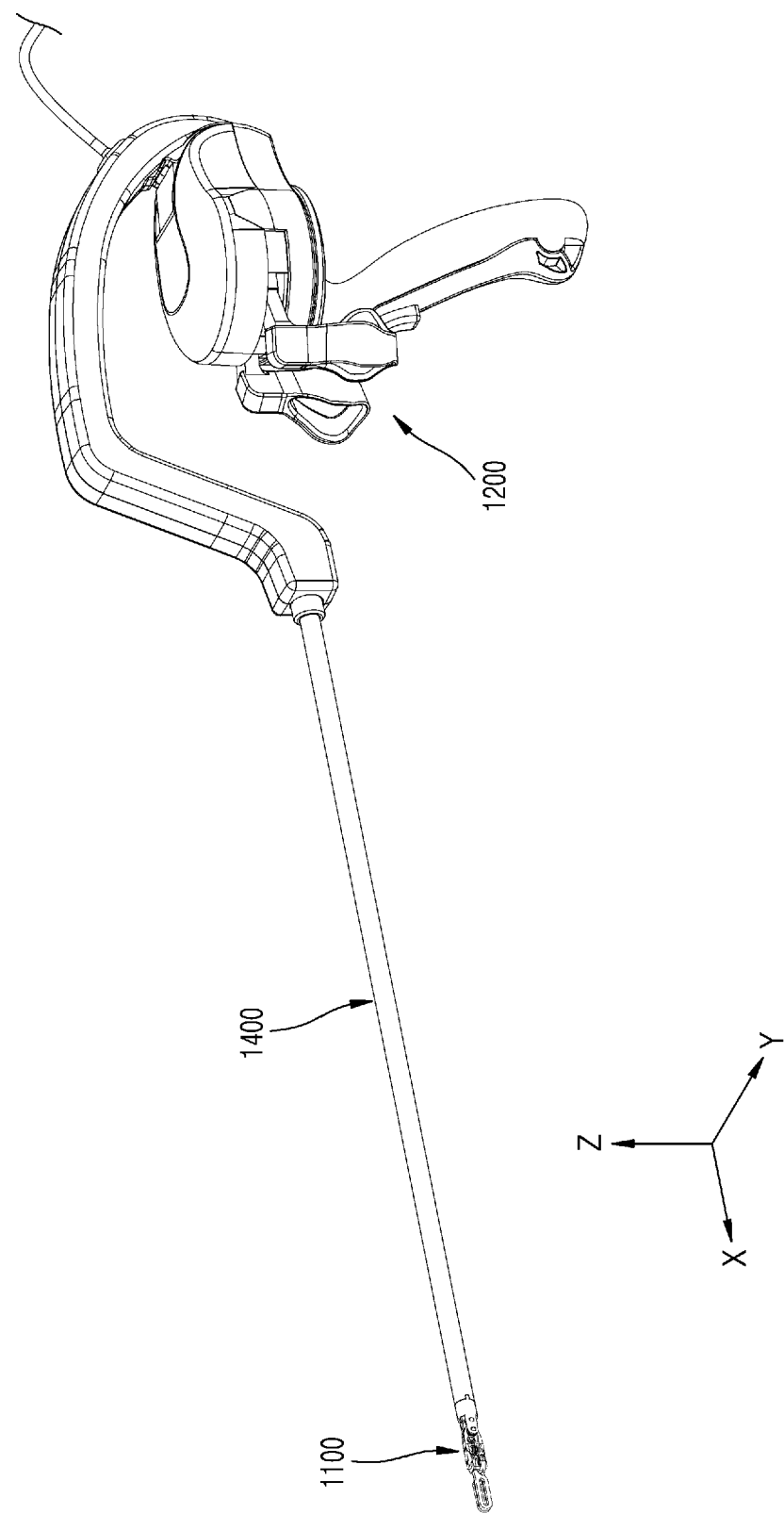
FIG. 59 is a diagram illustrating an example of use of an end tool of a surgical instrument according to a second embodiment of the present disclosure.
Figure 60:
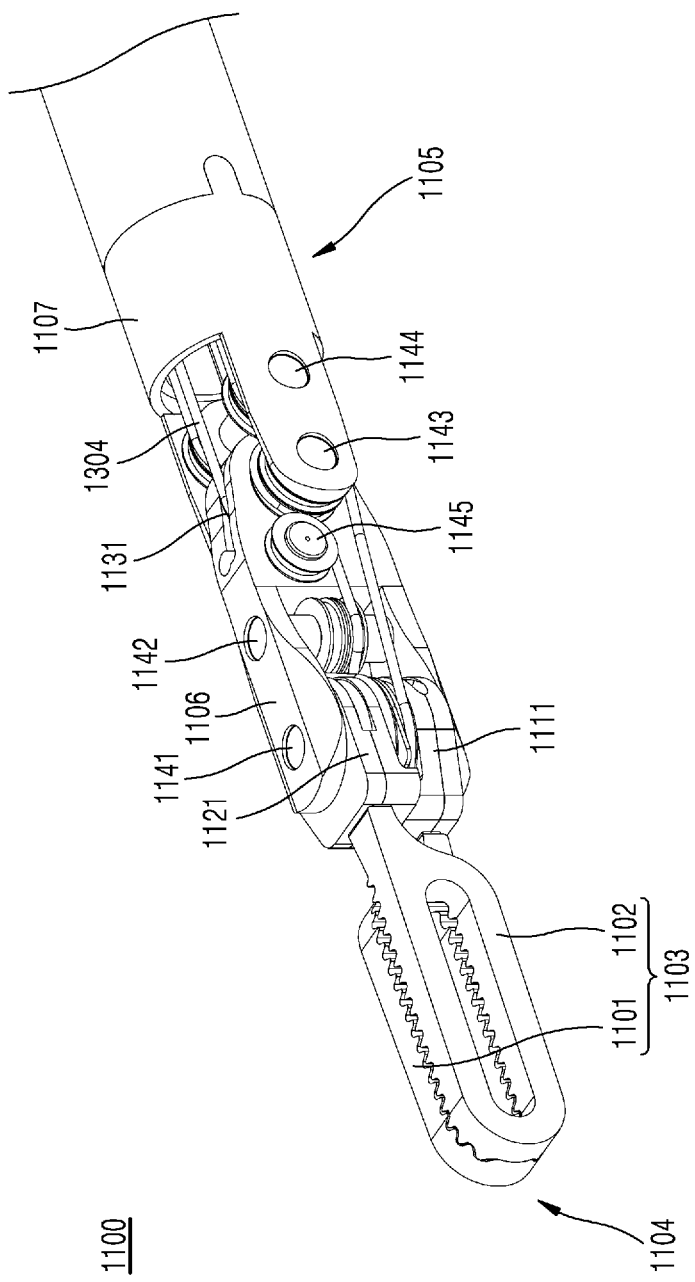
FIGS. 60 and 61 are perspective views illustrating the end tool of the surgical instrument according to the second embodiment of the present disclosure.
Figure 61:
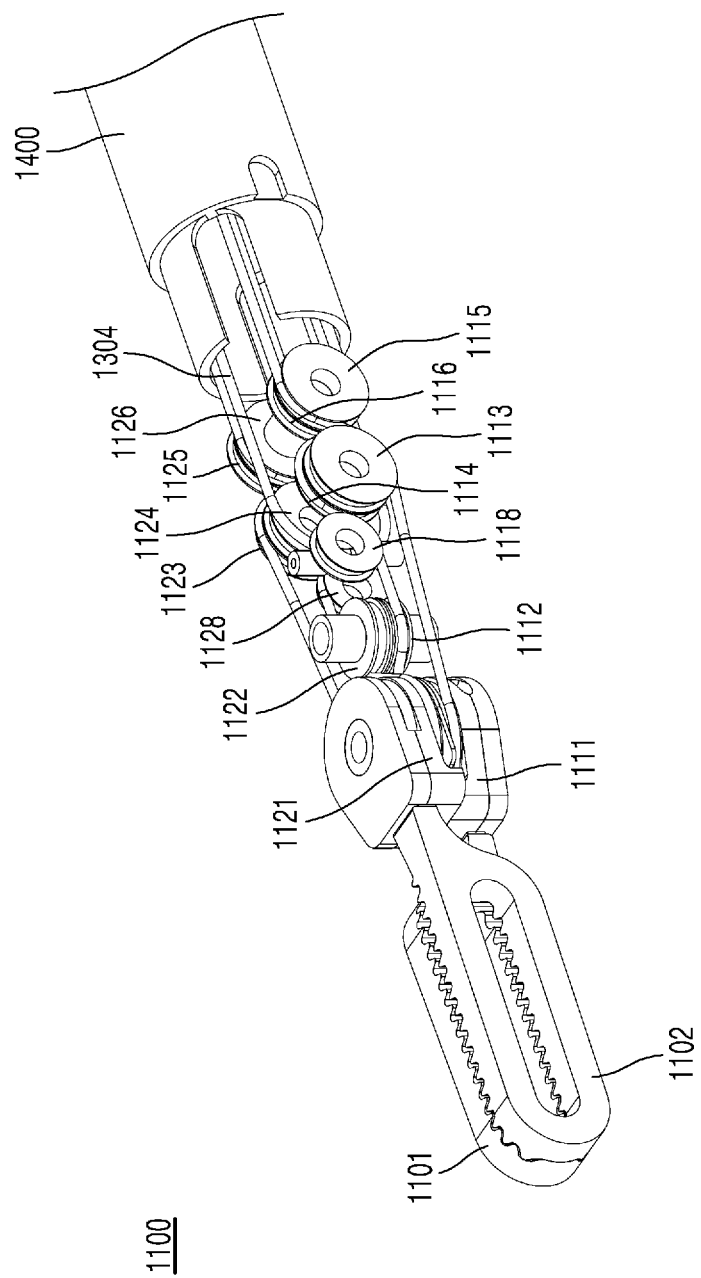
Figure 62:
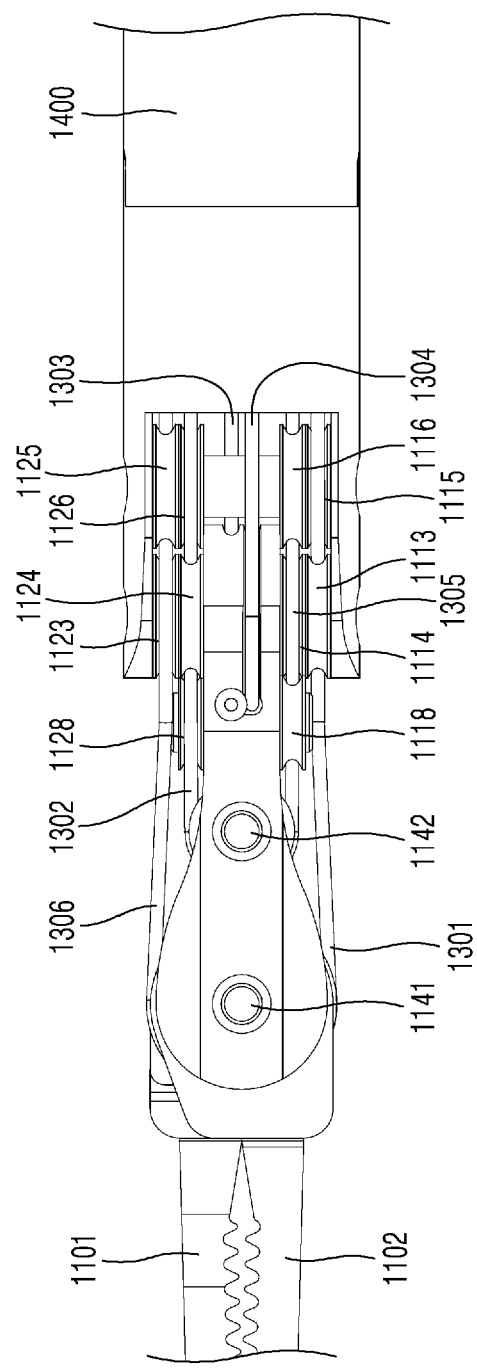
FIGS. 62, 63, 64, and 65 are plan views of the end tool of FIG. 60.
Figure 63:
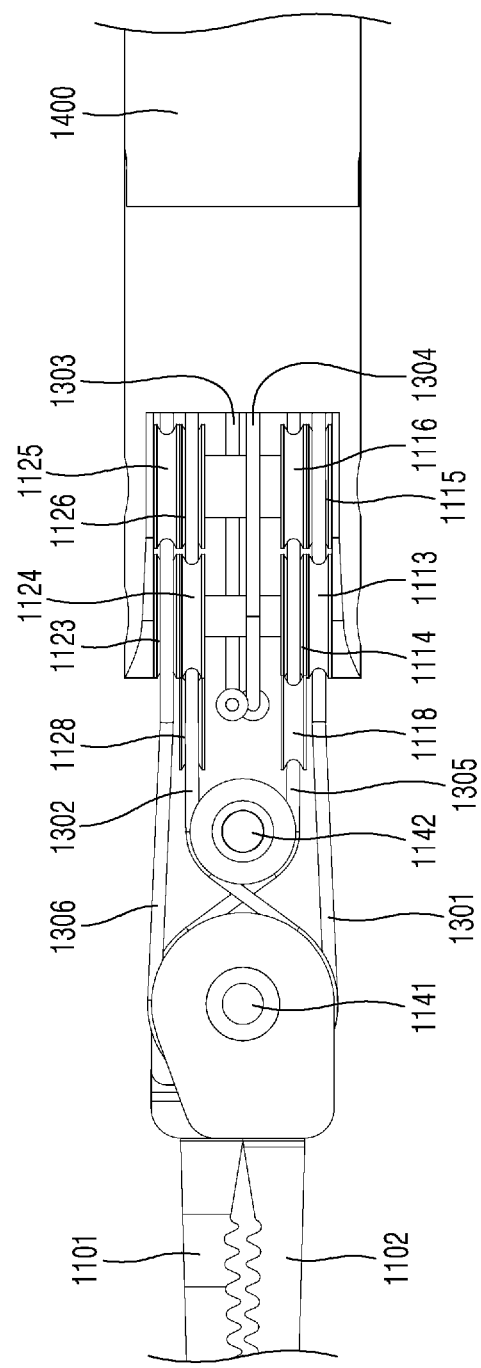
Figure 66:
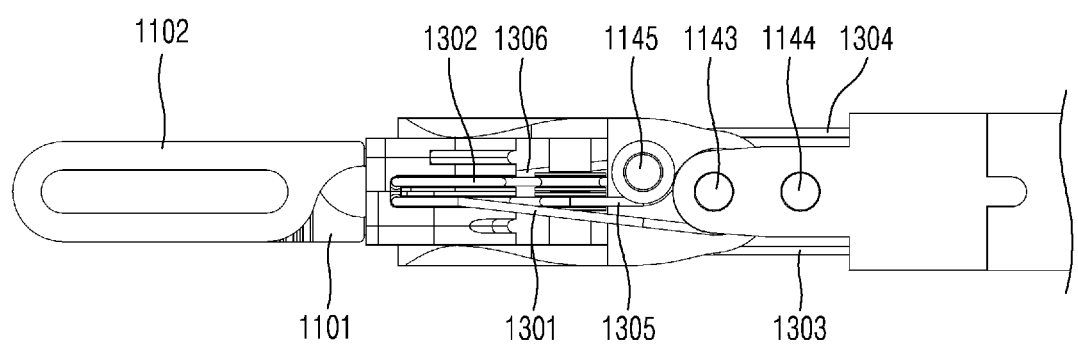
FIGS. 66, 67, and 68 are side views of the end tool of FIG. 60.
Figure 67:
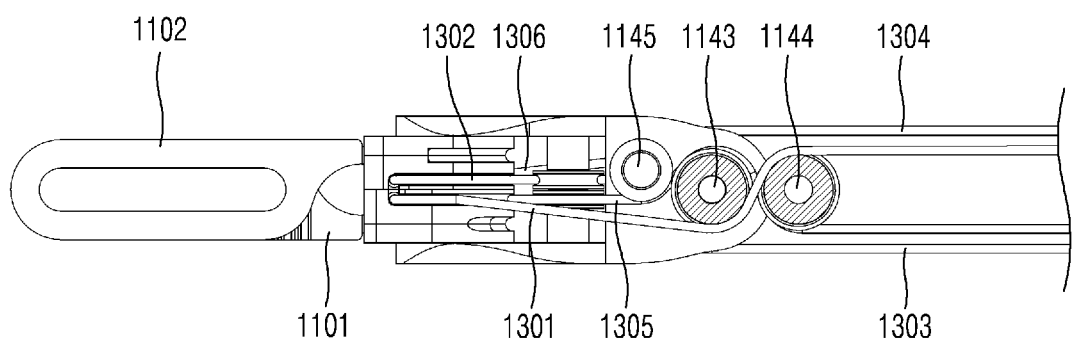
Figure 68:
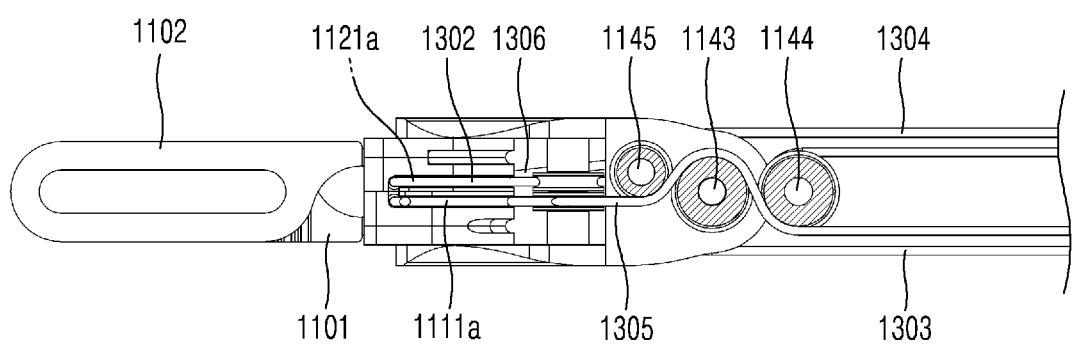
Figure 69:
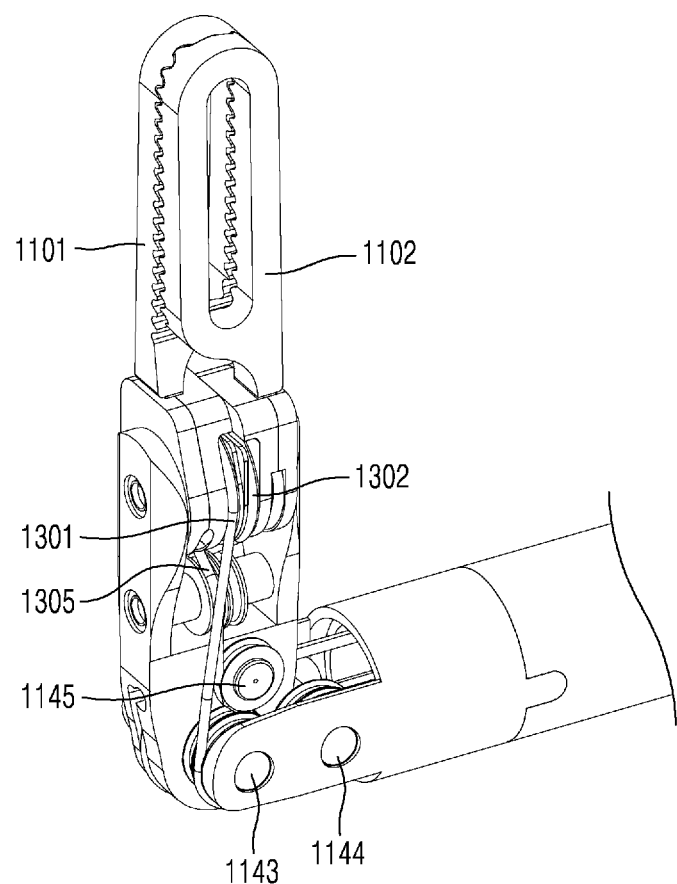
FIGS. 69 and 70 are perspective views illustrating a state in which the end tool of the surgical instrument of FIG. 60 is pitch-rotated by −90°.
Figure 70:
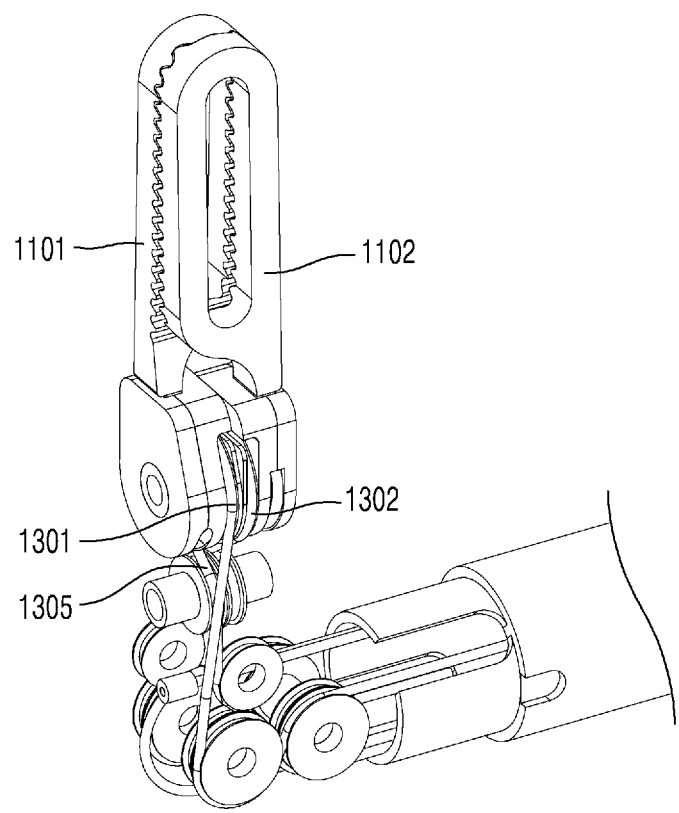
Figure 71:
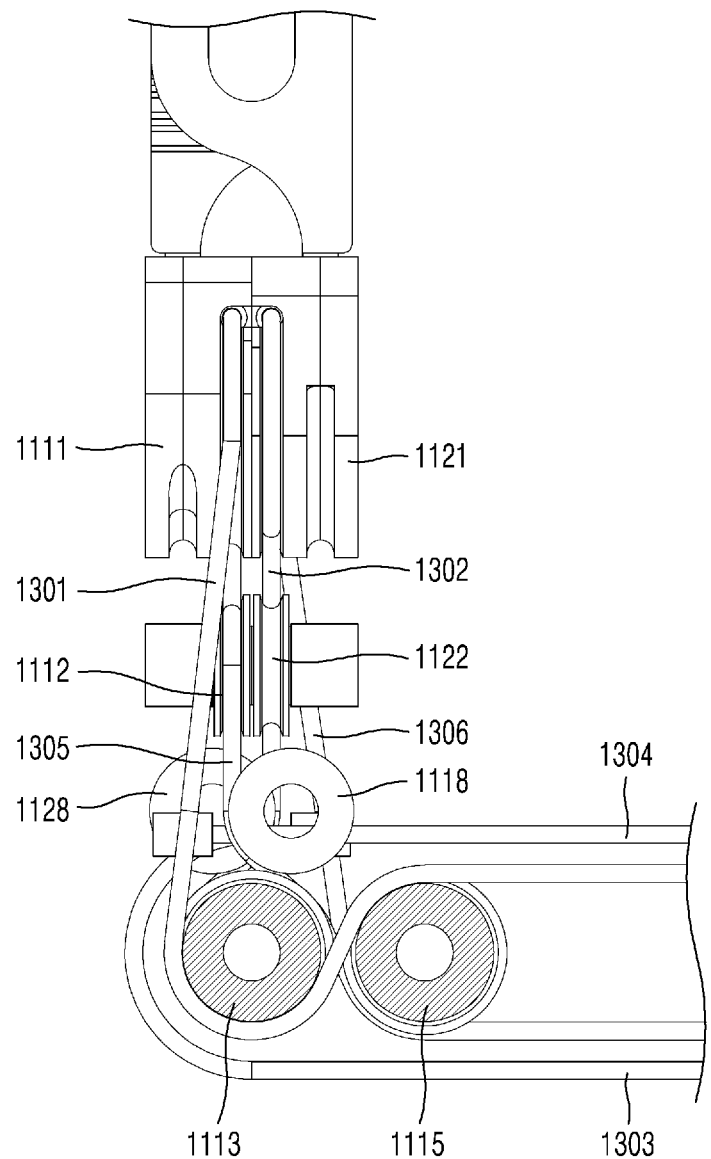
FIGS. 71 and 72 are side views illustrating a state in which the end tool of the surgical instrument of FIG. 60 is pitch-rotated by −90°.
Figure 72:
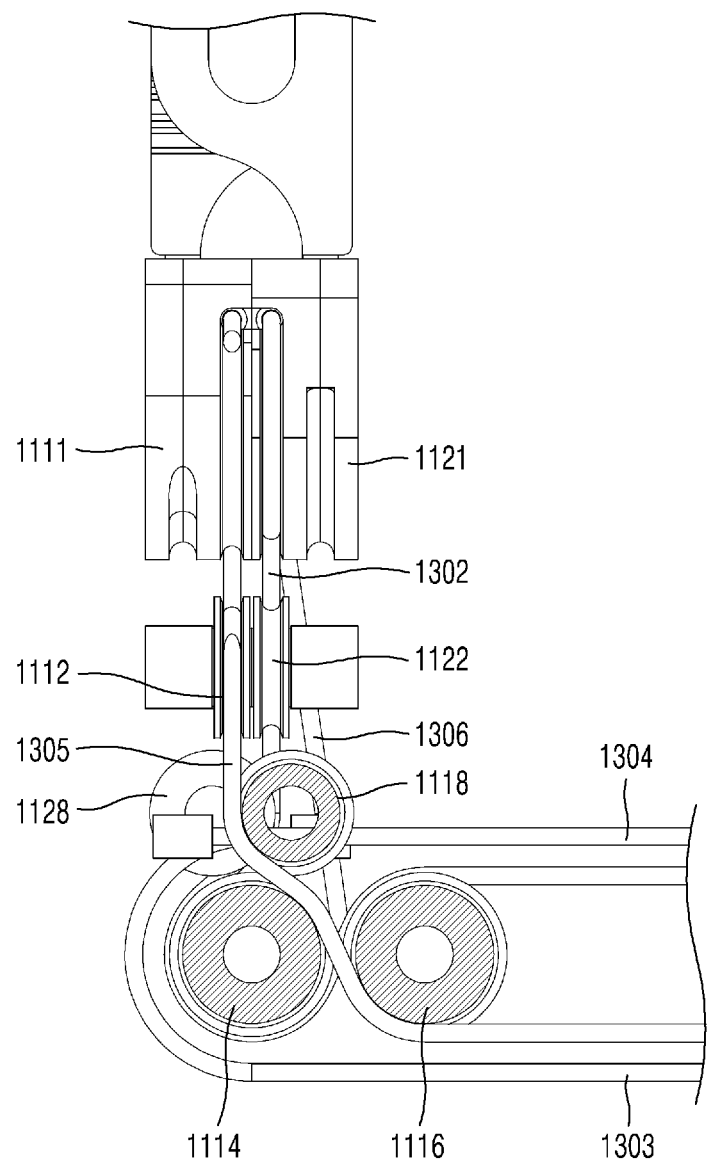
Figure 73:
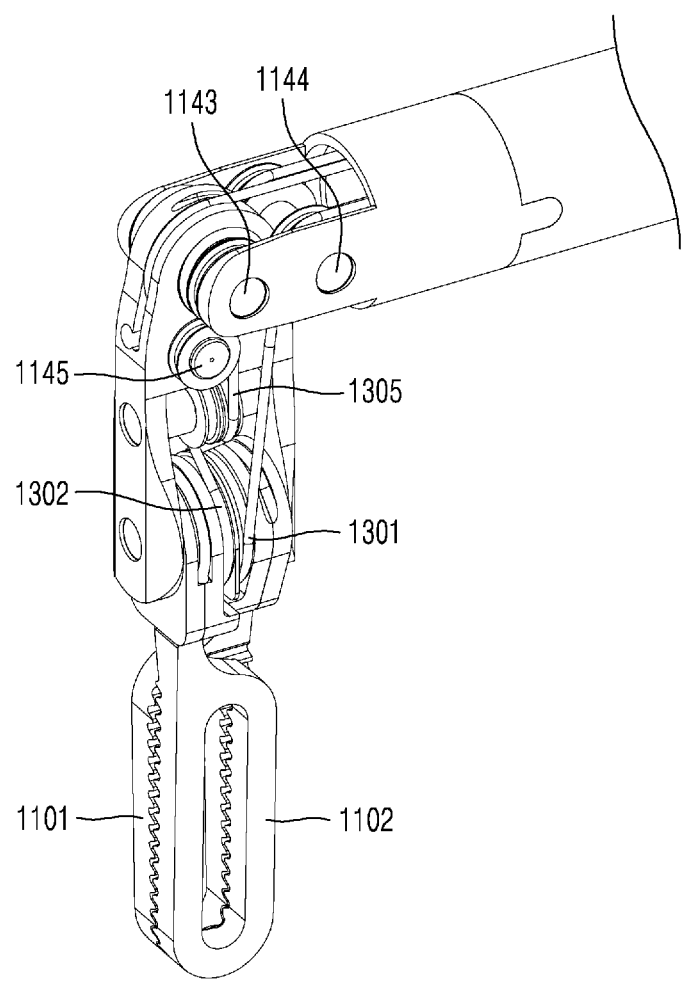
FIGS. 73 and 74 are perspective views illustrating a state in which the end tool of the surgical instrument of FIG. 60 is pitch-rotated by +90°.
Figure 74:
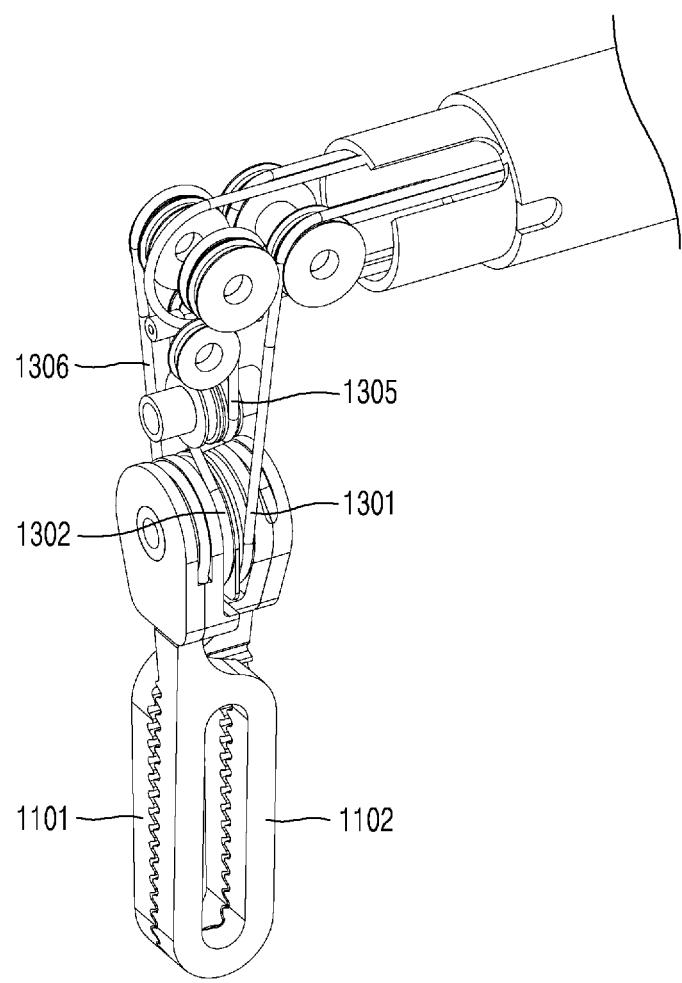
Figure 75:
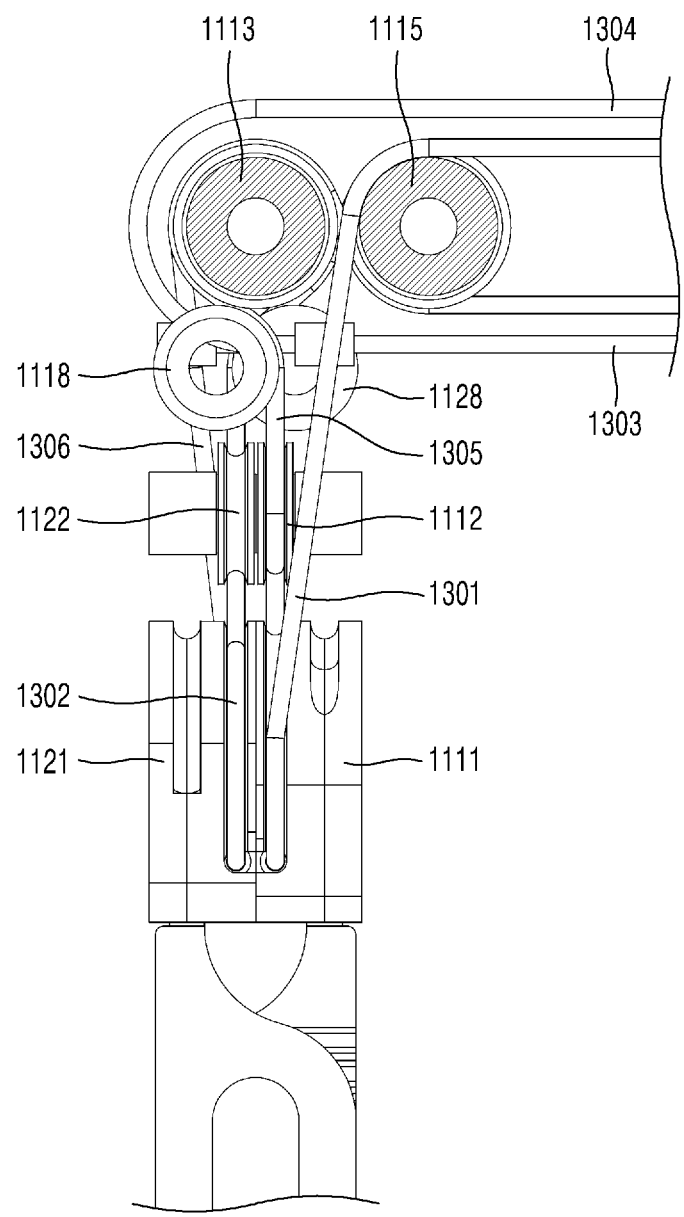
FIGS. 75 and 76 are side views illustrating a state in which the end tool of the surgical instrument of FIG. 60 is pitch-rotated by +90°.
Figure 76:
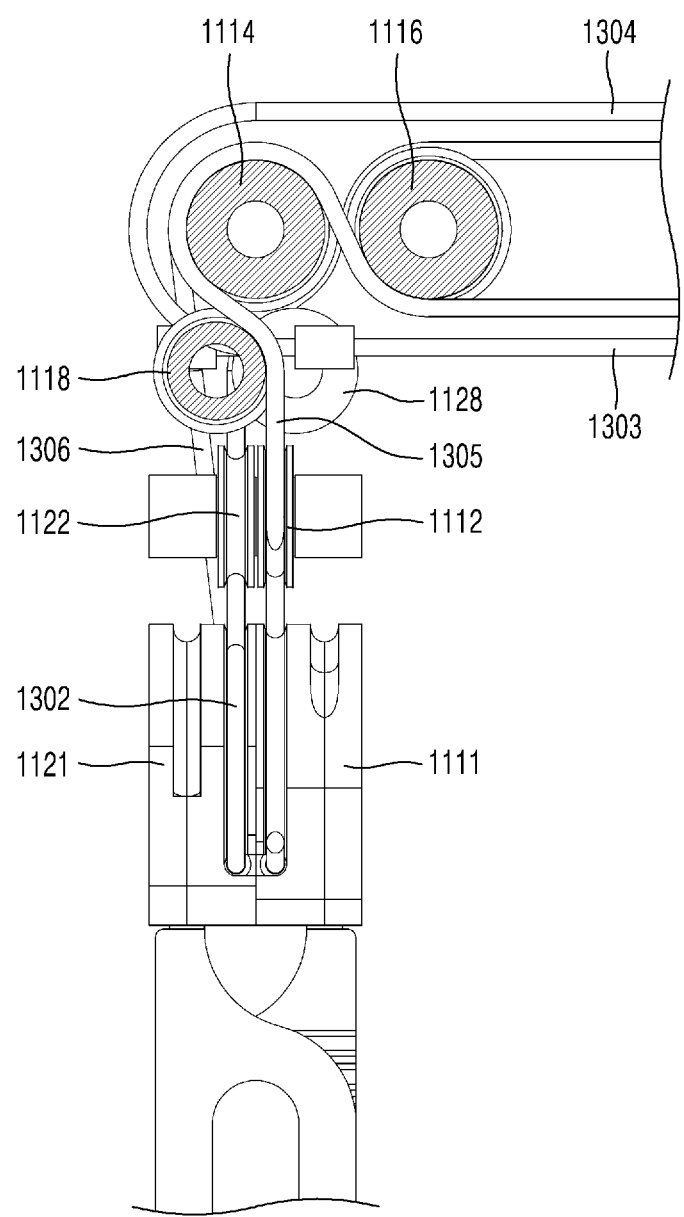

FIG. 59 is a diagram illustrating an example of use of an end tool of a surgical instrument according to the second embodiment of the present disclosure. FIGS. 60 and 61 are perspective views illustrating the end tool of the surgical instrument according to the second embodiment of the present disclosure. FIGS. 62, 63, 64, and 65 are plan views of the end tool of FIG. 60. FIGS. 66, 67, and 68 are side views of the end tool of FIG. 60. FIGS. 69 and 70 are perspective views illustrating a state in which the end tool of the surgical instrument of FIG. 60 is pitch-rotated by −90°. FIGS. 71 and 72 are side views illustrating a state in which the end tool of the surgical instrument of FIG. 60 is pitch-rotated by −90°. FIGS. 73 and 74 are perspective views illustrating a state in which the end tool of the surgical instrument of FIG. 60 is pitch-rotated by +90°. FIGS. 75 and 76 are side views illustrating a state in which the end tool of the surgical instrument of FIG. 60 is pitch-rotated by +90°.

Referring to FIGS. 59 to 76, a power transmission part 1300 of the end tool 1100 of the surgical instrument according to the second embodiment of the present disclosure may include a wire 1301, a wire 1302, a wire 1303, a wire 1304, a wire 1305, and a wire 1306. In the present embodiment, the wires are substantially the same as the wire 301, the wire 302, the wire 303, the wire 304, the wire 305, and the wire 306 of the first embodiment described above with reference to FIG. 5 and the like, and thus, detailed descriptions thereof will be omitted.

In addition, the power transmission part 1300 of the end tool 100 of the surgical instrument according to the second embodiment of the present disclosure may include a coupling member 1321, a coupling member 1322, a coupling member 1323, a coupling member 1324, a coupling member 1326, a coupling member 1327, a coupling member 1329, and the like, which are coupled to ends of the respective wires to combine the wires with the pulleys. In this regard, each of the coupling members may have various shapes as necessary, such as a ball shape, a tube shape, or the like. In the present embodiment, the coupling members are substantially the same as the coupling member 321, the coupling member 322, the coupling member 323, the coupling member 324, the coupling member 326, and the coupling member 327 of the first embodiment described above with reference to FIG. 5 and the like, and thus, detailed descriptions thereof will be omitted.

(End Tool)

Hereinafter, the end tool 1100 of the surgical instrument of FIG. 59 will be described in more detail.

Continuing to refer to FIGS. 59 to 76, the end tool 1100 of the second embodiment of the present disclosure includes a pair of jaws for performing a grip motion, that is, a first jaw 1101 and a second jaw 1102. In this regard, a component encompassing each of the first jaw 1101 and the second jaw 1102 or both the first jaw 1101 and the second jaw 1102 may be referred to as a jaw 1103.

In addition, the end tool 1100 may include a pulley 1111, a pulley 1112, a pulley 1113, a pulley 1114, a pulley 1115, a pulley 1116, a pulley 1117, and a pulley 1118, which are associated with a rotational motion of the first jaw 1101. In addition, the end tool 1100 may include a pulley 1121, a pulley 1122, a pulley 1123, a pulley 1124, a pulley 1125, a pulley 1126, a pulley 1127, and a pulley 1128, which are associated with a rotational motion of the second jaw 102. These pulleys will be described in more detail below.

In addition, the end tool 1100 of the second embodiment of the present disclosure may include an end tool hub 1106 and a pitch hub 1107.

A rotation axis 1141, a rotation axis 1142, and a rotation axis 1145 are inserted through the end tool hub 1106. In addition, the end tool hub 1106 may internally accommodate at least portions of the pulley 1111 and the pulley 1121 that are axially coupled to the rotation axis 1141. In addition, the end tool hub 1106 may internally accommodate at least portions of the pulley 1112 and the pulley 1122 that are axially coupled to the rotation axis 1142. In addition, the pulley 1117/pulley 1118 and the pulley 1127/pulley 1128 that are axially coupled to the rotation axis 1145 may be coupled to the end tool hub 1106.

The rotation axis 1143 and a rotation axis 1144 may be inserted through the pitch hub 1107, and the pitch hub 1107 may be axially coupled to the end tool hub 1106 and a pulley 1131 by the rotation axis 1143. Thus, the end tool hub 1106 and the pulley 1131 (formed with the end tool hub 1106 as one body) may be formed to be rotatable around the rotation axis 1143 with respect to the pitch hub 1107.

In addition, the pitch hub 1107 may internally accommodate at least portions of the pulley 1113, the pulley 1114, the pulley 1123, and the pulley 1124 that are axially coupled to the rotation axis 1143. In addition, the pitch hub 1107 may internally accommodate at least portions of the pulley 1115, the pulley 1116, the pulley 1125, and the pulley 1126 that are axially coupled to the rotation axis 1144.

In addition, the end tool 1100 of the second embodiment of the present disclosure may include the rotation axis 1141, the rotation axis 1142, the rotation axis 1145, the rotation axis 1143, and the rotation axis 1144. As described above, the rotation axis 1141, the rotation axis 1142, and the rotation axis 1145 may be inserted through the end tool hub 1106, and the rotation axis 1143 and the rotation axis 1144 may be inserted through the pitch hub 1107.

The rotation axis 1141, the rotation axis 1142, the rotation axis 1145, the rotation axis 1143, and the rotation axis 1144 may be arranged sequentially from a distal end 1104 of the end tool 1100 toward a proximal end 1105. Accordingly, starting from the distal end 1104, the rotation axis 1141 may be referred to as a first pin, the rotation axis 1142 may be referred to as a second pin, the rotation axis 1145 may be referred to as a two-and-a-halfth pin, the rotation axis 1143 may be referred to as a third pin, and the rotation axis 1144 may be referred to as a fourth pin.

In this regard, the rotation axis 1141 may function as a jaw pulley rotation axis, the rotation axis 1142 may function as a jaw auxiliary pulley rotation axis, the rotation axis 1143 may function as a pitch main rotation axis, and the rotation axis 1144 may function as a pitch sub-rotation axis of the end tool 1100. In addition, the rotation axis 1145 arranged between the rotation axis 1142 and the rotation axis 1143 may function as a pitch redundant rotation axis of the end tool 1100.

In the present embodiment, the end tool hub 1106, the pitch hub 1107, and the rotation axes 1141, 1142, 1143, 1144, and 1145 are substantially the same as the end tool hub 1106, the pitch hub 1107, and the rotation axes 1141, 1142, 1143, 1144, and 1145 that are described above with reference to FIG. 2 and the like, respectively, and thus, detailed descriptions thereof will be omitted.

Meanwhile, one or more pulleys may be fit into each of the rotation axes 1141, 1142, 1143, 1144, and 1145, and this will be described in detail below.

The pulley 1111 functions as a first jaw pulley, the pulley 1121 functions as a second jaw pulley, and these two components may be collectively referred to as a jaw pulley.

The pulley 1111 and the pulley 1121, which are jaw pulleys, are formed to face each other, and are formed to be rotatable independently of each other around the rotation axis 1141, which is a jaw pulley rotation axis. In this regard, the drawings illustrate that the pulley 1111 and the pulley 1121 are formed to be rotated around one rotation axis 1141, but it is needless to say that each jaw pulley may be formed to be rotatable around a separate shaft. In this regard, the first jaw 1101 may be fixedly coupled to the pulley 1111 to be rotated together with the pulley 1111, and the second jaw 1102 may be fixedly coupled to the pulley 1121 to be rotated together with the pulley 1121. Yaw and actuation motions of the end tool 1100 are performed according to rotation of the pulley 1111 and the pulley 1121. That is, when the pulley 1111 and the pulley 1121 are rotated in the same direction around the rotation axis 1141, the yaw motion is performed, and when the pulley 1111 and the pulley 1121 are rotated in opposite directions around the rotation axis 1141, the actuation motion is performed.

In this regard, the first jaw 1101 and the pulley 1111 may be formed as separate members and coupled to each other, or the first jaw 1101 and the pulley 1111 may be formed as one body. Similarly, the second jaw 1102 and the pulley 1121 may be formed as separate members and coupled to each other, or the second jaw 1102 and the pulley 1121 may be formed as one body.

In this regard, a groove 1111a around which the wire 1301/wire 1305, which are first wires, are wound in the pulley 1111, which is a first jaw pulley, and a groove 1121a around which the wire 1302/wire 1306, which are second wires, are wound in the pulley 1121, which is a second jaw pulley, are arranged adjacent to each other. Thus, the wire 1301/wire 1305, which are first jaw wires, and the wire 1302 and the wire 1306, which are second jaw wires, are arranged adjacent to each other in the Z-axis direction, and thus, there may not be a space in which a separate structure is to be arranged, between the first jaw wires and the second jaw wires.

The pulley 1112 functions as a first jaw auxiliary pulley, the pulley 1122 functions as a second jaw auxiliary pulley, and these two components may be collectively referred to as a jaw auxiliary pulley.

In detail, the pulley 1112 and the pulley 1122, which are jaw auxiliary pulleys, may be additionally provided on one side of the pulley 1111 and the pulley 1121. In other words, the pulley 1112, which is a jaw auxiliary pulley, may be arranged between the pulley 1111 and the pulley 1113/pulley 1114. In addition, the pulley 1122, which is a jaw auxiliary pulley, may be arranged between pulley 1121 and pulley 1123/pulley 1124. The pulley 1112 and the pulley 1122 may be formed to be rotatable independently of each other around the rotation axis 1142. In this regard, the drawings illustrate that the pulley 1112 and the pulley 1122 are formed to be rotated around one rotation axis 1142, but it is needless to say that the pulley 1112 and the pulley 1122 may be formed to be rotatable around separate shafts, respectively. Such an auxiliary pulley will be described below in more detail.

The pulley 1113 and the pulley 1114 may function as first jaw pitch main pulleys, the pulley 1123 and the pulley 1124 may function as second jaw pitch main pulleys, and these two components may be collectively referred to as a pitch main pulley.

The pulley 1115 and the pulley 1116 may function as first jaw pitch sub-pulleys, the pulley 1125 and the pulley 1126 may function as second jaw pitch sub-pulleys, and these two components may be collectively referred to as a pitch sub-pulley.

Meanwhile, according to the present disclosure, the pulley 1117, the pulley 1118, the pulley 1127, and the pulley 1128, which are pitch redundant pulleys, are further arranged between the pulley 1112 and the pulley 1122, which are jaw auxiliary pulleys, and the pulley 1113, the pulley 1114, the pulley 1123, and the pulley 1124, which are pitch main pulleys.

The pulley 1117 and the pulley 1118 may function as first jaw pitch redundant pulleys, the pulley 1127 and the pulley 1128 may function as second jaw pitch redundant pulleys, and these two components may be collectively referred to as a pitch redundant pulley.

In addition, the rotation axis 1145 functioning as a pitch redundant rotation axis may be further provided, and the rotation axis 1145 may be inserted through the end tool hub 1106. In this regard, the rotation axis 1145 may be formed to be substantially parallel to the rotation axis 1143, which is a pitch main rotation axis, and the rotation axis 1144, which is a pitch sub-rotation axis. In this regard, the rotation axis 1145 is arranged between the rotation axis 1142, which is the second pin, and the rotation axis 1143, which is the third pin, and thus may be referred to as the two-and-a-halfth pin in terms of its position.

The pitch redundant pulleys may serve to change insertion/withdrawal paths of jaw wires entering from the proximal end of the end tool to the distal end, or coming out from the distal end to the proximal end. This will be described in more detail below.

Accordingly, the rotation axis 1141, the rotation axis 1142, the rotation axis 1145, the rotation axis 1143, and the rotation axis 1144 may be sequentially arranged from the distal end 1104 of the end tool 1100 toward the proximal end 1105.

In addition, the pulley 1111, the pulley 1112, the pulley 1117/pulley 1118, the pulley 1113/pulley 1114, and the pulley 1115/pulley 1116, which are associated with rotation of the first jaw 1101, may be sequentially arranged from the distal end 1104 of the end tool 1100 toward the proximal end 1105.

In addition, the pulley 1121, the pulley 1122, the pulley 1127/pulley 1128, the pulley 1123/pulley 1124, and the pulley 1125/pulley 1126, which are associated with rotation of the second jaw 1102, may be sequentially arranged from the distal end 1104 of the end tool 1100 toward the proximal end 1105.

Hereinafter, components associated with the rotation of the pulley 1111 will be described.

The pulley 1113 and the pulley 1114 are paired to function as first jaw pitch main pulleys. That is, the pulley 1113 and the pulley 1114 function as main rotation pulleys for a pitch motion of the first jaw 1101. In this regard, the wire 1301, which is a first jaw wire, is wound around the pulley 1113, and the wire 1305, which is a first jaw wire, is wound around the pulley 1114.

The pulley 1115 and the pulley 1116 are paired to function as first jaw pitch sub-pulleys. That is, the pulley 1115 and the pulley 1116 function as sub-rotation pulleys for a pitch motion of the first jaw 1101. In this regard, the wire 1301, which is a first jaw wire, is wound around the pulley 1115, and the wire 1305, which is a first jaw wire, is wound around the pulley 1116.

The pulley 1117 and the pulley 1118 are paired to function as first jaw redundant pulleys. That is, the pulley 1117 and the pulley 1118 function as redundant rotation pulleys for a pitch motion of the first jaw 1101. In this regard, the wire 1301, which is a first jaw wire, is wound around the pulley 1117, and the wire 1305, which is a first jaw wire, is wound around the pulley 1118.

In this regard, the pulley 1117 and the pulley 1118 are arranged on one side of the pulley 1111 and the pulley 1112 to face each other. In this regard, the pulley 1117 and the pulley 1118 are formed to be rotatable independently of each other around the rotation axis 1145, which is a pitch redundant rotation axis. In addition, the pulley 1113 and the pulley 1114 are arranged on one sides of the pulley 1117 and the pulley 1118, respectively, to face each other. In this regard, the pulley 1113 and the pulley 1114 are formed to be rotatable independently of each other around the rotation axis 1143, which is a pitch main rotation axis. In addition, the pulley 1115 and the pulley 1116 are arranged on one sides of the pulley 1113 and the pulley 1114, respectively, to face each other. In this regard, the pulley 1115 and the pulley 1116 are formed to be rotatable independently of each other around the rotation axis 1144, which is a pitch sub-rotation axis. In this regard, the drawings illustrate that the pulley 1117, the pulley 1118, the pulley 1113, the pulley 1114, the pulley 1115, and the pulley 1116 are formed to be rotatable around the Y-axis direction, but the concept of the present disclosure is not limited thereto, and the rotation axes of the respective pulleys may be formed in various directions according to their configurations.

The wire 1301, which is a first jaw wire, is wound to sequentially come into contact with at least portions of the pulley 1115, the pulley 1113, the pulley 1117, and the pulley 1111. In addition, the wire 1305 connected to the wire 1301 by the coupling member 1323 is wound to sequentially come into contact with at least portions of the pulley 1111, the pulley 1112, the pulley 1118, the pulley 1114, and the pulley 1116.

In other words, the wire 1301 and the wire 1305, which are first jaw wires, are wound to sequentially come into contact with at least portions of the pulley 1115, the pulley 1113, the pulley 1117, the pulley 1111, the pulley 1112, the pulley 1118, the pulley 1114, and the pulley 1116, and are formed to move along the above pulleys while rotating the above pulleys.

Figure 64:
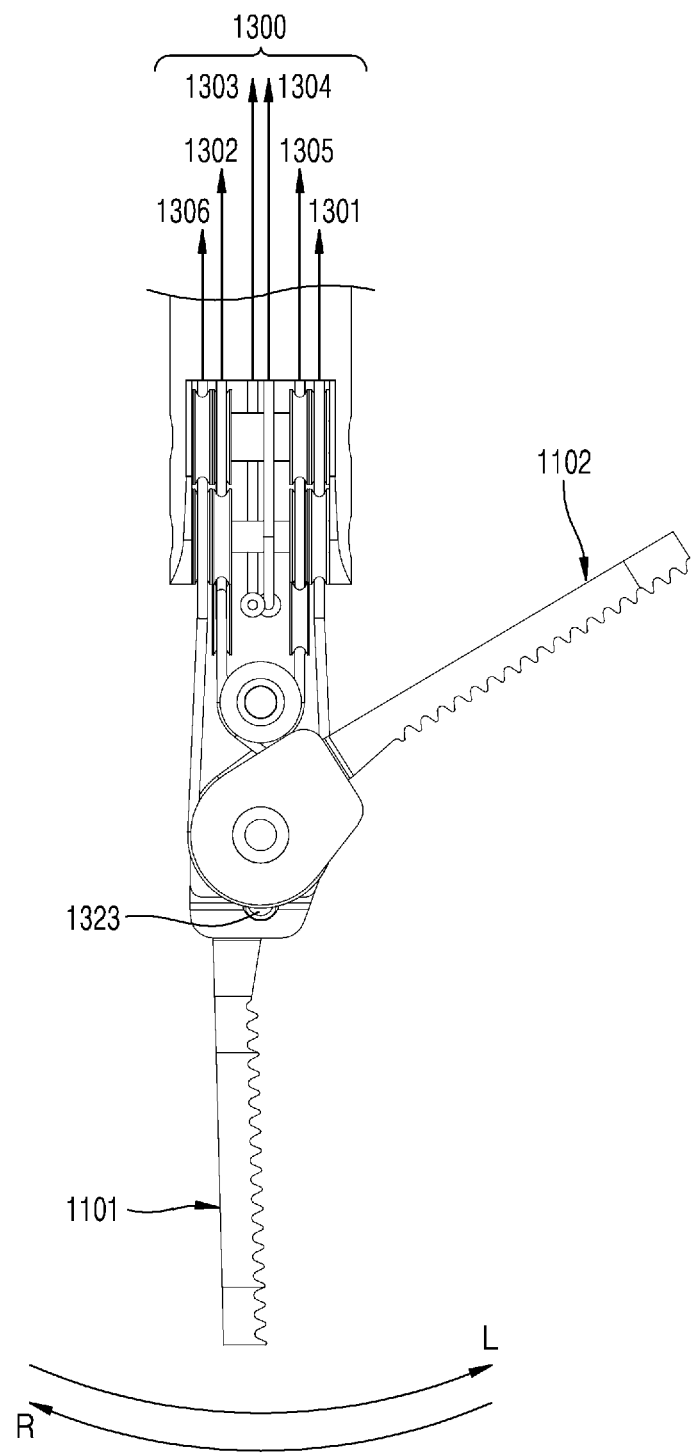
Figure 65:
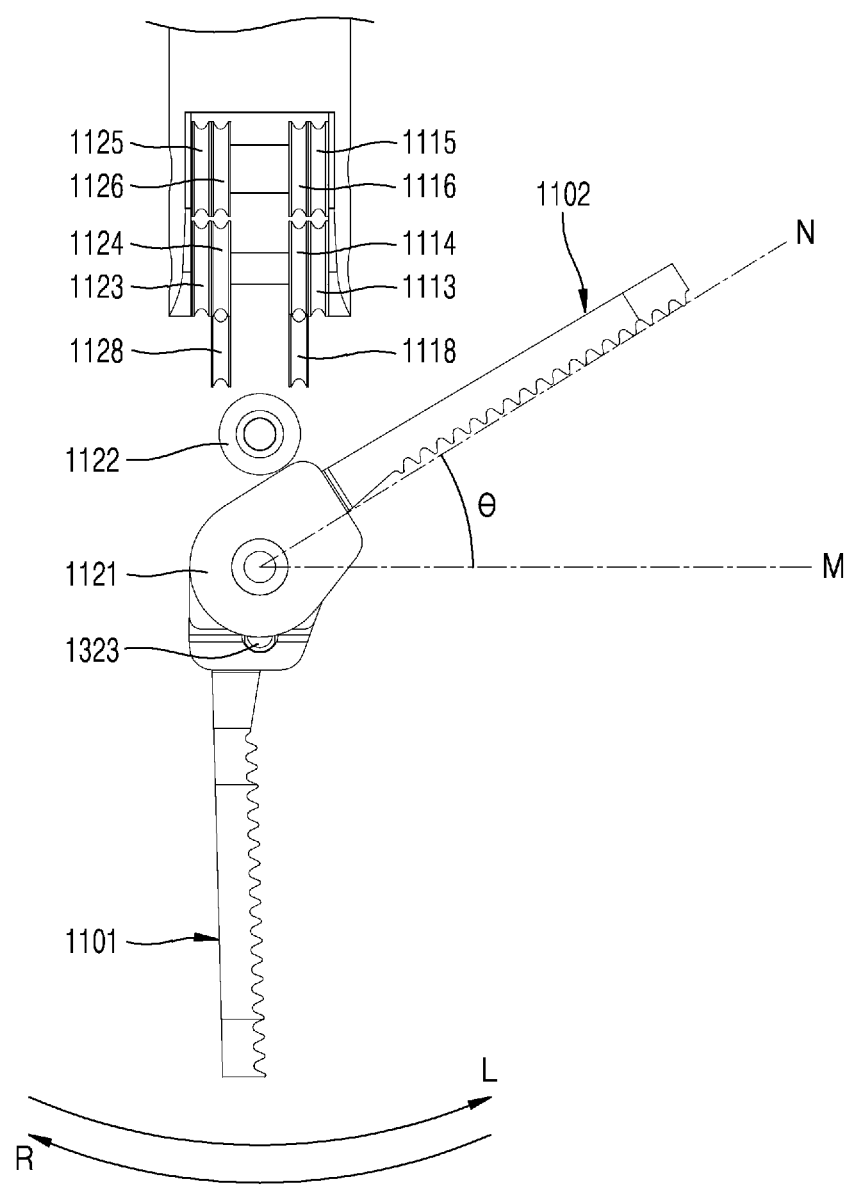

Accordingly, when the wire 1301 is pulled in the direction of an arrow 1301 of FIG. 64, the coupling member 1323 to which the wire 1301 is coupled and the pulley 1111 coupled to the coupling member 1323 are rotated in the direction of an arrow L of FIG. 64. On the contrary, when the wire 1305 is pulled in the direction of an arrow 1305 of FIG. 64, the coupling member 1323 to which the wire 1305 is coupled and the pulley 1111 coupled to the coupling member 1323 are rotated in the direction of an arrow R of FIG. 64.

Next, components associated with the rotation of the pulley 1121 will be described.

The pulley 1123 and the pulley 1124 are paired to function as second jaw pitch main pulleys. That is, the pulley 1123 and the pulley 1124 function as main rotation pulleys for a pitch motion of the second jaw 1102. In this regard, the wire 1306, which is a second jaw wire, is wound around the pulley 1123, and the wire 1302, which is a second jaw wire, is wound around the pulley 1124.

The pulley 1125 and the pulley 1126 are paired to function as second jaw pitch sub-pulleys. That is, the pulley 1125 and the pulley 1126 may function as sub-rotation pulleys for a pitch motion of the second jaw 1102. In this regard, the wire 1306, which is a second jaw wire, is wound around the pulley 1125, and the wire 1302, which is a second jaw wire, is wound around the pulley 1126.

The pulley 1127 and the pulley 1128 are paired to function as second jaw pitch redundant pulleys. That is, the pulley 1127 and the pulley 1128 function as redundant rotation pulleys for a pitch motion of the second jaw 1102. In this regard, the wire 1306, which is a second jaw wire, is wound around the pulley 1127, and the wire 1302, which is a second jaw wire, is wound around the pulley 1128.

In this regard, the pulley 1127 and the pulley 1128 are arranged on one side of the pulley 1121 and the pulley 1122 to face each other. In this regard, the pulley 1127 and the pulley 1128 are formed to be rotatable independently of each other around the rotation axis 1145, which is a pitch redundant rotation axis. In addition, the pulley 1123 and the pulley 1124 are arranged on one sides of the pulley 1127 and the pulley 1128, respectively, to face each other. In this regard, the pulley 1123 and the pulley 1124 are formed to be rotatable independently of each other around the rotation axis 1143, which is a pitch main rotation axis. In addition, the pulley 1125 and the pulley 1126 are arranged on one sides of the pulley 1123 and the pulley 1124, respectively, to face each other. In this regard, the pulley 1125 and the pulley 1126 are formed to be rotatable independently of each other around the rotation axis 1144, which is a pitch sub-rotation axis. In this regard, the drawings illustrate that the pulley 1127, the pulley 1128, the pulley 1123, the pulley 1124, the pulley 1125, and the pulley 1126 are formed to be rotatable around the Y-axis direction, but the concept of the present disclosure is not limited thereto, and the rotation axes of the respective pulleys may be formed in various directions according to their configurations.

The wire 1306, which is a second jaw wire, is wound to sequentially come into contact with at least portions of the pulley 1125, the pulley 1123, the pulley 1127, and the pulley 1121. In addition, the wire 1302 connected to the wire 1306 by the coupling member 1326 is wound to sequentially come into contact with at least portions of the pulley 1121, the pulley 1122, the pulley 1128, the pulley 1124, and the pulley 1126.

In other words, the wire 1306 and the wire 1302, which are second jaw wires, are wound to sequentially come into contact with at least portions of the pulley 1125, the pulley 1123, the pulley 1127, the pulley 1121, the pulley 1122, the pulley 1128, the pulley 1124, and the pulley 1126, and are formed to move along the above pulleys while rotating the above pulleys.

Accordingly, when the wire 1306 is pulled in the direction of an arrow 1306 of FIG. 64, the coupling member 1326 to which the wire 1306 is coupled and the pulley 1121 coupled to the coupling member 1326 are rotated in the direction of the arrow R of FIG. 64. On the contrary, when the wire 1302 is pulled in the direction of an arrow 302 of FIG. 64, the coupling member 1326 to which the wire 1302 is coupled and the pulley 1121 coupled to the coupling member 1326 are rotated in the direction of an arrow L of FIG. 64.

In this regard, according to the present disclosure, two strands of jaw wires wound around one jaw pulley are wound around pitch main pulleys in opposite directions, such that a pitch motion is easily controlled.

In detail, when the side above, in the +Z-axis direction, a plane passing between the pulley 1111, which is a first jaw pulley, and the pulley 1121, which is a second jaw pulley (i.e., an XY plane) is defined as an upper side and the side below the plane in the −Z-axis direction is defined as a lower side, any one (e.g., the wire 1301) of the two strands of the first jaw wires may enter the pulley 1113, which is a first jaw pitch main pulley, from the lower side of the XY plane, and the other strand (e.g., the wire 1305) may come out of the pulley 1114, which is a first jaw pitch main pulley, from the upper side of the XY plane. In other words, it may be described as a structure in which the jaw wire enters the first jaw pitch main pulley from the lower side and comes out from the upper side. (The second jaw wire enters the second jaw pitch main pulley from the upper side and comes out from the lower side)

In other words, the wire 1301, which is one strand of the first jaw wires, sequentially comes into contact with the upper side of the pulley 1115, the lower side of the pulley 1113, and the lower side of the pulley 1117, and then comes into contact with the pulley 1111. Next, the wire 1305, which is the other strand of the first jaw wires, is wound around the pulley 1111 and the pulley 1112, and then sequentially comes into contact with the lower side of the pulley 1118, the upper side of the pulley 1114, and the lower side of the pulley 1116, and then comes out toward the connection part 400. Accordingly, the first jaw wire comes out of the connection part 400, enters the pulley 1113 from the lower side, then passes through each pulley, then passes through the upper side of the pulley 1114, and then enters back the connection part 400.

Similarly, the wire 1306, which is one strand of the second jaw wires, sequentially comes into contact with the lower side of the pulley 1125, the upper side of the pulley 1123, and the upper side of the pulley 1127, and then comes into contact with the pulley 1121. Next, the wire 1302, which is the other strand of the second jaw wires, is wound around the pulley 1121 and the pulley 1122, and then sequentially comes into contact with the upper side of the pulley 1128, the lower side of the pulley 1124, and the upper side of the pulley 1126, and then comes out toward the connection part 400. Accordingly, the second jaw wire comes out of the connection part 400, enters the pulley 1123 from the upper side, then passes through each pulley, then passes through the lower side of the pulley 1124, and then enters back the connection part 400.

In other words, it may also be described that, any one wire of the two strands of the first jaw wires is wound around the first jaw pitch main pulley in any one of the clockwise direction and the counterclockwise direction while moving toward the end tool 1100 from a connection part 1400, and the other wire is wound around the first jaw pitch main pulley in the other one of the clockwise direction and the counterclockwise direction while moving toward the end tool 1100 from the connection part 1400. That is, as illustrated in FIGS. 66, 67, and 68, the wire 1301 is wound in the clockwise direction while moving toward the end tool 1100 from the connection part 1400, and the wire 1305 is wound in the counterclockwise direction while moving toward the end tool 1100 from the connection part 400.

Similarly, it may also be described that, any one wire of the two strands of the second jaw wires is wound around the second jaw pitch main pulley in any one of the clockwise direction and the counterclockwise direction while moving toward the end tool 1100 from the connection part 1400, and the other wire is wound around the second jaw pitch main pulley in the other one of the clockwise direction and the counterclockwise direction while moving toward the end tool 1100 from the connection part 1400. That is, as illustrated in FIGS. 66, 67, and 68, the wire 1302 is wound in the clockwise direction while moving toward the end tool 1100 from the connection part 1400, and the wire 1306 is wound in the counterclockwise direction while moving toward the end tool 1100 from the connection part 400.

As such, the end tool 1100 of the surgical instrument according to an embodiment of the present disclosure may obtain an effect of facilitating control of the pitch motion as the two strands of the jaw wires wound around one jaw pulley are wound around the pitch main pulleys in opposite directions. That is, during a pitch motion, the drive part first jaw pulley (see 211 of FIG. 11) and the drive part second jaw pulley (see 221 of FIG. 11) are rotated to wind or unwind the jaw wires, and thus perform a kind of compensation for the pitch motion, enabling the pitch motion of the end tool 1100.

First Modified Example of Second Embodiment

Hereinafter, the end tool 1100 of the surgical instrument according to a first modified example of the second embodiment of the present disclosure will be described. In this regard, the end tool 1100 of the surgical instrument according to the first modified example of the second embodiment of the present disclosure is different from the end tool of the surgical instrument according to the first embodiment of the present disclosure described above in that some of the pulleys are omitted. Hereinafter, the configuration that is different from that of the first embodiment will be described in detail.

Figure 77:
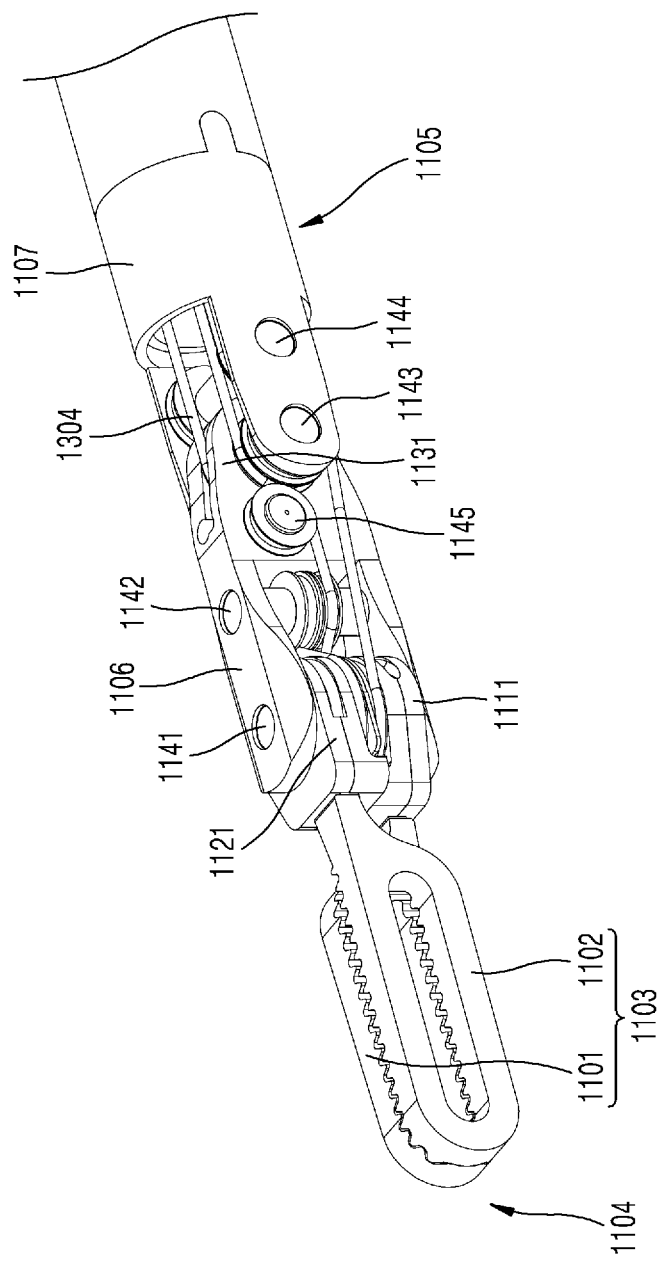
FIGS. 77 and 78 are perspective views illustrating an end tool of a surgical instrument according to a first modified example of the second embodiment of the present disclosure.
Figure 78:
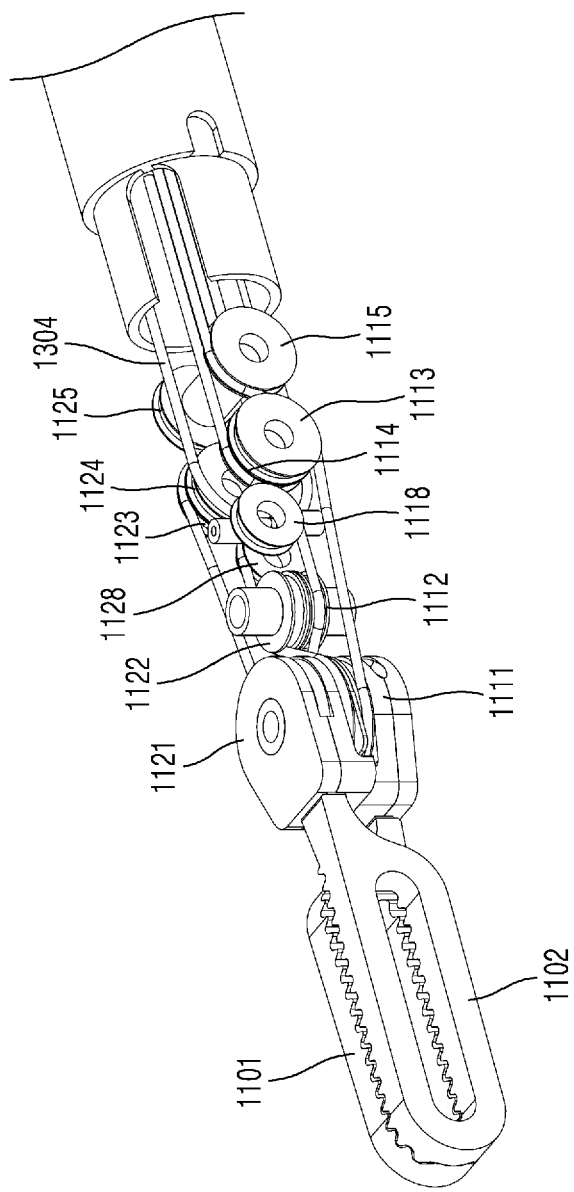
Figure 79:
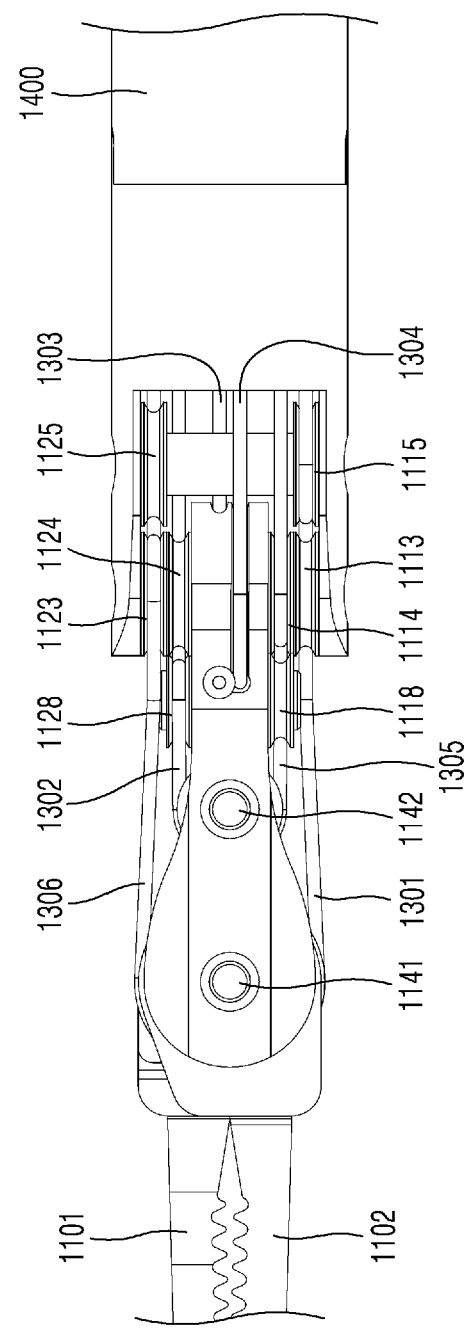
FIGS. 79 and 80 are plan views of the end tool of FIG. 77.
Figure 80:
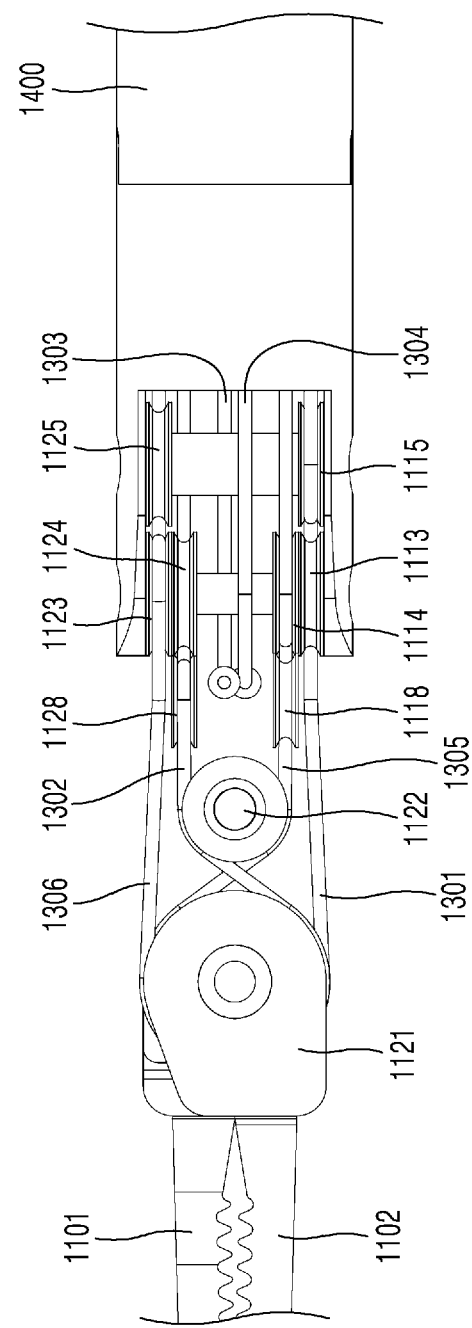
Figure 81:
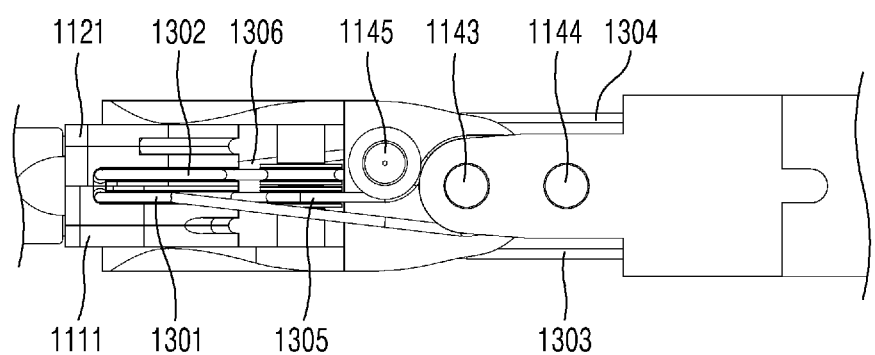
FIGS. 81, 82, and 83 are side views of the end tool of FIG. 77.
Figure 82:
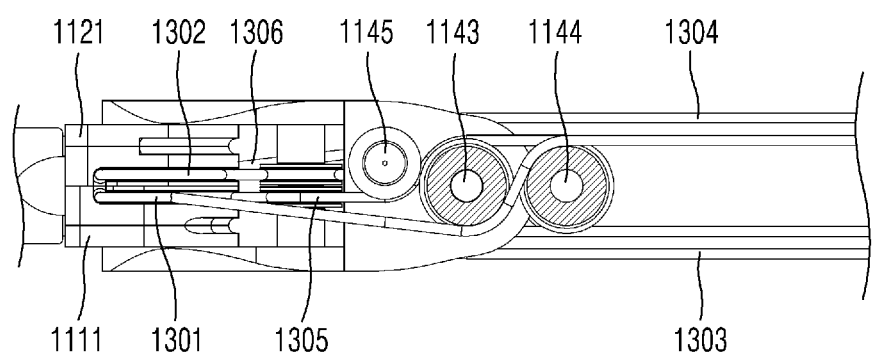
Figure 83:
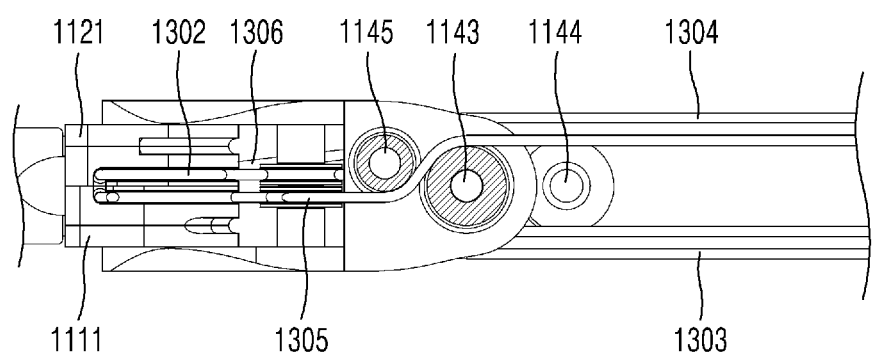
Figure 84:
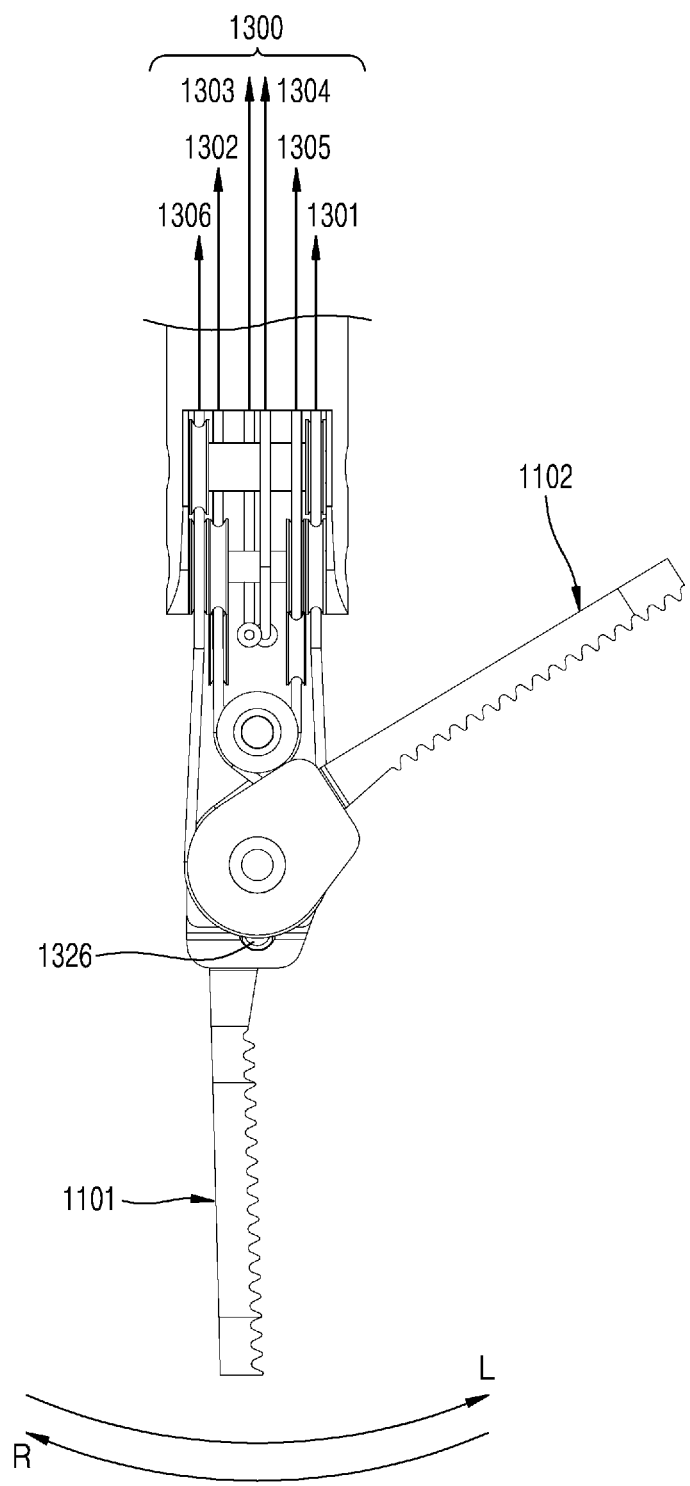
FIGS. 84 and 85 are plan views of the end tool of FIG. 77.
Figure 85:
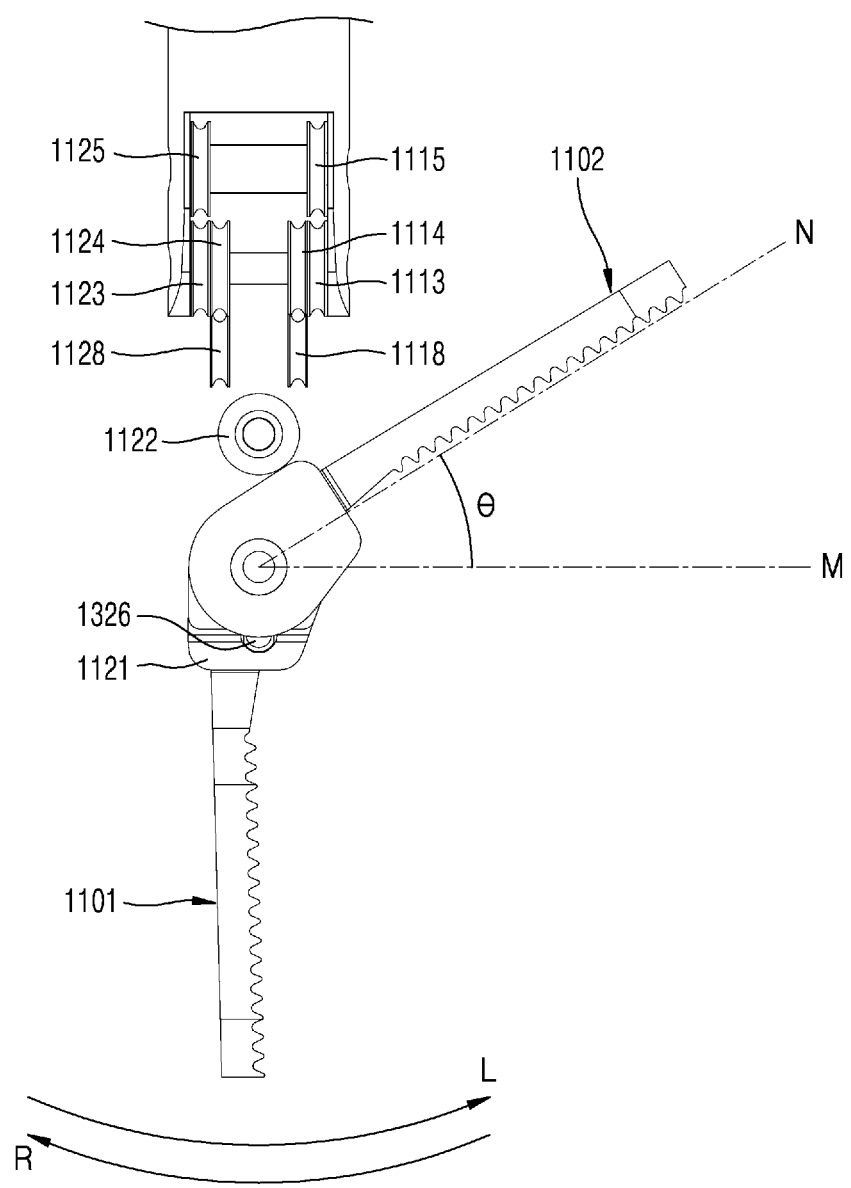
Figure 86:
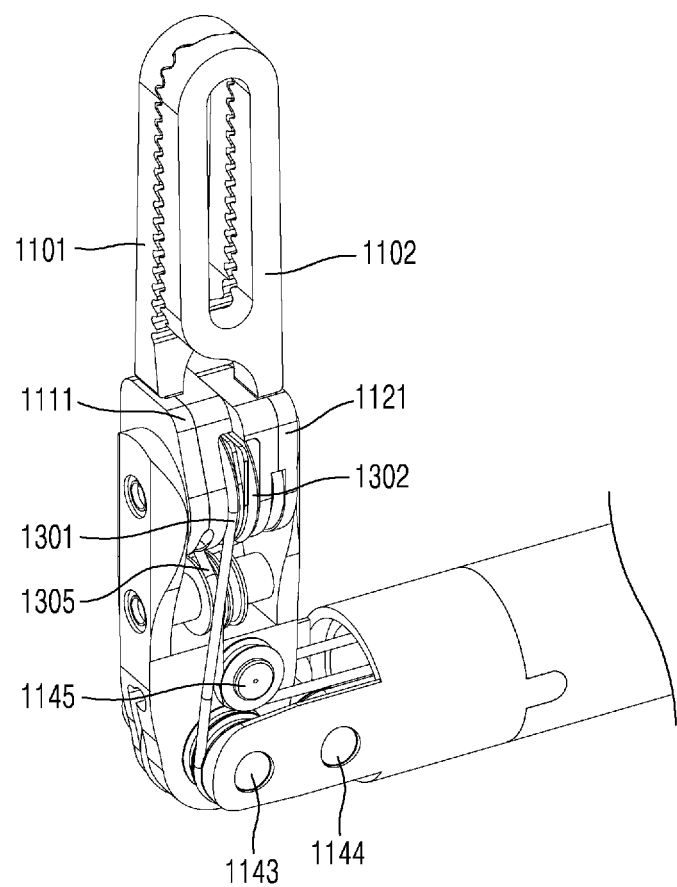
FIGS. 86 and 87 are perspective views illustrating a state in which the end tool of the surgical instrument of FIG. 77 is pitch-rotated by −90°.
Figure 87:
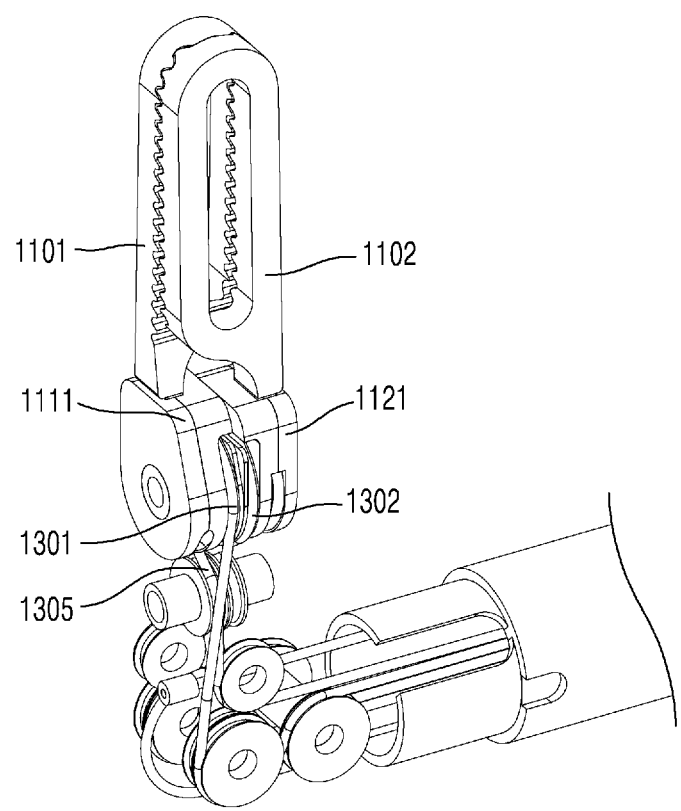
Figure 88:
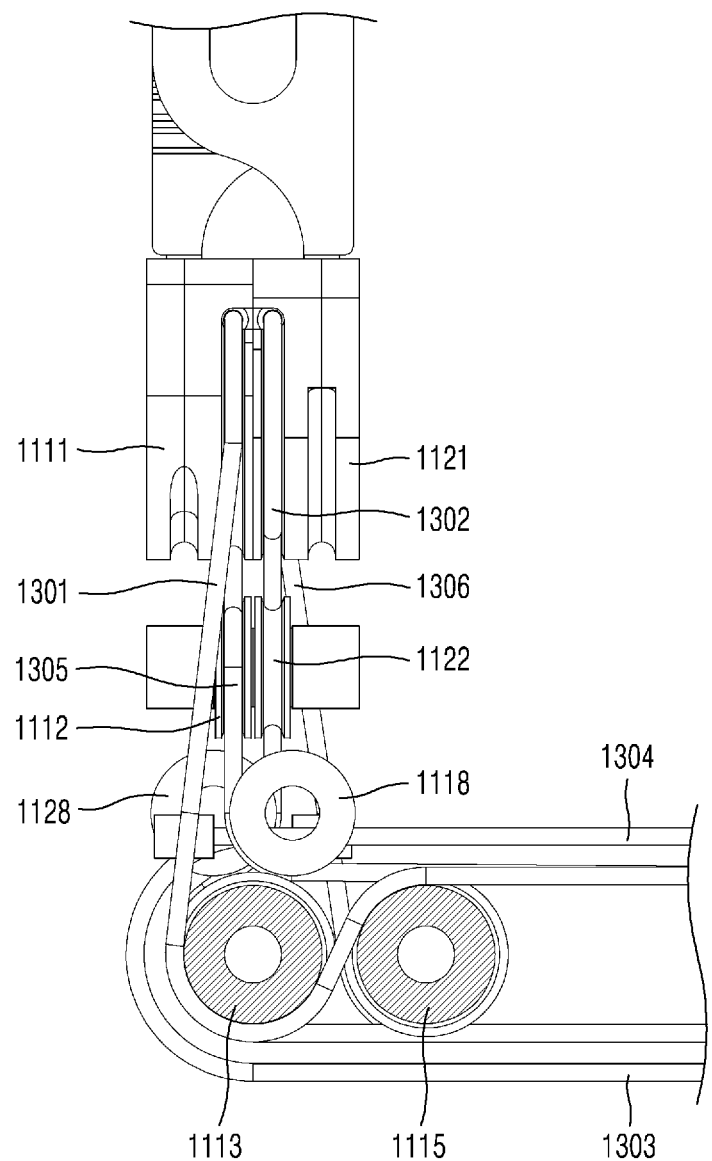
FIGS. 88 and 89 are side views illustrating a state in which the end tool of the surgical instrument of FIG. 77 is pitch-rotated by −90°.
Figure 89:
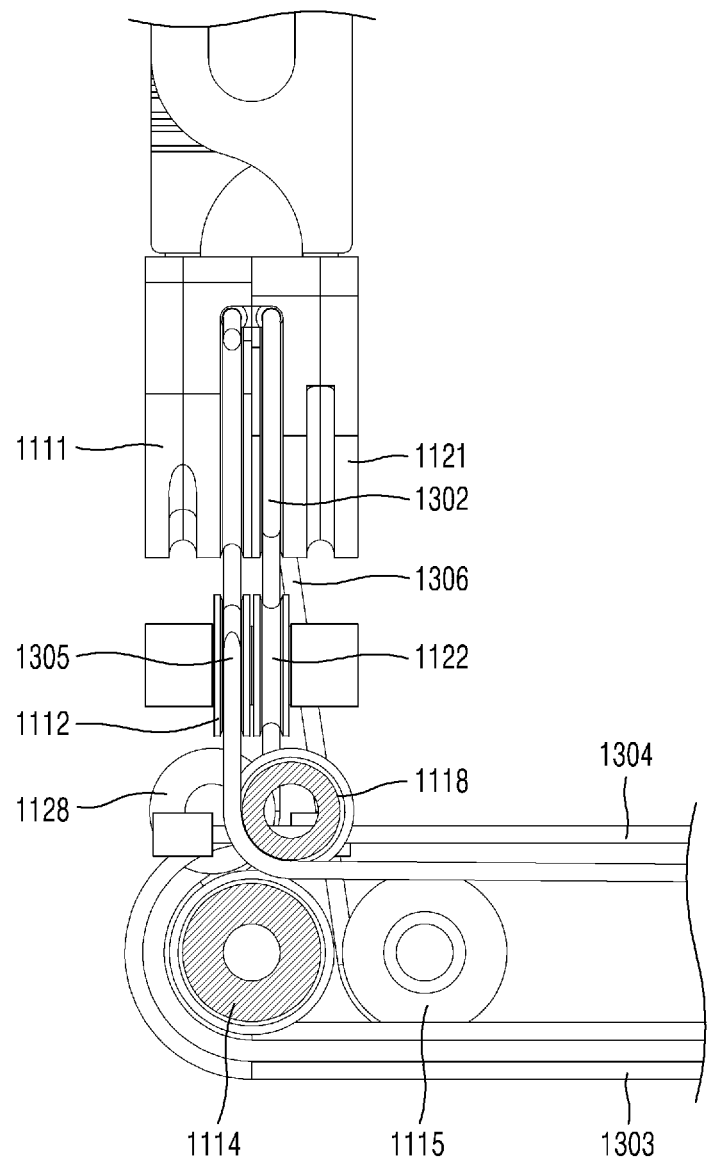
Figure 90:
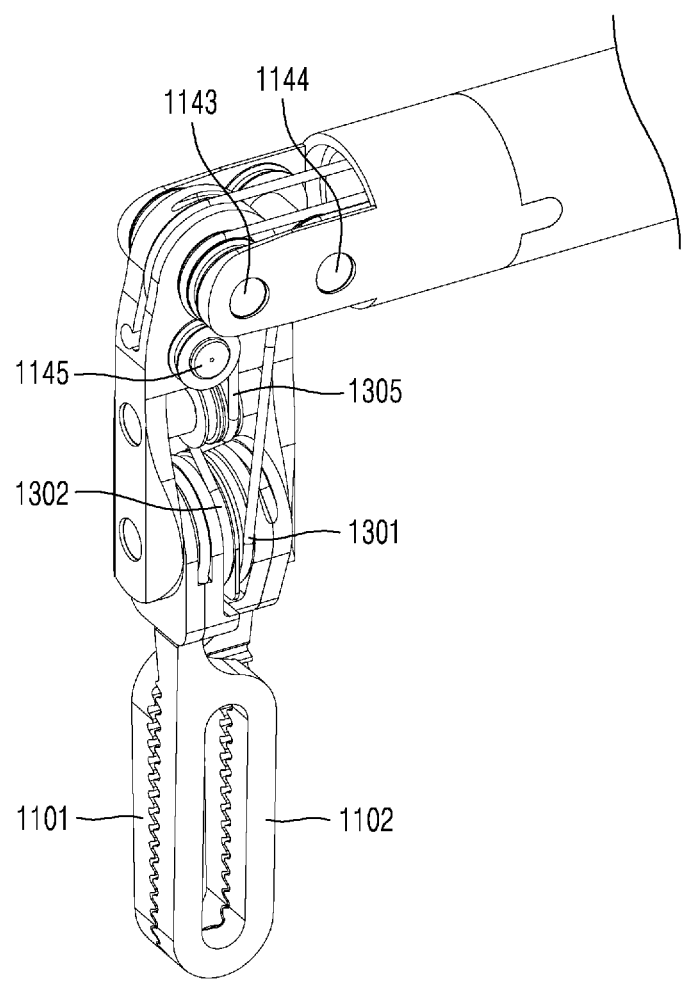
FIGS. 90 and 91 are perspective views illustrating a state in which the end tool of the surgical instrument of FIG. 77 is pitch-rotated by +90°.
Figure 91:
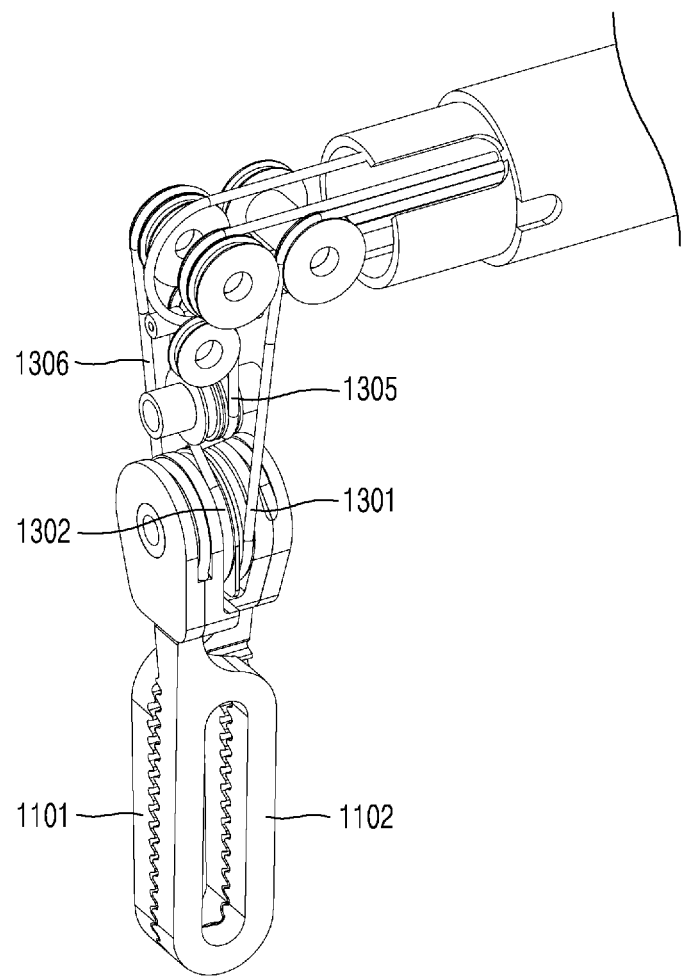
Figure 92:
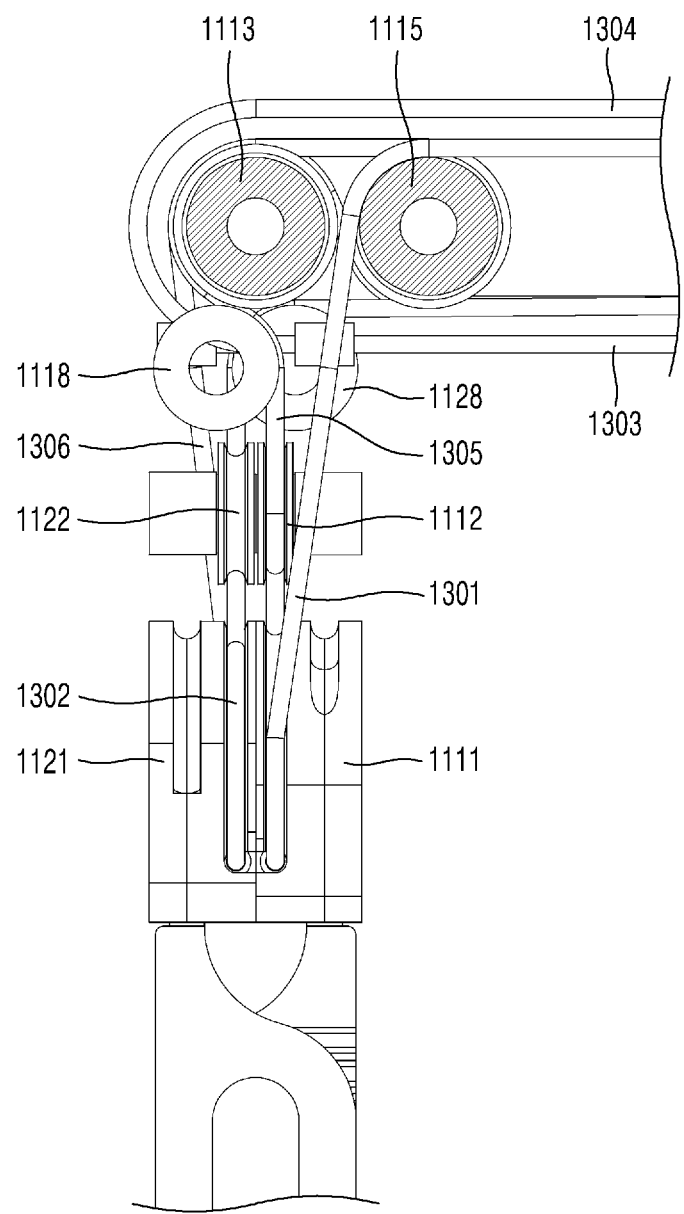
FIGS. 92 and 93 are side views illustrating a state in which the end tool of the surgical instrument of FIG. 77 is pitch-rotated by +90°.
Figure 93:
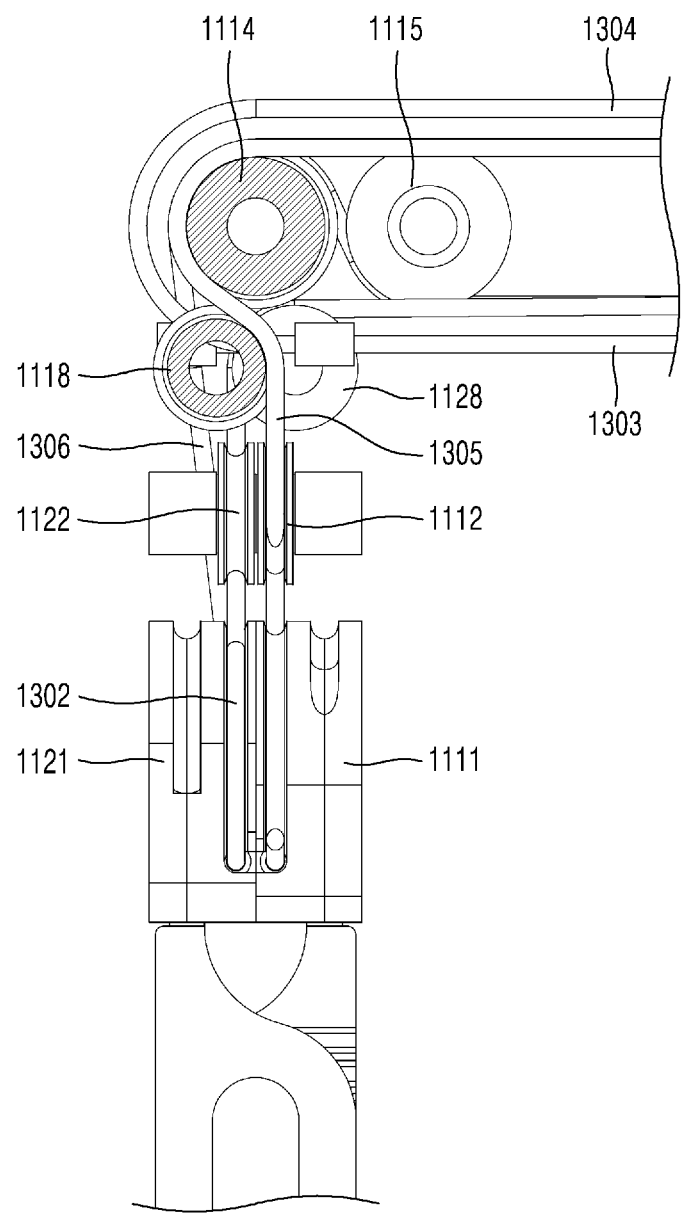

FIGS. 77 and 78 are perspective views illustrating an end tool of a surgical instrument according to the first modified example of the second embodiment of the present disclosure. FIGS. 79 and 80 are plan views of the end tool of FIG. 77. FIGS. 81, 82, and 83 are side views of the end tool of FIG. 77. FIGS. 84 and 85 are plan views of the end tool of FIG. 77. FIGS. 86 and 87 are perspective views illustrating a state in which the end tool of the surgical instrument of FIG. 77 is pitch-rotated by −90°. FIGS. 88 and 89 are side views illustrating a state in which the end tool of the surgical instrument of FIG. 77 is pitch-rotated by −90°. FIGS. 90 and 91 are perspective views illustrating a state in which the end tool of the surgical instrument of FIG. 77 is pitch-rotated by +90°. FIGS. 92 and 93 are side views illustrating a state in which the end tool of the surgical instrument of FIG. 77 is pitch-rotated by +90°.

Referring to FIGS. 77 to 93, the end tool 1100 according to the first modified example of the second embodiment of the present disclosure includes a pair of jaws for performing a grip motion, that is, the first jaw 1101 and the second jaw 1102. In this regard, a component encompassing each of the first jaw 1101 and the second jaw 1102 or both the first jaw 1101 and the second jaw 1102 may be referred to as the jaw 1103.

In addition, the end tool 1100 of the first modified example of the second embodiment of the present disclosure may include the end tool hub 1106 and the pitch hub 1107.

In addition, the end tool 1100 of the first modified example of the second embodiment of the present disclosure may include the rotation axis 1141, the rotation axis 1142, the rotation axis 1145, the rotation axis 1143, and the rotation axis 1144. As described above, the rotation axis 1141, the rotation axis 1142, and the rotation axis 1145 may be inserted through the end tool hub 1106, and the rotation axis 1143 and the rotation axis 1144 may be inserted through the pitch hub 1107.

In the present modified example, the end tool hub 1106, the pitch hub 1107, and the rotation axes 1141, 1142, 1143, 1144, and 1145 are substantially the same as the end tool hub 1106, the pitch hub 1107, and the respective rotation axes that are described above with reference to FIG. 2 and the like, respectively, and thus, detailed descriptions thereof will be omitted.

Meanwhile, the end tool 1100 may include the pulley 1111, the pulley 1112, the pulley 1113, the pulley 1114, the pulley 1115, the pulley 1117, and the pulley 1118, which are associated with a rotational motion of the first jaw 1101. In addition, the end tool 1100 may include the pulley 1121, the pulley 1122, the pulley 1123, the pulley 1124, the pulley 1125, the pulley 1127, and the pulley 1128, which are associated with a rotational motion of the second jaw 1102.

In this regard, in the end tool 1100 of the surgical instrument according to the first modified example of the second embodiment of the present disclosure, each of the first jaw pitch sub-pulley and the second jaw pitch sub-pulley includes only one pulley.

In detail, the end tool 1100 of the surgical instrument according to the second embodiment of the present disclosure illustrated in FIG. 60 and the like includes a pair of pulleys 1115 and 1116 as first jaw pitch sub-pulleys, and a pair of pulleys 1125 and 1126 as second jaw pitch sub-pulleys.

On the contrary, the end tool 1100 of the surgical instrument according to the first modified example of the second embodiment of the present disclosure is different from the second embodiment of the present disclosure illustrated in FIG. 60 and the like, in that it includes a single pulley 1115 as a first jaw pitch sub-pulley, and a single pulley 1125 as a second jaw pitch sub-pulley.

Accordingly, the pulley 1111, the pulley 1112, the pulley 1117/pulley 1118, the pulley 1113/pulley 1114, and the pulley 1115, which are associated with rotation of the first jaw 1101, may be sequentially arranged from the distal end 1104 of the end tool 1100 toward the proximal end 1105.

In addition, the pulley 1121, the pulley 1122, the pulley 1127/pulley 1128, the pulley 1123/pulley 1124, and the pulley 1125, which are associated with rotation of the second jaw 1102, may be sequentially arranged from the distal end 1104 of the end tool 1100 toward the proximal end 1105.

In this regard, the pulley 1116 and pulley 1126 of the end tool 1100 of the second embodiment of the present disclosure illustrated in FIG. 60 and the like are not pulleys around which wires are wound, but pulleys through which the wires pass in a straight line, and thus may be omitted as in the present modified example.

In other words, in the second embodiment of the present disclosure, two rows of first jaw pitch sub-pulleys and two rows of second jaw pitch sub-pulleys are provided, whereas in the first modified example of the second embodiment of the present disclosure, one row of a first jaw pitch sub-pulley and one row of a second jaw pitch sub-pulley are provided.

In this regard, the pulley 1117/pulley 1118 are arranged on one side of the pulley 1111 and the pulley 1112. In this regard, the pulley 1117/pulley 1118 are formed to be rotatable around the rotation axis 1145, which is a pitch redundant rotation axis. In addition, the pulley 1113 and the pulley 1114 are arranged on one side of the pulley 1117/pulley 1118 to face each other. In this regard, the pulley 1113 and the pulley 1114 are formed to be rotatable independently of each other around the rotation axis 1143, which is a pitch main rotation axis. In addition, the pulley 1115 is arranged on one side of the pulley 1113 and the pulley 1114. In this regard, the pulley 1115 is formed to be rotatable around the rotation axis 1144, which is a pitch sub-rotation axis. In this regard, the drawings illustrate that the pulley 1117, the pulley 1118, the pulley 1113, the pulley 1114, and the pulley 1115 are formed to be rotatable around the Y-axis direction, but the concept of the present disclosure is not limited thereto, and the rotation axes of the respective pulleys may be formed in various directions according to their configurations.

The wire 1301, which is a first jaw wire, is wound to sequentially come into contact with at least portions of the pulley 1115, the pulley 1113, the pulley 1117, and the pulley 1111. In addition, the wire 1305 connected to the wire 1301 by the coupling member 1323 is wound to sequentially come into contact with at least portions of the pulley 1111, the pulley 1112, the pulley 1118, and the pulley 1114.

In other words, the wire 1301 and the wire 1305, which are first jaw wires, are wound to sequentially come into contact with at least portions of the pulley 1115, the pulley 1113, the pulley 1117, the pulley 1111, the pulley 1112, the pulley 1118, and the pulley 1114, and are formed to move along the above pulleys while rotating the above pulleys.

Meanwhile, the pulley 1127/pulley 1128 are arranged on one side of the pulley 1121 and the pulley 1122. In this regard, the pulley 1127/pulley 1128 are formed to be rotatable around the rotation axis 1145, which is a pitch redundant rotation axis. In addition, the pulley 1123 and the pulley 1124 are arranged on one side of the pulley 1127/pulley 1128 to face each other. In this regard, the pulley 1123 and the pulley 1124 are formed to be rotatable independently of each other around the rotation axis 1143, which is a pitch main rotation axis. In addition, the pulley 1125 is arranged on one side of the pulley 1123 and the pulley 1124. In this regard, the pulley 1125 is formed to be rotatable around the rotation axis 1144, which is a pitch sub-rotation axis. In this regard, the drawings illustrate that the pulley 1127, the pulley 1128, the pulley 1123, the pulley 1124, the pulley 1125, and the pulley 1126 are formed to be rotatable around the Y-axis direction, but the concept of the present disclosure is not limited thereto, and the rotation axes of the respective pulleys may be formed in various directions according to their configurations.

The wire 1306, which is a second jaw wire, is wound to sequentially come into contact with at least portions of the pulley 1125, the pulley 1123, the pulley 1127, and the pulley 1121. In addition, the wire 1302 connected to the wire 1306 by the coupling member 1326 is wound to sequentially come into contact with at least portions of the pulley 1121, the pulley 1122, the pulley 1128, and the pulley 1124.

In other words, the wire 1306 and the wire 1302, which are second jaw wires, are wound to sequentially come into contact with at least portions of the pulley 1125, the pulley 1123, the pulley 1127, the pulley 1121, the pulley 1122, the pulley 1128, and the pulley 1124, and are formed to move along the above pulleys while rotating the above pulleys.

Accordingly, in the second embodiment of the present disclosure, two rows of first jaw pitch sub-pulleys and two rows of second jaw pitch sub-pulleys are provided, whereas in the first modified example of the second embodiment of the present disclosure, one row of a first jaw pitch sub-pulley and one row of a second jaw pitch sub-pulley are provided, and thus, an effect of reducing the number of parts and simplifying a manufacturing process may be achieved.

Third Embodiment of End Tool of Surgical Instrument

Hereinafter, an end tool 2100 of a surgical instrument according to a third embodiment of the present disclosure will be described. In this regard, the end tool 2100 of the surgical instrument according to the third embodiment of the present disclosure is different from the end tool (see 100 of FIG. 2 and the like) of the surgical instrument according to the first embodiment of the present disclosure described above, in the arrangement of the jaw pulleys and the jaw wires. The configuration that is different from that of the first embodiment will be described in detail below.

Figure 94:
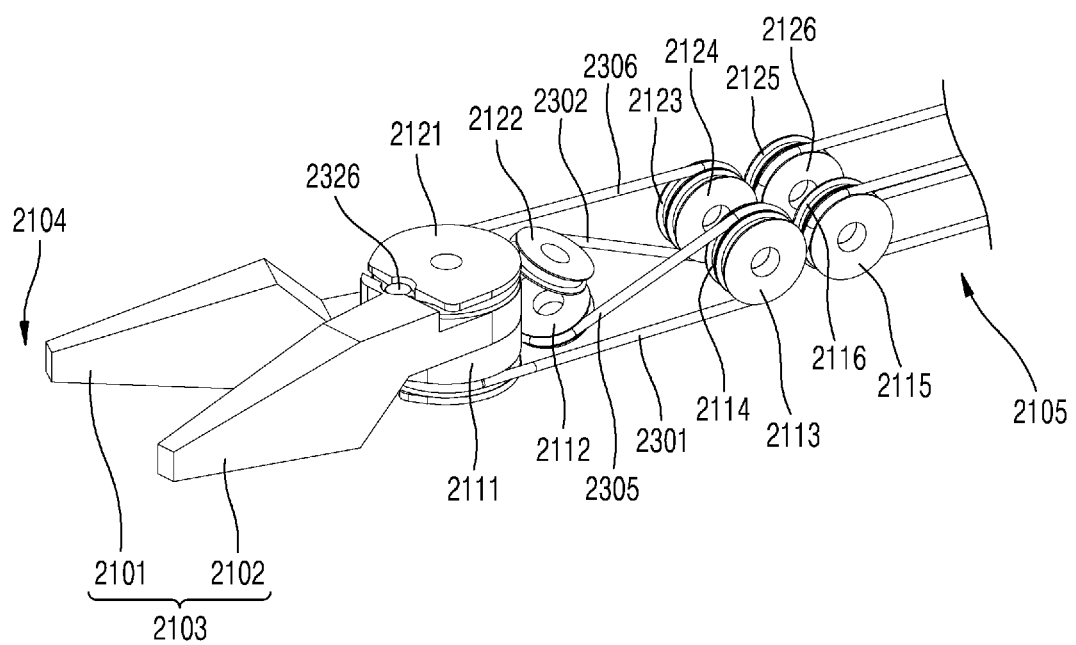
FIGS. 94, 95, 96, and 97 are perspective views illustrating an end tool of a surgical instrument according to a third embodiment of the present disclosure.
Figure 95:
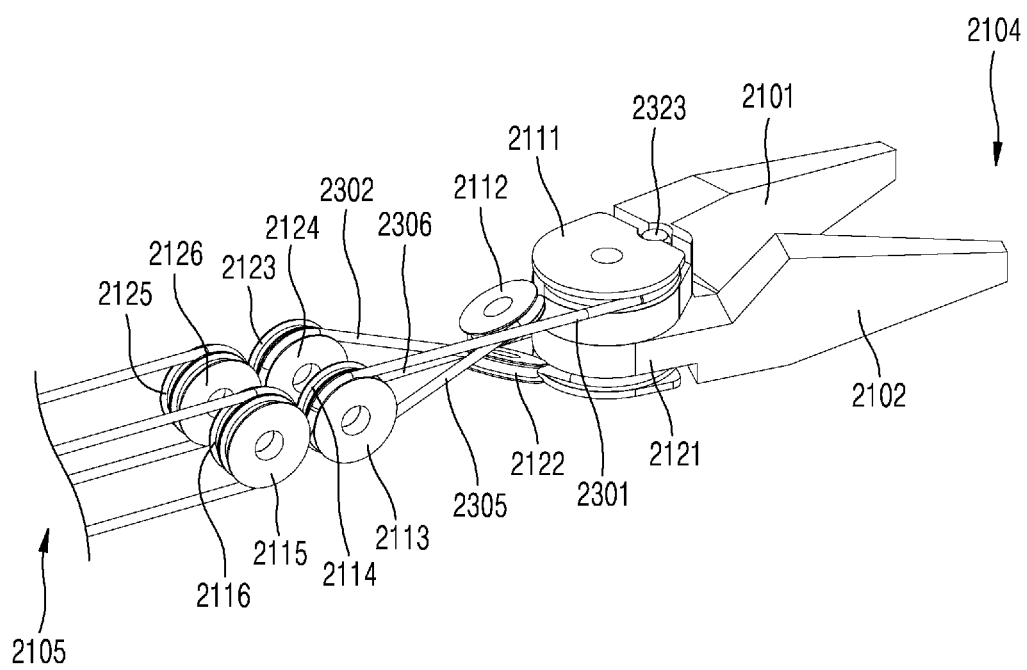
Figure 96:
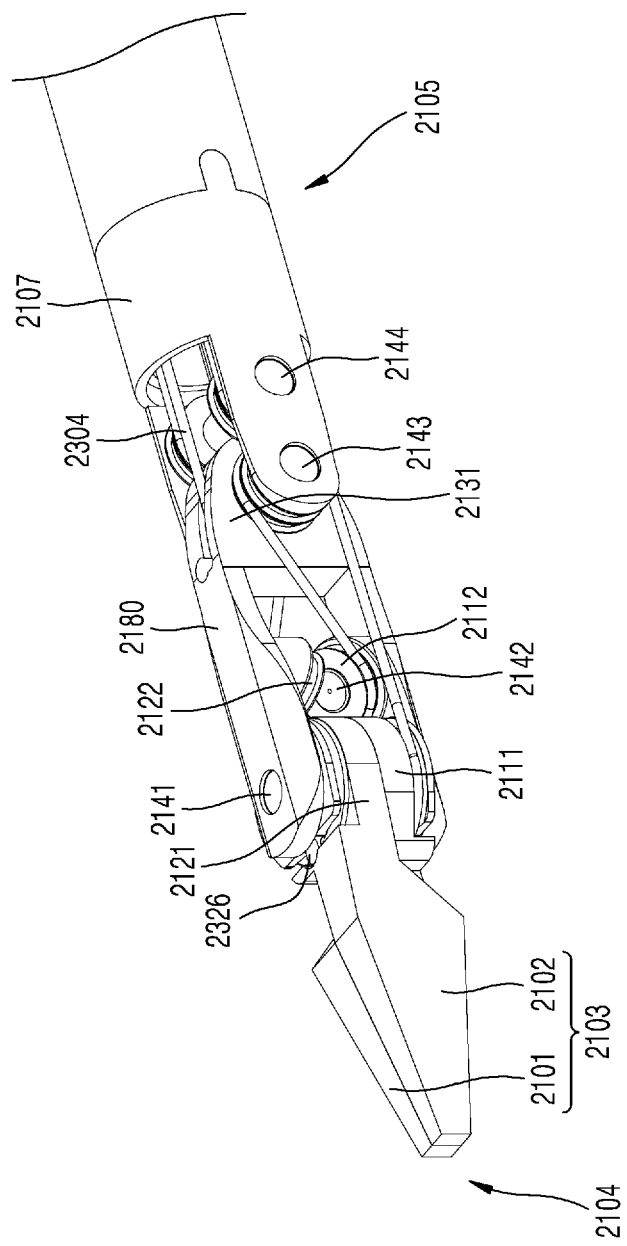
Figure 97:
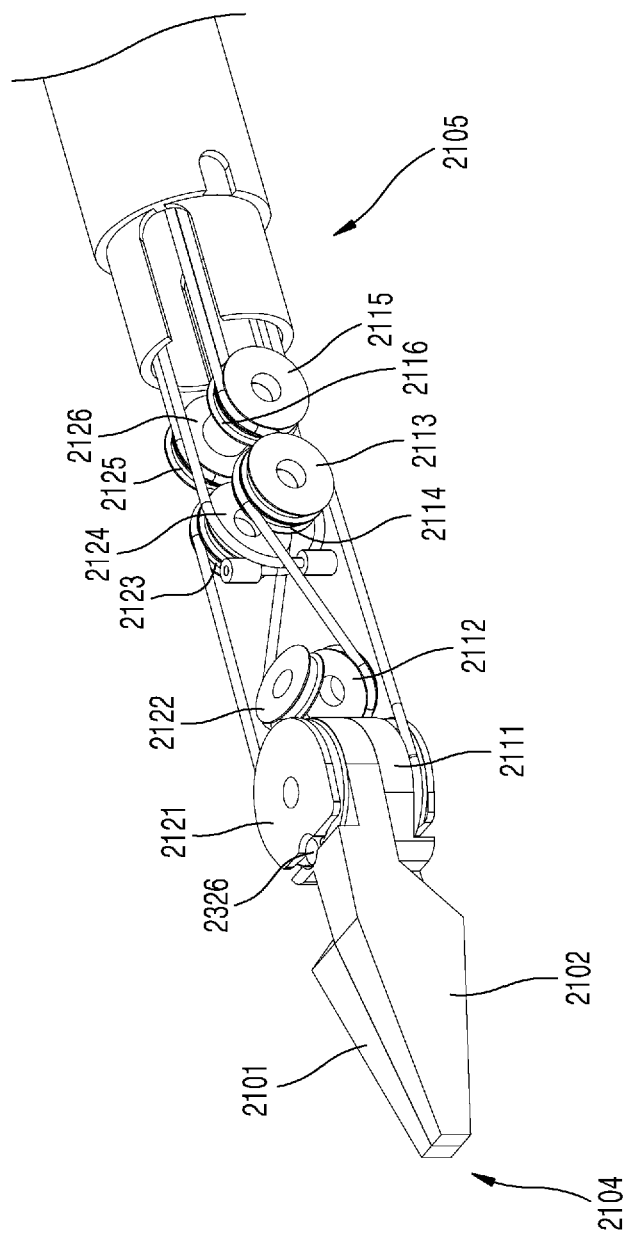
Figure 98:
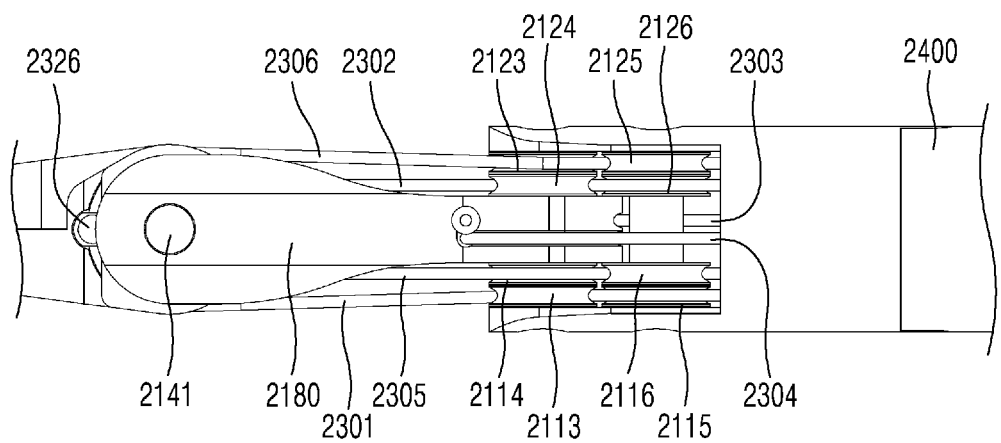
FIGS. 98 and 99 are plan views of the end tool of FIG. 94.
Figure 99:
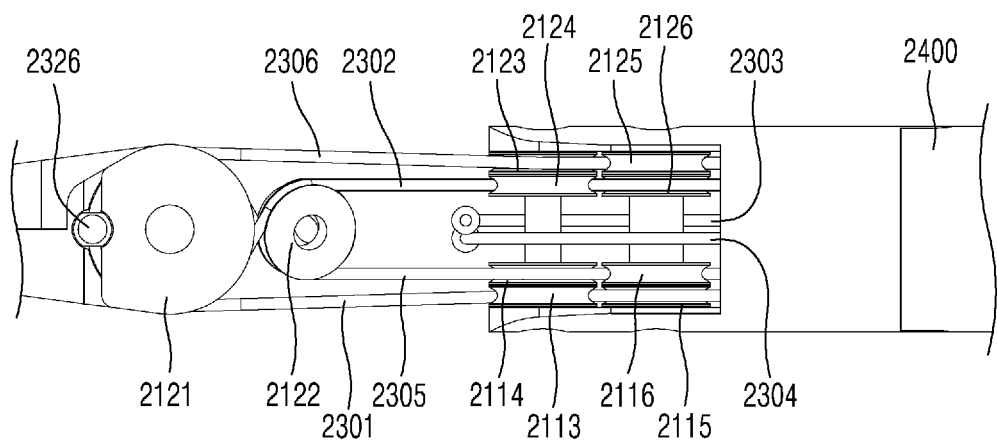
Figure 100:
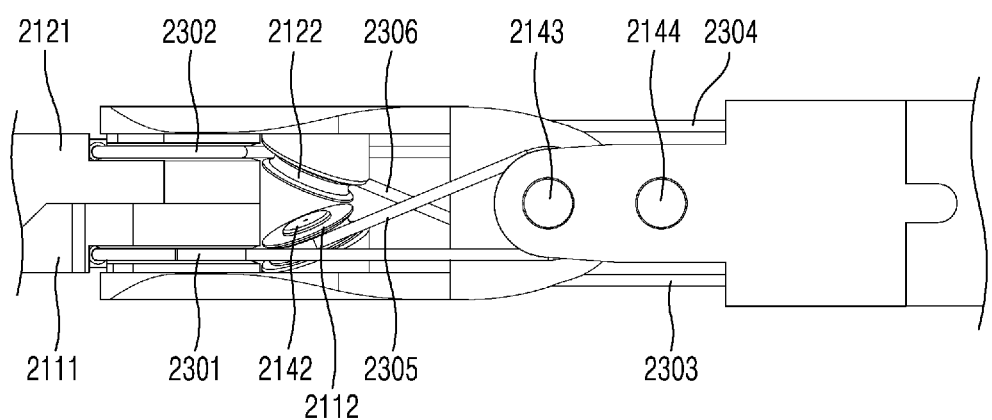
FIGS. 100, 101, and 102 are side views of the end tool of FIG. 94.
Figure 101:
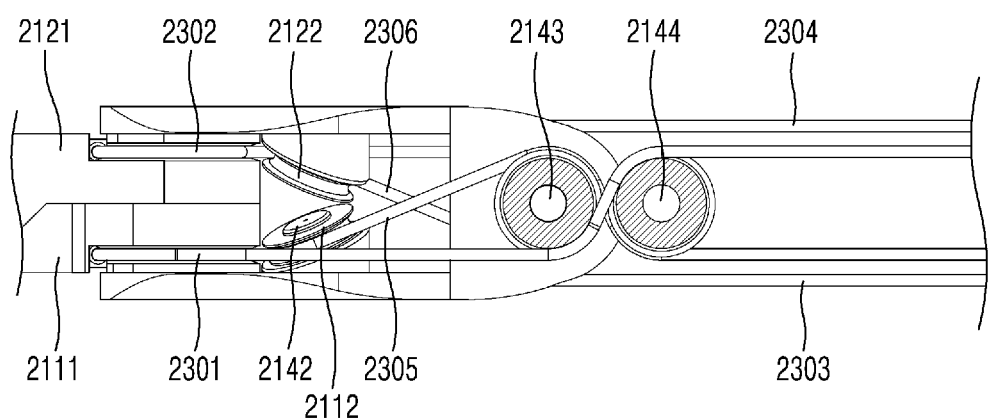
Figure 102:
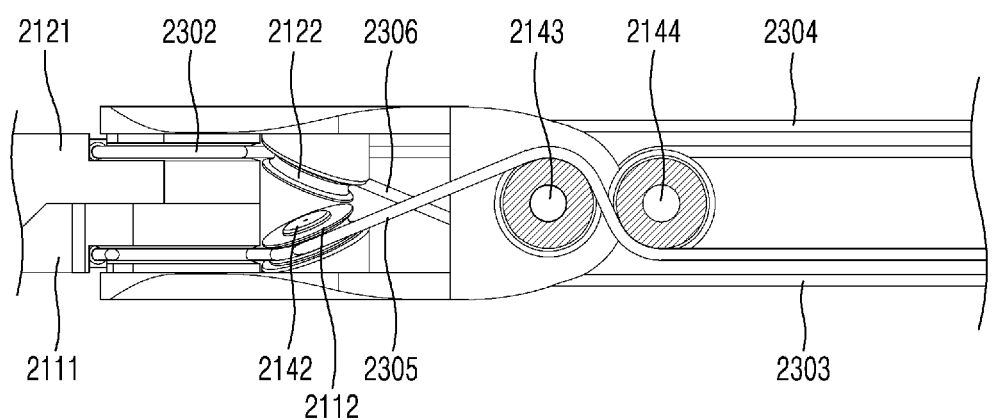
Figure 103:
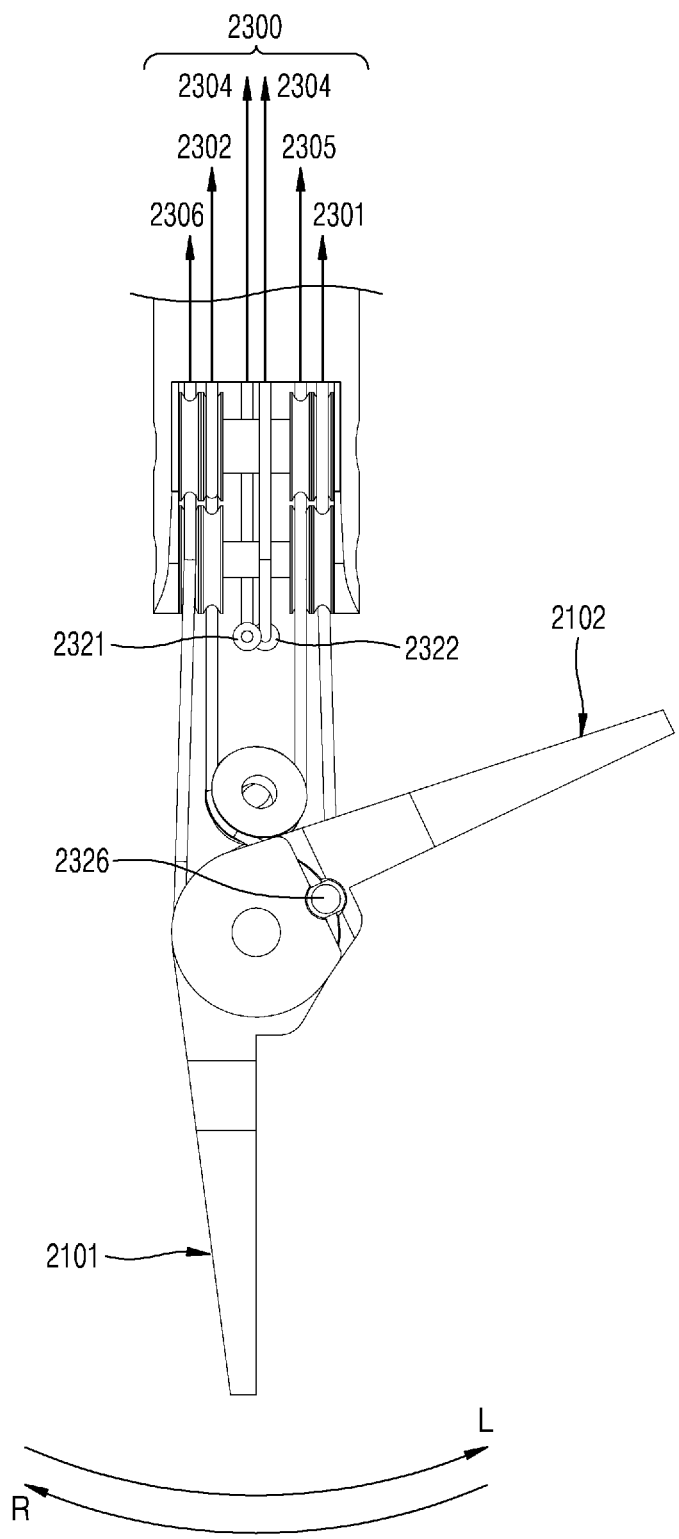
FIGS. 103 and 104 are plan views of the end tool of FIG. 94.
Figure 104:
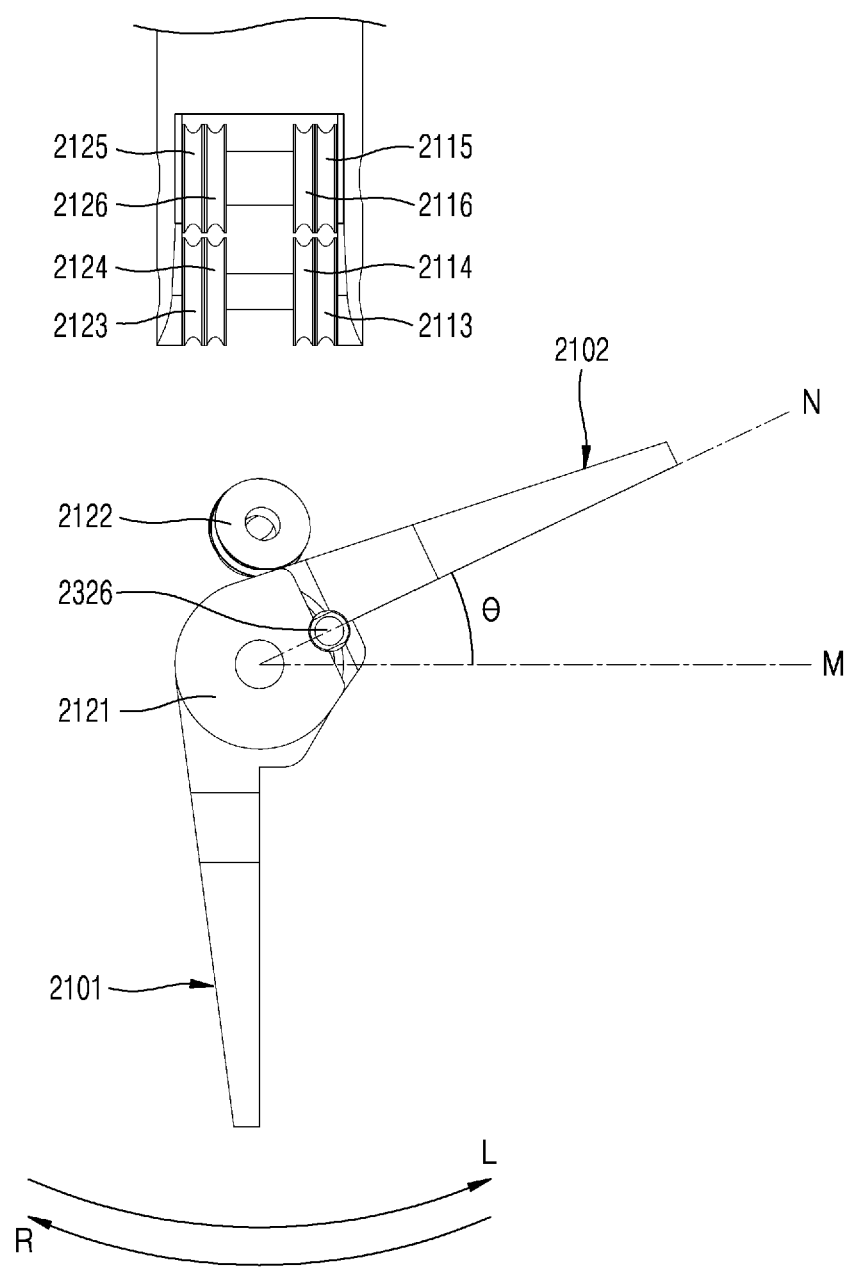
Figure 105:
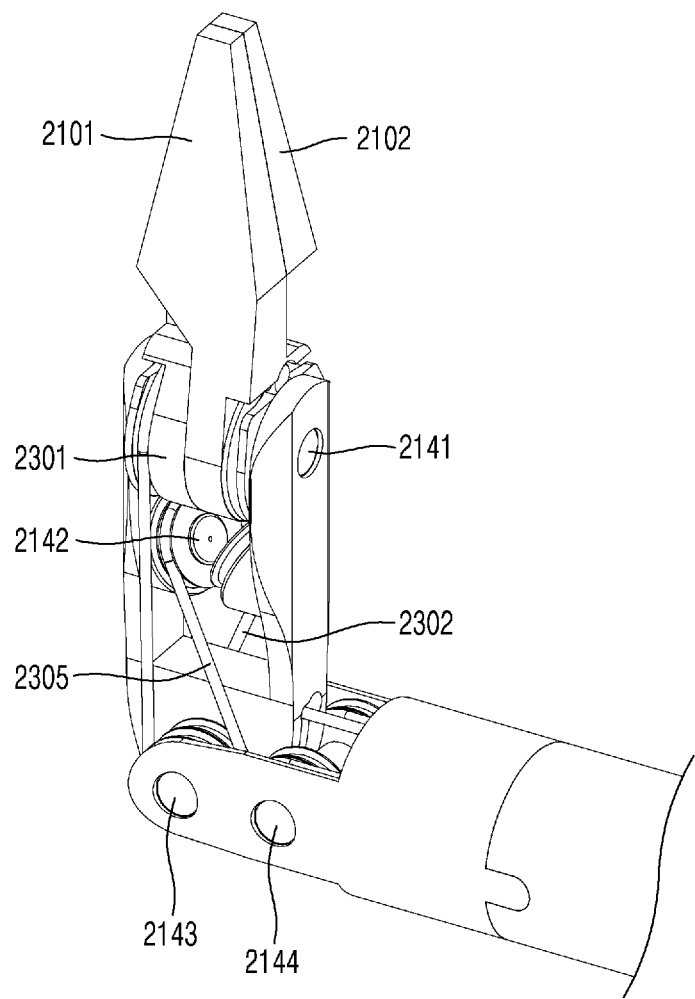
FIGS. 105 and 106 are perspective views illustrating a state in which the end tool of the surgical instrument of FIG. 94 is pitch-rotated by −90°.
Figure 106:
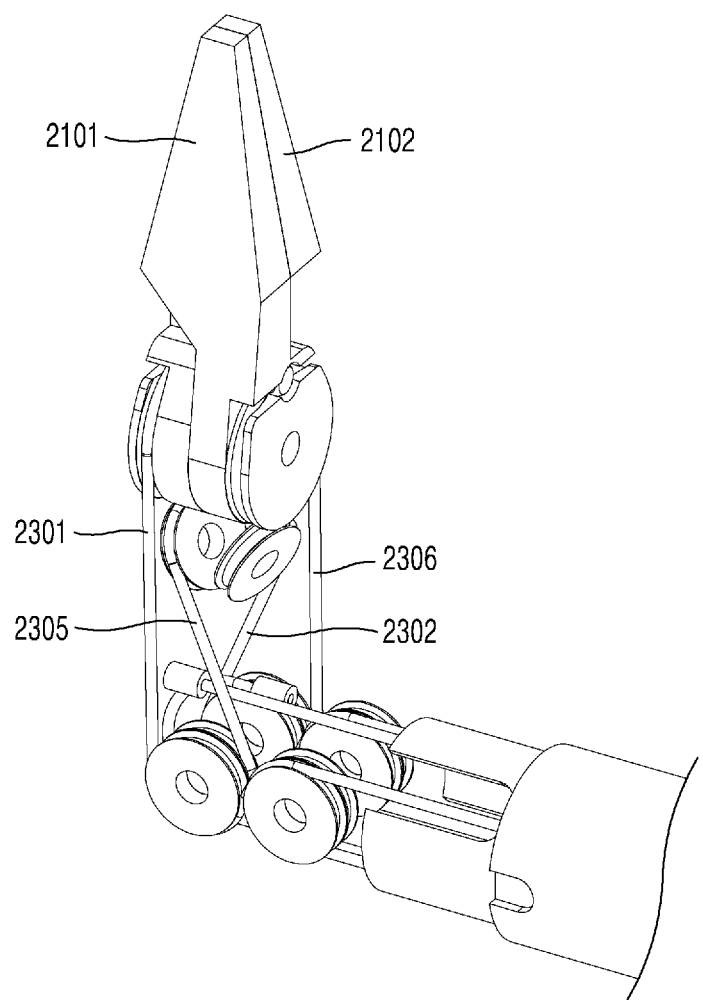
Figure 107:
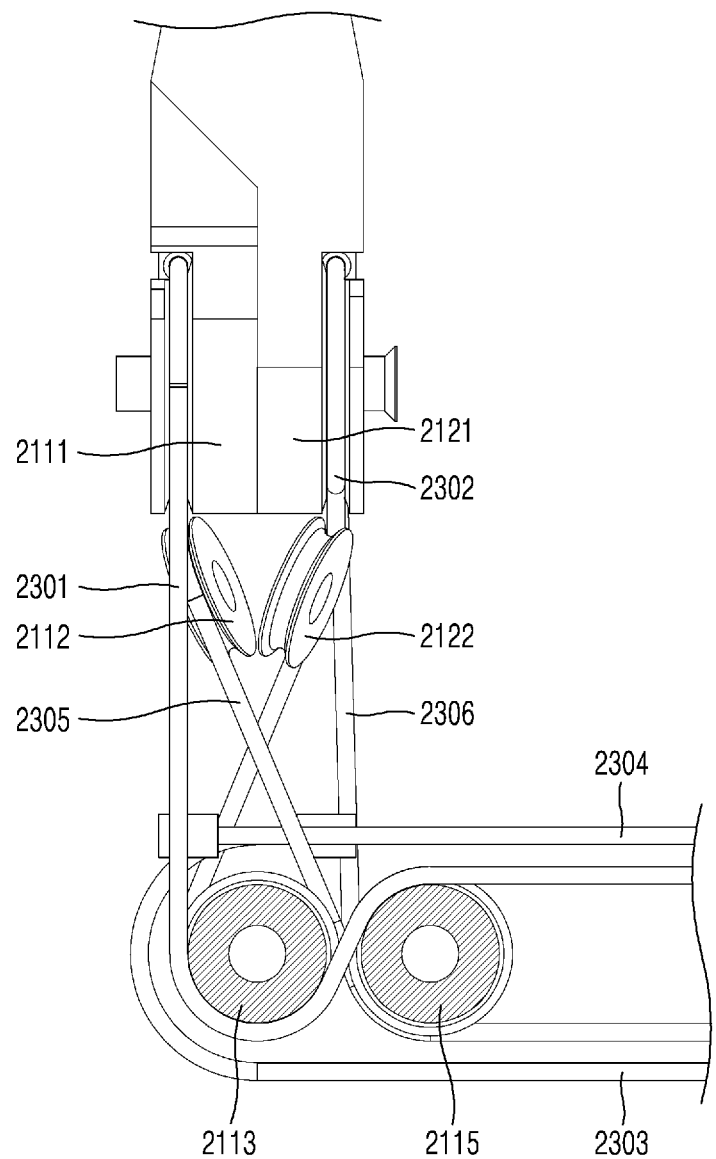
FIGS. 107 and 108 are side views illustrating a state in which the end tool of the surgical instrument of FIG. 94 is pitch-rotated by −90°.
Figure 108:
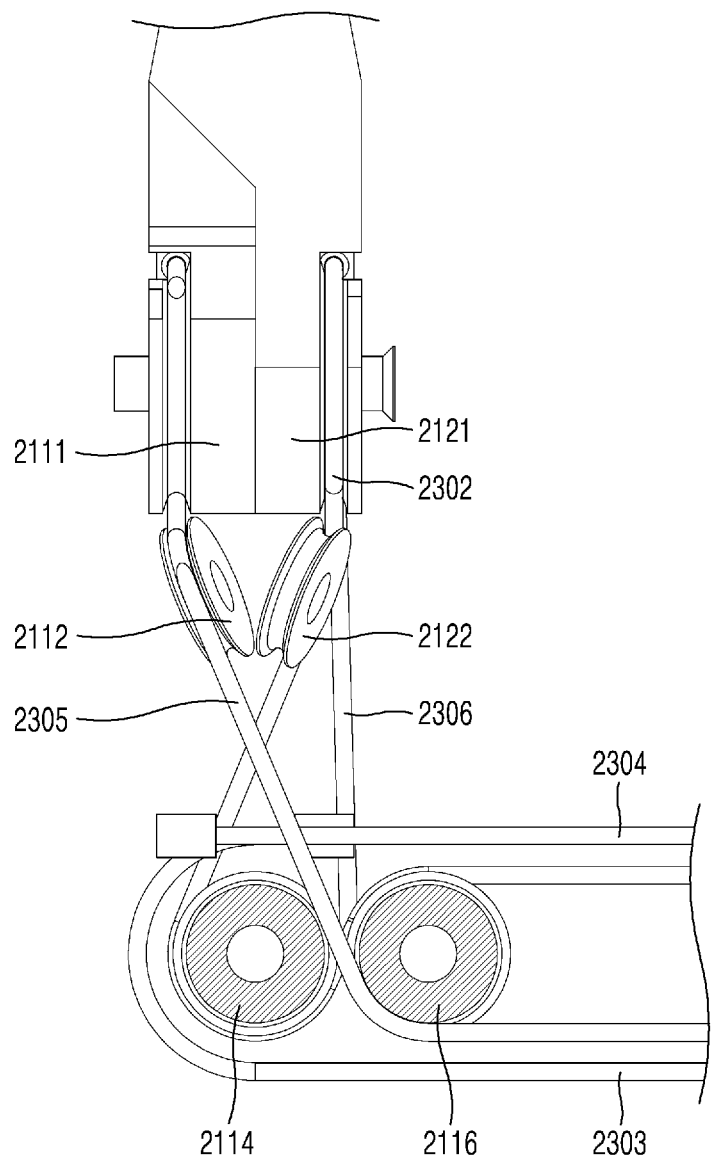
Figure 109:
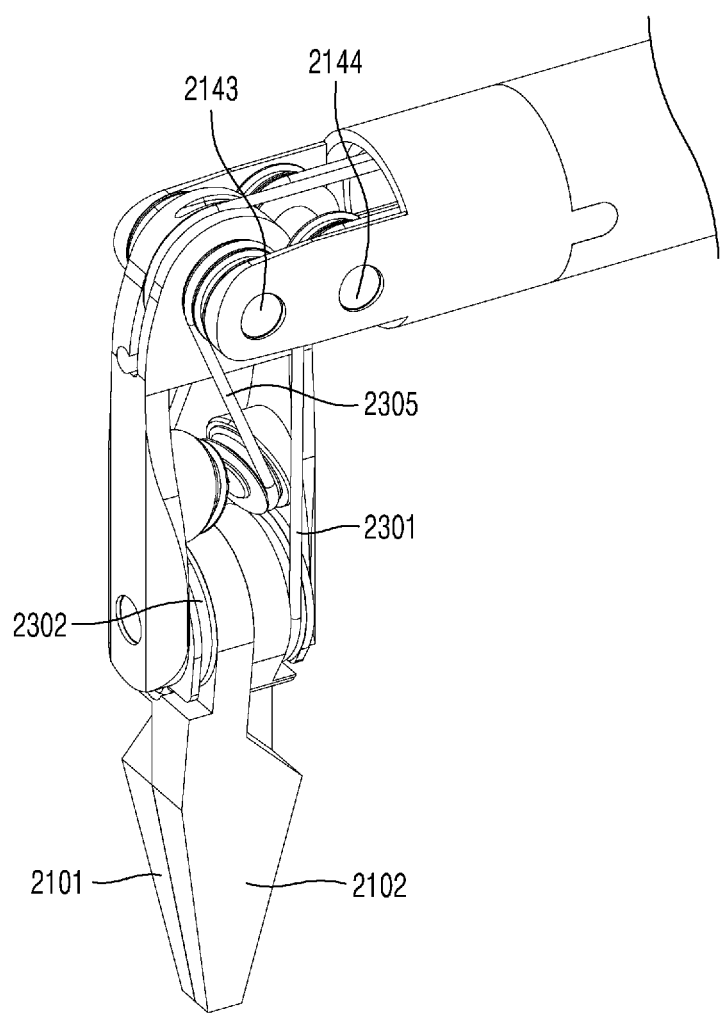
FIGS. 109 and 110 are perspective views illustrating a state in which the end tool of the surgical instrument of FIG. 94 is pitch-rotated by +90°.
Figure 110:
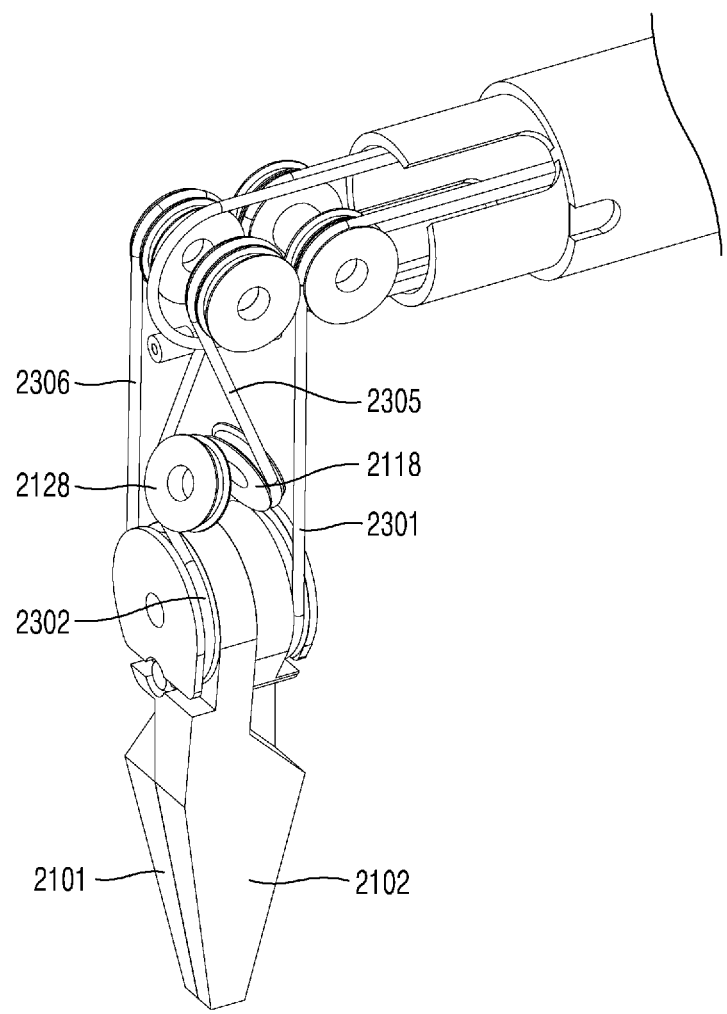
Figure 111:
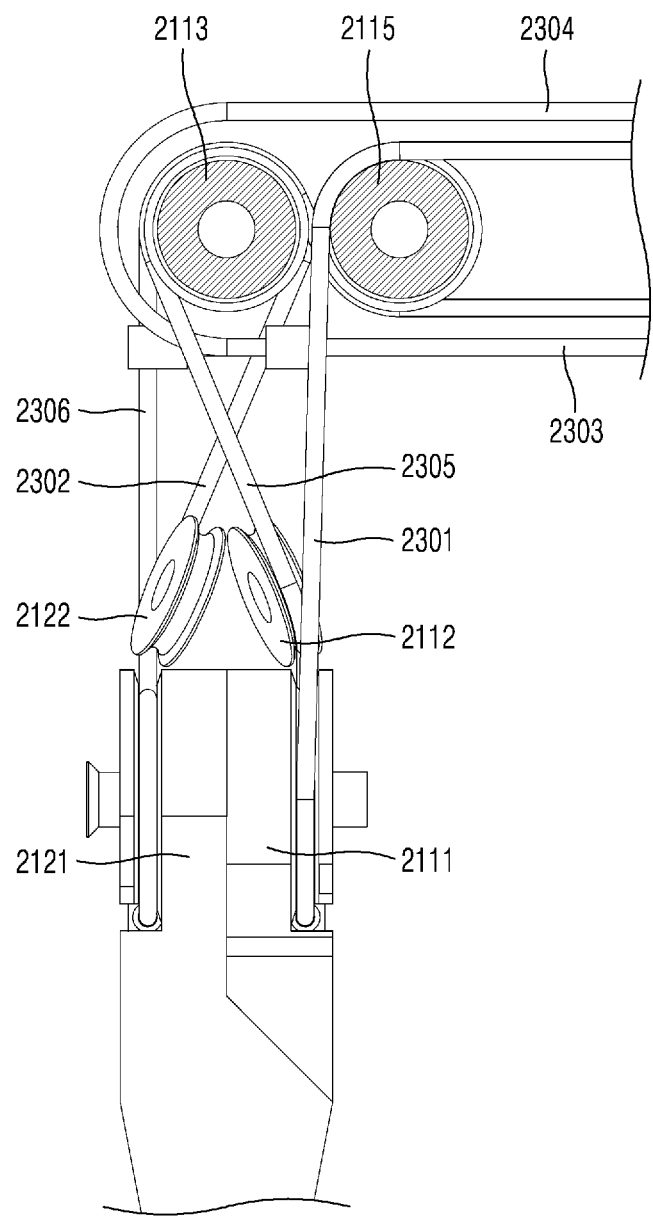
FIGS. 111 and 112 are side views illustrating a state in which the end tool of the surgical instrument of FIG. 94 is pitch-rotated by +90°.
Figure 112:
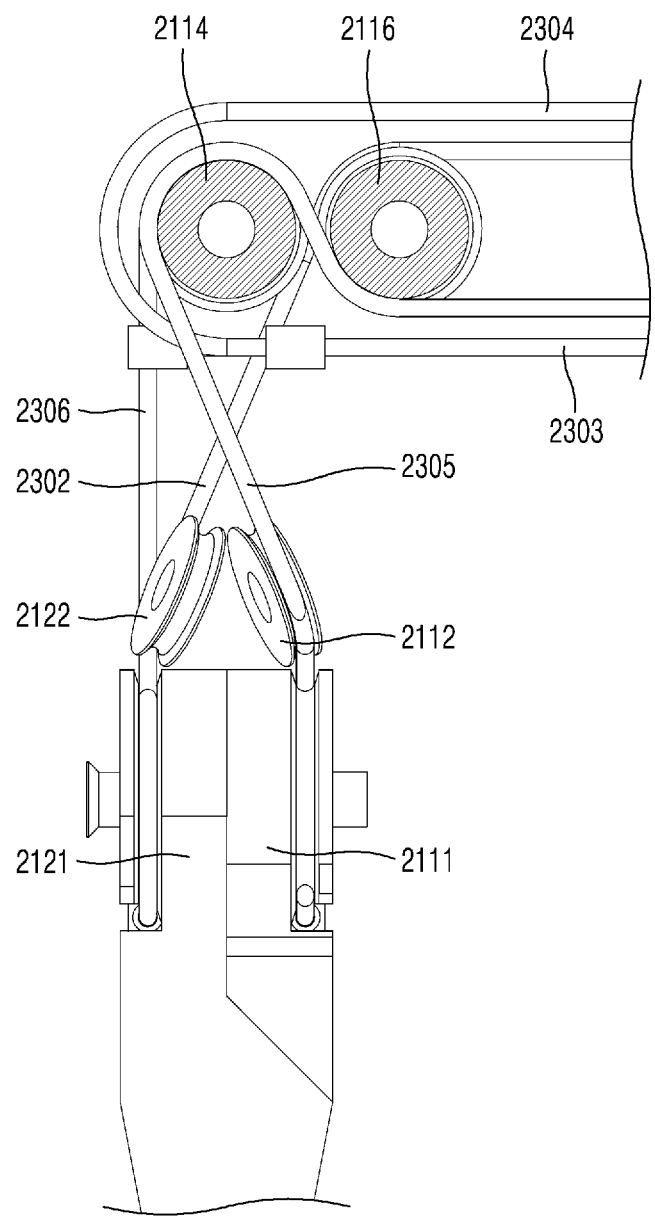
Figure 113:
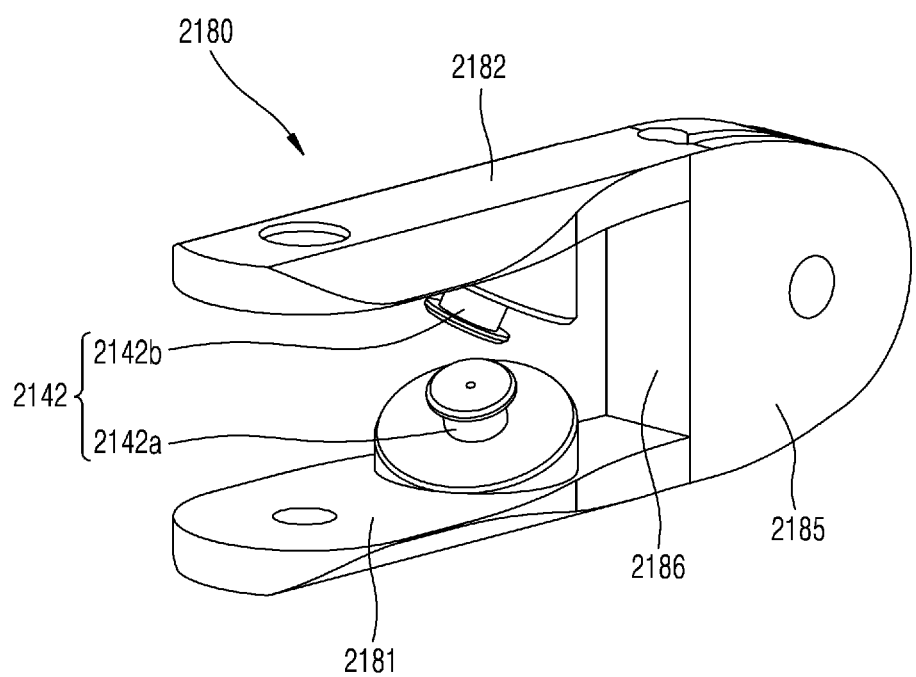
FIG. 113 is a perspective view of an end tool hub of the end tool of FIG. 94.
Figure 114:
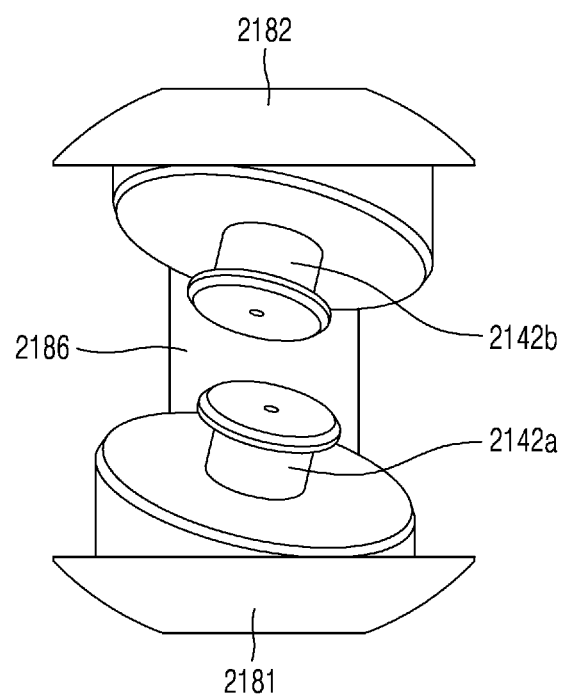
FIG. 114 is a front view of the end tool hub of the end tool of FIG. 94.
Figure 115:
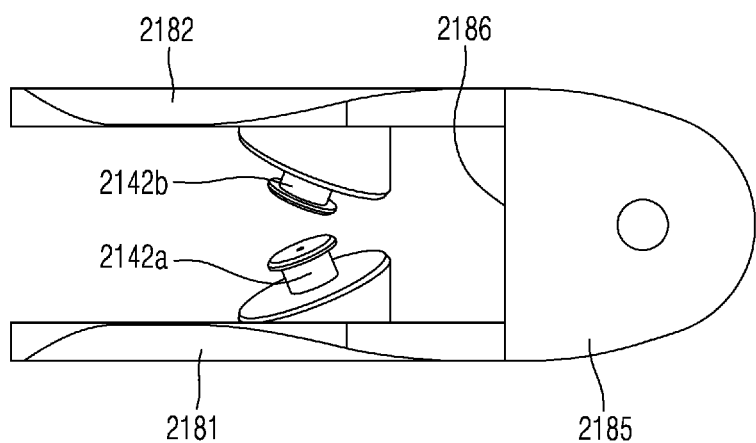
FIG. 115 is a side view of the end tool hub of the end tool of FIG. 94.

FIGS. 94, 95, 96, and 97 are perspective views illustrating an end tool of a surgical instrument according to the third embodiment of the present disclosure. FIGS. 98 and 99 are plan views of the end tool of FIG. 94. FIGS. 100, 101, and 102 are side views of the end tool of FIG. 94. FIGS. 103 and 104 are plan views of the end tool of FIG. 94. FIGS. 105 and 106 are perspective views illustrating a state in which the end tool of the surgical instrument of FIG. 94 is pitch-rotated by −90°. FIGS. 107 and 108 are side views illustrating a state in which the end tool of the surgical instrument of FIG. 94 is pitch-rotated by −90°. FIGS. 109 and 110 are perspective views illustrating a state in which the end tool of the surgical instrument of FIG. 94 is pitch-rotated by +90°. FIGS. 111 and 112 are side views illustrating a state in which the end tool of the surgical instrument of FIG. 94 is pitch-rotated by +90°. FIG. 113 is a perspective view of an end tool hub of the end tool of FIG. 94, FIG. 114 is a front view of the end tool hub of the end tool of FIG. 94, and FIG. 115 is a side view of the end tool hub of the end tool of FIG. 94.

Referring to FIGS. 94 to 115, a power transmission part 2300 of the end tool 2100 of the surgical instrument according to the third embodiment of the present disclosure may include a wire 2301, a wire 2302, a wire 2303, a wire 2304, a wire 2305, and a wire 2306. In the present embodiment, the wires are substantially the same as the wire 301, the wire 302, the wire 303, the wire 304, the wire 305, and the wire 306 of the first embodiment described above with reference to FIG. 5 and the like, and thus, detailed descriptions thereof will be omitted.

In addition, the power transmission part 2300 of the end tool 2100 of the surgical instrument according to the third embodiment of the present disclosure may include a coupling member 2321, a coupling member 2322, a coupling member 2323, a coupling member 2326, and the like, which are coupled to ends of the respective wires to combine the wires with the pulleys. In this regard, each of the coupling members may have various shapes as necessary, such as a ball shape, a tube shape, or the like. In the present embodiment, the coupling members are substantially the same as the coupling member 321, the coupling member 322, the coupling member 323, and the coupling member 326 of the first embodiment described above with reference to FIG. 5 and the like, and thus, detailed descriptions thereof will be omitted.

(End Tool)

Hereinafter, the end tool 2100 of the surgical instrument of FIG. 94 will be described in more detail.

Continuing to refer to FIGS. 94 to 115, the end tool 2100 of the third embodiment of the present disclosure includes a pair of jaws for performing a grip motion, that is, a first jaw 2101 and a second jaw 2102. In this regard, a component encompassing each of the first jaw 2101 and the second jaw 2102 or both the first jaw 2101 and the second jaw 2102 may be referred to as a jaw 2103.

In addition, the end tool 2100 may include a pulley 2111, a pulley 2112, a pulley 2113, a pulley 2114, a pulley 2115, and a pulley 2116, which are associated with a rotational motion of the first jaw 2101. In addition, the end tool 2100 may include a pulley 2121, a pulley 2122, a pulley 2123, a pulley 2124, a pulley 2125, and a pulley 2126, which are associated with a rotational motion of the second jaw 2102. These pulleys will be described in more detail below.

In addition, the end tool 2100 of the third embodiment of the present disclosure may include an end tool hub 2180 and a pitch hub 2107. The end tool hub 2180 will be described in more detail below.

In this regard, the end tool hub 2180 may internally accommodate at least portions of the pulley 2111 and the pulley 2121 that are axially coupled to a rotation axis 2141. In addition, the end tool hub 2180 may internally accommodate at least portions of the pulley 2112 and the pulley 2122 that are axially coupled to a rotation axis 2142.

A rotation axis 2143 and a rotation axis 2144 may be inserted through the pitch hub 2107, and the pitch hub 2107 may be axially coupled to the end tool hub 2180 and a pulley 2131 by the rotation axis 2143. Thus, the end tool hub 2180 and the pulley 2131 (formed with the end tool hub 2180 as one body) may be formed to be rotatable around the rotation axis 2143 with respect to the pitch hub 2107.

In addition, the pitch hub 2107 may internally accommodate at least portions of the pulley 2113, the pulley 2114, the pulley 2123, and the pulley 2124 that are axially coupled to the rotation axis 2143. In addition, the pitch hub 2107 may internally accommodate at least portions of the pulley 2115, the pulley 2116, the pulley 2125, and the pulley 2126 that are axially coupled to the rotation axis 2144.

In addition, the end tool 2100 of the third embodiment of the present disclosure may include the rotation axis 2141, the rotation axis 2142, the rotation axis 2143, and the rotation axis 2144.

The rotation axis 2141, the rotation axis 2142, the rotation axis 2143, and the rotation axis 2144 may be sequentially arranged from a distal end 2104 of the end tool 2100 toward a proximal end 2105. Accordingly, starting from the distal end 2104, the rotation axis 2141 may be referred to as a first pin, the rotation axis 2142 may be referred to as a second pin, the rotation axis 2143 may be referred to as a third pin, and the rotation axis 2144 may be referred to as a fourth pin.

In this regard, the rotation axis 2141 may function as a jaw pulley rotation axis, the rotation axis 2142 may function as both a jaw auxiliary pulley rotation axis and a pitch redundant rotation axis, the rotation axis 2143 may function as a pitch main rotation axis, and the rotation axis 2144 may function as a pitch sub-rotation axis of the end tool 2100.

Hereinafter, the end tool hub 2180 of the third embodiment of the present disclosure will be described in more detail, and in particular, the rotation axis 2142 of the end tool hub 2180, which serves as a jaw auxiliary pulley rotation axis, will be mainly described.

Referring to FIGS. 113 to 115, and the like, the end tool hub 2180 includes a first jaw pulley coupling part 2181, a second jaw pulley coupling part 2182, the rotation axis 2142, a pitch pulley coupling part 2185, and a guide part 2186. In addition, the rotation axis 2142 may include a first sub-shaft 2142*a* and a second sub-shaft 2142*b*.

In detail, the first jaw pulley coupling part 2181 and the second jaw pulley coupling part 2182 are formed to face each other such that the pulley 2111, the pulley 2112, the pulley 2121, and the pulley 2122 are accommodated therein. In addition, a through hole is formed in each of the jaw pulley coupling parts 2181 and 2182 such that the rotation axis 2141 passes through and axially couples the jaw pulley coupling parts 2181 and 2182, the pulley 2111, and the pulley 2121.

The first jaw pulley coupling part 2181 and the second jaw pulley coupling part 2182 are connected to each other by the guide part 2186. That is, the first jaw pulley coupling part 2181 and the second jaw pulley coupling part 2182 parallel to each other are coupled by the guide part 2186 formed in a direction substantially perpendicular thereto, such that the first jaw pulley coupling part 2181, the second jaw pulley coupling part 2182, and the guide part 2186 form a substantially "C" shape in which the pulley 2111, the pulley 2112, the pulley 2121, and the pulley 2122 are accommodated.

In other words, it may also be described that the first jaw pulley coupling part 2181 and the second jaw pulley coupling part 2182 are formed to extend in the X-axis direction from both ends of the guide part 2186 that is elongated in the Z-axis direction.

The first sub-shaft 2142a may be formed on an inner surface of the first jaw pulley coupling part 2181, and the second sub-shaft 2142b may be formed on the second jaw pulley coupling part 2182. In other words, it may also be described that the second rotation axis 2142, which is a jaw auxiliary pulley rotation axis, is formed by being divided into the first sub-shaft 2142a and the second sub-shaft 2142b.

In detail, the first sub-shaft 2142a and the second sub-shaft 2142b may be formed to be inclined to a certain extent. In other words, the first sub-shaft 2142a and the second sub-shaft 2142b may be formed obliquely rather than parallel to any one of the X-axis, Y-axis, and Z-axis.

In addition, the pulley 2112 may be coupled to the first sub-shaft 2142a, and the pulley 2122 may be coupled to the second sub-shaft 2142b. In this regard, the pulley 2112 may function as both a first jaw auxiliary pulley and a first pitch redundant pulley. In addition, the pulley 2122 may function as both a second jaw auxiliary pulley and a second pitch redundant pulley. This will be described in detail below.

Meanwhile, the pulley 2131 that serves as an end tool pitch pulley may be formed in the pitch pulley coupling part 2185 at one end of the end tool hub 2180. In this regard, the pulley 2131 may be formed with the end tool hub 2180 as one body. That is, one end of the end tool hub 2180 may be formed in a disk shape or a semicircular shape, and a groove around which a wire may be wound may be formed on an outer circumferential surface of the groove, such that a kind of guide channel is formed. Alternatively, the pulley 2131 may be formed as a separate member from the end tool hub 2180 and coupled to the end tool hub 2180. The wire 2303 and the wire 2304 described above are coupled to the pulley 2131 serving as an end tool pitch pulley, and a pitch motion is performed as the pulley 2131 is rotated around the rotation axis 2143.

Meanwhile, one or more pulleys may be fit into each of the rotation axes 2141, 2142, 2143, and 2144, and this will be described in detail below.

The pulley 2111 functions as a first jaw pulley, the pulley 2121 functions as a second jaw pulley, and these two components may be collectively referred to as a jaw pulley.

The pulley 2111 and the pulley 2121, which are jaw pulleys, are formed to face each other, and are formed to be rotatable independently of each other around the rotation axis 2141, which is a jaw pulley rotation axis. In this regard, the drawings illustrate that the pulley 2111 and the pulley 2121 are formed to be rotated around one rotation axis 2141, but it is needless to say that each jaw pulley may be formed to be rotatable around a separate shaft. In this regard, the first jaw 2101 may be fixedly coupled to the pulley 2111 to be rotated together with the pulley 2111, and the second jaw 2102 may be fixedly coupled to the pulley 2121 to be rotated together with the pulley 2121. Yaw and actuation motions of the end tool 2100 are performed according to rotation of the pulley 2111 and the pulley 2121. That is, when the pulley 2111 and the pulley 2121 are rotated in the same direction around the rotation axis 2141, the yaw motion is performed, and when the pulley 2111 and the pulley 2121 are rotated in opposite directions around the rotation axis 2141, the actuation motion is performed.

In this regard, the first jaw 2101 and the pulley 2111 may be formed as separate members and coupled to each other, or the first jaw 2101 and the pulley 2111 may be formed as one body. Similarly, the second jaw 2102 and the pulley 2121 may be formed as separate members and coupled to each other, or the second jaw 2102 and the pulley 2121 may be formed as one body.

The pulley 2112 functions as a first jaw auxiliary pulley, the pulley 2122 functions as a second jaw auxiliary pulley, and these two components may be collectively referred to as a jaw auxiliary pulley. Simultaneously, the pulley 2112 may function as a first pitch redundant pulley, and the pulley 2122 may function as a second pitch redundant pulley.

In detail, the pulley 2112 and the pulley 2122, which are jaw auxiliary pulleys, may be additionally provided on one side of the pulley 2111 and the pulley 2121. In other words, the pulley 2112, which is a jaw auxiliary pulley, may be arranged between the pulley 2111 and the pulley 2113/pulley 2114. In addition, the pulley 2122, which is a jaw auxiliary pulley, may be arranged between pulley 2121 and pulley 2123/pulley 2124. The pulley 2112 may be formed to be rotatable around the first sub-shaft 2142a of the rotation axis 2142, and the pulley 2122 may be formed to be rotatable around the second sub-shaft 2142b of the rotation axis 2142.

The pulley 2113 and the pulley 2114 may function as first jaw pitch main pulleys, the pulley 2123 and the pulley 2124 may function as second jaw pitch main pulleys, and these two components may be collectively referred to as a pitch main pulley.

The pulley 2115 and the pulley 2116 may function as first jaw pitch sub-pulleys, the pulley 2125 and the pulley 2126 may function as second jaw pitch sub-pulleys, and these two components may be collectively referred to as a pitch sub-pulley.

Accordingly, the rotation axis 2141, the rotation axis 2142, the rotation axis 2143, and the rotation axis 2144 may be sequentially arranged from the distal end 2104 of the end tool 2100 toward the proximal end 2105.

In addition, the pulley 2111, the pulley 2112, the pulley 2113/pulley 2114, and the pulley 2115/pulley 2116, which are associated with rotation of the first jaw 2101, may be sequentially arranged from the distal end 2104 of the end tool 100 toward the proximal end 2105.

In addition, the pulley 2121, the pulley 2122, the pulley 2123/pulley 2124, and the pulley 2125/pulley 2126, which are associated with rotation of the second jaw 2102, may be sequentially arranged from the distal end 2104 of the end tool 100 toward the proximal end 2105.

Hereinafter, the pulley 2112 and the pulley 2122 will be described in more detail.

First, the pulley 2112 may function as a first jaw auxiliary pulley, and the pulley 2122 may function as a second jaw auxiliary pulley. The pulley 2112 and the pulley 2122 may come into contact with the wire 2305, which is a first jaw wire, and the wire 2302, which is a second jaw wire to change the arrangement path of the wire 2305 and the wire 2302 to a certain extent, and thus perform a function of increasing a rotation angle of each of the first jaw 2101 and the second jaw 2102. The role of the auxiliary pulley will be similar to that described in the first embodiment of the present disclosure.

Simultaneously, the pulley 2112 may function as a first pitch redundant pulley, and the pulley 2122 may function as a second pitch redundant pulley. The pitch redundant pulleys may serve to change insertion/withdrawal paths of jaw wires entering from the proximal end of the end tool to the distal end, or coming out from the distal end to the proximal end.

In this regard, a plane passing between the pulley 2111, which is a first jaw pulley, and the pulley 2121, which is a second jaw pulley, is defined as a first plane, the side above the first plane in the +Z-axis direction is defined as an upper side, and the side below the first plane in the −Z-axis direction is defined as a lower side.

The wire 2305, which is a first jaw wire, is located on the upper side of the first plane when passing through the pulley 2114, which is a first jaw pitch main pulley, then the path of the wire 2305 is changed as the wire 2305 passes through the pulley 2112, which is a first pitch redundant pulley, and when the wire 2305 passes through the pulley 2111, which is a first jaw pulley, the wire 2305 is located on the lower side of the first plane.

In this regard, the first sub-shaft 2142*a* and the pulley 2112 coupled thereto are formed to be inclined with respect to the first plane, to serve to guide the path of the wire 2305 such that the wire 2305, which is located on the upper side of the first plane when in contact with the pulley 2114, is located on the lower side of the first plane when in contact with the pulley 2111.

That is, as illustrated in FIG. 114, the first sub-shaft 2142*a* and the pulley 2112 coupled thereto may be formed to be inclined to a certain extent on a YZ plane. In addition, as illustrated in FIG. 115, the first sub-shaft 2142*a* and the pulley 2112 coupled thereto may be formed to be inclined to a certain extent on an XZ plane.

Similarly, the wire 2302, which is a second jaw wire, is located on the lower side of the first plane when passing through the pulley 2124, which is a second jaw pitch main pulley, then the path of the wire 2302 is changed as the wire 2302 passes through the pulley 2122, which is a second pitch redundant pulley, and when the wire 2302 passes through the pulley 2121, which is a second jaw pulley, the wire 2302 is located on the upper side of the first plane.

In this regard, the second sub-shaft 2142*b* and the pulley 2122 coupled thereto are formed to be inclined with respect to the first plane, to serve to guide the path of the wire 2302 such that the wire 2302, which is located on the lower side of the first plane when in contact with the pulley 2124, is located on the upper side of the first plane when in contact with the pulley 2121.

That is, as illustrated in FIG. 114, the second sub-shaft 2142*b* and the pulley 2122 coupled thereto may be formed to be inclined to a certain extent on a YZ plane. In addition, as illustrated in FIG. 115, the second sub-shaft 2142*b* and the pulley 2122 coupled thereto may be formed to be inclined to a certain extent on an XZ plane.

Hereinafter, components associated with the rotation of the pulley 2111 will be described.

The pulley 2113 and the pulley 2114 are paired to function as first jaw pitch main pulleys. That is, the pulley 2113 and the pulley 2114 function as main rotation pulleys for a pitch motion of the first jaw 2101. In this regard, the wire 2301, which is a first jaw wire, is wound around the pulley 2113, and the wire 2305, which is a first jaw wire, is wound around the pulley 2114.

The pulley 2115 and the pulley 2116 are paired to function as first jaw pitch sub-pulleys. That is, the pulley 2115 and the pulley 2116 function as sub-rotation pulleys for a pitch motion of the first jaw 2101. In this regard, the wire 2301, which is a first jaw wire, is wound around the pulley 2115, and the wire 2305, which is a first jaw wire, is wound around the pulley 2116.

In this regard, the pulley 2113 and the pulley 2114 are arranged on one side of the pulley 2111 and the pulley 2112 to face each other. In this regard, the pulley 2113 and the pulley 2114 are formed to be rotatable independently of each other around the rotation axis 2143, which is a pitch main rotation axis. In addition, the pulley 2115 and the pulley 2116 are arranged on one sides of the pulley 2113 and the pulley 2114, respectively, to face each other. In this regard, the pulley 2115 and the pulley 2116 are formed to be rotatable independently of each other around the rotation axis 2144, which is a pitch sub-rotation axis. In this regard, the drawings illustrate that the pulley 2113, the pulley 2114, the pulley 2115, and the pulley 2116 are formed to be rotatable around the Y-axis direction, but the concept of the present disclosure is not limited thereto, and the rotation axes of the respective pulleys may be formed in various directions according to their configurations.

The wire 2301, which is a first jaw wire, is wound to sequentially come into contact with at least portions of the pulley 2115, the pulley 2113, and the pulley 2111. In addition, the wire 2305 connected to the wire 2301 by the coupling member 2323 is wound to sequentially come into contact with at least portions of the pulley 2111, the pulley 2112, the pulley 2114, and the pulley 2116.

In other words, the wire 2301 and the wire 2305, which are first jaw wires, are wound to sequentially come into contact with at least portions of the pulley 2115, the pulley 2113, the pulley 2111, the pulley 2112, the pulley 2114, and the pulley 2116, and are formed to move along the above pulleys while rotating the above pulleys.

Accordingly, when the wire 2301 is pulled in the direction of an arrow 2301 of FIG. 103, the coupling member 2323 to which the wire 2301 is coupled and the pulley 2111 coupled to the coupling member 2323 are rotated in the direction of an arrow L of FIG. 103. On the contrary when the wire 2305 is pulled in the direction of an arrow 2305 of FIG. 103, the coupling member 2323 to which the wire 2305 is coupled and the pulley 2111 coupled to the coupling member 2323 are rotated in the direction of an arrow R of FIG. 103.

Next, components associated with the rotation of the pulley 2121 will be described.

The pulley 2123 and the pulley 2124 are paired to function as second jaw pitch main pulleys. That is, the pulley 2123 and the pulley 2124 function as main rotation pulleys for a pitch motion of the second jaw 2102. In this regard, the wire 2306, which is a second jaw wire, is wound around the pulley 2123, and the wire 2302, which is a second jaw wire, is wound around the pulley 2124.

The pulley 2125 and the pulley 2126 are paired to function as second jaw pitch sub-pulleys. That is, the pulley 2125 and the pulley 2126 may function as sub-rotation pulleys for a pitch motion of the second jaw 2102. In this regard, the wire 2306, which is a second jaw wire, is wound around the pulley 2125, and the wire 2302, which is a second jaw wire, is wound around the pulley 2126.

In this regard, the pulley 2123 and the pulley 2124 are arranged on one side of the pulley 2121 and the pulley 2122 to face each other. In this regard, the pulley 2123 and the pulley 2124 are formed to be rotatable independently of each other around the rotation axis 2143, which is a pitch main rotation axis. In addition, the pulley 2125 and the pulley 2126 are arranged on one sides of the pulley 2123 and the pulley 2124, respectively, to face each other. In this regard, the pulley 2125 and the pulley 2126 are formed to be rotatable independently of each other around the rotation axis 2144, which is a pitch sub-rotation axis. In this regard, the drawings illustrate that the pulley 2123, the pulley 2124, the pulley 2125, and the pulley 2126 are formed to be rotatable around the Y-axis direction, but the concept of the present disclosure is not limited thereto, and the rotation axes of the respective pulleys may be formed in various directions according to their configurations.

The wire 2306, which is a second jaw wire, is wound to sequentially come into contact with at least portions of the pulley 2125, the pulley 2123, and the pulley 2121. In addition, the wire 2302 connected to the wire 2306 by the coupling member 2326 is wound to sequentially come into contact with at least portions of the pulley 2121, the pulley 2122, the pulley 2124, and the pulley 2126.

In other words, the wire 2306 and the wire 2302, which are second jaw wires, are wound to sequentially come into contact with at least portions of the pulley 2125, the pulley 2123, the pulley 2121, the pulley 2122, the pulley 2124, and the pulley 2126, and are formed to move along the above pulleys while rotating the above pulleys.

Accordingly, when the wire 2306 is pulled in the direction of an arrow 2306 of FIG. 103, the coupling member 2326 to which the wire 2306 is coupled and the pulley 2121 coupled to the coupling member 2326 are rotated in the direction of an arrow R of FIG. 103. On the contrary, when the wire 2302 is pulled in the direction of an arrow 2302 of FIG. 103, the coupling member 2326 to which the wire 2302 is coupled and the pulley 2121 coupled to the coupling member 2326 are rotated in the direction of an arrow L of FIG. 103.

In this regard, according to the present disclosure, two strands of jaw wires wound around one jaw pulley are wound around pitch main pulleys in opposite directions, such that a pitch motion is easily controlled.

In detail, when the side above, in the +Z-axis direction, a plane passing between the pulley 2111, which is a first jaw pulley, and the pulley 2121, which is a second jaw pulley (i.e., an XY plane) is defined as an upper side and the side below the plane in the −Z-axis direction is defined as a lower side, any one (e.g., the wire 2301) of the two strands of the first jaw wires may enter the pulley 2113, which is a first jaw pitch main pulley, from the lower side of the XY plane, and the other strand (e.g., the wire 2305) may come out of the pulley 2114, which is a first jaw pitch main pulley, from the upper side of the XY plane. In other words, it may be described as a structure in which the first jaw wire enters the first jaw pitch main pulley from the lower side and comes out from the upper side. (The second jaw wire enters the second jaw pitch main pulley from the upper side and comes out from the lower side)

In other words, the wire 2301, which is one strand of the first jaw wires, sequentially comes into contact with the upper side of the pulley 2115 and the lower side of the pulley 2113, and then comes into contact with the pulley 2111. Next, the wire 2305, which is the other strand of the first jaw wires, is wound around the pulley 2111 and the pulley 2112, and then sequentially comes into contact with the upper side of the pulley 2114, and the lower side of the pulley 2116, and then comes out toward the connection part 400. Accordingly, the first jaw wire comes out of a connection part 2400, enters the pulley 2113 from the lower side, then passes through each pulley, then passes through the upper side of the pulley 2114, and then enters back the connection part 400.

Similarly, the wire 2306, which is one strand of the second jaw wires, sequentially comes into contact with the lower side of the pulley 2125 and the upper side of the pulley 2123, and then comes into contact with the pulley 2121. Next, the wire 2302, which is the other strand of the second jaw wires, is wound around the pulley 2121 and the pulley 2122, and then sequentially comes into contact with the lower side of the pulley 2124 and the upper side of the pulley 2126, and then comes out toward the connection part 400. Accordingly, the second jaw wire comes out of the connection part 400, enters the pulley 2123 from the upper side, then passes through each pulley, then passes through the lower side of the pulley 2124, and then enters back the connection part 2400.

In other words, it may also be described that, any one wire of the two strands of the first jaw wires is wound around the first jaw pitch main pulley in any one of the clockwise direction and the counterclockwise direction while moving toward the end tool 2100 from a connection part 2400, and the other wire is wound around the first jaw pitch main pulley in the other one of the clockwise direction and the counterclockwise direction while moving toward the end tool 2100 from the connection part 2400. That is, as illustrated in FIGS. 100, 101, and 102, the wire 2301 is wound in the clockwise direction while moving toward the end tool 2100 from the connection part 2400, and the wire 2305 is wound in the counterclockwise direction while moving toward the end tool 2100 from the connection part 400.

Similarly, it may also be described that, any one wire of the two strands of the second jaw wires is wound around the second jaw pitch main pulley in any one of the clockwise direction and the counterclockwise direction while moving toward the end tool 2100 from the connection part 2400, and the other wire is wound around the second jaw pitch main pulley in the other one of the clockwise direction and the counterclockwise direction while moving toward the end tool 2100 from the connection part 2400. That is, as illustrated in FIGS. 100, 101, and 102, the wire 2302 is wound in the clockwise direction while moving toward the end tool 2100 from the connection part 2400, and the wire 2306 is wound in the counterclockwise direction while moving toward the end tool 2100 from the connection part 400.

As such, the end tool 2100 of the surgical instrument according to an embodiment of the present disclosure may obtain an effect of facilitating control of the pitch motion as the two strands of the jaw wires wound around one jaw pulley are wound around the pitch main pulleys in opposite directions. That is, during a pitch motion, the drive part first jaw pulley (see 211 of FIG. 11) and the drive part second jaw pulley (see 221 of FIG. 11) are rotated to wind or unwind the jaw wires, and thus perform a kind of compensation for the pitch motion, enabling the pitch motion of the end tool 2100.

As such, the present disclosure has been described with reference to one embodiment shown in the drawings, but it will be understood that this is merely exemplary, and those of ordinary skill in the art will understand that various modifications and variations of the embodiments are possible therefrom. Accordingly, the true technical protection scope of the present disclosure should be defined by the technical spirit of the appended claims.

INDUSTRIAL APPLICABILITY

The present disclosure relates to an end tool of a surgical instrument, and more particularly, may be used for an end tool provided in a surgical instrument that is mountable on a robotic arm or manually operable for use in laparoscopic surgery or various other surgeries.

The invention claimed is:

1. An end tool of a surgical instrument, the end tool comprising:
   a first jaw;
   a second jaw formed to face the first jaw;
   a first jaw pulley coupled to the first jaw and formed to be rotatable around a first shaft;
   a second jaw pulley coupled to the second jaw, formed to be rotatable around a shaft that is substantially the same as or parallel to the first shaft, and formed to face the first jaw pulley;
   a pair of first jaw pitch main pulleys formed on one side of the first jaw pulley, and formed to be rotatable around a second shaft forming a predetermined angle with the first shaft;
   a pair of second jaw pitch main pulleys formed on one side of the second jaw pulley, and formed to be rotatable around a shaft that is substantially the same as or parallel to the second shaft;
   a first jaw pitch redundant pulley arranged between the first jaw pulley and the pair of first jaw pitch main pulleys, and formed to be rotatable around a third shaft;
   a second jaw pitch redundant pulley arranged between the second jaw pulley and the pair of second jaw pitch main pulleys, and formed to be rotatable around a fourth shaft;
   a first jaw wire coupled to the first jaw pulley to rotate the first jaw pulley, and wound around at least portions of the pair of first jaw pitch main pulleys;
   a second jaw wire coupled to the second jaw pulley to rotate the second jaw pulley, and wound around at least portions of the pair of second jaw pitch main pulleys;
   an end tool hub formed to accommodate at least portions of the first jaw and the second jaw;
   a pitch hub axially coupled to the end tool hub to be rotatable with respect to the end tool hub;
   an end tool pitch pulley formed at a proximal end of the end tool hub; and
   a pitch wire coupled to the end tool pitch pulley to rotate the end tool pitch pulley.

2. The end tool of claim 1, wherein, among two strands of the first jaw wire coupled to the first jaw pulley, when moving from a proximal end to a distal end of the end tool, any one strand of the first jaw wire is wound around any one of the pair of first jaw pitch main pulleys in any one of a clockwise direction and a counterclockwise direction, and
   the other strand of the first jaw wire is wound around the other one of the pair of first jaw pitch main pulleys in the other one of the clockwise direction and the counterclockwise direction.

3. The end tool of claim 1, wherein, with respect to a plane perpendicular to the first shaft and passing between the first jaw pulley and the second jaw pulley, among two strands of the first jaw wire coupled to the first jaw pulley, any one strand of the first jaw wire comes into contact with an upper side of any one of the pair of first jaw pitch main pulleys, and
   the other strand of the first jaw wire comes into contact with a lower side of the other one of the pair of first jaw pitch main pulleys.

4. The end tool of claim 1, wherein the first jaw wire, when moving from a proximal end to a distal end of the end tool, sequentially comes into contact with the pair of first jaw pitch main pulleys and the first jaw pitch redundant pulley.

5. The end tool of claim 4, wherein, with respect to a plane perpendicular to the first shaft and passing between the first jaw pulley and the second jaw pulley, any one of two strands of the first jaw wire coupled to the first jaw pulley sequentially comes into contact with a lower side of any one of the pair of first jaw pitch main pulleys, and a lower side of the first jaw pitch redundant pulley, and
   the other one of the two strands of the first jaw wire coupled to the first jaw pulley sequentially comes into contact with an upper side of the other one of the pair of first jaw pitch main pulleys, and a lower side of the first jaw pitch redundant pulley.

6. The end tool of claim 1, further comprising:
   a first jaw auxiliary pulley formed between the first jaw pulley and the first jaw pitch redundant pulley; and
   a second jaw auxiliary pulley formed between the second jaw pulley and the second jaw pitch redundant pulley.

7. The end tool of claim 6, wherein the first jaw wire is located on a common internal tangent of the first jaw pulley and the first jaw auxiliary pulley, and
   a rotation angle of the first jaw pulley is increased by the first jaw auxiliary pulley.

8. The end tool of claim 1, further comprising:
   one or more first jaw pitch sub-pulleys formed on one side of the pair of first jaw pitch main pulleys and rotatable around a shaft that is substantially parallel to the second shaft; and
   one or more second jaw pitch sub-pulleys formed on one side of the pair of second jaw pitch main pulleys and rotatable around a shaft that is substantially parallel to the second shaft.

9. The end tool of claim 8, wherein the one or more first jaw pitch sub-pulleys or the one or more second jaw pitch sub-pulleys comprise only one pulley.

10. The end tool of claim 1, wherein a yaw motion is performed as the first jaw and the second jaw are rotated around the first shaft, and
    a pitch motion is performed as the end tool hub is rotated around the second shaft.

11. The end tool of claim 1, wherein, when the end tool pitch pulley is rotated by the pitch wire, as the entire end tool hub is rotated together with the end tool pitch pulley, lengths by which the first jaw wire is wound around the pair of first jaw pitch main pulleys and the pair of second jaw pitch main pulleys change.

12. The end tool of claim 11, wherein, when the end tool pitch pulley is rotated by the pitch wire, the first jaw wire is moved by an external force-to a certain extent, in order to compensate for changes in the lengths by which the first jaw wire is wound around the pair of first jaw pitch main pulleys and the pair of second jaw pitch main pulleys.

13. The end tool of claim 1, wherein the first jaw pitch redundant pulley or the second jaw pitch redundant pulley is formed with the end tool hub as one body.

14. The end tool of claim 1, wherein the third shaft and the fourth shaft are substantially parallel to the second shaft.

15. The end tool of claim 1, wherein the third shaft and the fourth shaft are formed to be inclined with respect to the first shaft and the second shaft, respectively.

16. The end tool of claim 1, wherein a groove on the first jaw pulley around which the first jaw wire is wound, and
    a groove on the second jaw pulley around which the second jaw wire is wound are formed to be spaced apart from each other to a certain extent.

17. The end tool of claim 1, wherein a groove on the first jaw pulley around which the first jaw wire is wound, and a groove on the second jaw pulley around which the second jaw wire is wound are formed adjacent to each other.

18. The end tool of claim 1, wherein the first jaw pitch redundant pulley or the second jaw pitch redundant pulley comprises only one pulley.

19. A surgical instrument comprising:
the end tool of the surgical instrument of claim 1;
a drive part configured to provide a certain driving force for rotation of the end tool; and
a connection part extending in a first direction (an X-axis) and having one end, to which the end tool is coupled, and another end, to which the drive part is coupled, to connect the drive part to the end tool.

20. The surgical instrument of claim 19, wherein, when a drive part pitch pulley of the drive part is rotated for a pitch motion, a drive part first jaw pulley and a drive part second jaw pulley of the drive part are rotated together to compensate for the pitch motion.

21. An end tool of a surgical instrument, the end tool comprising:
a first jaw;
a second jaw formed to face the first jaw;
a first jaw pulley coupled to the first jaw and formed to be rotatable around a first shaft;
a second jaw pulley coupled to the second jaw, formed to be rotatable around a shaft that is substantially the same as or parallel to the first shaft, and formed to face the first jaw pulley;
a pair of first jaw pitch main pulleys formed on one side of the first jaw pulley, and formed to be rotatable around a second shaft forming a predetermined angle with the first shaft;
a pair of second jaw pitch main pulleys formed on one side of the second jaw pulley, and formed to be rotatable around a shaft that is substantially the same as or parallel to the second shaft;
a first jaw pitch redundant pulley arranged between the first jaw pulley and the pair of first jaw pitch main pulleys, and formed to be rotatable around a third shaft;
a second jaw pitch redundant pulley arranged between the second jaw pulley and the pair of second jaw pitch main pulleys, and formed to be rotatable around a fourth shaft;
a first jaw wire coupled to the first jaw pulley to rotate the first jaw pulley, and wound around at least portions of the pair of first jaw pitch main pulleys; and
a second jaw wire coupled to the second jaw pulley to rotate the second jaw pulley, and wound around at least portions of the pair of second jaw pitch main pulleys,
wherein, with respect to a plane perpendicular to the first shaft and passing between the first jaw pulley and the second jaw pulley, among two strands of the first jaw wire coupled to the first jaw pulley, any one strand of the first jaw wire comes into contact only with an upper side of any one of the pair of first jaw pitch main pulleys, and
the other strand of the first jaw wire comes into contact only with a lower side of the other one of the pair of first jaw pitch main pulleys.

* * * * *